(12) United States Patent
Shekdar et al.

(10) Patent No.: US 9,872,514 B2
(45) Date of Patent: *Jan. 23, 2018

(54) COMPOUNDS, COMPOSITIONS, AND METHODS FOR REDUCING OR ELIMINATING BITTER TASTE

(71) Applicants: Chromocell Corporation, North Brunswick, NJ (US); Kraft Foods Group Brands LLC, Northfield, IL (US)

(72) Inventors: Kambiz Shekdar, New York, NY (US); Daniel Lavery, Princeton, NJ (US); Joseph Gunnet, Flemington, NJ (US); Jessica Langer, Highland Park, NJ (US); Jane V. Leland, Wilmette, IL (US); David Hayashi, Chicago, IL (US); Peter H. Brown, Glenview, IL (US); Louise Slade, Morris Plains, NJ (US); William P. Jones, Skokie, IL (US)

(73) Assignee: Chromocell Corporation, North Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/178,149

(22) Filed: Jun. 9, 2016

(65) Prior Publication Data
US 2017/0000178 A1  Jan. 5, 2017

Related U.S. Application Data

(60) Continuation of application No. 14/480,853, filed on Sep. 9, 2014, now Pat. No. 9,408,407, which is a division of application No. 13/641,213, filed as application No. PCT/US2011/032780 on Apr. 15, 2011, now Pat. No. 8,865,779.

(60) Provisional application No. 61/324,367, filed on Apr. 15, 2010, provisional application No. 61/324,416, filed on Apr. 15, 2010, provisional application No. 61/324,364, filed on Apr. 15, 2010, provisional application No. 61/324,407, filed on Apr. 15, 2010.

(51) Int. Cl.
| | | |
|---|---|---|
| A61K 47/00 | (2006.01) |
| A23L 27/00 | (2016.01) |
| A61K 47/06 | (2006.01) |
| A61K 47/08 | (2006.01) |
| A61K 47/10 | (2017.01) |
| A61K 47/12 | (2006.01) |
| A61K 47/14 | (2017.01) |
| A61K 47/22 | (2006.01) |
| A61K 47/44 | (2017.01) |
| C07C 63/06 | (2006.01) |
| C07C 69/78 | (2006.01) |
| C07D 311/20 | (2006.01) |
| C07D 311/22 | (2006.01) |
| C07D 311/72 | (2006.01) |
| A23L 27/20 | (2016.01) |
| A23L 27/16 | (2016.01) |
| A61K 47/02 | (2006.01) |

(52) U.S. Cl.
CPC ............... *A23L 27/86* (2016.08); *A23L 27/16* (2016.08); *A23L 27/203* (2016.08); *A23L 27/204* (2016.08); *A23L 27/2024* (2016.08); *A23L 27/2052* (2016.08); *A61K 47/02* (2013.01); *A61K 47/06* (2013.01); *A61K 47/08* (2013.01); *A61K 47/10* (2013.01); *A61K 47/12* (2013.01); *A61K 47/14* (2013.01); *A61K 47/22* (2013.01); *A61K 47/44* (2013.01); *C07C 63/06* (2013.01); *C07C 69/78* (2013.01); *C07D 311/20* (2013.01); *C07D 311/22* (2013.01); *C07D 311/72* (2013.01); *A23V 2002/00* (2013.01)

(58) Field of Classification Search
USPC ....................................................... 514/784
See application file for complete search history.

(56) References Cited

U.S. PATENT DOCUMENTS

| | | |
|---|---|---|
| 2,492,588 A | 12/1949 | Marhofer et al. |
| 3,919,318 A | 11/1975 | Acton et al. |
| 4,187,863 A | 2/1980 | Kovats et al. |
| 4,347,858 A | 9/1982 | Klemarczyk et al. |
| 4,983,394 A | 1/1991 | Hussein et al. |
| 5,602,184 A | 2/1997 | Myers et al. |
| 5,719,180 A | 2/1998 | Shudo et al. |
| 5,958,496 A | 9/1999 | Amino et al. |
| 6,020,505 A | 2/2000 | Hirose et al. |
| 7,576,049 B2 | 8/2009 | Shaath et al. |

(Continued)

FOREIGN PATENT DOCUMENTS

| | | |
|---|---|---|
| CN | 1572755 A | 2/2005 |
| EP | 0821055 A2 | 1/1998 |
| EP | 0941671 A2 | 9/1999 |
| EP | 1321140 A1 | 6/2003 |
| EP | 2198859 A1 | 6/2010 |

(Continued)

OTHER PUBLICATIONS

Vendramini et al., "Phenolic Compounds in Acerola Fruit (*Malpighia punicifolia*, L.)," Journal of the Brazilian Chemical Society, 15(5):664-668 (2004).

(Continued)

*Primary Examiner* — Rei Tsang Shiao
(74) *Attorney, Agent, or Firm* — Marcus Sands; Sabine Epelbaum

(57) ABSTRACT

The present invention provides edible compositions comprising a compound of the present invention, food products comprising such edible compositions and methods of preparing such food products. The present invention also provides methods of reducing the amount of NaCl in a food product, methods of reducing the sodium intake in a diet, and methods of reducing bitter taste in a food product.

16 Claims, 52 Drawing Sheets

(56) References Cited

U.S. PATENT DOCUMENTS

| | | | | |
|---|---|---|---|---|
| 8,865,779 | B2* | 10/2014 | Shekdar | A23L 27/16 514/784 |
| 9,408,407 | B2 | 8/2016 | Shekdar et al. | |
| 2003/0228402 | A1 | 12/2003 | Franklin et al. | |
| 2005/0158329 | A1 | 7/2005 | Ghosh | |
| 2006/0257543 | A1 | 11/2006 | Tachdjian et al. | |
| 2007/0077300 | A1 | 4/2007 | Wynn et al. | |
| 2008/0317923 | A1 | 12/2008 | Ley et al. | |
| 2009/0035337 | A1 | 2/2009 | Artiga-Gonzalez et al. | |
| 2009/0035444 | A1 | 2/2009 | Salemme et al. | |
| 2010/0035340 | A1 | 2/2010 | Drayna et al. | |
| 2010/0056621 | A1 | 3/2010 | Behrens et al. | |
| 2010/0184796 | A1 | 7/2010 | Behrens et al. | |
| 2010/0215740 | A1 | 8/2010 | Pilgaonkar et al. | |
| 2011/0045069 | A1 | 2/2011 | Ley et al. | |

FOREIGN PATENT DOCUMENTS

| | | | |
|---|---|---|---|
| EP | 2305048 | A1 | 4/2011 |
| EP | 2324833 | A1 | 5/2011 |
| JP | 2003073282 | A | 3/2003 |
| JP | 2004018431 | A | 1/2004 |
| JP | 2005013138 | A | 1/2005 |
| JP | 2005015686 | A | 1/2005 |
| JP | 2005082594 | A | 3/2005 |
| JP | 2005187360 | A | 7/2005 |
| JP | 2006025706 | A | 2/2006 |
| JP | 2007002005 | A | 1/2007 |
| JP | 2009517063 | A | 4/2009 |
| JP | 11060503 | | 5/2011 |
| JP | 11221042 | | 5/2011 |
| JP | 44004651 | | 6/2011 |
| JP | 2011115149 | A | 6/2011 |
| WO | WO1993010677 | | 6/1993 |
| WO | WO1994020080 | | 9/1994 |
| WO | WO1997004666 | | 2/1997 |
| WO | WO2000036933 | | 6/2000 |
| WO | WO2004029087 | A2 | 4/2004 |
| WO | WO2004087096 | A1 | 10/2004 |
| WO | WO2006087991 | A1 | 8/2006 |
| WO | WO2006101807 | A1 | 9/2006 |
| WO | WO2008119196 | A1 | 10/2008 |
| WO | WO2008119197 | A1 | 10/2008 |
| WO | WO2009015504 | A2 | 2/2009 |
| WO | WO2009112800 | A1 | 9/2009 |
| WO | WO2009137838 | A1 | 11/2009 |
| WO | WO2009140784 | A1 | 11/2009 |
| WO | WO2010023874 | A1 | 3/2010 |

OTHER PUBLICATIONS

Ata Wia et al., "Effect of Freezing of Jasmine Flowers on their Jasmine Concrete and Absolute Qualities", Egyptian Journal of Food Science, 16(1-2):237-247 (1988).
Papas et al. CAS: 142: 349067, 2005.
Bayer aspirin, 2005.
Amazon Camphor, 2005.
eBay Borneol, 2005.
Sigma-Alorich pinocarveol.
Sigma-Alorich Myrtenyl acetate, 2005.
Sigma-Alorich Myrtenol, 2005.
Sigma-Alorich Verbenone, 2005.
Sigma-Alorich Pinene, 2005.
Adam et al., "Clues to early diagenetic sulfurization processes from mild chemical cleavage oflabile sulfur-rich geomacromolecules," Geochimica et Cosmochimica Acta, 64(20):3485-3503 (2000).
Alsosalt Salt Substitute, www.alsosalt.com, downloaded Jan. 31, 2011 (2 pages).
Bang et al., "Phytol, SSADH inhibitory diterpenoid ofLactuca sativa," Archives of Pharmacal Research, 25(5):643-646 (2002).
Bauer et al., "Common Fragrance and Flavor Materials: Preparation, Properties, and Uses," Fourth Edition, Wiley-VCR Verlag GmbH, pp. 1-282 (2001).

Behrens et al., Structural requirements for bitter taste receptor activation, AChemS 2009 Annual Meeting, Sarasota, FL, Poster PI 41, Apr. 22-26, 2009 (4 pages).
Brockhoff et al., "Structural requirements of bitter taste receptor activation," PNAS, 107(24):11110-11115 (2010).
Doyle et al., "Sodium reduction and its effect on food safety, food quality, and human health," Comprehensive Reviews in Food Science and Food Safety, 9(1):44-56 (2009).
Hebting et al., "Biomarker evidence for a major preservation pathway of sedimentary organic carbon," Science, 312:1627-1631 (2006).
Kim et al., "Terpene and Phenolic Constituents ofLactuca indica," Archives of Pharmacal Research, 31(8):983-988 (2008).
Kuhn et al., "Bitter taste receptors for saccharin and acesulfame K," Journal of Neuroscience, 24( 45): 10260-10265 (2004).
Kumar et al., "Formulation evaluation of mouth dissolving tablets of Fenofibrate using sublimation technique," International Journal ofChemTech Research, 1(4):840-850 (2009).
Lee et al., "Phytochemical constituens ofCirsium setidens Nakai and their cytotoxicity against human cancer cell lines," Archives in Pharmacal Research 25(5):628-635 (2002).
Maguire, "Reducing Salt in SA Food," Web publication, pp. 1-2 (2007) http://www.developtechnology.co.za/index2. php?option=com content&do pdf= 1 &id= 19926.
http://www.colawp.com/colas/400/cola467 recipe.html.
Rodriguez-Garcia et al., "Evaluation of the antioxidant activity of three microalgal species for use as dietary supplements and in the preservation of foods," Food Chemistry, 108(3):1023-1026 (2008).
Senatore et al., "Chemical composition of the essential oil from aerial parts of *Stachys palustris* L. (Lamiaceae) growing wild in southern Italy," Croatica ChemicaActa, 80(1):135-139 (2007).
Slack et al., "Inhibition of bitter taste receptors," AChemS 2009 Annual Meeting, Sarasota, FL, Poster PI 95, Apr. 22-26, 2009 (4 pages).
Slack et al., "Modulation of bitter taste perception by a small molecule hTAS2R antagonist," Curr Biol., 20(12): 1104-1109 (2010).
Stevenson et al., "Resistance to extinction of conditioned odor perceptions: evaluative conditioning is not unique," Journal of Experimental Psychology: Learning, Memory and Cognition, 26(2):423-40 (2000).
The Good Scents Company Information Systems ( available at www.thegoodscentscompany.com, accessed Mar. 16, 2011).
Trost et al., "Taste+ odor interactions in compound aversion conditioning," Learning and Behavior, 32(4):440-453 (2004).
Winnig et al., "Saccharin: Artificial sweetener, bitter tastant, and sweet taste inhibitor," Sweetness and Sweeteners, Chapter 16, pp. 230-240 Chapter DOI: 10.1021/bk-2008-0979.ch016 ACS Symposium Series, vol. 979 http:/ /pubs.acs.org/doi/abs/10.1021/bk-2008-0979 .chO 16.
Winnig et al., "Saccharin: Artificial sweetener, bitter tastant, and sweet taste inhibitor," the 231 st ACS National Meeting Spring, 2006, poster AGFD 111, Atlanta, GA Mar. 26-30, 2006 (1 page).
Arun et al., "Evaluation of hot melt coating as taste masking tool," International Research Journal of Pharmacy, 2(8): 169-172 (2011).
Brown et al., "Diet and Refsun's Disease: The determination of phytanic acid and phytol in certain foods and the application of this knowledge to the choice of suitable convenience food for patients with Refsum's Disease," Journal of Human Nutrition and Dietetics, 6(4):295-305 (1993).
Pezoa et al., "Development of a Formulation of Sustained Release Potassium Chloride," Drug Development and Industrial Pharmacy, I 7(13):1875-1882 (1991).
Bezman et al., "Differential Effects of Tomato (*Lycopersicon esculentum* Mill) Matrix on the Volatility ofImportant Aroma Compounds," Journal of Agricultural and Food Chemistry, 51(3):722-726 (2003).
Lilic et al., "Possibility of replacement of sodium chloride by potassium chloride in cooked sausages—sensory characteristics and health aspects," Biotechnology in Animal Husbandry, 24(1-2):133-138 (2008).

(56) References Cited

OTHER PUBLICATIONS

Marais, "Terpenes in the Aroma of Grapes and Wines: A Review," South African Journal of Enology and Viticulture, 4(2):49-58 (1983).
Potassium: Tips for People with Chronic Kidney Disease (CKD), US Department of Health and Human Services, National Institutes of Health & National Kidney Disease Education Program, NIH Publication No. 11-7 407, Revised Sep. 2011 [online], <URL: http://nkdep.nih.gov/resources/nutrition-potassium-508.pdf> (2 pages).

* cited by examiner

FIGURE 1E
| No. | Test Compound Structure | KCl solution | KCl foodstuff | Potassium lactate solution | Potassium lactate foodstuff |
|---|---|---|---|---|---|
| 10 | 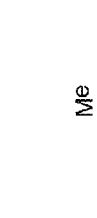 | <br>1 ppm<br>n=12<br>b | 10/18<br>0.1 ppm<br>d | <br>0.1 ppm<br>n=8<br>d | — |
| 11 | 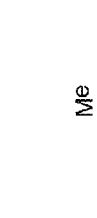 | 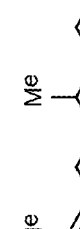<br>10 ppm<br>n=9<br>b | 10/20<br>5 ppm<br>d | <br>10 ppm<br>n=5<br>d | — |

FIGURE 1G
| No. | Test Compound Structure | KCl solution | KCl foodstuff | Potassium lactate solution | Potassium lactate foodstuff |
|---|---|---|---|---|---|
| 15 | 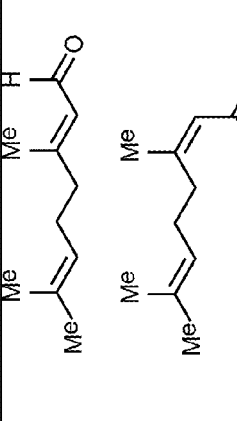 (mixture) | 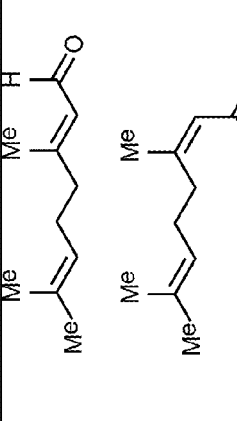 1 ppm n=6 a | -- | -- | -- |
| 17 | 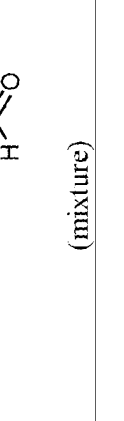 |  1 ppm n=8 d | -- | -- | -- |

FIGURE 1H

| No. | Test Compound Structure | KCl solution | KCl foodstuff | Potassium lactate solution | Potassium lactate foodstuff |
|---|---|---|---|---|---|
| 18 | (structure: Me, OMe, OMe, Me, HO, Me) | 10 ppm n=7 d | --- | --- | --- |
| 19 | (structure: Me, OH, Me, Me) | 10 ppm n=13 a | --- | --- | --- |
| 20 | (structure: Me, O, H, Me, Me) | No Blocking Effect | --- | --- | --- |

FIGURE 1K

| No. | Test Compound Structure | KCl solution | KCl foodstuff | Potassium lactate solution | Potassium lactate foodstuff |
|---|---|---|---|---|---|
| 25 | ![structure] Me, Me, Me, O-C(=O)-iBu | 10 ppm n=8 d | -- | -- | -- |
| 26 | ![structure] Me, Me, Me, O-C(=O)-CH2-Ph | 1 ppm n=9 b | 9/18 0.1 ppm d | 10 ppm n=5 b | -- |

FIGURE 1M
| No. | Test Compound Structure | KCl solution | KCl foodstuff | Potassium lactate solution | Potassium lactate foodstuff |
|---|---|---|---|---|---|
| 31 |  | 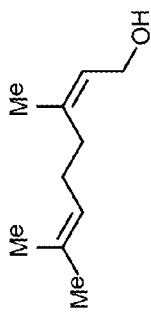<br>10 ppm<br>n=11<br>b | 25/44<br>10 ppm<br>d | 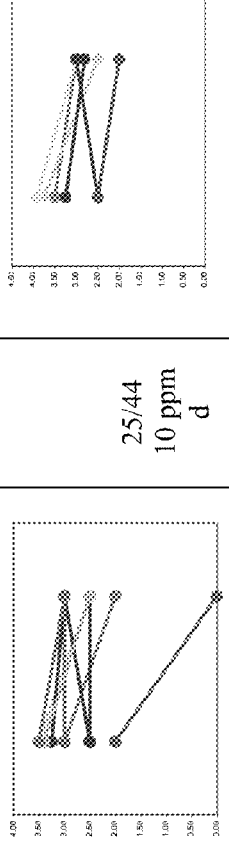<br>10 ppm<br>n=8<br>b | -- |
| 32 | 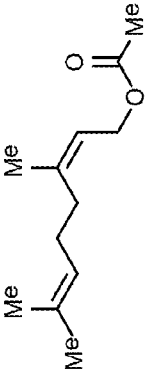 | <br>1 ppm<br>n=15<br>d | -- | -- | -- |

FIGURE 1N

| No. | Test Compound Structure | KCl solution | KCl foodstuff | Potassium lactate solution | Potassium lactate foodstuff |
|---|---|---|---|---|---|
| 33 | ![structure with Me, Me, Me, O, O-nPr] | 1 ppm<br>n=6<br>d | -- | -- | -- |
| 34 | ![structure with Me, Me, Me, O, O-iPr] | 10 ppm<br>n=13<br>b | 12/24<br>10 ppm<br>d | 1 ppm<br>n=8<br>c | 13/26<br>10 ppm<br>d |

FIGURE 10
| No. | Test Compound Structure | KCl solution | KCl foodstuff | Potassium lactate solution | Potassium lactate foodstuff |
|---|---|---|---|---|---|
| 36 | 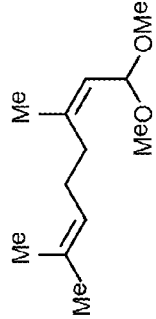 | 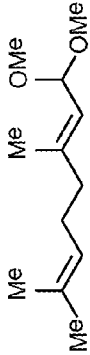 1 ppm n=9 a | -- | -- | -- |
| 37 | NEROLI, BIGARADE OIL (CITRUS AURANTIUM L.) | 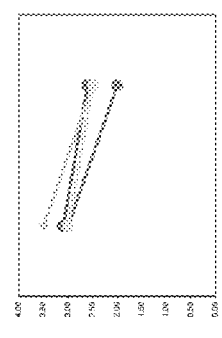 10 ppm n=4 c | 13/26 0.1 ppm d | No Blocking Effect | -- |

FIGURE 1P
| No. | Test Compound Structure | KCl solution | KCl foodstuff | Potassium lactate solution | Potassium lactate foodstuff |
|---|---|---|---|---|---|
| 38 | CITRONELLA, OIL (CYMBOPOGON NARDUS RENDLE) | <br>1 ppm<br>n=9<br>d | -- | -- | -- |
| 39 | GERANIUM, OIL (PELARGONIUM SPP.) | <br>10 ppm<br>n=12<br>d | -- | -- | -- |

| No. | Test Compound Structure | KCl solution | KCl foodstuff | Potassium lactate solution | Potassium lactate foodstuff |
|---|---|---|---|---|---|
| 40 | GERANIUM, EAST INDIAN, OIL (CYMBOPOGON MARTINI STAPF.) | 10 ppm n=6 d | -- | -- | -- |

FIGURE 2A

Solution Testing – The left data point in the solution charts represents the bitterness or metallic taste/impression score of the KCl/potassium lactate standard. The right data point in the solution charts represents the bitterness or metallic taste/impression score of the Test Solution. The concentration of the Test Compound used in each experiment is recited below the chart. In addition, the statistical significance of the Solution Testing data, determined using a paired T-test analysis, is presented wherein "a" represents $p < 0.1$; "b" represents $p < 0.05$; "c" represents $p < 0.01$; and "d" represents $p > 0.1$ (data not shown).

Foodstuff Testing – The fraction represents the number of tasters that discerned a decrease in the bitterness or metallic taste/impression of the Test Foodstuff. In addition, the concentration of the Test Compound used in each experiment is recited. Further, the statistical significance of the Foodstuff Testing data, determined using binomial distribution analysis, is presented wherein "a" represents $p < 0.1$; "b" represents $p < 0.05$; "c" represents $p < 0.01$; and "d" represents $p > 0.1$ (data not shown).

"--" denotes that the solution or foodstuff was not tested.

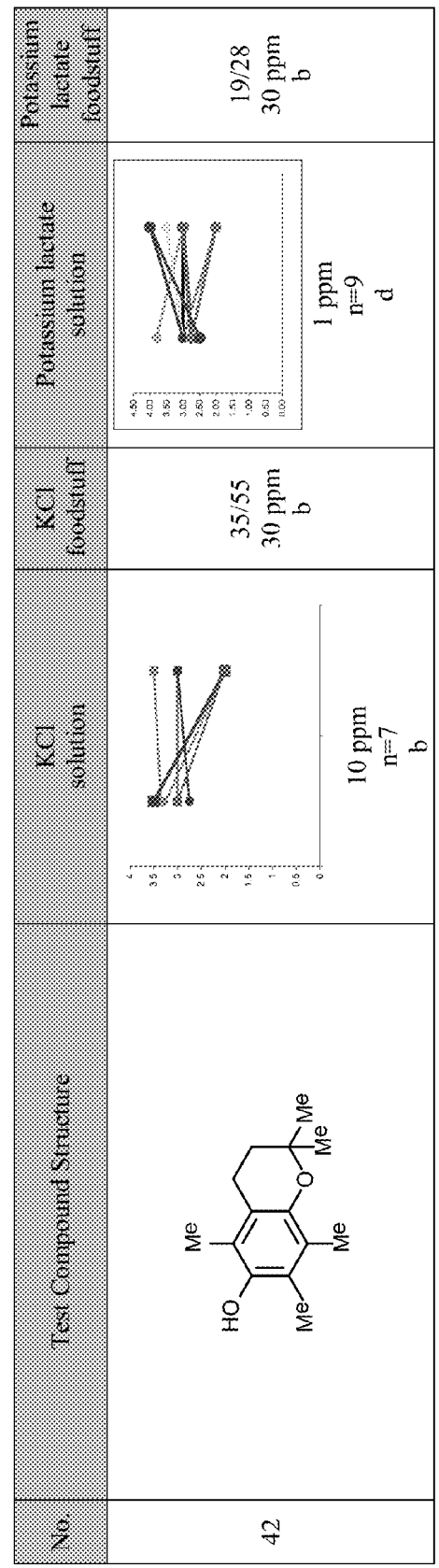

FIGURE 2C
| No. | Test Compound Structure | KCl solution | KCl foodstuff | Potassium lactate solution | Potassium lactate foodstuff |
|---|---|---|---|---|---|
| 45 | 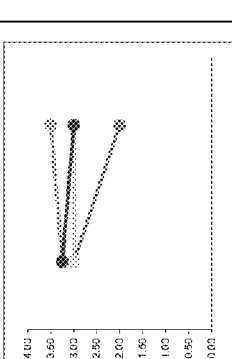 | 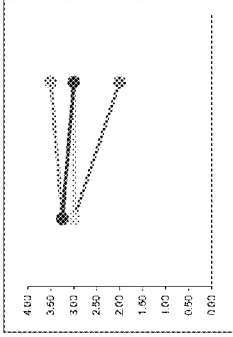 1 ppm n=5 d | -- | -- | -- |
| 47 | 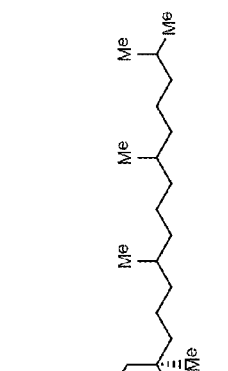 | 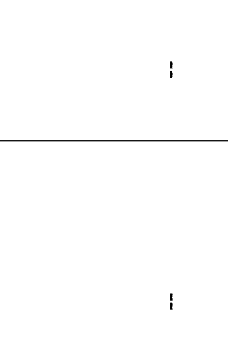 1 ppm n=5 d | -- | -- | -- |

FIGURE 3D

| No. | Test Compound Structure | KCl solution | KCl foodstuff | Potassium lactate solution | Potassium lactate foodstuff |
|---|---|---|---|---|---|
| 60 | salicylic acid (2-hydroxybenzoic acid) | 1 ppm<br>n=8<br>d | -- | -- | -- |
| 61 | methyl 4-hydroxybenzoate | 1 ppm<br>n=8<br>d | -- | -- | -- |

FIGURE 4A
| No. | Test Compound Structure | KCl solution | KCl foodstuff | Potassium lactate solution | Potassium lactate foodstuff |
|---|---|---|---|---|---|
| 73 | 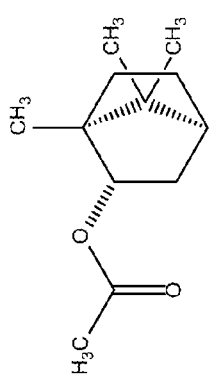 | 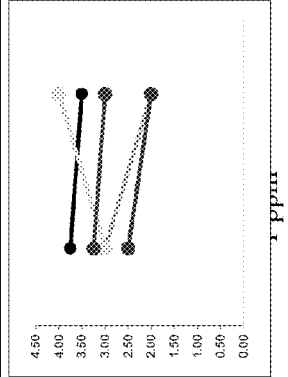 1 ppm n=6 d | --- | --- | --- |
| 74 | 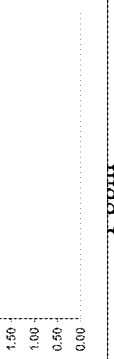 | 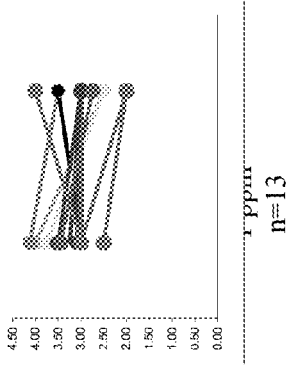 1 ppm n=13 b | 28/52 10 ppm d | 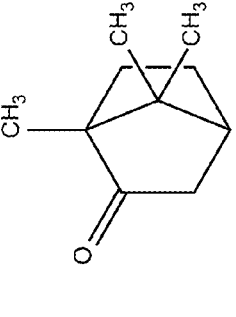 1 ppm n=6 c | 27/52 1 ppm d |

FIGURE 4B
| No. | Test Compound Structure | KCl solution | KCl foodstuff | Potassium lactate solution | Potassium lactate foodstuff |
|---|---|---|---|---|---|
| 76 | 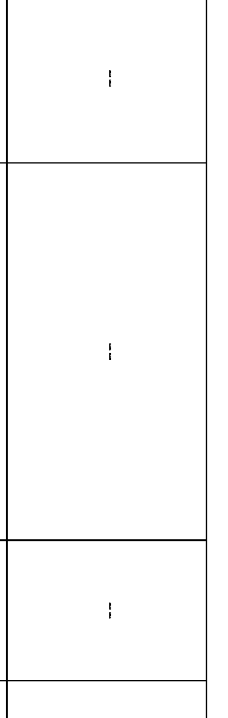 | 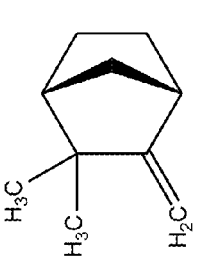 n=8 | --- | --- | --- |
| 78 | 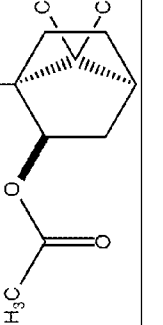 | 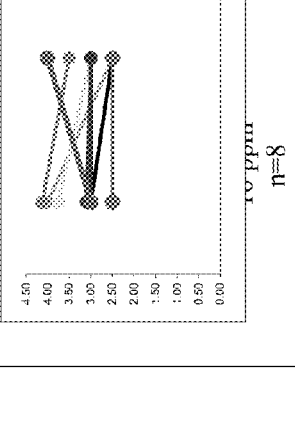 n=6 | --- | --- | --- |
| 80 | 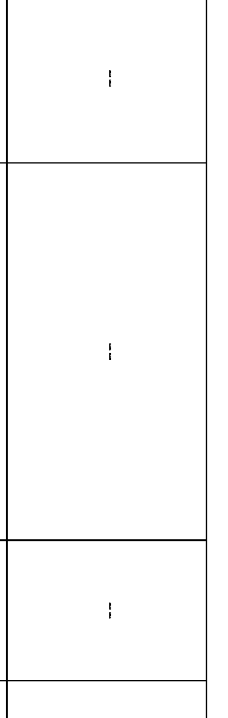 | No Blocking Effect | --- | --- | --- |

FIGURE 4C

| No. | Test Compound Structure | KCl solution | KCl foodstuff | Potassium lactate solution | Potassium lactate foodstuff |
|---|---|---|---|---|---|
| 81 | | n=8 | -- | -- | -- |
| 84 | | n=8 | -- | -- | -- |

FIGURE 4F
| No | Test Compound Structure | KCl solution | KCl foodstuff | Potassium lactate solution | Potassium lactate foodstuff |
|---|---|---|---|---|---|
| 94 | 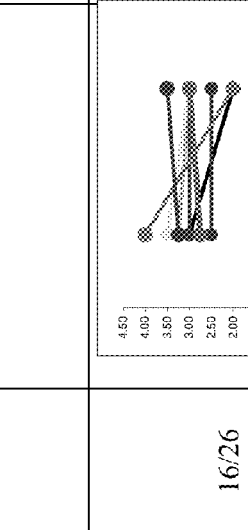 | 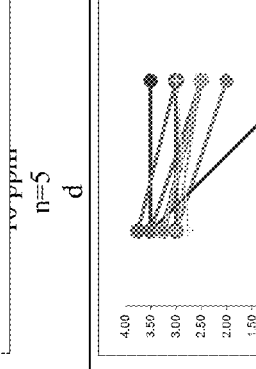 10 ppm n=5 d | --- | --- | --- |
| 95 | 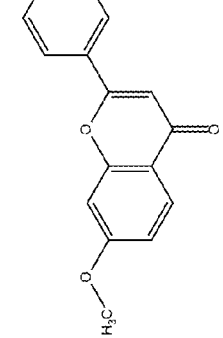 | 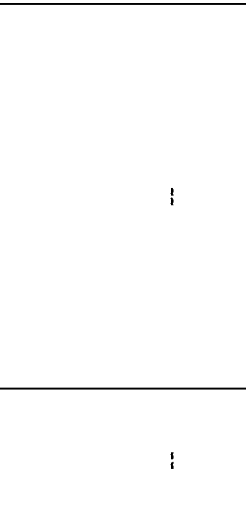 0-1 ppm n=16 c | 16/26 1 ppm d | 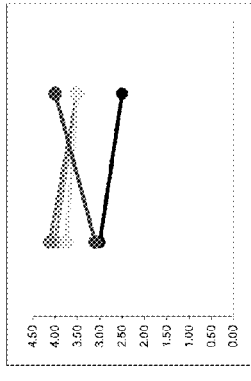 1 ppm n=9 b | 18/24 10 ppm b |

FIGURE 4K

| No. | Test Compound Structure | KCl solution | KCl foodstuff | Potassium lactate solution | Potassium lactate foodstuff |
|---|---|---|---|---|---|
| 107 | (catechin gallate-like structure) | ~6 ppm, n=5 | --- | --- | --- |
| 108 | (catechin gallate-like structure) | ~7 ppm, n=8 | --- | --- | --- |
| 109 | (flavone structure) | No Blocking Effect | --- | --- | --- |

FIGURE 4L

| No | Test Compound Structure | KCl solution | KCl foodstuff | Potassium lactate solution | Potassium lactate foodstuff |
|---|---|---|---|---|---|
| 110 | ![structure with OCH3, OH groups on flavone] | No Blocking Effect | -- | -- | -- |
| 111 | ![structure with OH, OH groups on flavonol] | (graph) 10 ppm n=7 b | 22/42 1 ppm d | -- | -- |
| 112 | ![structure with OH on flavonol] | No Blocking Effect | -- | -- | -- |

FIGURE 4M

| No. | Test Compound Structure | KCl solution | KCl foodstuff | Potassium lactate solution | Potassium lactate foodstuff |
|---|---|---|---|---|---|
| 113 | [piperidine amide of piperine-like compound structure] | 1 ppm<br>n=7<br>d | --- | --- | --- |
| 114 | [piperonal / benzo[d][1,3]dioxole-5-carbaldehyde structure] | 10 ppm<br>n=6<br>a | 18/30<br>1 ppm<br>d | --- | --- |
| 115 | Black Pepper Oil (mixture of structures) | No Blocking Effect | --- | --- | --- |

FIGURE 4N
| No. | Test Compound Structure | KCl solution | KCl foodstuff | Potassium lactate solution | Potassium lactate foodstuff |
|---|---|---|---|---|---|
| 116 | 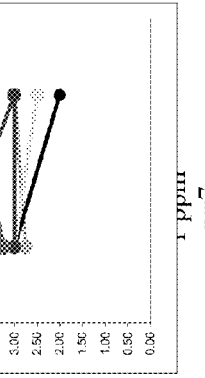 | 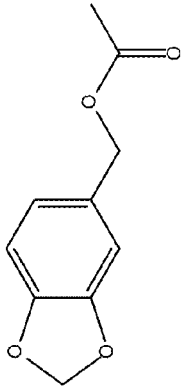 τ ppm n=12 d | -- | -- | -- |
| 117 | 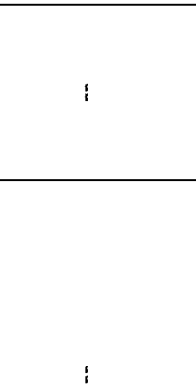 | 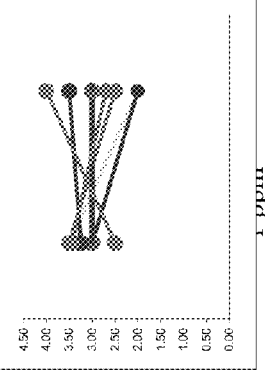 τ ppm n=7 d | -- | -- | -- |

FIGURE 40

| No. | Test Compound Structure | KCl solution | KCl foodstuff | Potassium lactate solution | Potassium lactate foodstuff |
|---|---|---|---|---|---|
| 118 | ![structure: safrole-like, benzodioxole with propenyl CH₃] | n=9, b | -- | -- | -- |
| 119 | Camphor Oil (mixture of structures) | n=7, d | -- | -- | -- |

FIGURE 4Q
| No. | Test Compound Structure | KCl solution | KCl foodstuff | Potassium lactate solution | Potassium lactate foodstuff |
|---|---|---|---|---|---|
| 122 | 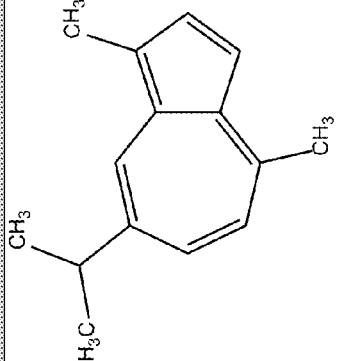 | 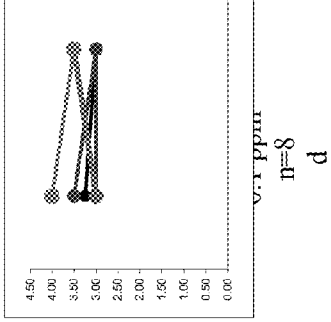<br>n=8<br>d | -- | -- | -- |
| 123 | 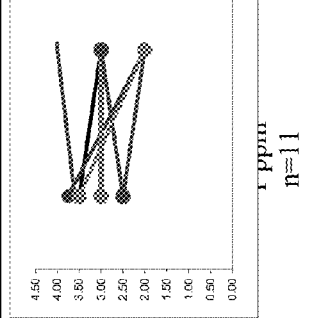 | 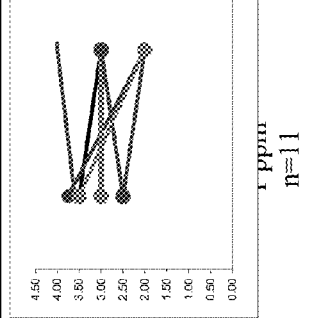<br>n=11<br>a | -- | -- | -- |

FIGURE 4R

| No. | Test Compound Structure | KCl solution | KCl foodstuff | Potassium lactate solution | Potassium lactate foodstuff |
|---|---|---|---|---|---|
| 124 | (guaiacol structure: phenol with OCH₃) | chart, 0.1 ppm, n=9, d | -- | -- | -- |
| 126 | (bicyclic sesquiterpene structure) | chart, 1 ppm, n=6, c | -- | -- | -- |
| 127 | (long-chain phenolic ketone structure) | -- | -- | -- | -- |

FIGURE 4T

| No. | Test Compound Structure | KCl solution | KCl foodstuff | Potassium lactate solution | Potassium lactate foodstuff |
|---|---|---|---|---|---|
| 130 | (structure: methoxy-substituted pyrido-indole with CH₃) | n=9 | -- | -- | -- |
| 132 | (structure: methoxybenzofuran with phenyl diketone) | n=6 | -- | -- | -- |

COMPOUNDS, COMPOSITIONS, AND METHODS FOR REDUCING OR ELIMINATING BITTER TASTE

CROSS REFERENCE TO RELATED APPLICATIONS

This application is a continuation of U.S. patent application Ser. No. 14/480,853, filed Sep. 9, 2014 (allowed), which is a divisional of U.S. patent application Ser. No. 13/641,213, filed Dec. 21, 2012, now U.S. Pat. No. 8,865,779, issued Oct. 21, 2014, which is United States National Stage Application under 35 U.S.C. §371 of International Application No. PCT/US2011/032780, filed Apr. 15, 2011 (expired), which claims the benefit of U.S. Provisional Application No. 61/324,416, filed Apr. 15, 2010, U.S. Provisional Application No. 61/324,407, filed Apr. 15, 2010, U.S. Provisional Application No. 61/324,367, filed Apr. 15, 2010, and U.S. Provisional Application No. 61/324,364, filed Apr. 15, 2010, the contents of which are hereby incorporated by reference in their entireties.

FIELD OF THE INVENTION

The present invention relates to flavor in edible compositions.

BACKGROUND OF THE INVENTION

The sense of taste, e.g., in human, can detect at least five traditional tastes: sweet, sour, salty, bitter, and umami (savory). Many nutritious substances including vegetables, foods, food ingredients and nutrients comprise bitter tastants and/or have a bitter taste. In addition, many pharmaceutical substances important to maintain or improve health comprise bitter tastants and/or have a bitter taste. While certain food products and consumer products have desirable bitter tastes, including coffee, beer and dark chocolate, in many contexts, consumers dislike such bitter tastes, for example, many consumers dislike the perception of certain bitter tastants and/or bitter taste and will avoid food or pharmaceutical products with an undesirable bitter tastant or bitter taste in favor of food and pharmaceutical products that have reduced levels of undesirable bitter tastants or that have reduced or that completely lack bitter taste. This aversion to products containing undesirable bitter tastants and/or having undesirable bitter taste may be caused by perception of bitter tastants and/or bitter taste mediated by activation of bitter receptors present in the oral cavity and/or in the gastrointestinal tract. In many cases, consumer dislike of bitter tastants and/or bitter taste prevents or hampers improvement of the nutritive quality and safety of foods as desired levels of nutrients or preservatives comprising bitter tastants and/or having bitter taste cannot be used. Also, dislike of or aversion to the bitter tastants or bitter taste of some pharmaceutical agents negatively impacts compliance with prescribed regimens for their use.

For instance, several additives, preservatives, emulsifiers and foodstuffs used in the production of food products comprise bitter tastants and/or have a bitter taste. While these additives, preservatives, emulsifiers and foodstuffs may affect the taste of a food product, they may also be important for improving the shelf life, nutritive quality, or texture of the food product. For example, the increasing trend of hypertension and cardiovascular disease has been attributed, in past, to the high sodium intake of the Western diet. Accordingly, substitution of sodium chloride with another salty tasting compound, is desirable. The most common sodium chloride substitute is potassium chloride, which, to a portion of the population, is perceived as possessing a bitter taste in addition to its salty taste. The bitter taste of potassium chloride limits the extent to which it may be used to replace sodium chloride in foods without causing undesired bitter taste for the portion of the population sensitive to it.

Another common food additive, sodium lactate, has a broad antimicrobial action, is effective at inhibiting spoilage, and growth of pathogenic bacteria, and is commonly used in food products (e.g., meat and poultry products) to extend shelf life and increase food safety. Due to its sodium content, however, sodium lactate, can be undesirable as a preservative. Potassium lactate, which has similar antimicrobial properties, has been used in lieu of sodium lactate. However, potassium lactate is also associated with a bitter taste which limits the extent to which it may be used to replace sodium lactate in foods without causing undesired bitter taste.

In addition, the increasing incidence of obesity and diabetes has been attributed, in part, to the high sugar intake of many diets. Accordingly, substitution of sugar with another sweet tasting compound is desirable. Artificial and natural sugar substitutes that may be used to reduce sugar in foods are often associated with bitter taste which again limit the extent to which these may be used to replace sugar in foods without causing adverse bitter taste. For example, a common sugar substitute is Acesulfame K, which also has a bitter taste in addition to its sweet taste.

Without being limited by theory, bitter, sweet, and umami tastants and compounds typically elicit a taste response via G-protein coupled receptors, while salty and sour tastants and compounds are typically hypothesized to elicit a taste response via ion channels. Bitter taste receptors belong to the T2R (also referred to as TAS2R) family of G-protein coupled receptors that induce intracellular calcium concentration changes in response to a bitter tastant. T2R receptors act via gustducin, a taste-specific G-protein. There are at least twenty-five different members of the T2R family, suggesting that the perception of bitter taste is complex, involving several different tastant-receptor interactions. Compounds capable of modulating the activation and/or signaling of bitter taste receptors in the oral cavity and/or the gastrointestinal tract could be effective to allow desired usage levels of bitter tastants or bitter tasting substances in food and pharmaceutical products without resulting in consumer dislike of such products due to perception of the increased levels of bitter tastants or bitter tastes. In some instances, blockers or modulators of bitter taste receptors and bitter taste may reduce the perception of bitter tastants and/or bitter taste via the bitter taste receptors and/or taste transduction signaling machinery present in the oral cavity and/or the gastrointestinal tract.

Traditionally in food preparation and pharmaceuticals, bitter taste was masked using sweeteners and other tastants, including salt. In some cases, however, this is undesirable or insufficient because it can alter, mask, or interfere with other testes/flavors/impressions (e.g., non bitter tastes or desired bitter tastes) in the food product Additionally, this approach has rarely been able to completely mask the bitter taste present in such food products or pharmaceuticals. For that reason, compounds which reduce bitter taste instead of, or in addition to, masking agents are preferred.

It is, therefore, desirable to provide compounds that may be added to food products, consumer products and pharmaceuticals comprising bitter tastants or having a bitter taste to eliminate, modulate or reduce the perception of the bitter tastants or bitter taste or to reduce the corresponding activation of the bitter receptors in the oral cavity and/or the gastrointestinal tract. Similarly, it is desirable to provide food products, consumer products, and pharmaceutical compositions comprising such compounds. It is also desirable to decrease the sodium intake of a subject using such compounds to eliminate, modulate or reduce the perception of bitter taste associated with salt substitutes. It is further desirable to decrease the sugar intake of a subject using such compounds to eliminate, modulate or reduce the perception of bitter taste associated with sugar substitutes.

SUMMARY OF THE INVENTION

The present invention provides compounds that modulate bitter taste, edible compositions comprising such compounds, and methods of preparing such edible compositions. The present invention also provides methods of reducing the amount of sodium or sugar in an edible composition and methods of reducing bitter taste of an edible composition. The present invention further provides a method of reducing, modulating or eliminating the bitter taste of a food, consumer or pharmaceutical product in a subject. The present invention also provides a method of modulating, particularly reducing the activation of a bitter taste receptor.

One aspect of the present invention provides edible compositions for reducing bitter taste of a bitter tastant. In some embodiments, the edible composition comprises a terpenoid compound. In some embodiments, the terpenoid compound is a compound having a molecular weight less than about 1030, 500, or 300 daltons. In certain embodiments, the terpenoid compound is a compound of Formula II), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), and Formula (IIh) or Compounds 1-41 or a comestibly or biologically acceptable salt or derivative thereof, or an enantiomer or diastereomer thereof.

In certain embodiments, the compound of Formula (I) is selected from the group consisting of damascene compounds (e.g., β-damascene, trans-α-damascene), ionone compounds (e.g., β-ionone, α-ionone, γ-ionone, and dihydro-α-ionone, particularly either β-ionone or α-ionone), nerol, geranyl isovalerate, geranyl acetone, neryl acetate, geranyl propionate, geranyl butyrate, citronellyl propionate, citronellyl isobutyrate, citral diethyl acetal, geranyl phenylacetate, geranyl formate, DL-citronellol, neryl isovalerate, citronellyl acetate, citral dimethyl acetal, citral, geranial, neral, neryl butyrate, citronellal, hydroxycitronellal, citronellyl valerate, geraniol, neryl isobutyrate, geranyl acetate, citronellyl formate, and hydroxycitronellal dimethyl acetal or a comestibly or biologically acceptable salt or derivative thereof, or an enantiomer or diastereomer thereof.

In some embodiments, the edible composition comprises a chroman compound. In some embodiments, the chroman compound is a compound having a molecular weight less than about 1000, 500, or 300 daltons. In certain embodiments, the chroman compound is a compound of Formula (V), Formula (VIa), Formula (VIb), or Formula (VIIa) or Compounds 42-53 or a comestibly or biologically acceptable salt or derivative thereof, or an enantiomer or diastereomer thereof.

In certain embodiments, the compound of Formula (V) is selected from the group consisting of pentamethyl-6-chromanol, α-tocopherol, (+)-δ-tocopherol, (+)-α-tocopherol acetate, D-α-tocopherol succinate, DL-α-tocopherol acetate, Vitamin E acetate, 4-chromanol and dihydrocoumarin.

In some embodiments, the edible composition comprises a benzo ring-containing compound. In some embodiments, the benzo ring-containing compound is a compound having a molecular weight less than about 1000, 500, or 300 daltons. In certain embodiments, the benzo ring-containing compound is a compound of Formula (VIII), Formula (IXa), Formula (IXb), Formula (IXe), or Formula (IXd) or Compounds 54-71 or a comestibly or biologically acceptable salt or derivative thereof, or an enantiomer or diastereomer thereof.

In certain embodiments, the compound of Formula (VIII) is selected from the group consisting of benzoic acid, ethyl benzoate, propyl benzoate, phenylethyl benzoate, 4-hydroxybenzoic acid, methyl para-hydroxybenzoate, ethyl/para-hydroxybenzoate, butyl paraben, 4-methoxybenzoic acid, 3-methoxybenzoic acid, 2-methoxybenzoic acid, 4-propoxybenzoic acid, methyl-ortho-methoxy benzoate, para-hydroxybenzyl alcohol, α-methylbenzyl alcohol, and 4-(1-hydroxyethyl)-2-methoxyphenol.

In some embodiments, the edible composition comprises one or more polycyclic compounds. In some embodiments, the polycyclic compound is a compound having a molecular weight less than about 1000, 500, 300 or 200 daltons. In certain embodiments, the polycyclic compound has a bicyclic core with a one-carbon transannular bridge, such as a compound of Formula (XI) or Formula (XII) or Compounds 72-94 or a comestibly or biologically acceptable salt or derivative thereof, or an enantiomer or diastereomer thereof.

The present invention also includes edible compositions comprising a compound according to any one of Compounds 95-134 or comestibly or biologically acceptable salts or derivatives thereof, or enantiomers or diastereomers thereof.

In some embodiments, the edible composition comprises (a) a compound of the invention; and (b) a bitter tastant. In some embodiments, the compound of the invention is a compound having a molecular weight less than about 1000, 500, or 300 daltons. In certain embodiments, the compound of the invention is a compound of Formula (I), Formula (Ia), Formula (IIa), Formula (IIIa), Formula (IIb), Formula ((IIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

In another embodiment, the edible composition comprises (a) any one of Compounds 1-134, or combinations thereof; and (b) a bitter tastant.

In another embodiment, the edible composition comprises (a) any one of Compounds 1-58, or 61-134, or combinations thereof; and (b) a bitter tastant.

According to the invention, the bitter tastant can be inherent in, e.g., a food product (such as coffee or chocolate) or can be a component of an edible composition (such as a bitter tasting preservative). In some embodiments, the bitter tastant present in the edible composition is a bitter tasting salt. In some embodiments, the bitter tastant present in the edible composition is a potassium salt, a magnesium salt, or a calcium salt. In some embodiments, the bitter tastant is a potassium salt. In some embodiments, the bitter tastant present in the edible compositions is KCl. In other embodiments, the bitter tastant present in the edible composition is potassium lactate.

In some embodiments, the edible composition further comprises a sodium salt. In some embodiments the edible composition further comprises NaCl. In other embodiments, the edible composition further comprises sodium lactate. In some embodiments, the edible composition further comprises sugar.

In another aspect of the invention, the edible composition is a food product comprising at least one compound of the invention. In certain embodiments, the compound of the invention is a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof. In another embodiment, the compound of the invention is any one of Compounds 1-134, or combinations thereof.

In another aspect of the present invention, the edible composition is a pharmaceutical composition comprising a bitter lasting pharmaceutically active ingredient and a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof. In another embodiments, the pharmaceutical composition comprises a bitter tasting pharmaceutically active ingredient and any one of Compounds 1-134, or combinations thereof.

In yet other embodiments, the edible composition is a pharmaceutical composition comprising a pharmaceutically active ingredient, a bitter tastant, and a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof. In yet other embodiments, the pharmaceutical composition comprises a pharmaceutically active ingredient, a bitter tastant, and any one of Compounds 1-134, as described herein, or combinations thereof.

In another aspect of the present invention, the edible composition is a consumer product comprising a bitter tastant and a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof. In another embodiments, the consumer product comprises a bitter tastant and any one of Compounds 1-134, or combinations thereof.

Yet another embodiment of the present invention provides a consumer product for reducing bitter taste, of a bitter tastant, wherein said consumer product comprises a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof. In yet other embodiments, the consumer product for reducing bitter taste of a bitter tastant comprises any one of Compounds 1-134, as described herein, or combinations thereof.

In a further aspect, the present invention provides a method of preparing an edible composition comprising:
 (a) providing a comestibly acceptable carrier; and
 (b) adding to the comestibly acceptable carrier of (a) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

In another embodiment the method of preparing an edible composition comprises:
 (a) providing a comestibly acceptable carrier; and
 (b) adding to the comestibly acceptable carrier of (a) any one of Compounds 1-134, or combinations thereof.

In some embodiments, the edible composition is a food product, a consumer product or a pharmaceutical composition. In some embodiments, the comestibly acceptable carrier is a foodstuff, a food product, or a pharmaceutically acceptable carrier.

In some embodiments, the comestibly acceptable carrier in (a) is inherently bitter. In such embodiments, the comestibly acceptable carrier may inherently contain a bitter tastant (i.e., the comestibly acceptable carrier is bitter without addition of a bitter tastant). In some embodiments, the inherent bitter tastant is a bitter tasting salt. In some embodiments, the inherently bitter foodstuff comprises a potassium salt, a magnesium salt, or a calcium salt. In some embodiments, the inherently bitter foodstuff comprises a potassium salt, such as KCl.

In other embodiments, the method of preparing an edible composition further comprises: (c) adding a bitter tastant. In some embodiments, the bitter tastant used in the methods of preparing an edible composition is a bitter tasting salt. In some embodiments, the bitter tastant used in the methods of preparing an edible composition is a potassium salt, a magnesium salt, or a calcium salt. In some embodiments, the bitter tastant used in the methods of preparing an edible composition is a potassium salt. In some embodiments, the bitter tastant used in the methods of preparing an edible composition is KCl. In other embodiments, the bitter tastant used in the methods of preparing an edible composition is potassium lactate.

In some embodiments, the edible composition further comprises a sodium salt in some embodiments, the edible composition further comprises NaCl. In some embodiments, the edible composition further comprises sodium lactate. In some embodiments, the edible composition further comprises sugar.

The present invention also provides a method of reducing the amount of sodium in an edible composition. In some embodiments, such methods comprise:
  (a) replacing an amount of one or more sodium salts used in preparing an edible composition with an amount of one or more potassium salts; and
  (b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

In another embodiment, the method of reducing the amount of sodium in an edible composition comprises:
  (a) replacing an amount of one or more sodium salts used in preparing an edible composition with an amount of one or more potassium salts; and
  (b) incorporating into the edible composition an effective amount of any one of Compounds 1-134, or combinations thereof.

In some embodiments, the edible composition is a food product, a consumer product or a pharmaceutical composition.

In some embodiments of the present invention, the method of reducing the amount of sodium in an edible composition, comprises incorporating into the edible composition an amount of the compound sufficient to permit replacement of up to 25% of the sodium present in an edible composition with potassium. In other embodiments, the amount of the compound incorporated into the edible composition is sufficient to permit replacement of up to 50% of the sodium present in an edible composition with potassium. In yet other embodiments, the amount of the compound incorporated into the edible composition is sufficient to permit replacement of up to 75% of the sodium present in an edible composition with potassium. In other embodiments, the amount of the compound incorporated into the edible composition is sufficient to permit replacement of up to 100% of the sodium present in an edible composition with potassium. In some embodiments, the edible composition maintains a salty flavor.

The present invention also provides a method of reducing the amount of NaCl in an edible composition. In some embodiments, such methods comprise:
  (a) replacing an amount of NaCl used in preparing an edible composition with an amount of KCl; and
  (b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

In another embodiment, the method of reducing the amount of NaCl in an edible composition comprise:
  (a) replacing an amount of NaCl used in preparing an edible composition with an amount of KCl; and
  (b) incorporating into the edible composition an effective amount of any one of Compounds 1-134, or combinations thereof.

In some embodiments of the present invention, the method of reducing the amount of sodium in an edible composition, comprises incorporating into the edible composition an amount of the compound sufficient to permit replacement of up to 25% of the NaCl present in an edible composition with KCl. In other embodiments, the amount of the compound incorporated into the edible composition is sufficient to permit replacement of up to 50% of the NaCl present in an edible composition with KCl. In yet other embodiments, the amount of the compound incorporated into the edible composition is sufficient to permit replacement of up to 75% of the NaCl present in an edible composition with KCl. In other embodiments, the amount of the compound incorporated into the edible composition is sufficient to permit replacement of up to 100% of the NaCl present in an edible composition with KCl. In some embodiments, the edible composition maintains a salty flavor.

In another embodiment, the present invention provides a method of reducing the amount of sodium lactate in an edible composition comprises:
  (a) replacing an amount of sodium lactate used in preparing an edible composition with an amount of potassium lactate; and
  (b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

In another embodiment, the invention provides a method of reducing the amount of sodium lactate in an edible composition comprising:
  (a) replacing an amount of sodium lactate used in preparing an edible composition with an amount of potassium lactate; and
  (b) incorporating into the edible composition an effective amount of any one of Compounds 1-134, or combinations thereof.

In some embodiments, the edible composition is a food product, a consumer product or a pharmaceutical composition.

In some embodiments of the present invention, the method of reducing the amount of sodium lactate in an edible composition, comprises incorporating into the edible composition an amount of the compound sufficient to permit replacement of up to 25% of the sodium lactate present in an edible composition with potassium lactate. In other embodiments, the amount of the compound incorporated into the edible composition is sufficient to permit replacement of up to 50% of the sodium lactate present in an edible composition with potassium lactate. In yet other embodiments, the amount of the compound incorporated into the edible composition is sufficient to permit replacement of up to 75% of the sodium lactate present in an edible composition with potassium lactate. In other embodiments, the amount of the compound incorporated into the edible composition is sufficient to permit replacement of up to 100% of the sodium lactate present in an edible composition with potassium lactate. In some embodiments, the edible composition has the same shelf life as an edible composition comprising sodium lactate.

In another embodiment, the invention provides a method of reducing the amount of sugar in an edible composition comprising:
(a) replacing an amount of sugar used in preparing an edible composition with an amount of Acesulfame K; and
(b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

In another embodiment, the invention provides a method of reducing the amount of sugar in an edible composition comprising:
(a) replacing an amount of sugar used in preparing an edible composition with an amount of Acesulfame K; and
(b) incorporating into the edible composition an effective amount of any one of Compounds 1-134, or combinations thereof.

In some embodiments, the edible composition is a food product, a consumer product or a pharmaceutical composition.

In some embodiments of the present invention, the method of reducing the amount of sugar in an edible composition, comprises incorporating into the edible composition an amount of the compound sufficient to permit replacement of up to 25% of the sugar present in an edible composition with Acesulfame K. In other embodiments, the amount of the compound incorporated into the edible composition is sufficient to permit replacement of up to 50% of the sugar present in an edible composition with Acesulfame K. In yet other embodiments, the amount of the compound incorporated into the edible composition is sufficient to permit replacement of up to 75% of the sugar present in an edible composition with Acesulfame K. In other embodiments, the amount of the compound incorporated into the edible composition is sufficient to permit replacement of up to 100% of the sugar present in an edible composition with Acesulfame K. In some embodiments, the edible composition maintains a sweet flavor.

The present invention also provides a method of reducing the sodium intake of a subject. Such method comprises:
(a) replacing an amount of NaCl used in preparing an edible composition with an amount of KCl; and
(b) incorporating into the edible imposition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, thereby reducing the sodium intake of the subject.

In another embodiment, the method of reducing the sodium intake of a subject comprises:
(a) replacing an amount of NaCl used in preparing an edible composition with an amount of KCl; and
(b) incorporating into the edible composition an effective amount of any one of Compounds 1-134, or combinations thereof, thereby reducing the sodium intake of the subject.

In another embodiment, the method of reducing the sodium intake of a subject comprises:
(a) replacing an amount of sodium lactate used in preparing an edible composition with an amount of potassium lactate; and
(b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, thereby reducing the sodium intake of the subject.

In another embodiment, the method of reducing the sodium intake of a subject comprises:
(a) replacing an amount of sodium lactate used in preparing an edible composition with an amount of potassium lactate; and
(b) incorporating into the edible composition an effective amount of any one of Compounds 1-134, or combinations thereof, thereby reducing the sodium intake of the subject.

In some embodiments, the edible composition is a food product, a consumer product or a pharmaceutical composition.

In some embodiments of the present invention, the methods of reducing the sodium intake of a subject further comprise (c) identifying a subject in need thereof. In some embodiments, the methods of reducing the sodium intake of a subject comprise incorporating into the edible composition an amount of the compound sufficient to reduce sodium intake by up to 25% using potassium replacement. In other embodiments, the amount of compound added in (b) is sufficient to reduce sodium intake by up to 50% using potassium replacement. In yet other embodiments, the amount of compound added in (b) is sufficient to reduce sodium intake by up to 75% using potassium replacement. In other embodiments, the amount of compound added in (b) is sufficient to reduce sodium intake by up to 100% using potassium replacement.

The present invention also provides a method of reducing sugar intake of a subject comprising:
(a) replacing an amount of sugar used in preparing an edible composition with an amount of Acesulfame K; and
(b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, thereby reducing the sugar intake of the subject.

In another embodiment, the method of reducing the sugar intake of a subject comprises:
(a) replacing an amount of sugar used in preparing an edible composition with an amount of Acesulfame K; and
(b) incorporating into the edible composition an effective amount of any one of Compounds 1-134, or combinations thereof, thereby reducing the sugar intake of the subject.

In some embodiments, the edible composition is a food product, a consumer product or a pharmaceutical composition.

In some embodiments of the present invention, the methods of reducing the sugar intake of a subject further comprises (c) identifying a subject in need thereof. In some embodiments, the methods of reducing the sugar intake of a subject comprise incorporating into the edible composition an amount of the compound sufficient to reduce sugar intake by up to 25% using Acesulfame K replacement. In other embodiments, the amount of compound added in (b) is sufficient to reduce sugar intake by up to 50% using Acesulfame K replacement. In yet other embodiments, the amount of compound added in (b) is sufficient to reduce sugar intake by up to 75% using Acesulfame K replacement. In other embodiments, the amount of compound added in (b) is sufficient to reduce sugar intake by up to 100% using Acesulfame K replacement.

The present invention also provides a method of reducing the bitter taste attributed to a bitter tastant in an edible composition comprising adding an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, to the edible composition such that any bitter taste induced by the bitter tastant is reduced. In other embodiments, the compound added to the edible composition is any one of Compounds 1-134, or combinations thereof.

The present invention further provides a method of reducing the bitter taste attributed to a bitter tastant in an edible composition comprising ingesting an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, before, along with, or after the edible composition such that any bitter taste induced by the bitter tastant is reduced. In other embodiments, the compound ingested with the edible composition is any one of Compounds 1-134, or combinations thereof.

In some embodiments, the edible composition is a food product, a consumer product or a pharmaceutical composition.

In some embodiments, the method reduces the bitter taste induced by the bitter tastant by up to 25%, In some embodiments, the method reduces the bitter taste induced by the bitter tastant by up to 50%. In other embodiments, the bitter taste induced by the bitter tastant is reduced by up to 75%. In yet other embodiments, the bitter taste induced by the bitter tastant is reduced by up to 100%. In some embodiments, the bitter tastant present in the edible composition is a bitter tasting salt. In some embodiments, the bitter tastant present in the edible composition is a potassium salt, a magnesium salt, or a calcium salt. In some embodiments, the bitter tastant present in the edible compositions is KCl.

In further aspect, the present invention provides a method of preserving an edible composition comprising:
(a) providing an edible composition; and
(b) adding to the edible composition of (a) potassium lactate and an effective amount of a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

In another embodiment, the method of preserving an edible composition comprises:
(a) providing an edible composition; and
(b) adding to the edible composition of (a) potassium lactate and an effective amount of any one of Compounds 1-134, or combinations thereof.

The present invention also provides a method of reducing the amount of sodium in an edible composition white preserving the edible composition. In some embodiments, such method comprises:
(a) replacing an amount of sodium lactate used in preparing an edible composition with an amount of potassium lactate; and
(b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

The present invention also provides a method of reducing the amount of sodium in an edible composition while preserving the edible composition. In some embodiments, such method comprises:
(a) replacing an amount of sodium lactate used in preparing an edible composition with an amount of potassium lactate; and
(b) incorporating into the edible composition an effective amount of any one of Compounds 1-134, or combinations thereof.

In some embodiments, the edible composition is a food product. In some embodiments, the edible composition is a consumer product. In some embodiments, the edible composition is a pharmaceutical composition.

The present invention also provides a method of reducing or eliminating bitter taste in a subject utilizing an edible composition comprising a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof. In other embodiments, the composition that reduces or eliminates a bitter taste in a subject comprises any one of Compounds 1-134, or combinations thereof.

In some embodiments, the bitter taste is inherent. In some embodiments, the bitter taste is due to a bitter tasting salt. In some embodiments, the bitter taste is due to a potassium salt, a magnesium salt, or a calcium salt. In some embodiments, the bitter taste is due to KCl. In other embodiments, the bitter taste is due to potassium lactate.

The present invention also provides a method of inhibiting or reducing the activation and/or signaling of a bitter taste receptor, wherein the method comprises contacting a bitter taste receptor with a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof. In other embodiments, the method comprises contacting a bitter taste receptor with any one of Compounds 1-134, or combinations thereof. In some embodiments, the bitter taste receptor is in the oral cavity. In other embodiments, the bitter taste receptor is in the gastrointestinal tract, for example, in the stomach. In other embodiments, the bitter taste receptor is in an in vitro assay.

Particular embodiments of the invention are set forth in the following numbered paragraphs:

1. A composition comprising a compound according to Formula (I):

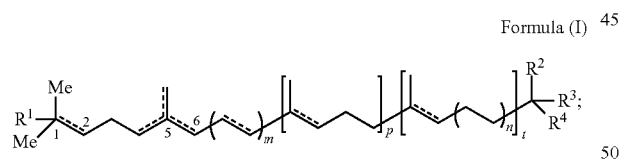

Formula (I)

or a comestibly or biologically acceptable salt or derivative thereof, or an enantiomer or diastereomer thereof, wherein, as valence and stability permit;

$R^1$ is absent or is selected from the group consisting of hydrogen, $C_{1-10}$alkyl, $C_{1-10}$haloalkyl, $C_{2-10}$alkenyl, $C_{2-10}$alkynyl, hydroxyl, $C_{1-10}$acylamino, $C_{2-10}$acyloxy, $C_{1-10}$carbonate, $C_{1-10}$alkoxy, phenyloxy, phenyl-$C_{1-6}$alkyloxy, $C_{1-5}$heteteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-10}$carbamate, $C_{1-10}$urea, sulfhydryl, $C_{1-10}$alkylthio, sulfate, sulfonate, sulfamoyl, sulfonamido, sulfonyl, wherein heterocyclic or heteroaromatic rings, independently for each occurrence, comprise 1-4 heteroatoms selected from N, O, and S;

$R^2$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^3$ is selected from the group consisting of hydrogen $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroaryl, and $C_{1-5}$heteroaryl-$C_{3-6}$alkyl, wherein heterocyclic or heteroaromatic rings, independently for each occurrence, comprise 1-4 heteroatoms selected from N, O, and S;

$R^4$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

or $R^3$ and $R^4$ together form =O or —O—$C_{1-10}$alkyl-O—;

wherein any of $R^1$, $R^2$, $R^3$, and $R^4$, independently, is optionally substituted with 1-3 substituents selected from the group consisting of $C_{1-10}$alkyl, $C_{1-10}$haloalkyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl; and wherein heterocyclic or heteroaromatic rings, independently for each occurrence, comprise 1-4 heteroatoms selected from N, O, and S; and m is 0-2;
n is 0-2;
p is 0-2;
t is 0-2;
wherein $C_1$ and $C_6$ in formula (I) optionally are bonded together to form a 6-membered ring; and
wherein all dotted bonds indicate optional carbon-carbon double bonds;
wherein the composition is edible and capable of reducing bitter taste of a bitter tastant.

2. The composition according to paragraph 1, wherein as valence and stability permit:
$R^1$ is absent or is selected from the group consisting of hydroxyl, $C_{1-6}$alkoxy, and $C_{1-6}$acyloxy;
$R^2$ is selected from the group consisting of hydrogen, $C_{1-6}$alkyl, $C_{2-6}$alkenyl, and $C_{2-6}$alkynyl;
$R^3$ is selected from the group consisting of hydrogen and $C_{1-6}$alkoxy;
$R^4$ is selected from the group consisting of hydroxyl, $C_{1-6}$alkoxy, and $C_{1-6}$acyloxy;
or $R^3$ and $R^4$ together form =O;
wherein any of $R^1$, $R^2$, $R^3$, and $R^4$, independently, is optionally substituted as in paragraph 1; and
m is 0-2;
n is 0-2;
p is 0-2;
t is 0-2;
wherein $C_1$ and $C_6$ in Formula (I) optionally are bonded together to form a 6-membered ring; and
wherein all dotted bonds indicate optional carbon-carbon double bonds.

3. The composition according to paragraph 1, wherein as valence and stability permit:
$R^1$ is absent or is selected from the group consisting of hydroxyl, $C_{1-3}$alkoxy, and $C_{1-3}$acyloxy;
$R^2$ is selected from the group consisting of hydrogen, $C_{1-3}$alkyl, $C_{2-3}$alkenyl, and $C_{2-3}$alkynyl;
$R^3$ is selected from the group consisting of hydrogen and $C_{1-3}$alkoxy;
$R^4$ is selected from the group consisting of hydroxyl, $C_{1-3}$alkoxy, and $C_{1-3}$acyloxy;
m is 1;
n is 0;
p is 1; and
t is 1;
wherein all dotted bonds indicate optional carbon-carbon double bonds.

4. The composition according to paragraph 1, wherein said compound according to Formula (I) is a compound according to Formula (Ia):

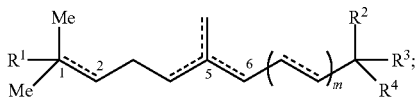

Formula (Ia)

or a comestibly or biologically acceptable salt or derivative thereof, or an enantiomer or diastereomer thereof, wherein, as valence and stability permit;
$R^1$ is absent or is selected from the group consisting of hydrogen, $C_{1-10}$alkyl, $C_{1-10}$haloalkyl, $C_{2-10}$alkenyl, $C_{2-10}$alkynyl, hydroxyl, $C_{1-10}$acylamino, $C_{2-10}$acyloxy, $C_{1-10}$carbonate, $C_{1-10}$alkoxy, phenyloxy, phenyl-$C_{1-6}$alkyloxy, $C_{1-5}$heteteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-10}$carbamate, $C_{1-10}$urea, sulfhydryl, $C_{1-10}$alkylthio, sulfate, sulfonate, sulfamoyl, sulfonamido, sulfonyl, wherein heterocyclic or heteroaromatic rings, independently for each occurrence, comprise 1-4 heteroatoms selected from N, O, and S;

$R^2$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^3$ is selected from the group consisting of hydrogen $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-10}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S;

$R^4$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;
or $R^3$ and $R^4$ together form =O or —O—$C_{1-10}$alkyl-O—;
wherein any of $R^1$, $R^2$, $R^3$, and $R^4$, independently, is optionally substituted with 1-3 substituents selected from the group consisting of $C_{1-10}$alkyl, $C_{1-10}$haloalkyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl; and wherein heterocyclic or heteroaromatic rings, independently for each occurrence, comprise 1-4 heteroatoms selected from N, O, and S; and
m is 0-2;
wherein $C_1$ and $C_6$ in Formula (Ia) optionally are bonded together to form a 6-membered ring; and
wherein all dotted bonds indicate optional carbon-carbon double bonds,
5. The composition according to paragraph 4, wherein as valence and stability permit;
$R^1$ is absent or is selected from the group consisting of hydroxyl, $C_{1-6}$alkoxy, and $C_{1-6}$acyloxy;
$R^2$ is selected from the group consisting of hydrogen, $C_{3-6}$alkyl, $C_{2-6}$alkenyl, and $C_{2-6}$alkynyl;
$R^3$ is selected from the group consisting of hydrogen and $C_{1-6}$alkoxy;
$R^4$ is selected from the group consisting of hydroxyl, $C_{1-8}$alkoxy, and $C_{1-16}$acyloxy;
or $R^3$ and $R^4$ together form =O;
wherein any of $R^1$, $R^2$, $R^3$, and $R^4$, independently, is optionally substituted as noted above; and
m is 0-2;
wherein $C_2$ and $C_6$ in Formula (Ia) optionally are bonded together to form a 6-membered ring; and
wherein all dotted bonds indicate optional carbon-carbon double bonds.
6. The composition according to paragraph 1, wherein said compound according to Formula (I) is a compound according to Formula (IIa):

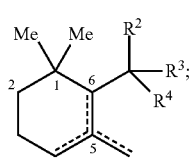

Formula (IIa)

or a comestibly or biologically acceptable salt or derivative thereof, or an enantiomer or diastereomer thereof, wherein, as valence and stability permit, $R^2$, $R^3$, and $R^4$ are as defined in paragraph 1.
7. The composition according to paragraph 6, wherein said compound according to Formula (IIa) is a compound according to Formula (IIIa):

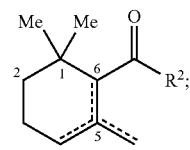

Formula (IIIa)

or a comestibly or biologically acceptable salt or derivative thereof or an enantiomer or diastereomer thereof, wherein, as valence and stability permit, $R^1$ is as defined in paragraph 6.
8. The composition according to paragraph 1, wherein said compound according to Formula (I) is a compound according to Formula (IIb):

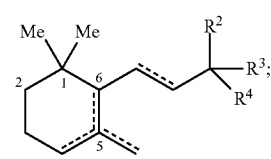

Formula (IIb)

or a comestibly or biologically acceptable salt or derivative thereof, or an enantiomer or diastereomer thereof, wherein, as valence and stability permit $R^2$, $R^3$, and $R^4$ are as defined in paragraph 8.
9. The composition according to paragraph 8, wherein said compound according to Formula (IIb) is a compound according to Formula (IIIb):

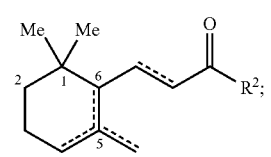

Formula (IIIb)

or a comestibly or biologically acceptable salt or derivative thereof, or an enantiomer or diastereomer thereof, wherein, as valence and stability permit, $R^2$ is as defined in paragraph 8.
10. The composition according to paragraph 1, wherein said compound according to Formula (I) is a compound according to Formula (IIc):

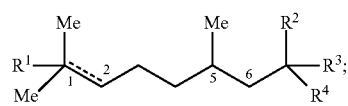

Formula (IIc)

or a comestibly or biologically acceptable salt or derivative thereof, or an enantiomer or diastereomer thereof, wherein, as valence and stability permit, $R^1$, $R^2$, $R^3$, and $R^4$ are as defined in paragraph 1.
11. The composition according to paragraph 10, wherein said compound according to Formula (IIc) is a compound according Formula (IIIc):

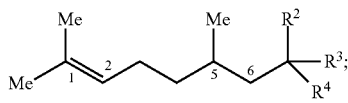

or a comestibly or biologically acceptable salt or derivative thereof, or an enantiomer or diastereomer thereof, wherein, as valence and stability permit, $R^2$, $R^3$, and $R^4$ are as defined in paragraph 10.

12. The composition according paragraph 11, wherein said compound according to Formula (IIIc) is a compound according to Formula (IVc):

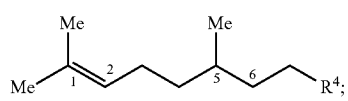

or a comestibly or biologically acceptable salt or derivative thereof, or an enantiomer or diastereomer thereof, wherein, as valence and stability permit, $R^4$ is as defined in paragraph 11.

13. The composition according to paragraph 11, wherein said compound according to Formula (I) is a compound according to Formula (IId):

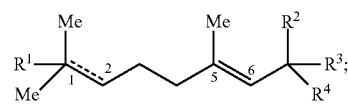

or a comestibly or biologically acceptable salt or derivative thereof, or an enantiomer or diastereomer thereof wherein, as valence and stability permit, $R^1$, $R^2$, $R^3$, and $R^4$ are as defined in paragraph 1.

14. The composition according to paragraph 13, wherein said compound according to Formula (IId) is a compound according to Formula (IIId):

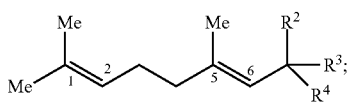

or a comestibly or biologically acceptable salt or derivative thereof or an enantiomer or diastereomer thereof wherein, as valence and stability permit, $R^2$, $R^3$, and $R^4$ are as defined in paragraph 13.

15. The composition according to paragraph 14, wherein said compound according to Formula (IIId) is a compound according to Formula (IVd):

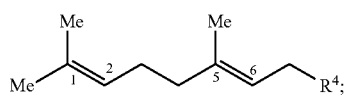

or a comestibly or biologically acceptable salt or derivative thereof, or an enantiomer or diastereomer thereof, wherein, as valence and stability permit, $R^4$ is as defined in paragraph 14.

16. The composition according to paragraph 1, wherein said compound according to formula (I) is a compound according to Formula (IIe):

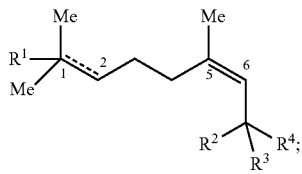

or a comestibly or biologically acceptable salt or derivative thereof or an enantiomer or diastereomer thereof wherein, as valence and stability permit, $R^1$, $R^2$, $R^3$, and $R^4$ are as defined in paragraph 1.

17. The composition according to paragraph 16, wherein said compound according to Formula (IIe) is a compound according to Formula (IIIe):

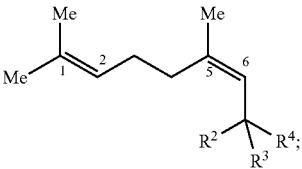

or a comestibly or biologically acceptable salt or derivative thereof or an enantiomer or diastereomer thereof wherein, as valence and stability permit, $R^2$, $R^3$, and $R^4$ are as defined in paragraph 16.

18. The composition according to paragraph 17, wherein said compound according to Formula (IIIe) is a compound according to Formula (IVe):

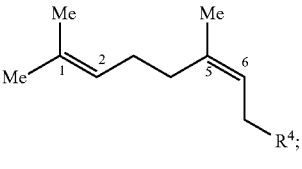

or a comestibly or biologically acceptable salt or derivative thereof, or an enantiomer or diastereomer thereof, wherein, as valence and stability permit, $R^4$ is as defined in paragraph 17.

19. The composition according to paragraph 1, wherein said compound according to Formula (I) is a compound according to Formula (IIf):

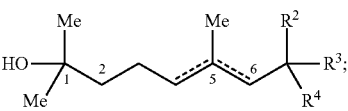

or a comestibly or biologically acceptable salt or derivative thereof or an enantiomer or diastereomer thereof wherein, as valence and stability permit, $R^2$, $R^3$, and $R^4$ are as defined in paragraph 1.

20. The composition according to paragraph 1, wherein said compound to Formula (I) is a compound according to Formula (IIg):

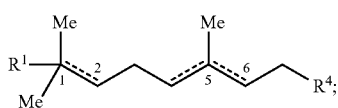

Formula (IIg)

or a comestibly or biologically acceptable salt or derivative thereof or an enantiomer or diastereomer thereof wherein, as valence and stability permit, $R^1$ and $R^4$ are as defined in paragraph 1.

21. The composition according to paragraph 1, wherein said compound according to Formula (I) is a compound according to Formula (IIh):

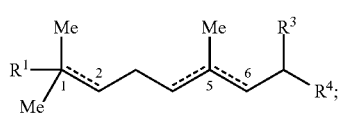

Formula (IIh)

or a comestibly or biologically acceptable salt or derivative thereof or an enantiomer or diastereomer thereof wherein, as valence and stability permit, $R^1$, $R^3$, and $R^4$ are as defined in paragraph 1.

22. The composition according to paragraph 1, wherein said compound according to Formula (I) is selected from the group consisting of:

Compound 1 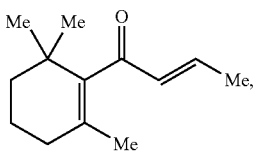 [SMILES: C/C=C/C(=O)C1=C(C)CCCC1(C)C]

Compound 2 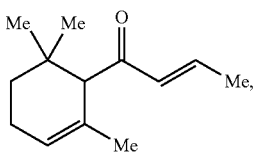 [SMILES: C/C=C/C(=O)C1C(C)=CCCC1(C)C]

Compound 3 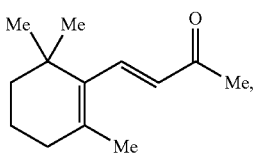

Compound 4 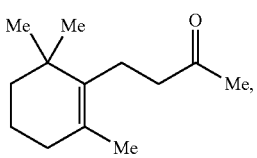 [SMILES: CC(=O)CCC1=C(C)CCCC1(C)C]

Compound 5 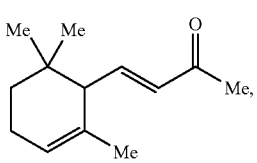 [SMILES: CC(=O)/C=C/C1C(C)=CCCC1(C)C]

Compound 6 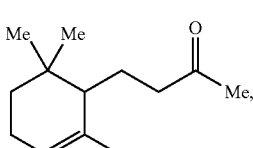

Compound 7 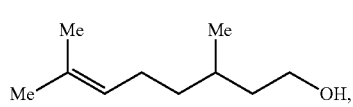 [SMILES: CC(C)=CCCC(C)CCO]

Compound 8 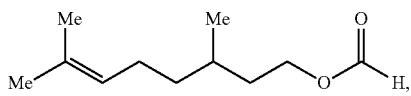

Compound 9 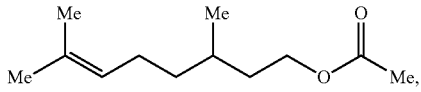 [SMILES: CC(=O)OCCC(C)CCC=C(C)C]

| | |
|---|---|
| Compound 10 | 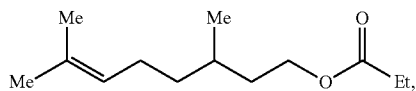 [SMILES: CCC(=O)OCCC(C)CCC=C(C)C] |
| Compound 11 | 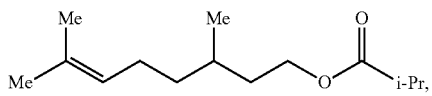 [SMILES: CC(C)=CCCC(C)CCOC(=O)C(C)C] |
| Compound 12 | 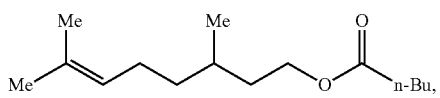 |
| Compound 13 | 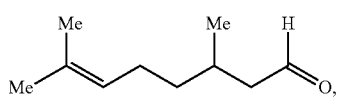 [SMILES: CC(C)=CCCC(C)CC=O] |
| Compound 14 (mixture) | 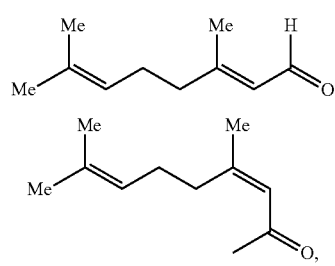 |
| Compound 15 (mixture) | 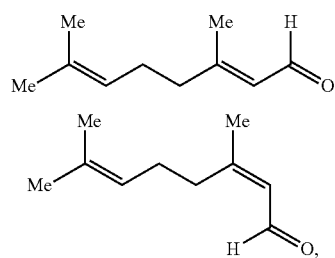 |
| Compound 16 | 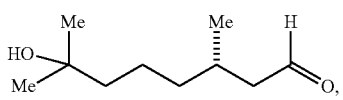 |
| Compound 17 | 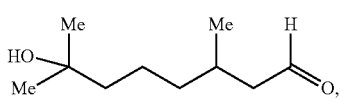 [SMILES: CC(CC=O)CCCC(C)(C)O] |
| Compound 18 | 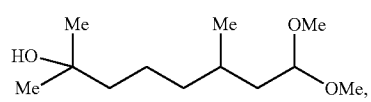 |
| Compound 19 | 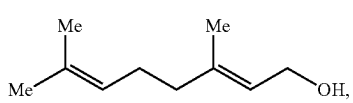 |
| Compound 20 | 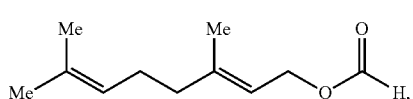 |
| Compound 21 | 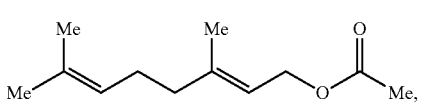 [SMILES: CC(=O)OC/C=C(\C)CCC=C(C)C] |

| | |
|---|---|
| Compound 22 | 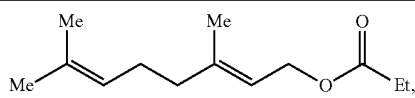 |
| Compound 23 | 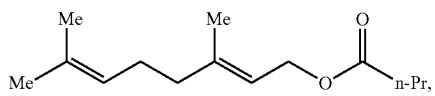 |
| Compound 24 | 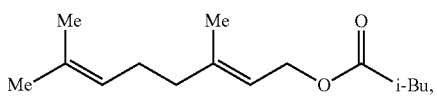 |
| Compound 25 | 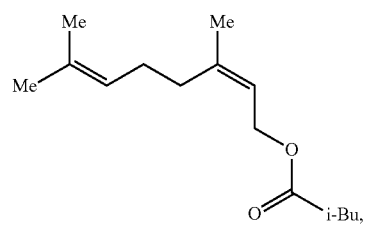 |
| Compound 26 | 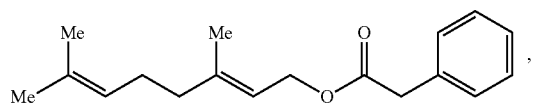 [SMILES: CC(C)=CCC/C(C)=C/COC(=O)Cc1ccccc1] |
| Compound 27 | 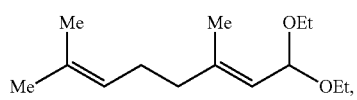 |
| Compound 28 (mixture) | 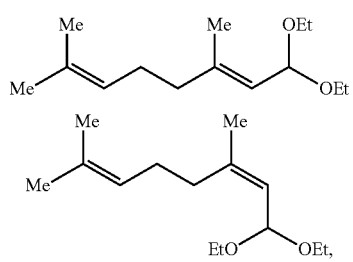 |
| Compound 29 | 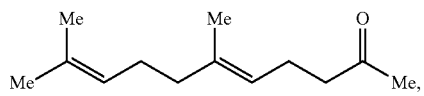 |
| Compound 30 | 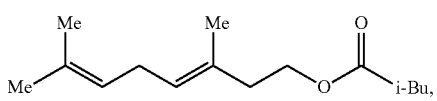 |
| Compound 31 | 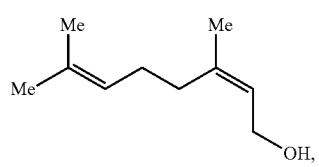 [SMILES: CC(C)=CCC/C(C)=C\CO] |
| Compound 32 | 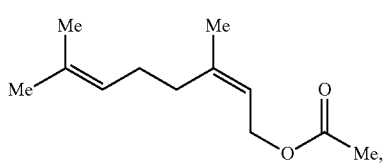 |

| Compound 33 | 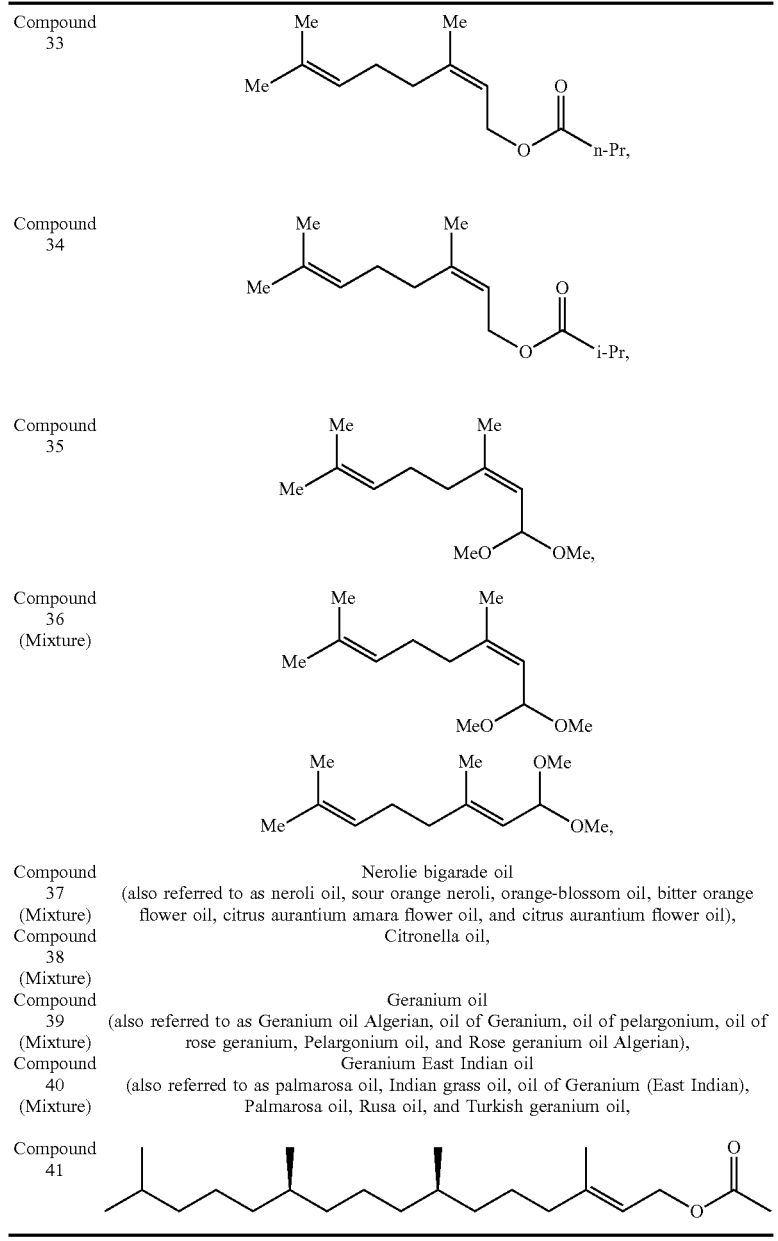 |
|---|---|
| Compound 34 | |
| Compound 35 | |
| Compound 36 (Mixture) | |
| Compound 37 (Mixture) | Nerolie bigarade oil (also referred to as neroli oil, sour orange neroli, orange-blossom oil, bitter orange flower oil, citrus aurantium amara flower oil, and citrus aurantium flower oil), |
| Compound 38 (Mixture) | Citronella oil, |
| Compound 39 (Mixture) | Geranium oil (also referred to as Geranium oil Algerian, oil of Geranium, oil of pelargonium, oil of rose geranium, Pelargonium oil, and Rose geranium oil Algerian), |
| Compound 40 (Mixture) | Geranium East Indian oil (also referred to as palmarosa, Indian grass oil, oil of Geranium (East Indian), Palmarosa oil, Rusa oil, and Turkish geranium oil, |
| Compound 41 | 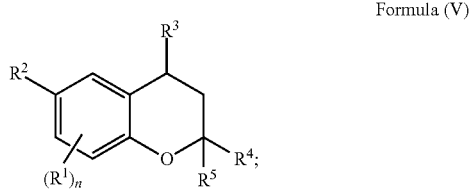 | comestibly or biologically acceptable derivatives thereof, or an enantiomer or diastereomer thereof.

25. A composition comprising a compound according to Formula (V):

Formula (V)

$R^2$, $R^3$, $R^4$, $R^5$, $(R^1)_n$ or a comestibly or biologically acceptable salts or derivative thereof, or an enantiomer or diastereomer thereof, wherein, as valence and stability permit:

$R^1$, independently for each occurrence, is selected from the group consisting of $C_{1-10}$alkyl, $C_{1-10}$haloalkyl, $C_{2-10}$alkenyl, $C_{2-10}$alkynyl, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{2-10}$acyloxy, $C_{1-10}$carbonate, $C_{1-10}$alkoxy, phenyloxy, phenyl-$C_{1-6}$alkyloxy, $C_{1-5}$heteteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-10}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroaryl, and $C_{3-5}$heteroaryl- $C_{3-6}$alkyl, wherein heterocyclic or heteroaromatic rings, independently for each occurrence, comprise 1-4 heteroatoms selected from N, O, and S;

$R^2$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, $diC_{1-10}$alkylamino, $monoC_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^3$ is selected from the group consisting of hydrogen $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, $diC_{1-10}$alkylamino, $monoC_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^4$ is selected from the group consisting of hydrogen, $C_{1-20}$alkyl, $C_{1-20}$haloalkyl, $C_{2-20}$alkenyl, $C_{2-20}$alkynyl, hydroxyl, $C_{1-10}$acyloxy, $C_{1-10}$alkoxy, phenyloxy, phenyl-$C_{1-6}$alkyloxy, $C_{1-5}$heteroaryloxy, $C_{1-5}$heteroaryl-$C_{1-6}$alkyloxy, $C_{3-10}$alkenyloxy, amino, $diC_{1-10}$alkylamino, $monoC_{1-10}$alkylamino, sulfhydryl, $C_{1-10}$alkylthio, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S;

$R^5$ is selected from the group consisting of hydrogen, $C_{1-20}$alkyl, $C_{1-20}$haloalkyl, $C_{2-20}$alkenyl, $C_{2-20}$alkynyl, hydroxyl, $C_{1-10}$acyloxy, $C_{1-10}$alkoxy, phenyloxy, phenyl-$C_{1-6}$alkyloxy, $C_{1-5}$heteroaryloxy, $C_{1-5}$heteroaryl-$C_{1-6}$alkyloxy, $C_{3-10}$alkenyloxy, amino, $diC_{1-10}$alkylamino, $monoC_{1-10}$alkylamino, sulfhydryl, $C_{1-10}$alkylthio, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S;

or $R^4$ and $R^5$ together form =O or —O—$C_{1-10}$alkyl-O—;

wherein any of $R^1$, $R^2$, $R^3$, and $R^4$, independently, is optionally substituted with 1-3 substituents selected from the group consisting of $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phosphoryl, phosphate, phosphonate, phosphinate, amino, $diC_{1-10}$alkylamino, $monoC_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S; and m is 0-3;

wherein the composition is edible and capable of reducing bitter taste of a bitter tastant.

24. The composition according to paragraph 23, wherein as valence and stability permit:

$R^1$ independently for each occurrence, is selected from the group consisting of halo, hydroxyl, $C_{1-6}$alkyl, $C_{1-6}$haloalkyl, $C_{2-6}$alkenyl, $C_{2-6}$alkynyl, and $C_{1-6}$alkoxy;

$R^2$ is selected from the group consisting of hydrogen, halo, hydroxyl, $C_{1-6}$alkyl, $C_{1-6}$haloalkyl, $C_{2-6}$alkenyl, $C_{2-6}$alkynyl, $C_{1-6}$alkoxy, $C_{1-6}$acyloxy, optionally substituted by hydroxyl, amino, mono- or disubstituted $C_{1-6}$alkyl amino, or carboxyl;

$R^3$ is selected from the group consisting of hydrogen, hydroxyl, $C_{1-6}$alkyl, $C_{2-6}$alkenyl, $C_{2-6}$alkynyl, and $C_{1-6}$alkoxy;

$R^4$ is selected from the group consisting of hydrogen, hydroxyl, $C_{1-21}$alkyl, $C_{2-21}$alkenyl, $C_{2-21}$alkynyl, and $C_{1-6}$alkoxy, wherein $R^4$ is optionally substituted by one or more occurrences of hydroxyl or acetyloxy;

$R^5$ is selected from the group consisting of hydrogen, hydroxyl, $C_{1-21}$alkyl, $C_{2-21}$alkenyl, $C_{2-21}$alkynyl, and $C_{1-6}$alkoxy, wherein $R^4$ is optionally substituted by one or more occurrences of hydroxyl or acetyloxy;

or $R^4$ and $R^5$ together form =O;

wherein any of $R^1$, $R^2$, $R^3$, $R^4$, and $R^5$, independently and independently for each occurrence, is optionally further substituted as in paragraph 1;

and n is 0-3.

25. The composition according to paragraph 23, wherein said compound according to Formula (V) is a compound according to Formula (VIa):

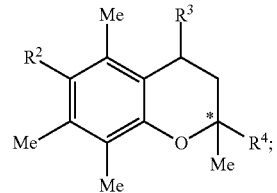

Formula (VIa)

or a comestibly or biologically acceptable salt or derivative thereof, or an enantiomer or diastereomer thereof, wherein, as valence and stability permit, $R^2$ and $R^4$ are as defined in paragraph 23, wherein the carbon marked with * optionally has R or S stereochemistry or is a mixture of R and S stereochemistry.

26. The composition according to paragraph 25, wherein said compound according to Formula (VIa) is a compound according to Formula (VIIa):

Formula (VIIa)

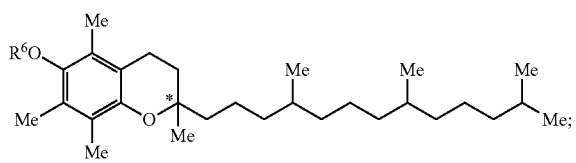

or a comestibly or biologically acceptable salt or derivative thereof, or an enantiomer or diastereomer thereof.

wherein, as valence and stability permit:

R⁶ is selected from the group consisting of hydrogen, $C_{1-6}$alkyl; or $C_{1-6}$acyl optionally substituted by hydroxyl, amino, mono- or disubstituted $C_{1-6}$alkyl amino, or carboxyl; and wherein the carbon marked with * optionally has R or S stereochemistry or is a mixture of R and S stereochemistry.

27. The composition according to paragraph 23, wherein said compound according to Formula (V) is a compound according to Formula (VIb):

Formula (VIb)

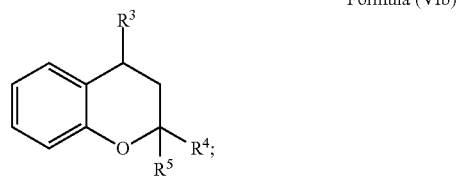

or a comestibly or biologically acceptable salt or derivative thereof, or an enantiomer or diastereomer thereof, wherein, as valence and stability permit, $R^3$, $R^4$, and $R^5$ are as defined in paragraph 23.

28. The composition according to paragraph 23, wherein said compound according to Formula (V) is selected from the group consisting of:

Compound 42

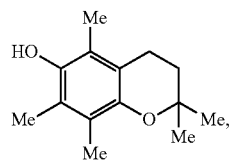

Compound 43

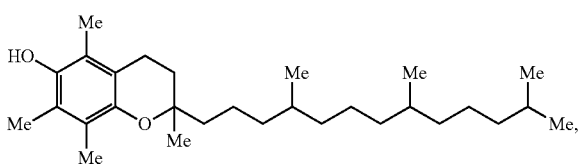

Compound 44

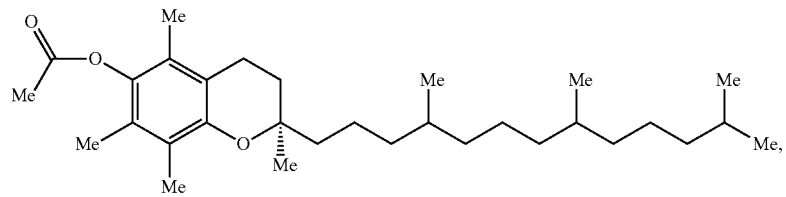

Compound 45

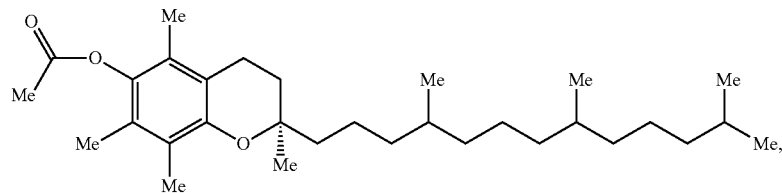

Compound 46

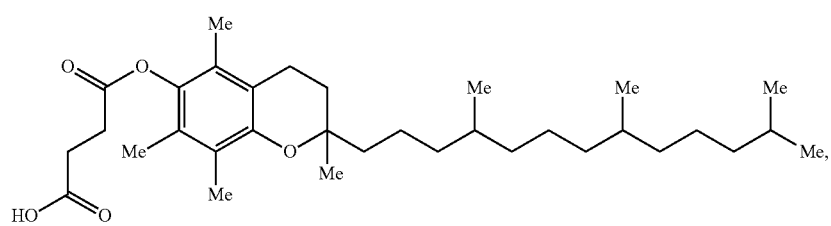

Compound 47

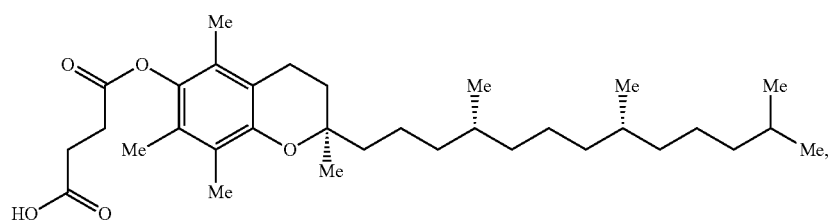

-continued

Compound 48
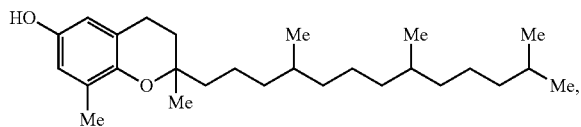

Compound 49
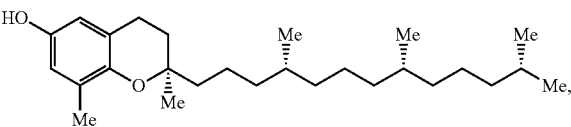

Compound 50
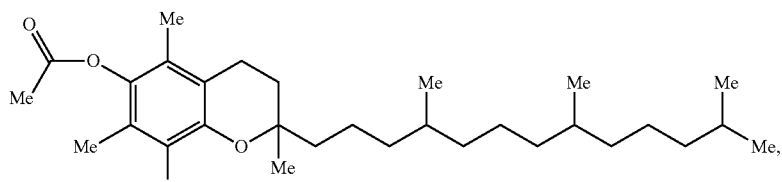

Compound 51
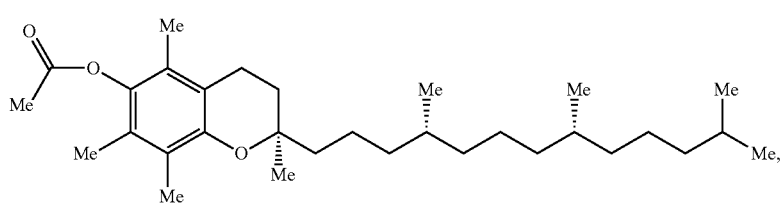

Compound 52
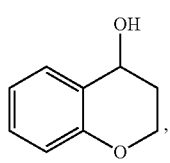

Compound 53
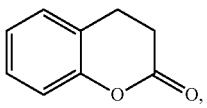

comestibly or biologically acceptable derivatives thereof, or enantiomers or diastereomers thereof.

29. A composition comprising a compound according to Formula (VIII):

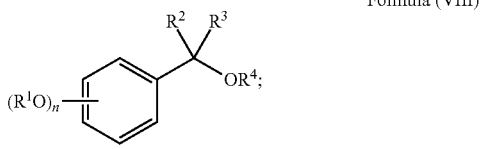

Formula (VIII)

or a comestibly or biologically acceptable salt or derivative thereof, or an enantiomer or diastereomer thereof.

wherein, as valence and stability permit:

$R^1$, independently for each occurrence, is selected from the group consisting of hydrogen, $C_{1-10}$alkyl, $C_{1-10}$haloalkyl, $C_{2-10}$alkenyl, $C_{2-10}$alkynyl, carboxyl, $C_{1-10}$alkoxycarbonyl, $C_{2-10}$alkenyloxycarbonyl, $C_{2-10}$alkynyloxycarbonyl, $C_{1-10}$acyl, phosphoryl, phosphonate, phosphinate, sulfonate, sulfamoyl, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroalkyl, and $C_{1-5}$heteroaryl-$C_{1-6}$alkyl, wherein heterocyclic or heteroaromatic rings, independently for each occurrence, comprise 1-4 heteroatoms selected from N, O, and S;

$R^2$ is selected from the group consisting of hydrogen, $C_{1-10}$alkyl, $C_{1-10}$haloalkyl, $C_{2-10}$alkenyl, $C_{2-10}$alkynyl, hydroxyl, $C_{1-10}$acyloxy, $C_{1-20}$alkoxy, phenyloxy, phenyl-$C_{1-6}$alkyloxy, $C_{1-5}$heteroaryloxy, $C_{1-5}$heteroaryl-$C_{1-6}$alkyloxy, $C_{3-10}$alkynyloxy, amino, di$C_{1-10}$alkylamino, mono$C_{1-10}$alkylamino, sulfhydryl, $C_{1-10}$alkylthio, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S;

$R^3$ is selected from the group consisting of hydrogen $C_{1-10}$alkyl, $C_{1-10}$haloalkyl, $C_{2-10}$alkenyl, $C_{2-10}$alkynyl, hydroxyl, $C_{1-10}$acyloxy, $C_{1-6}$alkoxy, phenyloxy, phenyl-$C_{1-6}$alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, amino, di$C_{1-10}$alkylamino, mono$C_{1-10}$alkylamino, sulfhydryl, $C_{1-10}$alkylthio, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroaryl, and $C_{1-5}$heteroaryl-$C_{1-6}$alkyl, $C_{1-5}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S;

or $R^2$ and $R^3$ together form =O or —O—$C_{1-10}$alkyl-O—;

$R^4$ is selected from the group consisting of hydrogen, $C_{1-10}$alkyl, $C_{1-10}$haloalkyl, $C_{2-10}$alkenyl, $C_{2-10}$alkynyl, carboxyl, $C_{1-10}$alkoxycarbonyl, $C_{2-10}$alkenyloxycarbonyl, $C_{2-10}$alkenyloxycarbonyl, $C_{1-10}$acyl, phosphoryl, phosphonate, phosphinate, cyano, sulfonate, sulfamoyl, sulfonyl, $C_{3-7}$carbocyclyl, $C_{3-7}$carbocyclyl-$C_{1-6}$alkyl, $C_{1-6}$heterocycl-$C_{3-6}$alkyl, $C_{6-10}$aryl, $C_{6-10}$aryl-$C_{1-6}$alkyl, $C_{1-5}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S;

wherein any of $R^1$, $R^2$, $R^3$, and $R^4$, independently and independently for each occurrence, is optionally substituted with 1-3 substituents selected from the group consisting of $C_{1-10}$alkyl, $C_{1-10}$haloalkyl, halo, hydroxyl, carboxyl, C$_{1-10}$alkoxycarbonyl, C$_{2-10}$alkenyloxycarbonyl, C$_{2-10}$alkynyloxycarbonyl, C$_{1-10}$acyl, C$_{1-10}$acylamino, C$_{1-10}$acyloxy, C$_{1-10}$carbonate, C$_{1-10}$alkoxy, phenyloxy, phosphoro, phosphate, phosphonate, phosphinate, amino, diC$_{1-10}$alkylamino, monoC$_{1-10}$alkylamino, C$_{1-13}$amido, C$_{1-10}$imino, C$_{1-10}$carbamate, C$_{1-6}$urea, cyano, nitro, azido, sulfhydryl, C$_{1-10}$alkylthio, sulfate, sulfonate, sulfamoyl, sulfonamido, sulfonyl, C$_{3-7}$carbocyclyl, C$_{3-7}$carbocyclyl-C$_{1-6}$alkyl, C$_{1-6}$heterocyclyl, C$_{1-6}$heterocycl, C$_{1-6}$heteroaryl-C$_{1-6}$alkyl, and wherein heterocyclic or heteroaromatic rings, independently for each occurrence, comprise 1-4 heteroatoms selected from N, O, and S; and n is 0-3;

wherein the composition is edible and capable of reducing bitter taste of a bitter tastant.

30. The composition according to paragraph 29, wherein as valence and stability permit:
R$^1$, independently for each occurrence, is selected from the group consisting of hydrogen, C$_{1-5}$alkyl, C$_{2-3}$alkyl, C$_{2-6}$alkenyl, C$_{2-6}$alkynyl, and C$_{1-6}$acyl;
R$^2$ is selected from the group consisting of hydrogen, C$_{1-6}$alkyl, C$_{2-6}$alkenyl, and C$_{2-6}$alkynyl;
R$^3$ is selected from the group consisting of hydrogen, C$_{1-6}$alkyl, C$_{2-6}$alkenyl, and C$_{2-6}$alkynyl;
R$^4$ is selected from the group consisting of hydrogen, C$_{1-6}$alkyl, C$_{2-6}$alkenyl, C$_{2-6}$alkynyl, C$_{1-6}$acyl, and C$_{6-10}$aryl-C$_{1-6}$alkyl;
wherein any of R$^1$, R$^2$, R$^3$, and R$^4$, independently and independently for each occurrence, is optionally further substituted as in paragraph 29; and
n is 0-3.

31. The composition according to paragraph 29, wherein said compound according to Formula (VIII) is a compound according to Formula (IXa):

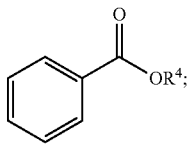

Formula (IXa)

or a comestibly or biologically acceptable salt or derivative thereof, or an enantiomer or diastereomer thereof, wherein, as valence and stability permit, R$^4$ is as defined in paragraph 29.

32. The composition according to paragraph 29, wherein said compound according to Formula (VIII) is a compound according to Formula (IXb):

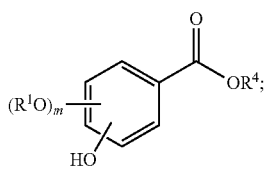

Formula (IXb)

or a comestibly or biologically acceptable salt or derivative thereof, or an enantiomer or diastereomer thereof,
wherein, as valence and stability permit:
R$^1$ and R$^4$ are as defined in paragraph 29; and
m is 0-2.

33. The composition according to paragraph 29, wherein said compound according to Formula (VIII) is a compound according to Formula (IXc):

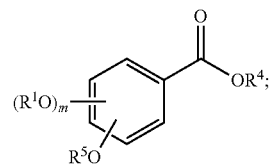

Formula (IXc)

or a comestibly or biologically acceptable salt or derivative thereof, or an enantiomer or diastereomer thereof,
wherein, as valence and stability permit:
R$^1$ and R$^4$ are as defined in paragraph 29;
R$^5$ is C$_{3-6}$alkyl; and
m is 0-2.

34. The composition according to paragraph 29, wherein said compound according to Formula (VIII) is a compound according to Formula (IXd):

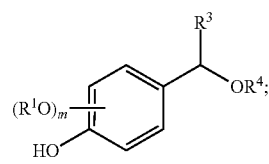

Formula (IXd)

or a comestibly or biologically acceptable salt or derivative thereof, or an enantiomer or diastereomer thereof,
wherein, as valence and stability permit:
R$^1$, R$^3$, and R$^4$ are as defined in paragraph 29; and
m is 0-2.

35. The composition according to paragraph 29, wherein said compound according to Formula (VIII) is selected from the group consisting of:

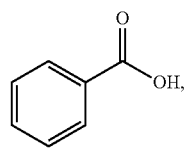

Compound 54

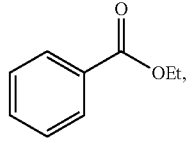

Compound 55

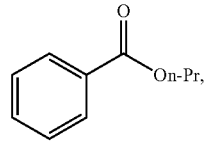

Compound 56

-continued

Compound 57
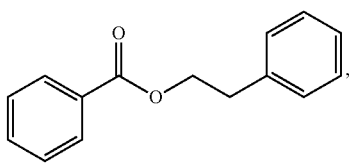

Compound 58
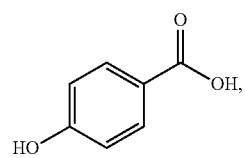

Compound 59
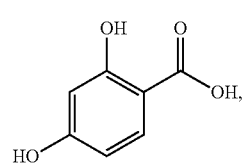

Compound 60
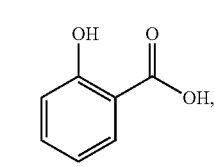

Compound 61
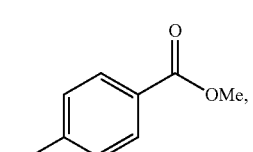

Compound 62
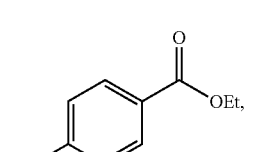

Compound 63
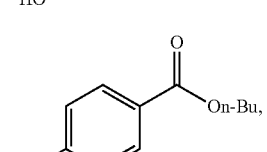

Compound 64
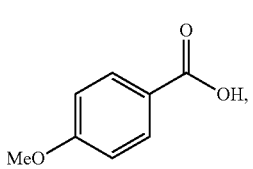

Compound 65
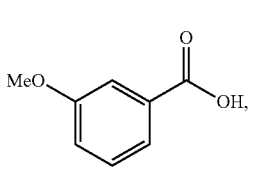

Compound 66
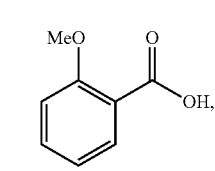

-continued

Compound 67
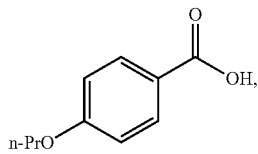

Compound 68
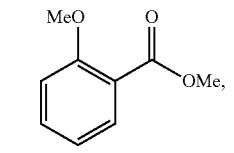

Compound 69
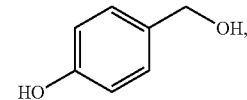

Compound 70
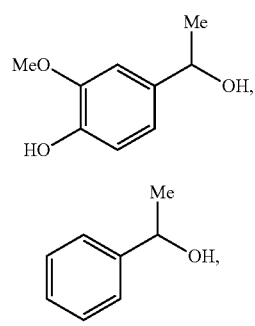

Compound 71
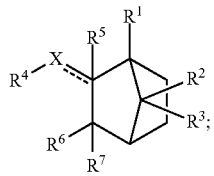

comestibly or biologically acceptable derivatives thereof, or enantiomers or diastereomers thereof.

36. A composition comprising a compound according to Formula (XI):

$$\text{Formula (XI)}$$

or a comestibly or biologically acceptable salt or derivative thereof, or an enantiomer or diastereomer thereof.
wherein, as valence and stability permit:
the bond with a dotted line optionally represents a single or double bond,
$R^1$, $R^2$, $R^3$, $R^6$, and $R^7$ are independently selected from the group consisting of hydrogen, $C_{1-10}$alkyl, $C_{2-10}$alkenyl, and $C_{2-10}$alkynyl.
wherein each of $R^1$, $R^2$, $R^3$, $R^6$, and $R^7$ may be optionally independently substituted with one or more substituents selected from the group consisting of halo, —OH, =O, —SH, =S, —NH$_2$, —CO$_2$H, —O($C_{2-10}$alkyl), —O($C_{2-10}$alkenyl), —O($C_{2-10}$alkynyl), —S($C_{1-10}$alkyl), —S($C_{2-10}$alkenyl), —S($C_{2-10}$alkynyl), —NH($C_{1-10}$alkyl), —NH($C_{2-10}$alkenyl), —NH($C_{2-10}$alkynyl), —N($C_{1-10}$alkyl)$_2$, —N($C_{2-10}$alkenyl)$_2$, and —N($C_{2-10}$alkynyl)$_2$, and
$R^4$ is absent or selected from the group consisting of hydrogen, $C_{1-10}$alkyl, $C_{2-10}$alkenyl, $C_{2-10}$alkynyl, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester, $C_{1-10}$alkylamide, $C_{1-10}$alkenylamide, $C_{1-10}$alkynylamide, $C_{1-10}$alkylthioester, $C_{1-10}$alkenylthioester, and $C_{1-10}$alkynylthioester;

wherein $R^2$ may be optionally substituted with one or more substituents selected from the group consisting of halo, —OH, =O, —SH, =S, —$NH_2$, —$CO_2H$, —O($C_{1-10}$alkyl), —O($C_{2-10}$alkenyl), —O($C_{2-10}$alkynyl), —S($C_{1-10}$alkyl), —S($C_{2-10}$alkenyl), —S($C_{1-10}$alkynyl), —NH($C_{1-10}$alkyl), —NH($C_{2-10}$alkenyl), —NH($C_{2-10}$alkynyl), —N($C_{1-10}$alkyl)$_2$, —N($C_{2-10}$alkenyl)$_2$, —N($C_{2-10}$alkynyl)$_2$, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester, $C_{1-10}$alkylamide, $C_{1-10}$alkenylamide, $C_{1-10}$alkynylamide, $C_{1-10}$alkylthioester, $C_{1-10}$alkenylthioester, and $C_{1-10}$alkynylthioester, $R^5$ is absent or selected from the group consisting of hydrogen, $C_{1-10}$alkyl, $C_{2-10}$alkenyl, and $C_{2-10}$alkynyl, wherein $R^5$ may be optionally independently substituted with one or more substituents selected from the group consisting of halo, —OH, =O, —SH, =S, —$NH_2$, —$CO_2H$, —O($C_{1-10}$alkyl), —O($C_{2-10}$alkenyl), —O($C_{2-10}$alkynyl), —S($C_{1-10}$alkyl), —S($C_{2-10}$alkenyl), —S($C_{2-10}$alkynyl), —NH($C_{1-10}$alkyl), —NH($C_{1-10}$alkenyl), —NH($C_{2-10}$alkynyl), —N($C_{1-10}$alkyl)$_2$, —N($C_{1-10}$alkenyl)$_2$, and —N($C_{1-10}$alkynyl)$_2$;

wherein $R^6$ and $R^7$ are optionally taken together to form =O, =S or =$C(R^a)_2$;

wherein each $R^a$ is independently selected from the group consisting of hydrogen, $C_{1-10}$alkyl, $C_{1-10}$alkenyl, and $C_{1-10}$alkynyl, wherein each $C_{1-10}$alkyl, $C_{2-10}$alkenyl, and $C_{2-10}$alkynyl may be optionally independently substituted with one or more substituents selected from the group consisting of halo, —OH, =O, —SH, =S, —$NH_2$, —$CO_2H$, —O($C_{1-10}$alkyl), —O($C_{2-10}$alkenyl), —O($C_{2-10}$alkynyl), —S($C_{1-10}$alkyl), —S($C_{2-10}$alkenyl), —S($C_{2-10}$alkynyl), —NH($C_{1-10}$alkyl), —N($C_{1-10}$alkenyl), —NH($C_{2-10}$alkynyl), —N($C_{1-10}$alkyl)$_2$, —N($C_{2-10}$alkenyl)$_2$, and —N($C_{2-10}$alkynyl)$_2$;

wherein when the bond with the dotted line represents a double bond and $R^4$ is present, X is selected from the group consisting of =$C(R^a)$— and =N—;

wherein when the bond with the dotted line represents a double bond and $R^4$ is absent, X is selected from the group consisting of =O and =S; and wherein when the bond with the dotted line represents a single bond, X is selected from the group consisting of —$C(R^a)_2$—, —$N(R^a)$—, —O—, and —S—;

provided that when the bond with the dotted line represents a double bond, $R^5$ is absent, and when the bond with the dotted line represents a single bond, $R^4$ is present;

wherein the composition is edible and capable of reducing bitter taste of a bitter tastant.

37. The composition according to paragraph 36, wherein as valence and stability permit:

$R^1$, $R^2$, $R^3$, $R^6$, and $R^7$ are independently selected from the group consisting of hydrogen, $C_{1-6}$alkyl, $C_{2-6}$alkenyl, and $C_{2-6}$alkynyl;

$R^4$ is absent or selected from the group consisting of hydrogen, $C_{1-6}$alkyl, $C_{2-6}$alkenyl, $C_{2-6}$alkynyl, $C_{1-6}$acyl, $C_{1-6}$acyloxy, $C_{1-6}$acylamino, $C_{1-6}$acylthioxy, $C_{1-6}$alkylester, $C_{1-6}$alkenylester, $C_{1-6}$alkynylester;

$R^5$ is absent or selected from the group consisting of hydrogen, $C_{1-6}$alkyl, $C_{2-6}$alkenyl, and $C_{2-6}$alkynyl;

wherein $R^6$ and $R^7$ are optionally taken together to form =O, =S or =$C(R^a)_2$;

wherein each $R^a$ is independently selected from the group consisting of hydrogen, $C_{2-6}$alkyl, $C_{2-6}$alkenyl, and $C_{2-6}$alkynyl;

wherein any of $R^1$, $R^2$, $R^3$, $R^4$, $R^5$, $R^6$, $R^7$, and $R^8$ are independently optionally substituted as in paragraph 36;

wherein when the bond with the dotted line represents a double bond and $R^4$ is present, X is selected from the group consisting of =$C(R^a)$— and =N—;

wherein when the bond with the dotted line represents a double bond and $R^4$ is absent, X is selected from the group consisting of =O and =S; and wherein when the bond with the dotted line represents a single bond, X is selected from the group consisting of —$C(R^a)_2$—, —$N(R^a)$—, —O—, and —S—;

provided that when the bond with the dotted line represents a double bond, $R^5$ is absent, and when the bond with the dotted line represents a single bond, $R^4$ is present.

38. The composition according to paragraph 37, wherein as valence and stability permit: $R^1$, $R^2$, $R^3$, $R^6$, and $R^7$ are independently selected from the group consisting of hydrogen, $C_{1-6}$alkyl, $C_{2-6}$alkenyl, and $C_{2-6}$alkynyl;

$R^4$ is absent or selected from the group consisting of hydrogen, $C_{1-6}$alkyl, $C_{2-6}$alkenyl, $C_{2-6}$alkynyl, $C_{1-6}$acyl, $C_{1-6}$acyloxy, $C_{1-6}$alkylester, $C_{1-6}$alkenylester, and $C_{1-6}$alkynylester;

wherein $R^4$ may be optionally substituted with one or more substituents selected from the group consisting of —OH, =O, —SH, and =S;

$R^5$ is absent or selected from the group consisting of hydrogen, $C_{1-6}$alkyl, $C_{2-6}$alkenyl, and $C_{2-6}$alkynyl;

wherein $R^6$ and $R^7$ are optionally taken together form =O, =S or =$C(R^a)_2$;

wherein each $R^a$ is independently selected from the group consisting of hydrogen, $C_{2-6}$alkyl, $C_{2-6}$alkenyl, and $C_{2-6}$alkynyl;

wherein when the bond with the dotted line represents a double bond and $R^4$ is present, X is selected from the group consisting of =$C(R^a)$— and =N—;

wherein when the bond with the dotted line represents a double bond and $R^4$ is absent, X is selected from the group consisting of =O and =S; and wherein when the bond with the dotted line represents a single bond, X is selected from the group consisting of —$C(R^a)_2$—, —$N(R^a)$—, —O—, and —S—;

provided that when the bond with the dotted line represents a double bond, $R^5$ is absent, and when the bond with the dotted line represents a single bond, $R^4$ is present.

39. The composition according to paragraph 38, wherein as valence and stability permit: $R^1$, $R^2$, $R^3$, $R^6$, and $R^7$ are independently selected from the group consisting of hydrogen, $C_{1-3}$alkyl, $C_{2-3}$alkenyl, and $C_{2-3}$alkynyl;

$R^4$ is absent or selected from the group consisting of hydrogen, $C_{1-6}$alkyl, $C_{2-6}$alkenyl, $C_{2-6}$alkynyl, and $C_{1-6}$acyl;

wherein $R^4$ may be optionally substituted with =O or =S;

$R^5$ is absent or selected from the group consisting of hydrogen, $C_{1-6}$alkyl, wherein $R^4$ may be optionally substituted with =O or =S;

$R^5$ is absent or selected from the group consisting of hydrogen, $C_{1-3}$alkyl, $C_{2-3}$alkenyl, and $C_{2-3}$alkynyl;

wherein $R^6$ and $R^7$ are optionally taken together to form =O, =S or —C($R^a$)$_2$;

wherein each $R^a$ is independently selected from the group consisting of hydrogen, $C_{2-3}$alkyl, $C_{2-3}$alkenyl, and $C_{2-3}$alkynyl;

wherein when the bond with the dotted line represents a double bond and $R^4$ is present, X is selected from the group consisting of =C($R^a$)— and =N—;

wherein when the bond with the dotted line represents a double bond and $R^4$ is absent, X is selected from the group consisting of =O and =S; and wherein when the bond with the dotted line represents a single bond, X is selected from the group consisting of —C($R^a$)$_2$—, —N($R^a$)—, —O—, and —S—;

provided that when the bond with the dotted line represents a double bond, $R^5$ is absent, and when the bond with the dotted line represents a single bond, $R^4$ is present.

40. The composition according to paragraph 39, wherein as valence and stability permit: $R^1$, $R^2$, $R^3$, $R^6$, and $R^7$ are independently selected from the group consisting of hydrogen, $C_{1-3}$alkyl, $C_{2-3}$alkenyl, and $C_{2-3}$alkynyl.

$R^4$ is absent or selected from the group consisting of hydrogen, $C_{1-6}$alkyl, $C_{2-6}$alkenyl, $C_{2-6}$alkynyl, and $C_{1-6}$acyl;

wherein $R^4$ may be optionally substituted with =O or =S;

$R^5$ is absent or selected from the group consisting of hydrogen, $C_{1-3}$alkyl, $C_{2-3}$alkenyl, and $C_{2-3}$alkynyl;

wherein $R^6$ and $R^7$ are optionally taken together to form =O, =S or —C($R^a$)$_2$;

wherein each $R^a$ is independently selected from the group consisting of hydrogen, $C_{2-3}$alkyl, $C_{2-3}$alkenyl, and $C_{2-3}$alkynyl;

wherein when the bond with the dotted line represents a double bond and $R^4$ is present, X is =C($R^a$)—;

wherein when the bond with the dotted line represents a double bond and $R^4$ is absent, X is selected from the group consisting of =O and =S; and wherein when the bond with the dotted line represents a single bond, X is selected from the group consisting of —C($R^a$)$_2$— and —O—;

provided that when the bond with the dotted line represents a double bond, $R^5$ is absent, and when the bond with the dotted line represents a single bond, $R^4$ is present.

41. A composition comprising a compound according to Formula (XII):

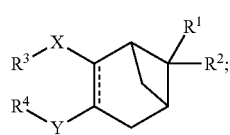

Formula (XII)

or a comestibly or biologically acceptable salt or derivative thereof, or an enantiomer or diastereomer thereof, wherein, as valence and stability permit:

the bond with a dotted line optionally represents a single or double bond, $R^1$ and $R^2$ are independently selected from the group consisting of hydrogen, $C_{1-10}$alkyl, $C_{2-10}$alkenyl, and $C_{2-10}$alkynyl;

wherein $R^1$ and $R^2$ may be optionally substituted with one or more substituents selected from the group consisting of halo, —OH, =O, —SH, =S, —NH$_2$, —CO$_2$H, —O($C_{1-10}$alkyl), —O($C_{2-10}$alkenyl), —O($C_{2-10}$alkynyl), —S($C_{1-10}$alkyl), —S($C_{2-10}$alkenyl), —S($C_{2-10}$alkynyl), —NH($C_{1-10}$alkyl), —NH($C_{2-10}$alkenyl), —NH($C_{2-10}$alkynyl), —N($C_{1-10}$alkyl)$_2$, —N($C_{2-10}$alkenyl)$_2$, and —N($C_{2-10}$alkenyl)$_2$;

$R^3$ and $R^4$ are independently selected from the group consisting of hydrogen, $C_{1-10}$alkyl, $C_{1-10}$alkenyl, $C_{2-10}$alkynyl, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester, $C_{1-10}$alkylamide, $C_{1-10}$alkenylamide, $C_{1-10}$alkynylamide, $C_{1-10}$alkylthioester, $C_{1-10}$alkenylthioester, $C_{1-10}$alkenylthioester, and $C_{1-10}$alkynylthioester;

wherein each of $R^1$ and $R^4$ may be optionally substituted with one or more substituents selected from the group consisting of halo, —OH, =O, —SH, =S, —NH$_2$, —CO$_2$H, —O($C_{1-10}$alkyl), —O($C_{2-10}$alkenyl), —O($C_{2-10}$alkynyl), —S($C_{1-10}$alkyl), —S($C_{2-10}$alkenyl), —S($C_{2-10}$alkynyl), NH($C_{1-10}$alkyl), NH($C_{1-10}$alkyl), —NH($C_{2-10}$alkenyl), —NH($C_{2-10}$alkynyl), —N($C_{1-10}$alkyl)$_2$, —N($C_{2-10}$alkenyl)$_2$, —N($C_{2-10}$alkynyl)$_2$, $C_{1-30}$acyl, $C_{3-10}$acyloxy, $C_{1-10}$acylamino, $C_{1-10}$acylthioxy, $C_{1-10}$alkylester, $C_{1-10}$alkenylester, $C_{1-10}$alkenylester, $C_{1-10}$alkylamide, $C_{1-10}$alkenylamide, $C_{1-10}$alkynylamide, $C_{1-10}$alkylthioester, $C_{1-10}$alkenylthioester, and $C_{1-10}$alkynylthioester; and X and Y are independently selected from the group consisting of a direct bond, $C_{1-10}$alkyl, $C_{2-10}$alkenyl, and $C_{2-10}$alkynyl, —N($R^a$)—, —O—, —S—, =O, and =S, provided that when X and Y is =O or =S, then $R^3$ and $R^4$, respectively, are absent, wherein $R^1$ is selected from the group consisting of hydrogen, $C_{1-10}$alkyl, $C_{2-10}$alkenyl, and $C_{2-10}$alkynyl wherein each $C_{1-10}$alkyl, $C_{2-10}$alkenyl, and $C_{2-10}$alkynyl may be optionally independently substituted with one or more substituents selected from the group consisting of halo, —OH, =O, —SH, =S, —NH$_2$, —CO$_2$H, —O($C_{1-10}$alkyl), —O($C_{2-10}$alkenyl), —O($C_{2-10}$alkynyl), —S($C_{1-10}$alkyl), —S($C_{2-10}$alkenyl), —S($C_{2-10}$alkynyl), —NH($C_{1-10}$alkyl), —NH($C_{2-10}$alkenyl), —NH($C_{2-10}$alkynyl), —N($C_{1-10}$alkyl)$_2$, —N($C_{2-10}$alkenyl)$_2$, and —N($C_{2-10}$alkynyl)$_2$;

wherein the composition is edible and capable of reducing bitter taste of a bitter tastant.

42. The composition according to paragraph 41, wherein as valence and stability permit:

the bond with a dotted line optionally represents a single or double bond, $R^1$ and $R^2$ are independently selected from the group consisting of hydrogen, $C_{1-10}$alkyl, $C_{1-10}$alkenyl, $C_{2-10}$alkynyl;

$R^3$ and $R^4$ are independently selected from the group consisting of hydrogen, $C_{1-6}$alkyl, $C_{2-6}$alkenyl, $C_{2-6}$alkynyl, $C_{1-6}$acyl, $C_{1-6}$acyloxy, $C_{1-6}$alkylester, $C_{1-6}$alkenylester, and $C_{1-6}$alkynylester, X and Y are independently selected from the group consisting of a direct bond, $C_{1-6}$alkyl, $C_{2-6}$alkenyl, $C_{2-10}$alkynyl, —N($R^a$)—, —O—, —S—, =O and =S, provided that when either X and Y is =O or =S, then $R^3$ and $R^4$, respectively, are absent, wherein any of wherein any of $R^1$, $R^2$, $R^3$, $R^4$, and $R^5$ are independently optionally substituted as noted in paragraph 41; and wherein $R^5$ is selected from the group consisting of hydrogen, $C_{1-6}$alkyl, $C_{2-6}$alkenyl, and $C_{2-6}$alkynyl.

43. The composition according to paragraph 42, wherein as valence and stability permit:

the bond with a dotted line optionally represents a single or double bond, $R^1$ and $R^2$ are independently selected from the group consisting of hydrogen, $C_{1-10}$alkyl, $C_{1-10}$alkenyl, $C_{2-10}$alkynyl;

$R^3$ and $R^4$ are independently selected from the group consisting of hydrogen, $C_{1-6}$alkyl, $C_{2-6}$alkenyl, $C_{2-6}$alkynyl, $C_{1-6}$acyl, $C_{1-6}$acyloxy, $C_{1-6}$acylamino, $C_{1-6}$acylthioxy, $C_{1-6}$alkylester, $C_{1-6}$alkenylester, and $C_{1-6}$alkynylester;

wherein each of $R^3$ and $R^4$ may be optionally independently substituted with one or more substituents selected from the group consisting of —O—, and —S—, =O and =S, $C_{1-6}$acyloxy, $C_{1-6}$alkylester, $C_{1-6}$alkenylester, $C_{1-6}$alkynylester, $C_{1-6}$alkylthioester, and $C_{1-6}$alkenylthioester;

X and Y are independently selected from the group consisting of a direct bond, $C_{1-6}$alkyl, $C_{2-6}$alkenyl, $C_{2-6}$alkynyl, —N($R^a$)—, —O—, —S—, =O, =S, provided that when either X or Y is =O or =S, then $R^3$ and $R^4$, respectively, are absent, and wherein $R^5$ is selected from the group consisting of hydrogen, $C_{1-6}$alkyl, $C_{2-6}$alkenyl, and $C_{2-6}$alkynyl.

44. The composition according to paragraph 43, wherein as valence and stability permit:

the bond with a dotted line optionally represents a single or double bond, $R^1$ and $R^2$ are independently selected from the group consisting of hydrogen, $C_{1-10}$alkyl, $C_{1-10}$alkenyl, $C_{2-10}$alkynyl;

$R^3$ and $R^4$ are independently selected from the group consisting of hydrogen, $C_{1-4}$alkyl, $C_{2-4}$alkenyl, $C_{2-4}$alkynyl, and $C_{1-4}$acyl wherein each of $R^3$ and $R^4$ may be optionally independently substituted with one or more substituents selected from the group consisting of —OH, =O, —SH, =S, $C_{1-4}$acyloxy, $C_{1-4}$, $C_{1-4}$acyloxy, $C_{1-4}$acylthioxy, $C_{1-4}$alkylester, $C_{1-4}$alkenylester, $C_{1-4}$alkynylester, $C_{1-4}$alkylthioester, $C_{1-4}$alkenylthioester, and $C_{2-6}$alkenylthioester;

X and Y are independently selected from the group consisting of a direct bond, $C_{1-6}$alkyl, $C_{2-6}$alkenyl, $C_{2-6}$alkynyl, —O—, —S—, =O, and =S, provided that when either X or Y is =O or =S, then $R^3$ and $R^4$, respectively, are absent.

45. The composition according to paragraph 44, wherein as valence and stability permit;

the bond with a dotted line optionally represents a single or double bond, $R^1$ and $R^2$ are independently selected from the group consisting of hydrogen, $C_{1-10}$alkyl, $C_{1-10}$alkenyl, $C_{2-10}$alkynyl;

$R^3$ and $R^4$ are independently selected from the group consisting of hydrogen, $C_{1-4}$alkyl, $C_{2-4}$alkenyl, $C_{2-4}$alkynyl, $C_{1-4}$acyl;

wherein $R^3$ and $R^4$ may be independently substituted with one or more substituents selected from the group consisting of —OH, =O, —SH, =S, $C_{1-4}$acyloxy, $C_{1-4}$alkylester, $C_{1-4}$alkenylester; $C_{1-4}$alkynylester; and X and Y are independently selected from the group consisting of a direct bond, $C_{1-6}$alkyl, $C_{2-6}$alkenyl, and $C_{2-6}$alkynyl, —O—, —S—, =O, and =S, provided that when either X or Y is =O or =S, then $R^3$ and $R^4$, respectively, are absent.

46. The composition according to paragraph 36, wherein said compound according to Formula (XI) is selected from the group consisting of:

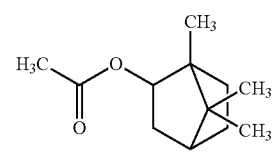

Compound 72

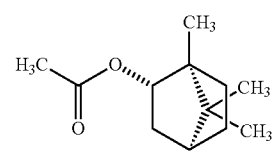

Compound 73

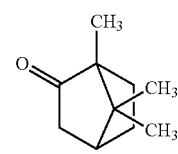

Compound 74

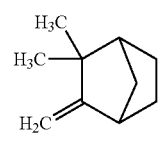

Compound 75

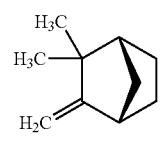

Compound 76

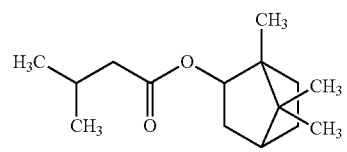

Compound 77

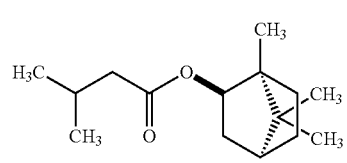

Compound 78

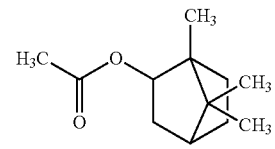

Compound 79

Compound 80
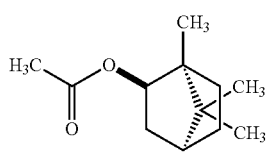

Compound 81
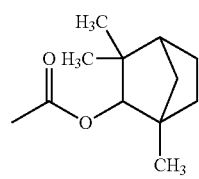

Compound 82
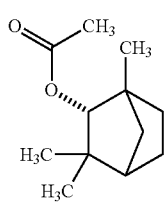

Compound 83
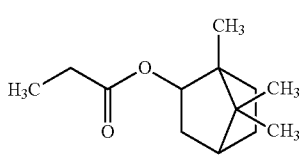

Compound 84
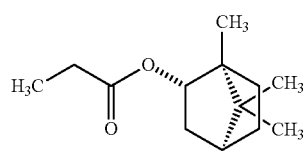

Compound 85
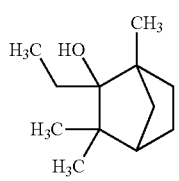

Compound 86
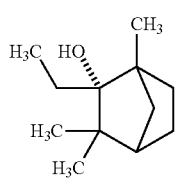

Compound 87
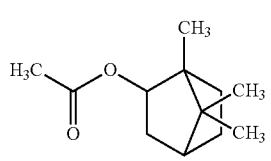

Compound 88
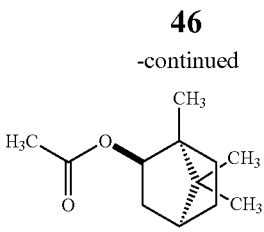

or comestibly or biologically acceptable derivatives thereof, or enantiomers or diastereomer thereof.

47. The composition according to paragraph 41, wherein said compound according to Formula (XII) is selected from the group consisting of:

Compound 89
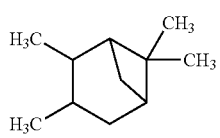

Compound 90
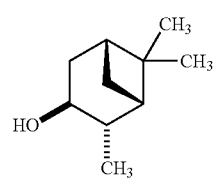

Compound 91
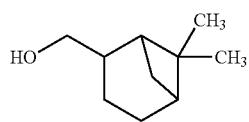

Compound 92
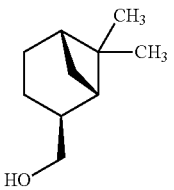

Compound 93
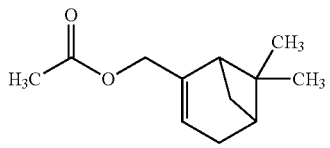

Compound 94
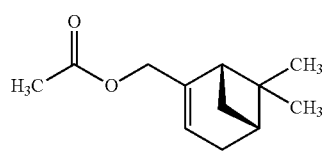

or comestibly or biologically acceptable derivatives thereof, or enantiomers or diastereomers thereof.

48. A composition comprising a compound selected from the group consisting of:

Compound 95
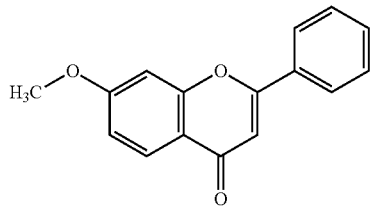
Compound 96
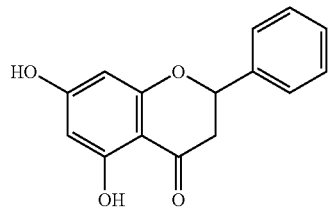 [SMILES: O=C1CC(c2ccccc2)Oc2cc(O)cc(O)c21]
Compound 97
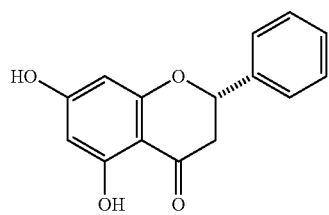 [SMILES: O=C1C[C@@H](c2ccccc2)Oc2cc(O)cc(O)c21]
Compound 98
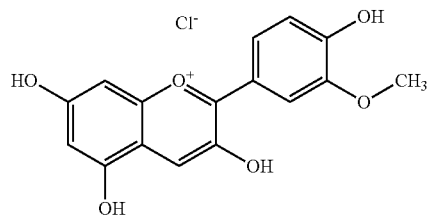 [SMILES: COc1cc(-c2[o+]c3cc(O)cc(O)c3cc2O)ccc1O ; [Cl-]]
Compound 99
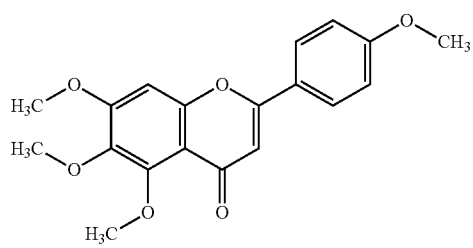
Compound 100
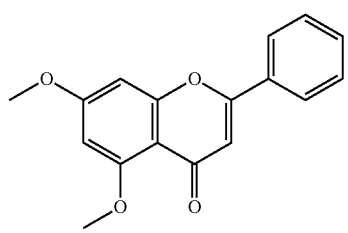 [SMILES: COc1cc(OC)c2c(=O)cc(-c3ccccc3)oc2c1]
Compound 101
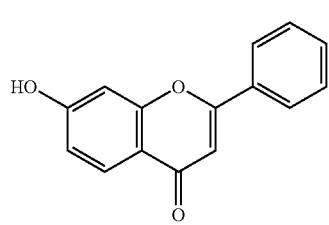 [SMILES: O=c1cc(-c2ccccc2)oc2cc(O)ccc12]

-continued
Compound 102
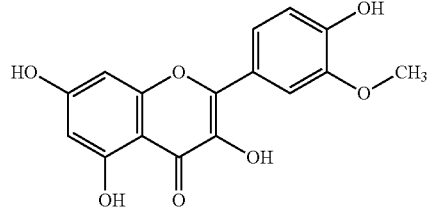 [SMILES: COc1cc(-c2oc3cc(O)cc(O)c3c(=O)c2O)ccc1O]
Compound 103
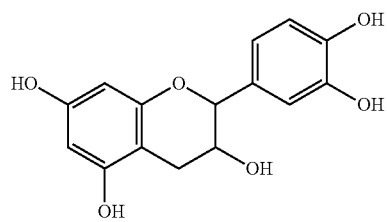 [SMILES: Oc1cc(O)c2c(c1)OC(c1ccc(O)c(O)c1)C(O)C2]
Compound 104
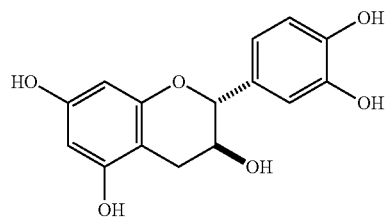 [SMILES: Oc1cc(O)c2c(c1)O[C@H](c1ccc(O)c(O)c1)[C@@H](O)C2]
Compound 105
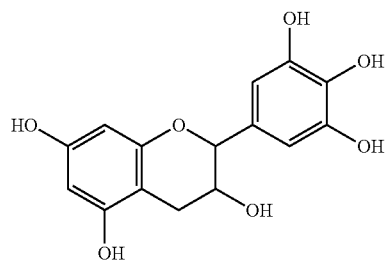
Compound 106
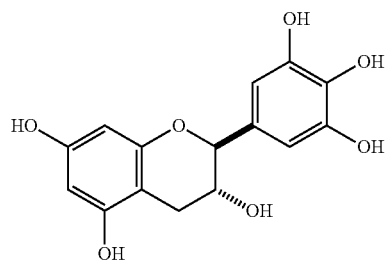 [SMILES: Oc1cc(O)c2c(c1)O[C@@H](c1cc(O)c(O)c(O)c1)[C@H](O)C2]
Compound 107
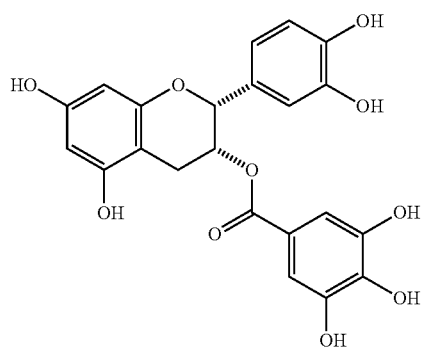 [SMILES: O=C(O[C@@H]1Cc2c(O)cc(O)cc2O[C@@H]1c1ccc(O)c(O)c1)c1cc(O)c(O)c(O)c1]

-continued
Compound 108
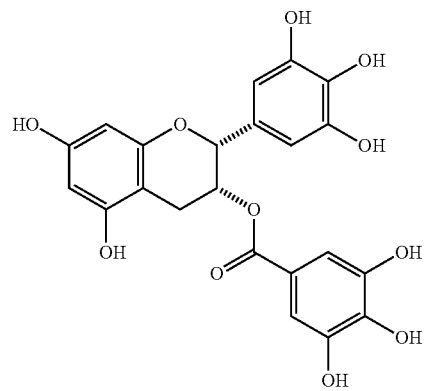 [SMILES: O=C(O[C@@H]1Cc2c(O)cc(O)cc2O[C@@H]1c1cc(O)c(O)c(O)c1)c1cc(O)c(O)c(O)c1]
Compound 109
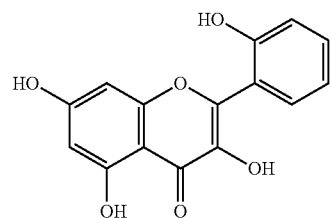 [SMILES: O=c1c(O)c(-c2ccccc2O)oc2cc(O)cc(O)c12]
Compound 110
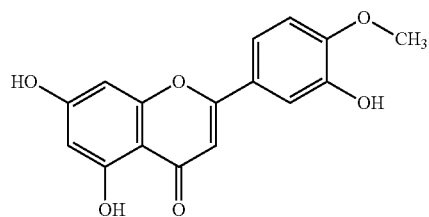 [SMILES: COc1ccc(-c2cc(=O)c3c(O)cc(O)cc3o2)cc1O]
Compound 111
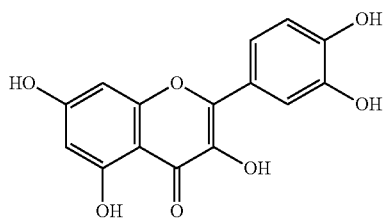 [SMILES: O=c1c(O)c(-c2ccc(O)c(O)c2)oc2cc(O)cc(O)c12]
Compound 112
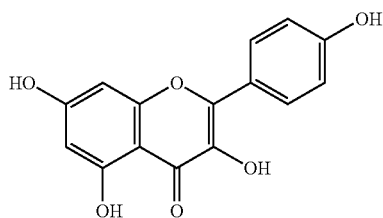 [SMILES: O=c1c(O)c(-c2ccc(O)cc2)oc2cc(O)cc(O)c12]
Compound 113
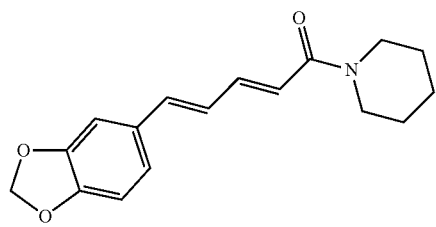 [SMILES: O=C(/C=C/C=C/c1ccc2c(c1)OCO2)N1CCCCC1]

-continued
| | |
|---|---|
| Compound 114 | 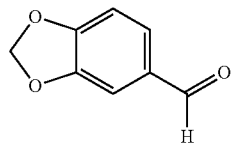 [SMILES: O=Cc1ccc2c(c1)OCO2] |
| Compound 115 | Black Pepper Oil (mixtue of structures) |
| Compound 116 | 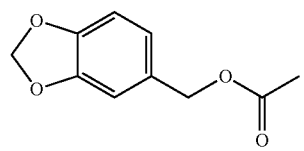 |
| Compound 117 | 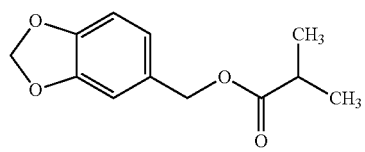 [SMILES: CC(C)C(=O)OCc1ccc2c(c1)OCO2] |
| Compound 118 | 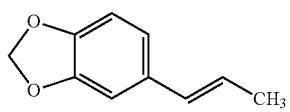 |
| Compound 119 | Camphor Oil (mixture of structures) |
| Compound 120 | 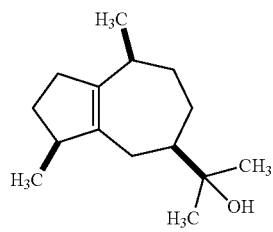 [SMILES: C[C@H]1CC[C@@H](C(C)(C)O)CC2=C1CC[C@@H]2C] |
| Compound 121 | 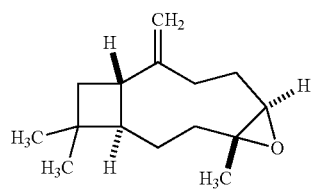 |
| Compound 122 | 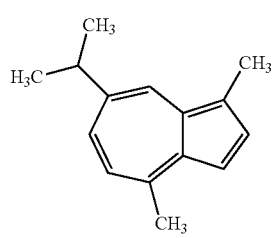 |
| Compound 123 | 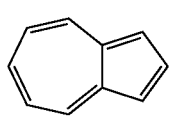 |
| Compound 124 | 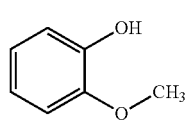 |

Compound 125 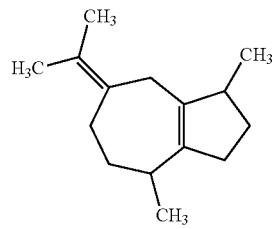
Compound 126 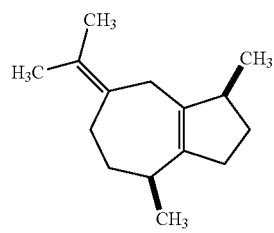
Compound 127 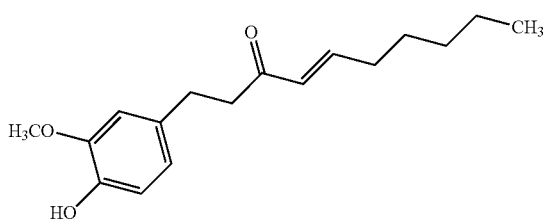 [SMILES: CCCCC/C=C/C(=O)CCc1ccc(O)c(OC)c1]
Compound 128   Ginger Oil (mixture of structures)
Compound 129   Ginger oleoresin (mixture of structures)
Compound 130 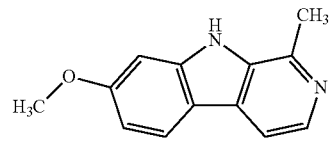 [SMILES: COc1ccc2c(c1)[nH]c1c(C)nccc12]
Compound 131 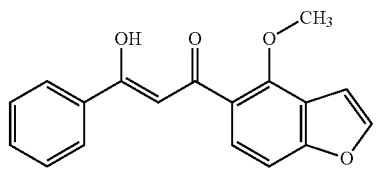 [SMILES: COc1c(C(=O)/C=C(\O)c2ccccc2)ccc2occc12]
Compound 132 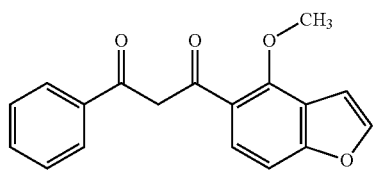
(Chromadex Cat. No. ASB-00016005-050)
Compound 133 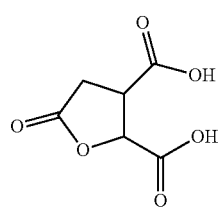 [SMILES: O=C1C[C@H](C(=O)O)[C@H](C(=O)O)O1]
(Sigma Cat. No. 116005)

-continued

Compound 134

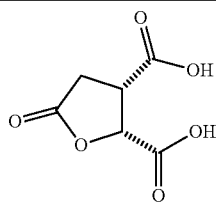

or a comestibly or biologically acceptable salt or derivative thereof, or an enantiomer or diastereomer thereof;
wherein the composition is edible and capable of reducing bitter taste of a bitter tastant.

49. A composition comprising:
(a) a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof; and
(b) a bitter tastant,
wherein the composition is edible.

50. The composition according to paragraph 49, wherein the bitter tastant is a foodstuff.

51. The composition according to paragraph 49, wherein the bitter tastant is a bitter tasting salt.

52. The composition according to paragraph 51, wherein the bitter tasting salt is a magnesium salt, a calcium salt, or a potassium salt.

53. The composition according to paragraph 52, wherein the potassium containing salt is KCl or potassium lactate.

54. The composition of any one of paragraphs 1-53, wherein the edible composition further comprises one or more components selected from the group consisting of: NaCl, sodium lactate, and sugar.

55. A food product comprising the compositions of any one of paragraphs 1-54.

56. A method of preparing an edible composition comprising:
(a) providing a comestibly acceptable carrier; and
(b) adding to the comestibly acceptable carrier of (a) a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

57. The method according to paragraph 56, wherein said comestibly acceptable carrier is inherently bitter.

58. The method according to paragraph 57, wherein the comestibly acceptable carrier comprises a bitter tasting salt.

59. The method according to paragraph 58, wherein the bitter tasting salt is a magnesium salt, a calcium salt, or a potassium salt.

60. The method according to paragraph 59, wherein the potassium salt is KCl or potassium lactate.

61. The method according to any one of paragraphs 56-60, wherein the edible composition further comprises one or more components selected from the group consisting of: NaCl, sodium lactate, and sugar.

62. The method according to paragraph 56, wherein the method further comprises:
(c) adding a bitter tastant.

63. The method according to paragraph 62, wherein the bitter tastant is a bitter tasting salt.

64. The method according to paragraph 63, wherein the bitter tasting salt is a magnesium salt, a calcium salt, or a potassium salt.

65. The method according in paragraph 64, wherein the potassium salt is KCl or potassium lactate.

66. The method according to any one of paragraphs 62-65, wherein the edible composition further comprises one or more components selected from the group consisting of: NaCl, sodium lactic, and sugar.

67. A method of reducing the amount of NaCl in an edible composition comprising:
(a) replacing an amount of NaCl used in preparing an edible composition with an amount of KCl; and
(b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

68. The method according to paragraph 67, wherein the amount of compound added in (b) is sufficient to permit replacement of the amount of NaCl typically present in the edible composition by up to 25%.

69. The method according to paragraph 67, wherein the amount of compound added in (b) is sufficient to permit replacement of the amount of NaCl typically present in the edible composition by up to 50%.

70. The method accenting to paragraph 67, wherein the amount of compound added in (b) is sufficient to permit replacement of the amount of NaCl typically present in the edible composition by up to 75%.

71. The method according to paragraph 67, wherein the amount of compound added in (b) is sufficient to permit replacement of the amount of NaCl typically present in the edible composition by up to 100%.

72. The method according to any one of paragraphs 67-7, wherein the edible exposition maintains a salty flavor.

73. A method of reducing the amount of sodium lactate in an edible composition comprising:
   (a) replacing an amount of sodium lactate used in preparing an edible composition with an amount of potassium lactate; and
   (b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134 as described herein, or combinations thereof.

74. The method according to paragraph 73, wherein the amount of compound added in (b) is sufficient to permit replacement of the amount of sodium lactate typically present in the edible composition by up to 25%.

75. The method according to paragraph 73, wherein the amount of compound added in (b) is sufficient to permit replacement of the amount of sodium lactate typically present in the edible composition by up to 50%.

76. The method according to paragraph 73, wherein the amount of compound added in (b) is sufficient to permit replacement of the amount of sodium lactate typically present in the edible composition by up to 75%.

77. The method according to paragraph 73, wherein the amount of compound added in (b) is sufficient to permit replacement of the amount of sodium lactate typically present in the edible composition by up to 100%.

78. The method according to any one of paragraphs 73-77, wherein the edible composition has the same shelf life as an edible composition comprising sodium lactate.

79. A method of reducing the amount of sugar in an edible composition comprising:
   (a) replacing an amount of sugar present an edible composition with an amount of Acesulfame K; and
   (b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

80. The method according to paragraph 79, wherein the amount of compound added in (b) is sufficient to permit replacement of the amount of sugar typically present in the edible composition by up to 25%.

81. The method according to paragraph 79, wherein the amount of compound added in (b) is sufficient to permit replacement of the amount of sugar typically present in the edible composition by up to 50%.

82. The method according to paragraph 79, wherein the amount of compound added in (b) is sufficient to permit replacement of the amount of sugar typically present in the edible composition by up to 75%.

83. The method according to paragraph 79, wherein the amount of compound added in (b) is sufficient to permit replacement of the amount of sugar typically present in the edible composition by up to 100%.

84. The method according to any one of paragraphs 79-83, wherein the edible composition maintains a sweet flavor.

85. A method of reducing the sodium intake of a subject, the method comprising:
   (a) replacing an amount of a sodium salt used in preparing an edible composition with an amount of a potassium salt; and
   (b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof or any one of Compounds 1-134, as described herein, or combinations thereof.

86. The method according to paragraph 85, wherein the sodium salt is NaCl and the potassium salt is KCl.

87. The method according to paragraph 85, wherein the sodium salt is sodium lactate, and the potassium salt is potassium lactate.

88. The method according to any one of paragraphs 85-87, wherein the method further comprises (c) identifying a subject in need thereof.

89. The method according to any one of paragraphs 85-88, wherein the amount of compound added in (b) is sufficient to reduce sodium intake by up to 25% by replacement with potassium.

90. The method according to any one of paragraphs 85-88, wherein the amount of compound added in (b) is sufficient to reduce sodium intake by up to 50% by replacement with potassium.

91. The method according to any one of paragraphs 85-88, wherein the amount of compound added in (b) is sufficient to reduce sodium intake by up to 75% by replacement with potassium.

92. The method according to any one of paragraphs 85-88, wherein the amount of compound added in (b) is sufficient to reduce sodium intake by up to 100% by replacement with potassium.

93. A method of reducing the sugar intake of a subject, the method comprising:
   (a) replacing an amount of sugar used in preparing an edible composition with an amount of a Acesulfame K; and
   (b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

94. The method according to paragraph 93, wherein the method further comprises (c) identifying a subject in need thereof.

95. The method according to paragraph 93 or 94, wherein the amount of compound added in (b) is sufficient to reduce sugar intake by up to 25% by replacement with Acesulfame K.

96. The method according to paragraph 93 or 94, wherein the amount of compound added in (b) is sufficient to reduce sugar intake by up to 50% by replacement with Acesulfame K.

97. The method according to paragraph 93 or 94, wherein the amount of compound added in (b) is sufficient to reduce sugar intake by up to 75% by replacement with Acesulfame K.

98. The method according to paragraph 93 or 94, wherein the amount of compound added in (b) is sufficient to reduce sugar intake by up to 100% by replacement with Acesulfame K.

99. A method of reducing bitter taste attributed to a bitter tastant in an edible composition comprising:
(a) adding an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof, to the edible composition such that any bitter taste induced by the bitter tastant is reduced.

100. A method of reducing bitter taste attributed to a bitter tastant in an edible composition comprising:
(a) ingesting an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), combinations thereof, or any one of Compounds 1-134, as described herein, or combinations thereof, along with the edible composition such that any bitter taste induced by the bitter tastant is reduced.

101. The method according to any one of paragraphs 56-100 or 102-111, wherein the edible composition is a food product, a consumer product, or a pharmaceutical composition.

102. The method according to any one of paragraphs 99-101, wherein the bitter taste induced by the bitter tastant is reduced by up to 25%.

103. The method according to any one of paragraphs 99-101, wherein the bitter taste induced by the bitter tastant is reduced by up to 50%.

104. The method according to any one of paragraphs 99-101, wherein the bitter taste induced by the bitter tastant is reduced by up to 75%.

105. The method according to any one of paragraphs 99-101, wherein the bitter taste induced by the bitter tastant is reduced by up to 100%.

106. The method according to any one of paragraphs 99-105, wherein the bitter tastant is a bitter tasting salt.

107. The method according to paragraph 106, wherein the bitter tasting salt is a magnesium salt, a calcium salt, or a potassium salt.

108. The method according to paragraph 107, wherein the potassium salt is KCl or potassium lactate.

109. The method according to any one of paragraphs 99-108, wherein the edible composition further comprises NaCl, sodium lactate, or sugar.

110. A method of preserving an edible composition comprising:
(a) providing an edible composition; and
(b) combining with the edible composition of (a) potassium lactate and a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof or any one of Compounds 1-134, as described herein, or combinations thereof.

111. A method of reducing the amount of sodium in an edible composition while preserving the edible composition, the method comprising:
(a) replacing an amount of sodium lactate used in preparing an edible composition with an amount of potassium lactate; and
(b) incorporating into the edible composition an effective amount of a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

112. A method of inhibiting, reducing, or eliminating a bitter taste in a subject comprising:
(a) placing a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof in the oral cavity of the subject.

113. The method according to paragraph 112, wherein the bitter taste is due to a bitter tasting salt.

114. The method according to paragraph 113, wherein the bitter taste is due to a magnesium salt, a calcium salt, or a potassium salt.

115. The method according to paragraph 114, wherein the bitter taste is due to KCl or potassium lactate.

116. A pharmaceutical composition comprising:
(a) a bitter tasting pharmaceutical active ingredient; and
(b) a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

117. A pharmaceutical composition comprising:
(a) a pharmaceutical active ingredient;
(b) a bitter tastant; and
(c) a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

118. A consumer product comprising:
(a) a bitter tasting ingredient; and
(b) a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

119. A consumer product for reducing bitter taste of a bitter tastant, wherein said consumer product comprises:
(a) a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

120. A method of inhibiting a bitter taste receptor comprising:
(a) contacting the bitter taste receptor with a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described herein, or combinations thereof.

121. The method according to paragraph 120, wherein the bitter taste receptor is in the oral cavity of a subject.

122. The method according to paragraph 120, wherein the bitter taste receptor is in the gastrointestinal tract of a subject.

123. The method according to paragraph 120, wherein the bitter taste receptor is present in an in vitro assay.

BRIEF DESCRIPTION OF THE DRAWINGS

FIGS. 2A-E disclose exemplary data for solution and foodstuff taste testing of the compositions comprising compounds of Formula (V) of the present invention.
Solution Testing—The left data point in the solution charts represents the bitterness or metallic taste/impression score of the KCl/potassium lactate standard. The right data point in the solution charts represents the bitterness or metallic taste/impression score of the Test Solution. The concentration of the Test Compound used in each experiment is recited below the chart. In addition, the statistical significance of the Solution Testing data, determined using a paired T-test analysis, is presented wherein "a" represents $p<0.1$; "b" represents $p<0.05$; "c" represents $p<0.01$; and "d" represents $p>0.1$ (data not shown).
Foodstuff Testing—The fraction represents the number of tasters that discerned a decrease in the bitterness or metallic taste/impression of the Test Foodstuff. In addition, the concentration of the Test Compound used in each experiment is recited. Further, the statistical significance of the Foodstuff Testing data, determined using binomial distribution analysis, is presented wherein "a" represents $p<0.1$; "b" represents $p<0.05$; "c" represents $p<0.01$; and "d" represents $p>0.1$ (data not shown).
"--" denotes that the solution or foodstuff was not tested.

FIGS. 3A-I disclose exemplary data for solution and foodstuff taste testing of the compositions comprising compounds of Formula (VIII) of the present invention. Solution Testing—The left data point in the solution charts represents the bitterness or metallic taste/impression score of the KCl/potassium lactate standard. The right data point in the solution charts represents the bitterness or metallic taste/impression score of the Test Solution. The concentration of the Test Compound used in each experiment is recited below the chart. In addition, the statistical significance of the Solution Testing data, determined using a paired T-test analysis, is presented wherein "a" represents $p<0.1$; "b" represents $p<0.05$; "c" represents $p<0.01$; and "d" represents $p>0.1$ (data not shown).

Foodstuff Testing—The fraction represents the number of tasters that discerned a decrease in the bitterness or metallic taste/impression of the Test Foodstuff. In addition, the concentration of the Test Compound used in each experiment is recited. Further, the statistical significance of the Foodstuff Testing data, determined using binomial distribution analysis, is presented wherein "a" represents $p<0.1$; "b" represents $p<0.05$; "c" represents $p<0.01$; and "d" represents $p>0.1$ (data not shown).

"--" denotes that the solution or foodstuff was not tested.

Figure 1A:
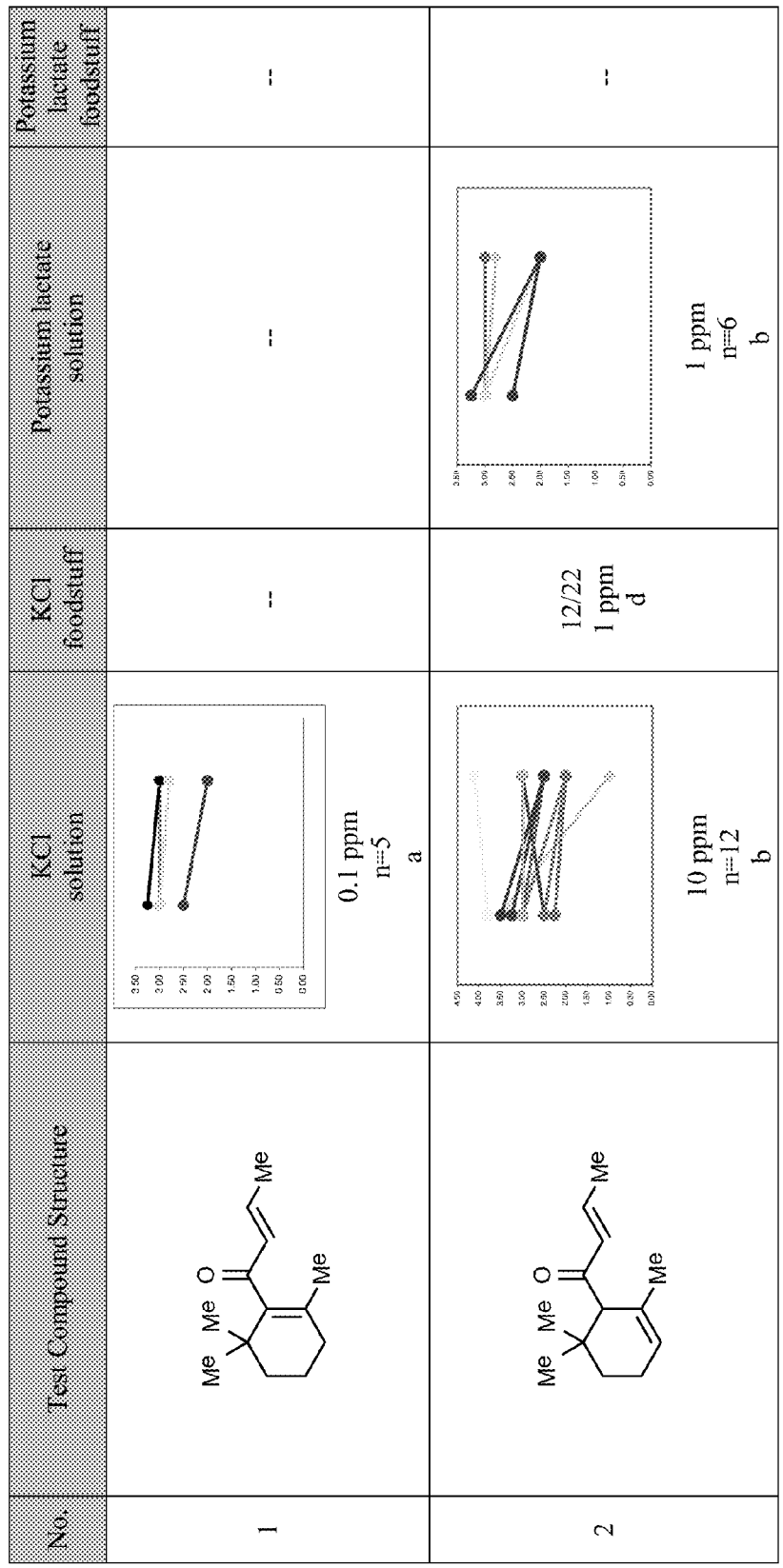
FIGS. 1A-Q disclose exemplary data for solution and foodstuff taste testing of the compositions comprising compounds of Formula (I) of the present invention.
Solution Testing—The left data point in the solution charts represents the bitterness or metallic taste/impression score of the KCl/potassium lactate standard. The right data point in the solution charts represents the bitterness or metallic taste/impression score of the Test Solution. The concentration of the Test Compound used in each experiment is recited below the chart. In addition, the statistical significance of the Solution Testing data, determined using a paired T-test analysis, is presented wherein "a" represents $p<0.1$; "b" represents $p<0.05$; "c" represents $p<0.01$; and "d" represents $p>0.1$ (data not shown).
Foodstuff Testing—The fraction represents the number of tasters that discerned a decrease in the bitterness or metallic taste/impression of the Test Foodstuff. In addition, the concentration of the Test Compound used in each experiment is recited. Further, the statistical significance of the Foodstuff Testing data, determined using binomial distribution analysis, is presented wherein "a" represents $p<0.1$; "b" represents $p<0.05$; "c" represents $p<0.01$; and "d" represents $p>0.1$ (data not shown).
"--" denotes that the solution or foodstuff was not tested.
Figure 1B:
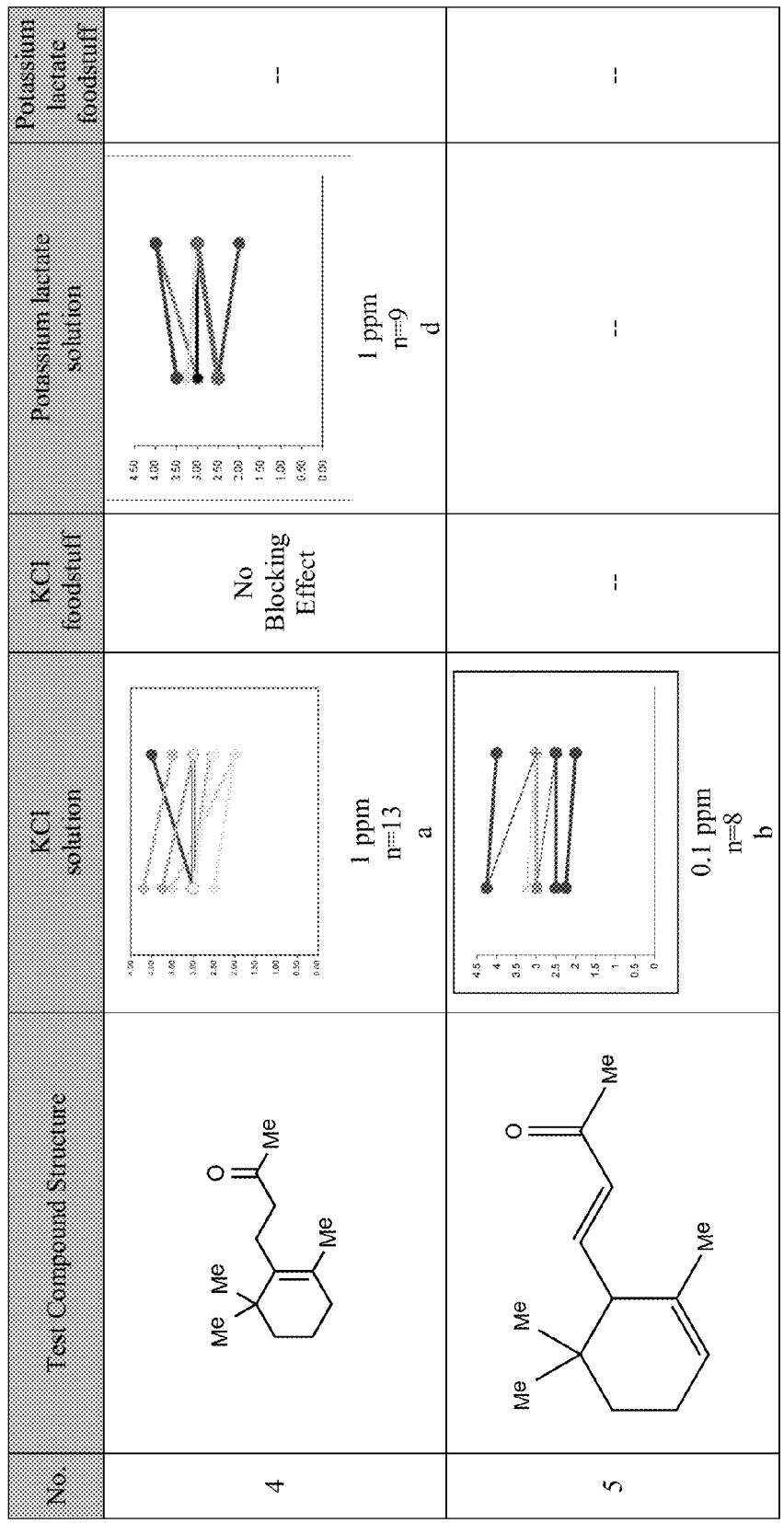
Figure 1C:
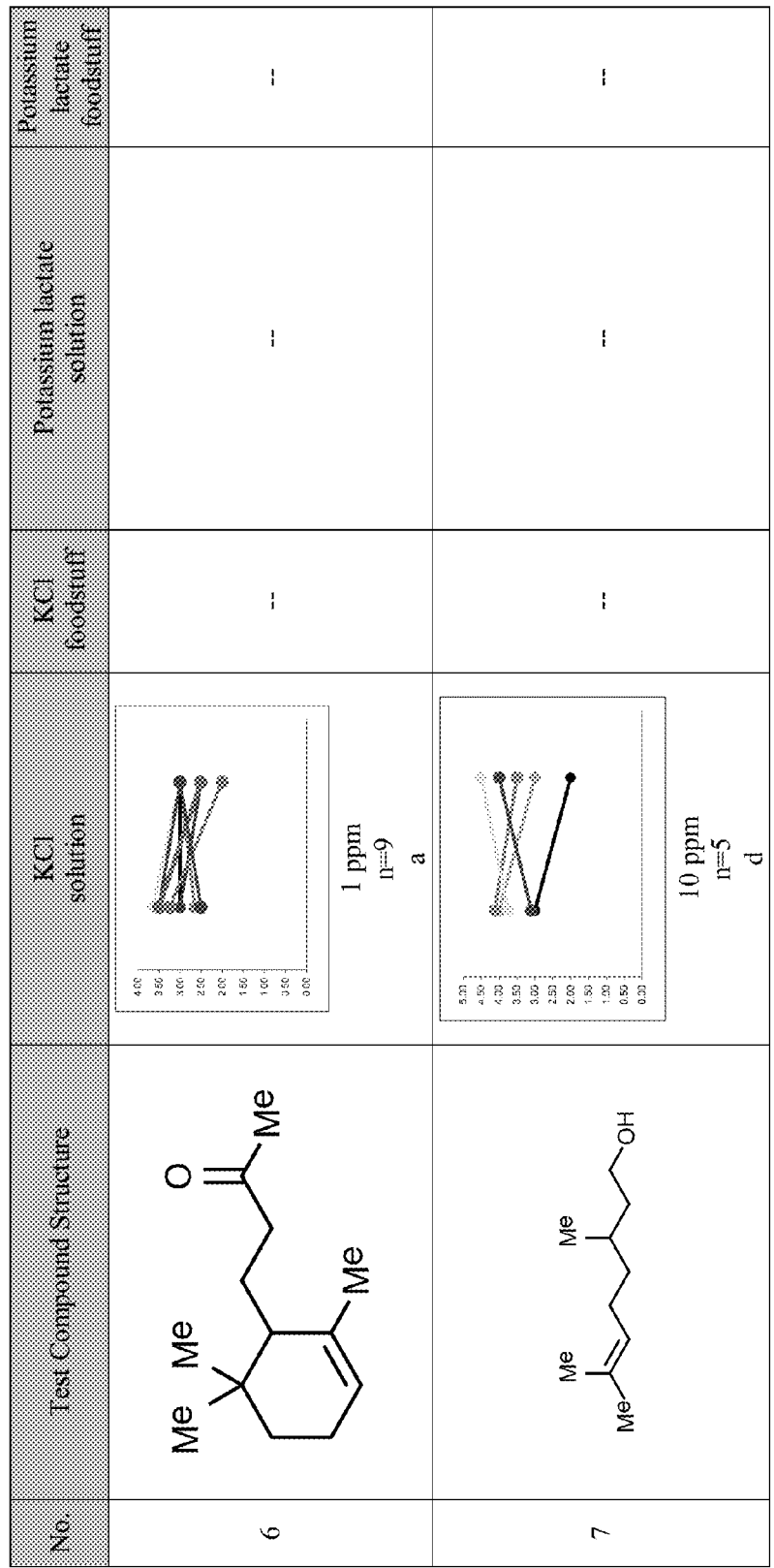
Figure 1D:
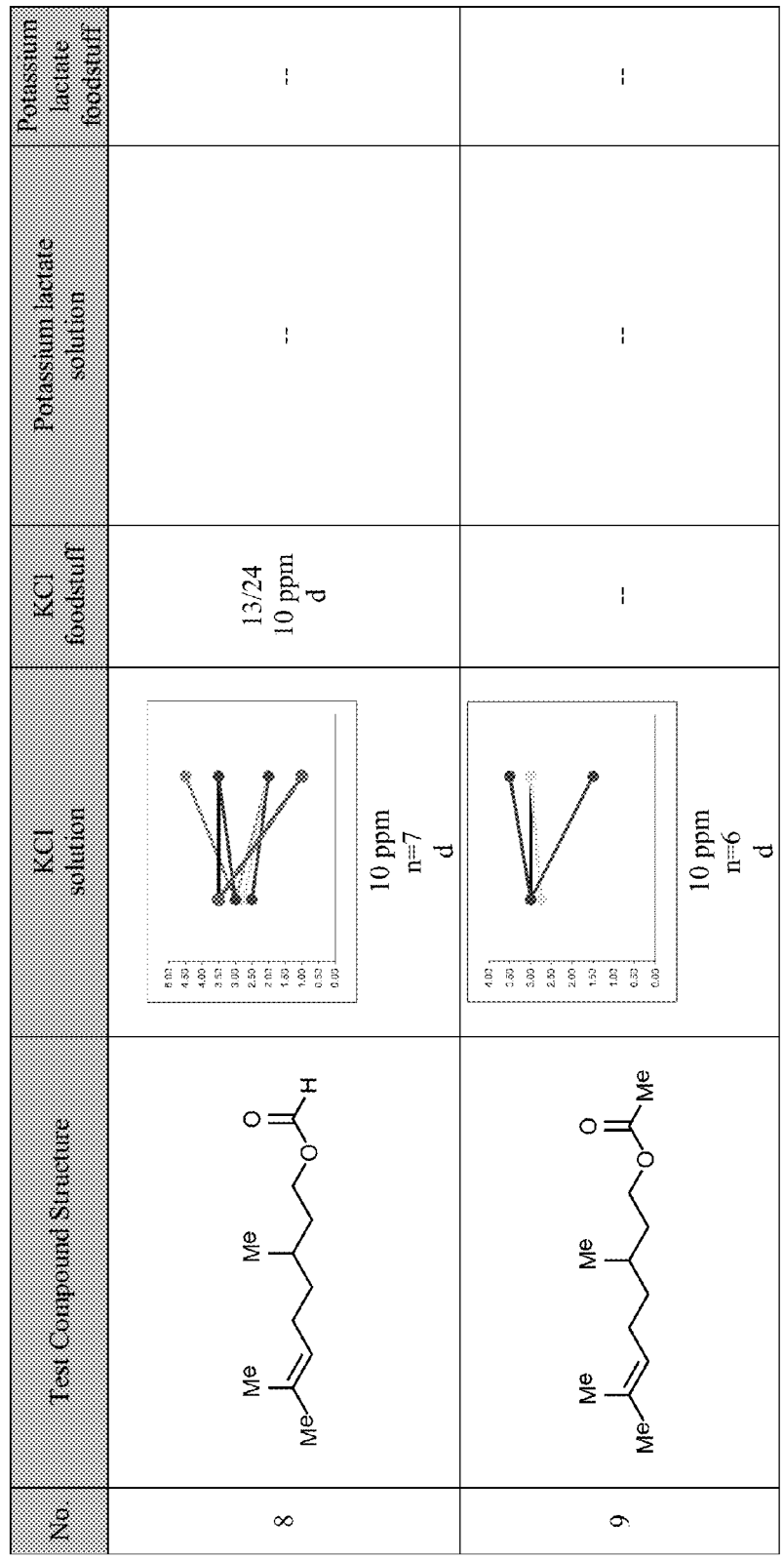
Figure 1F:
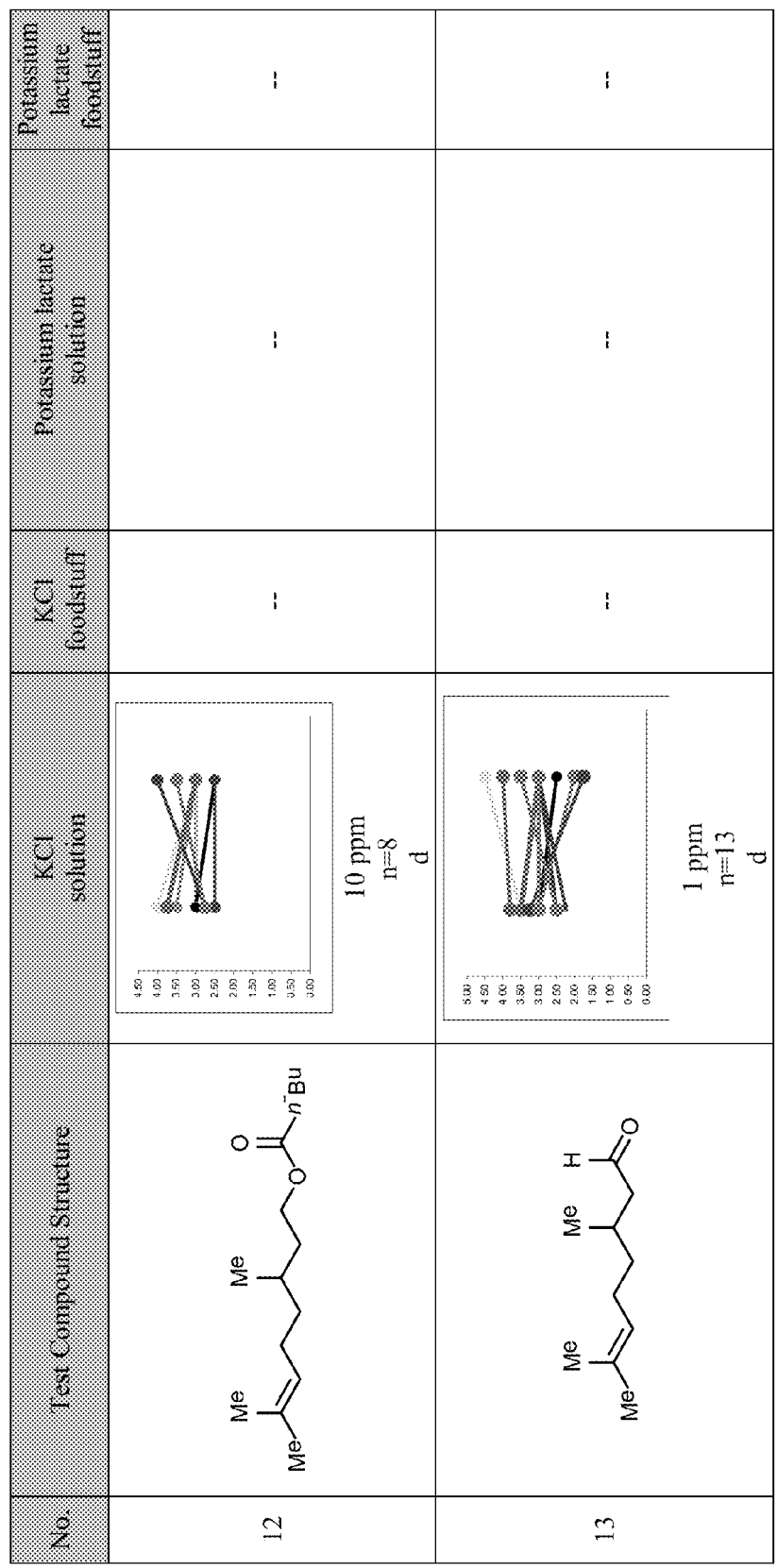
Figure 1I:
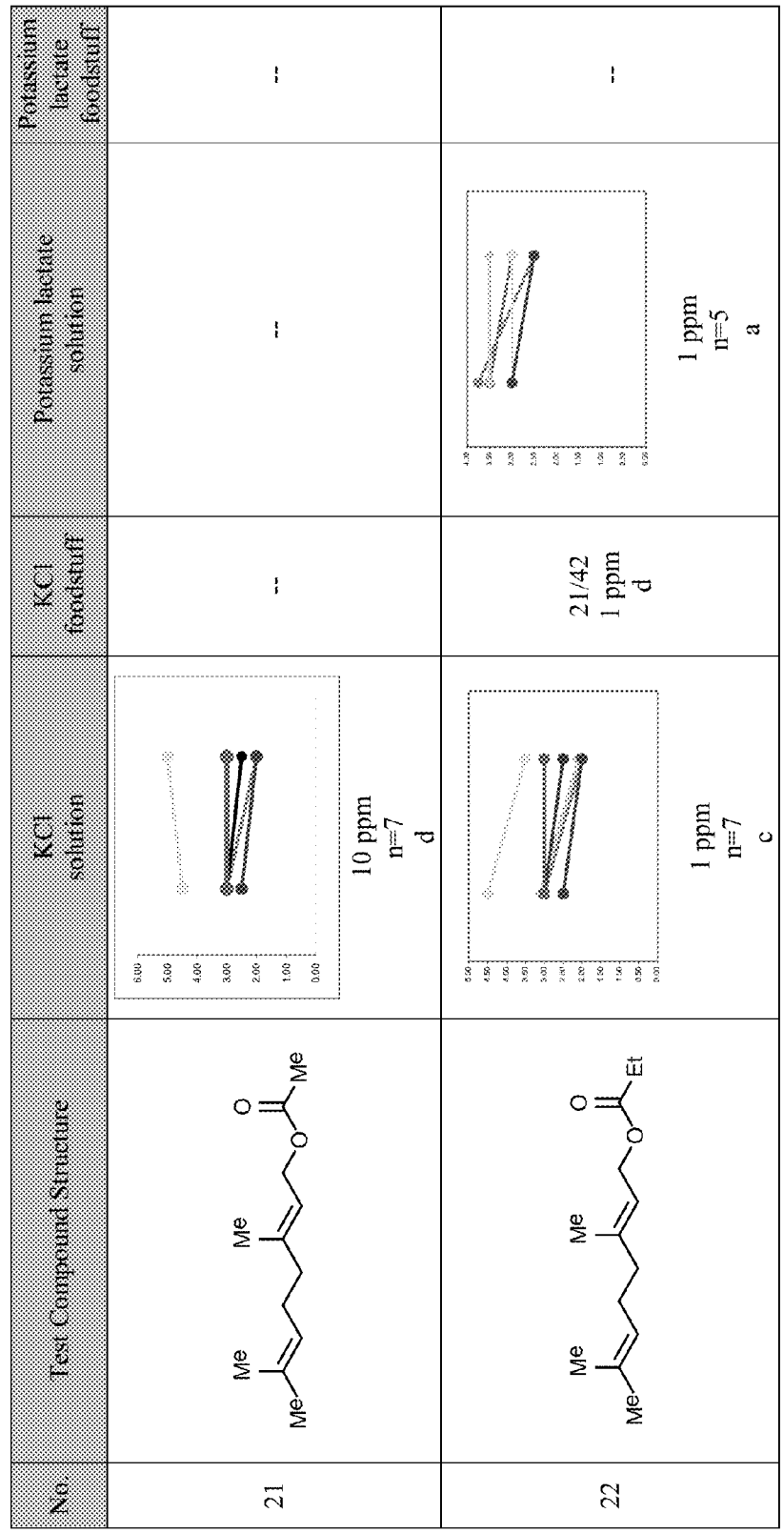
Figure 1J:
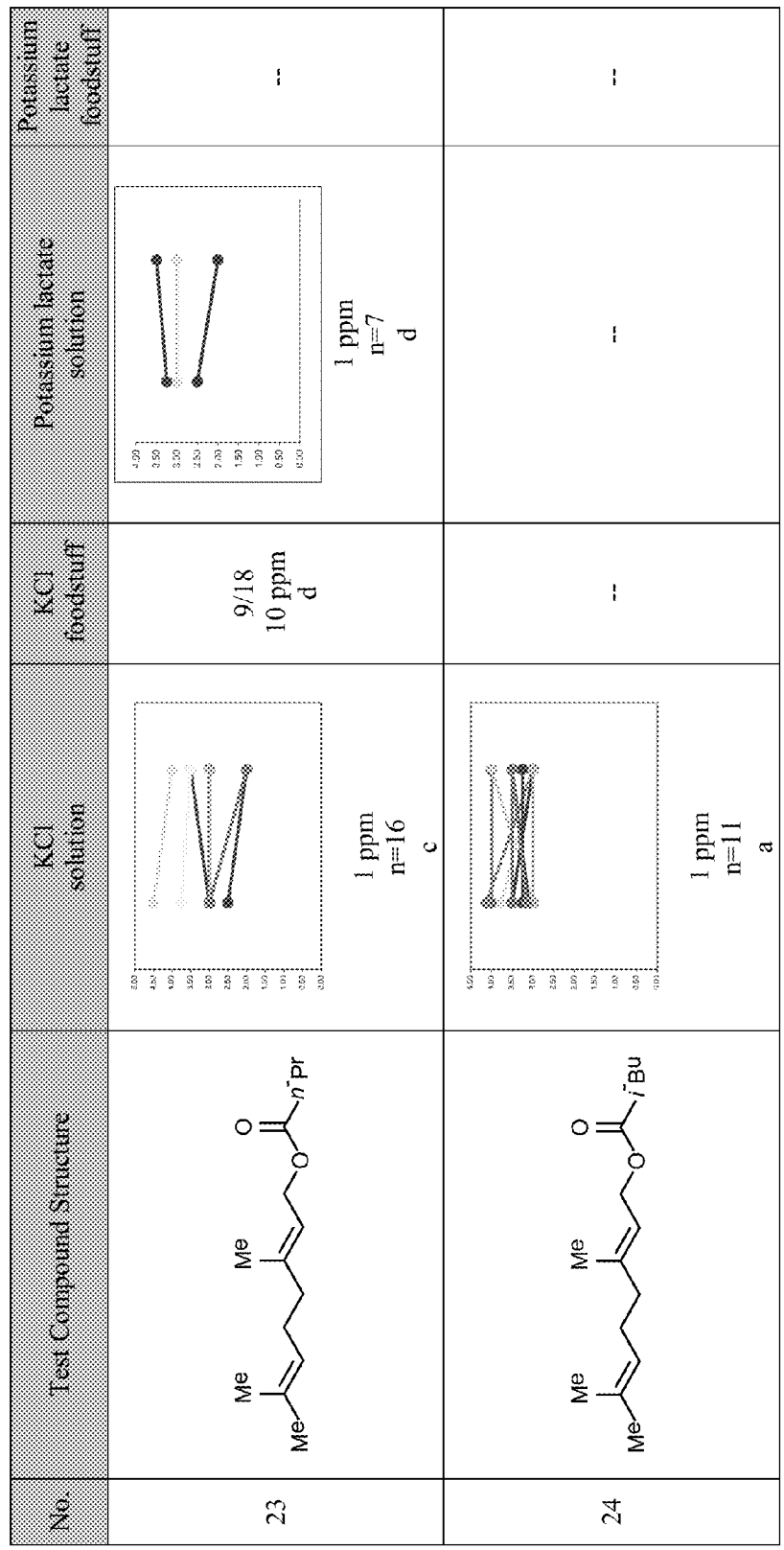
Figure 1L:
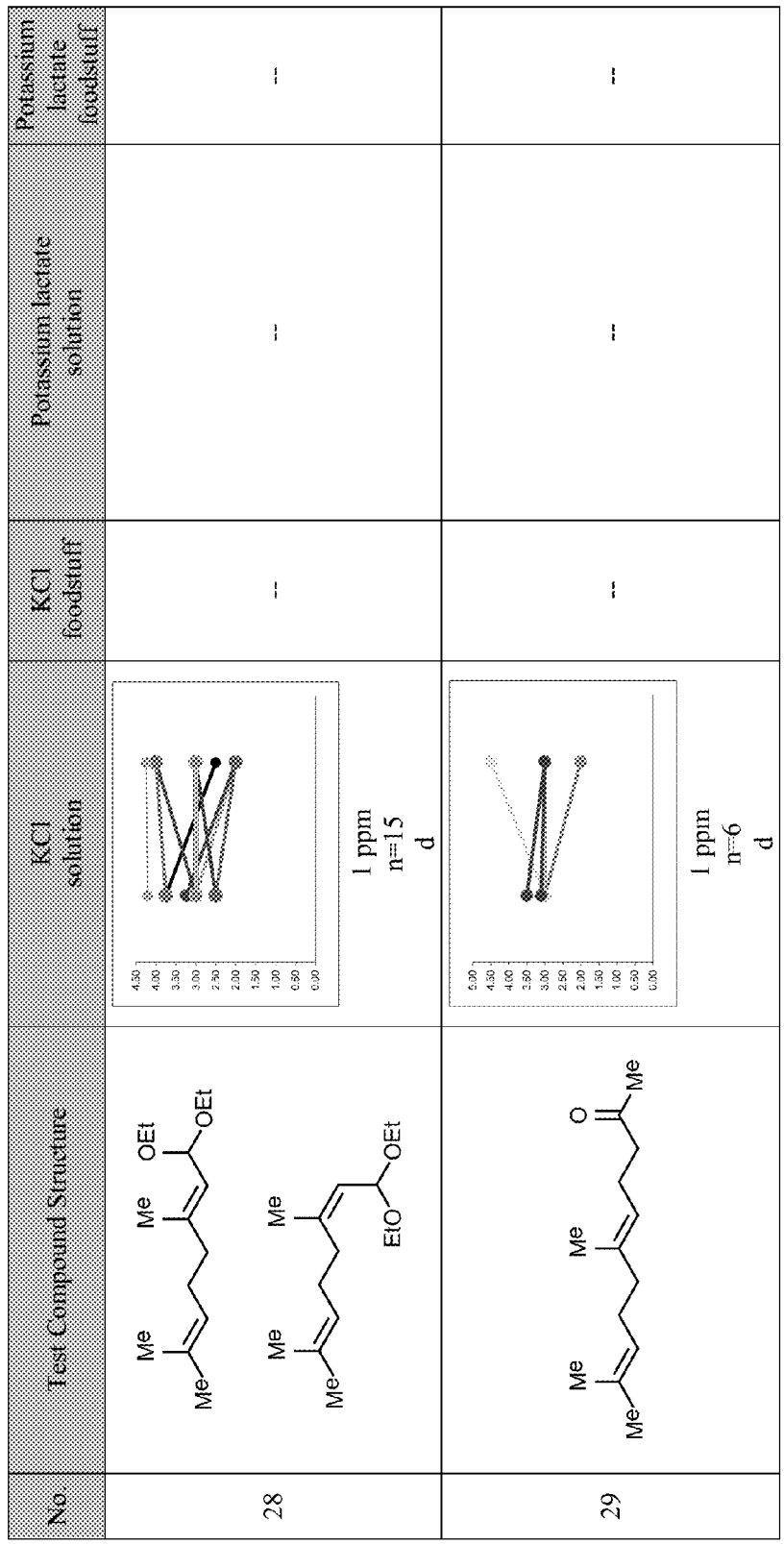
Figure 1Q:
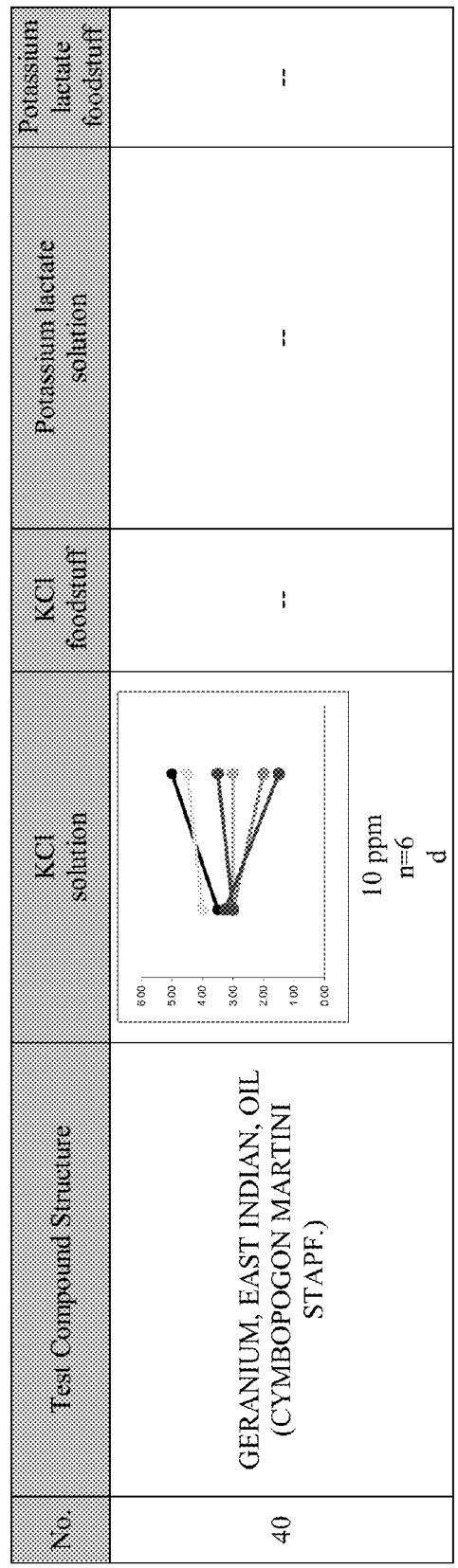
Figure 2B:
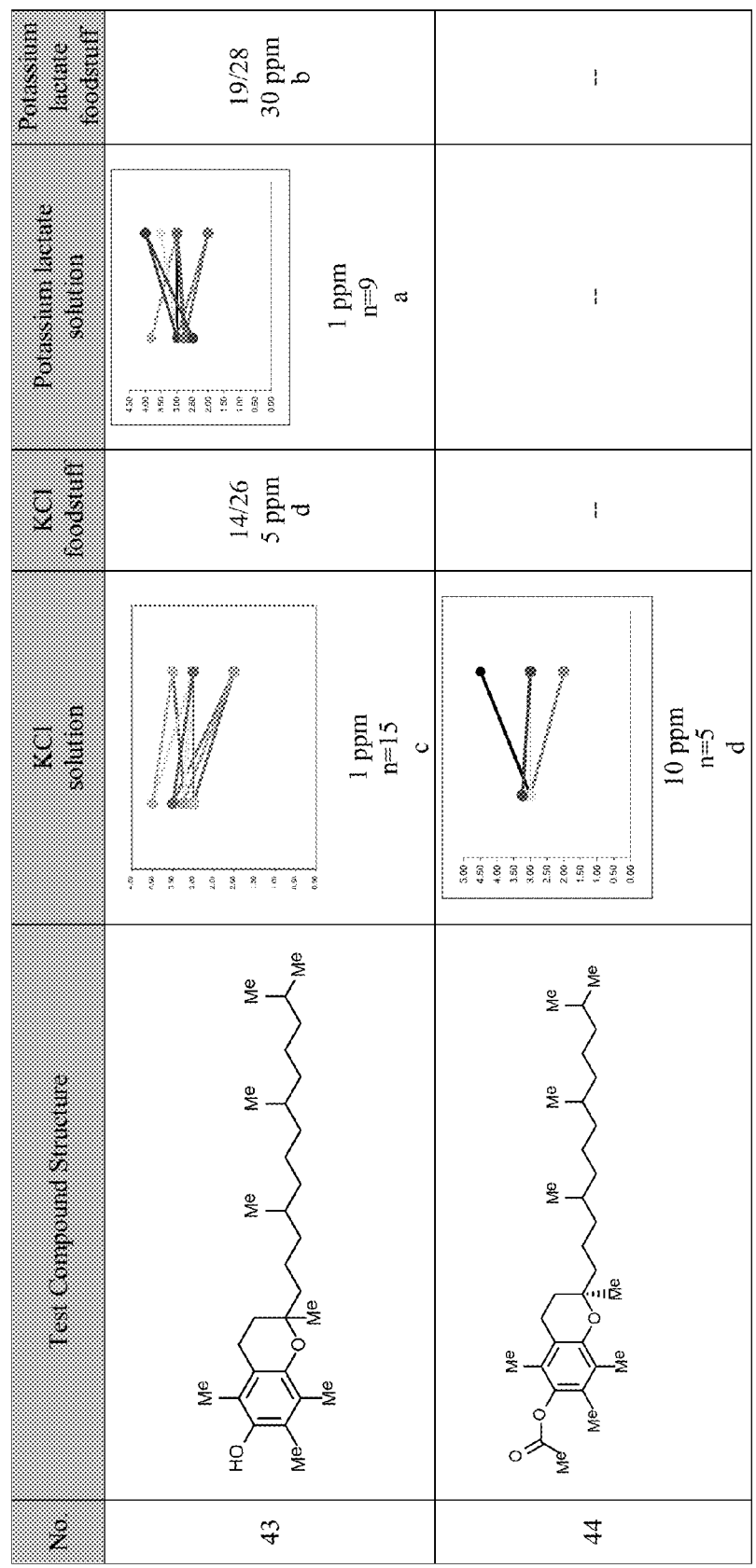
Figure 2D:
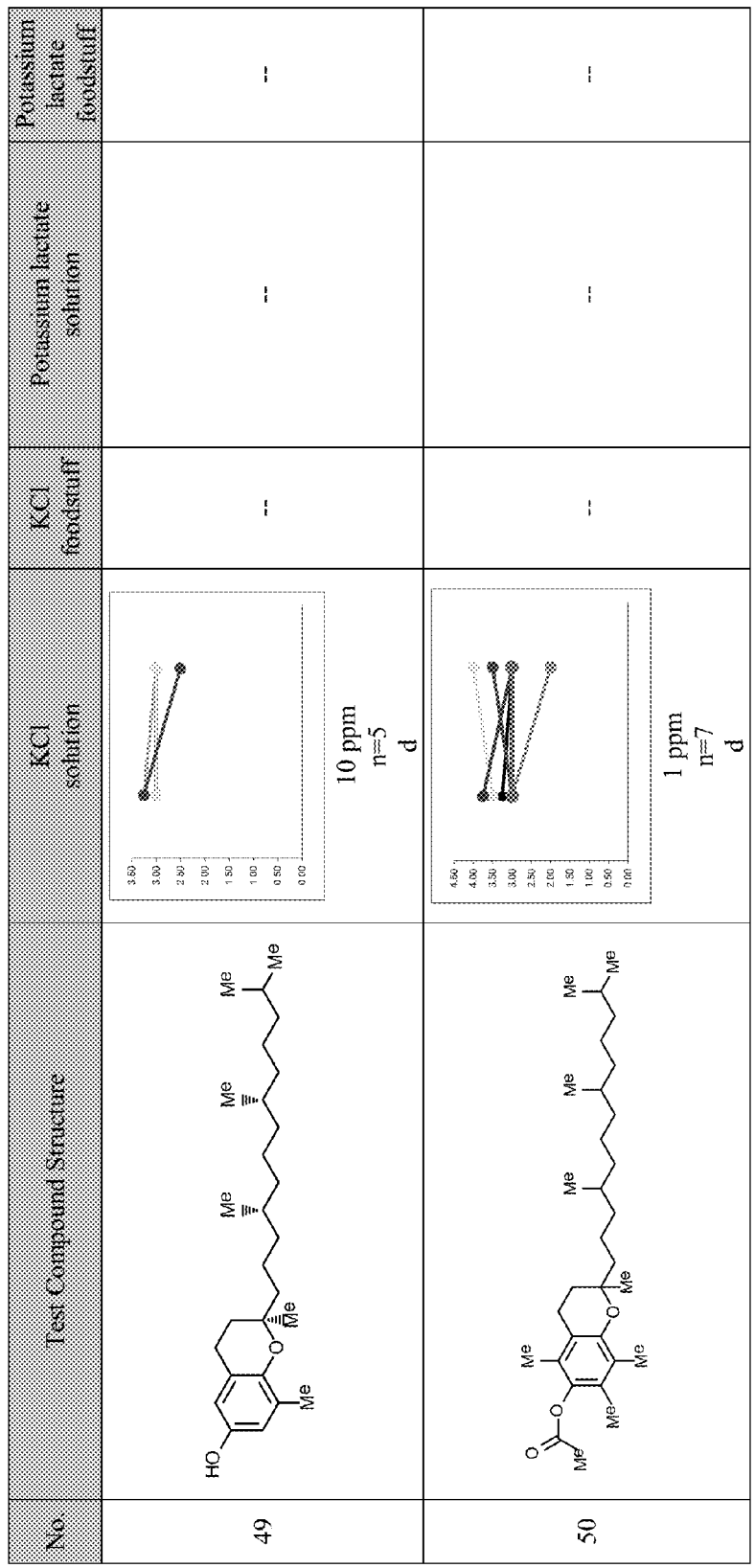
Figure 2E:
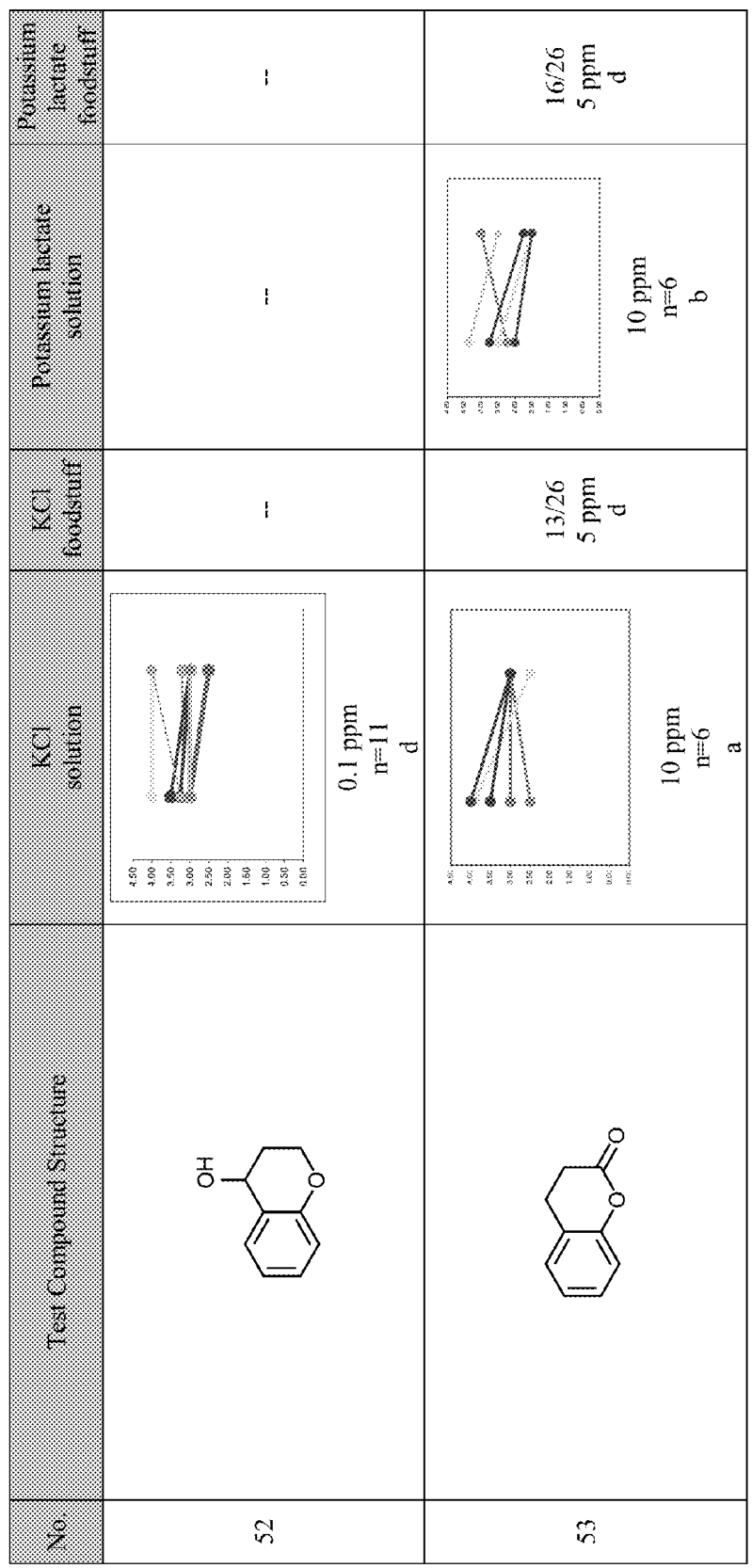
Figure 3A:
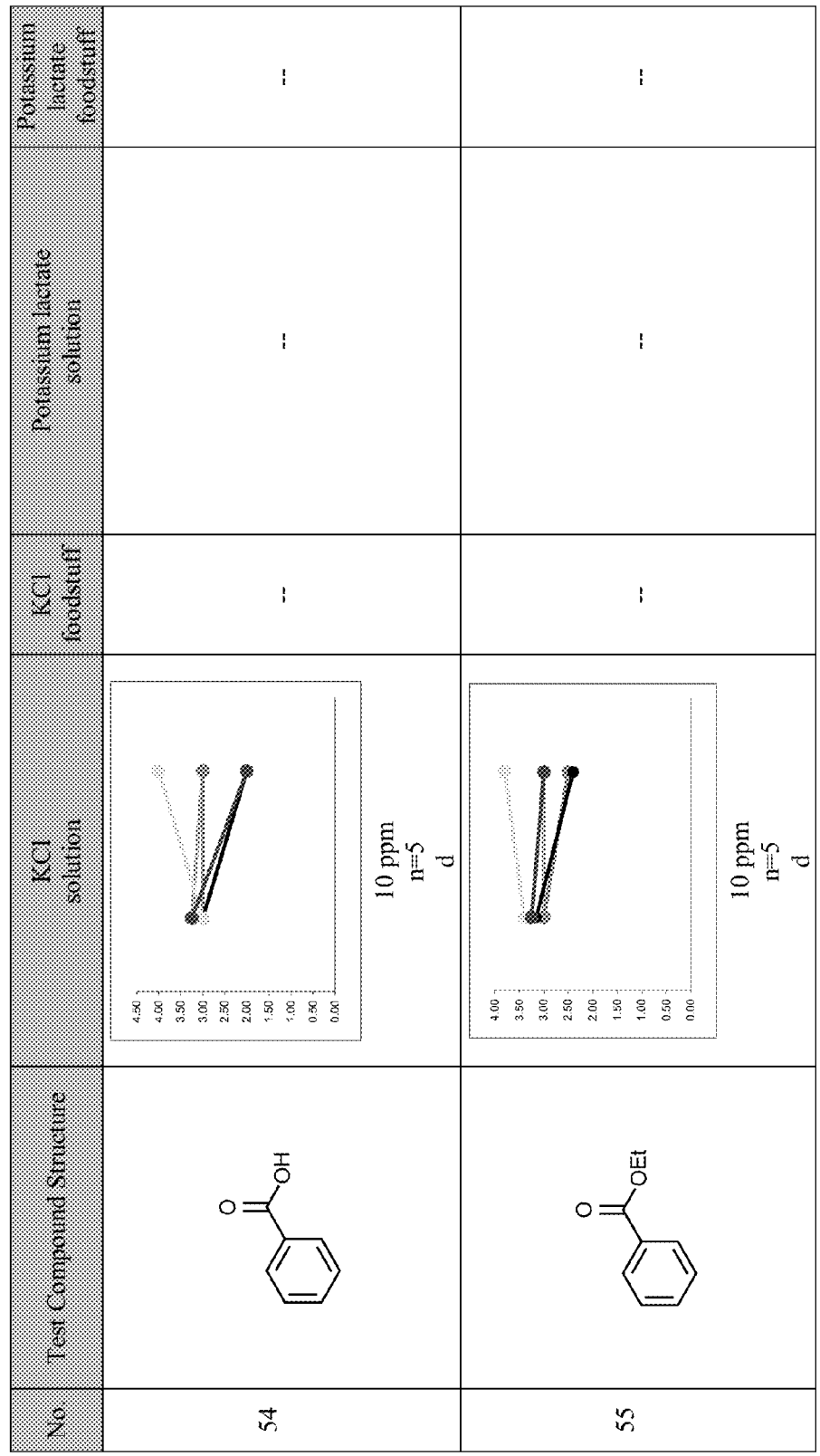
Figure 3B:
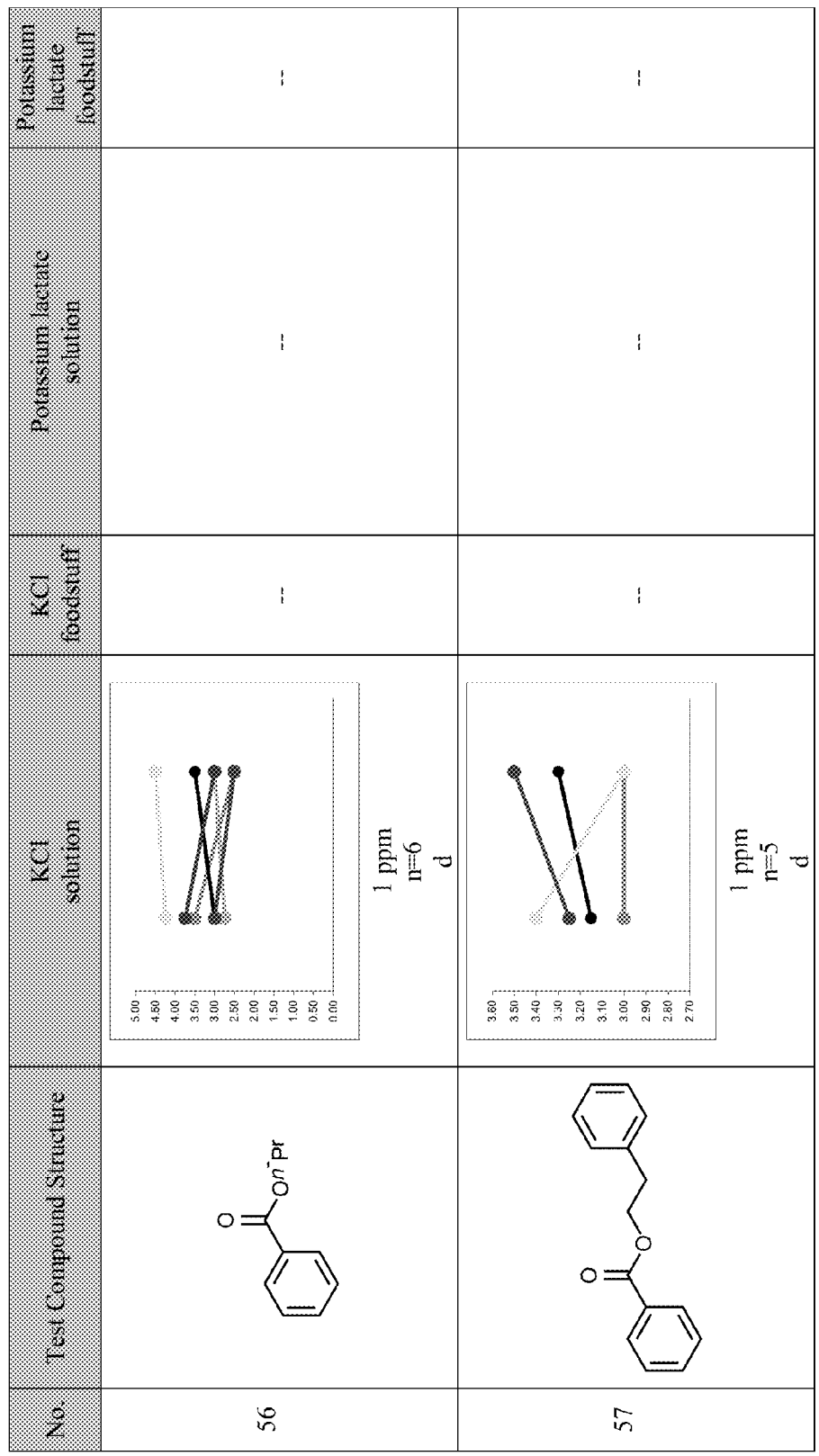
Figure 3C:
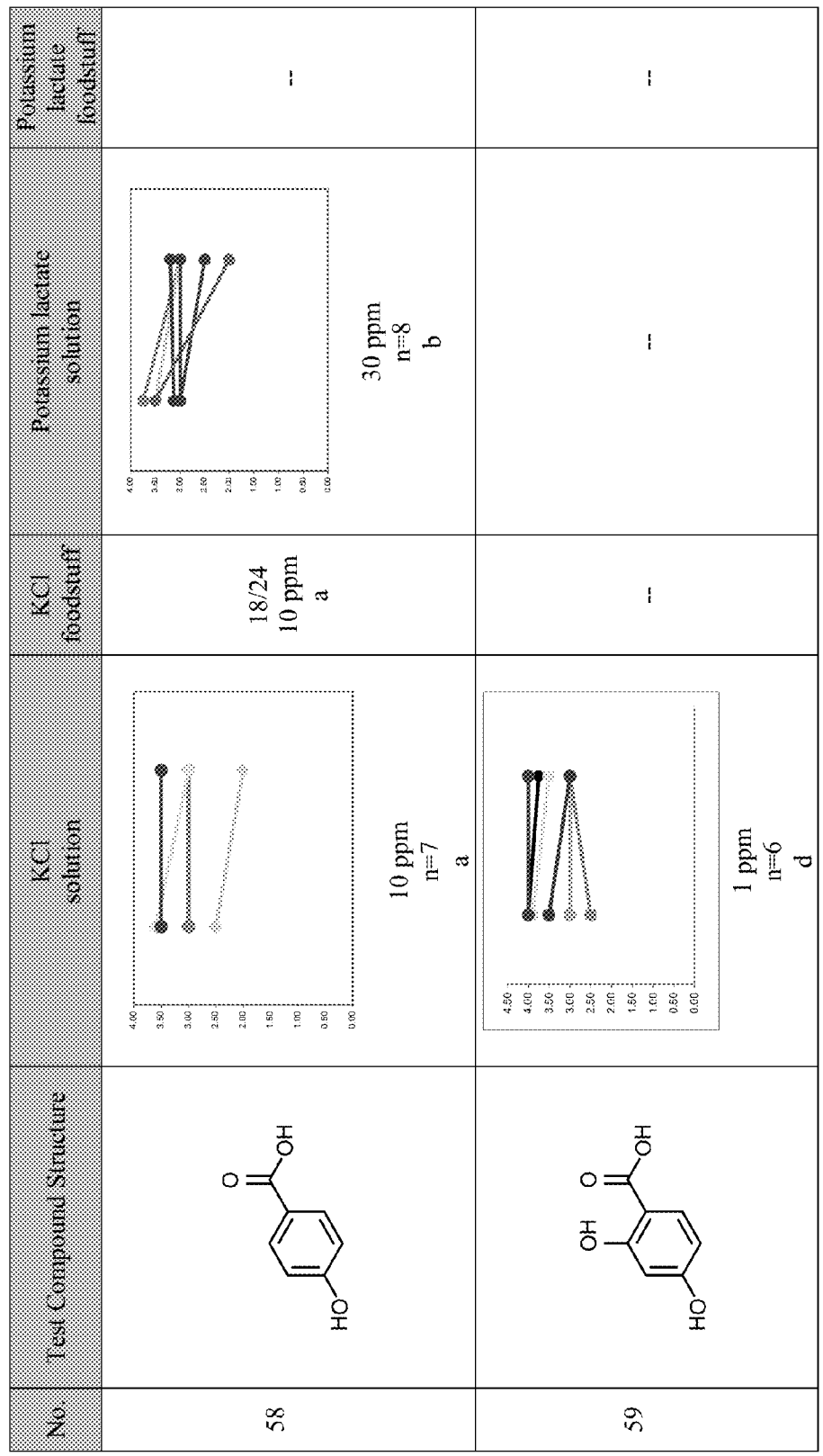
Figure 3E:
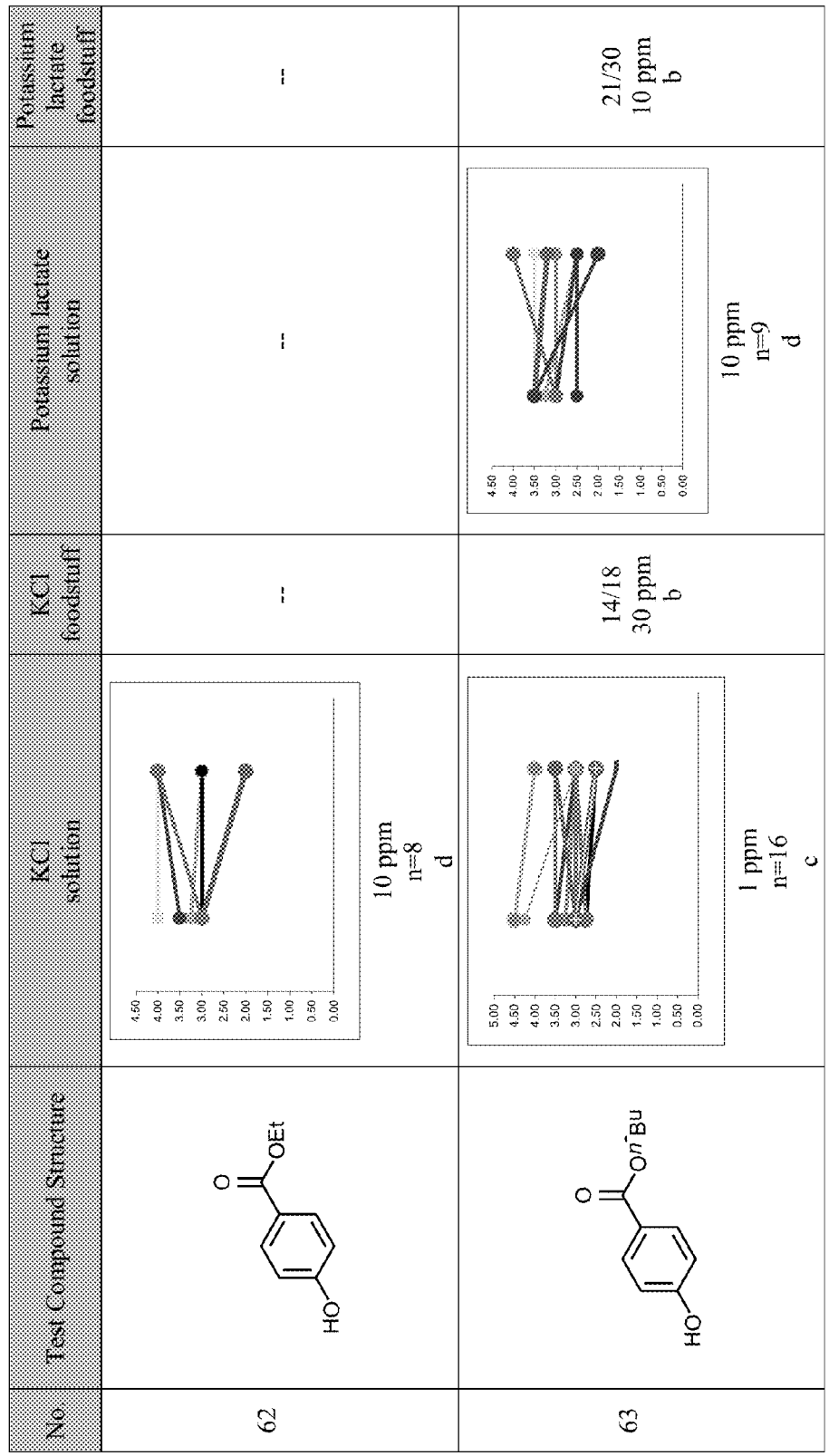
Figure 3F:
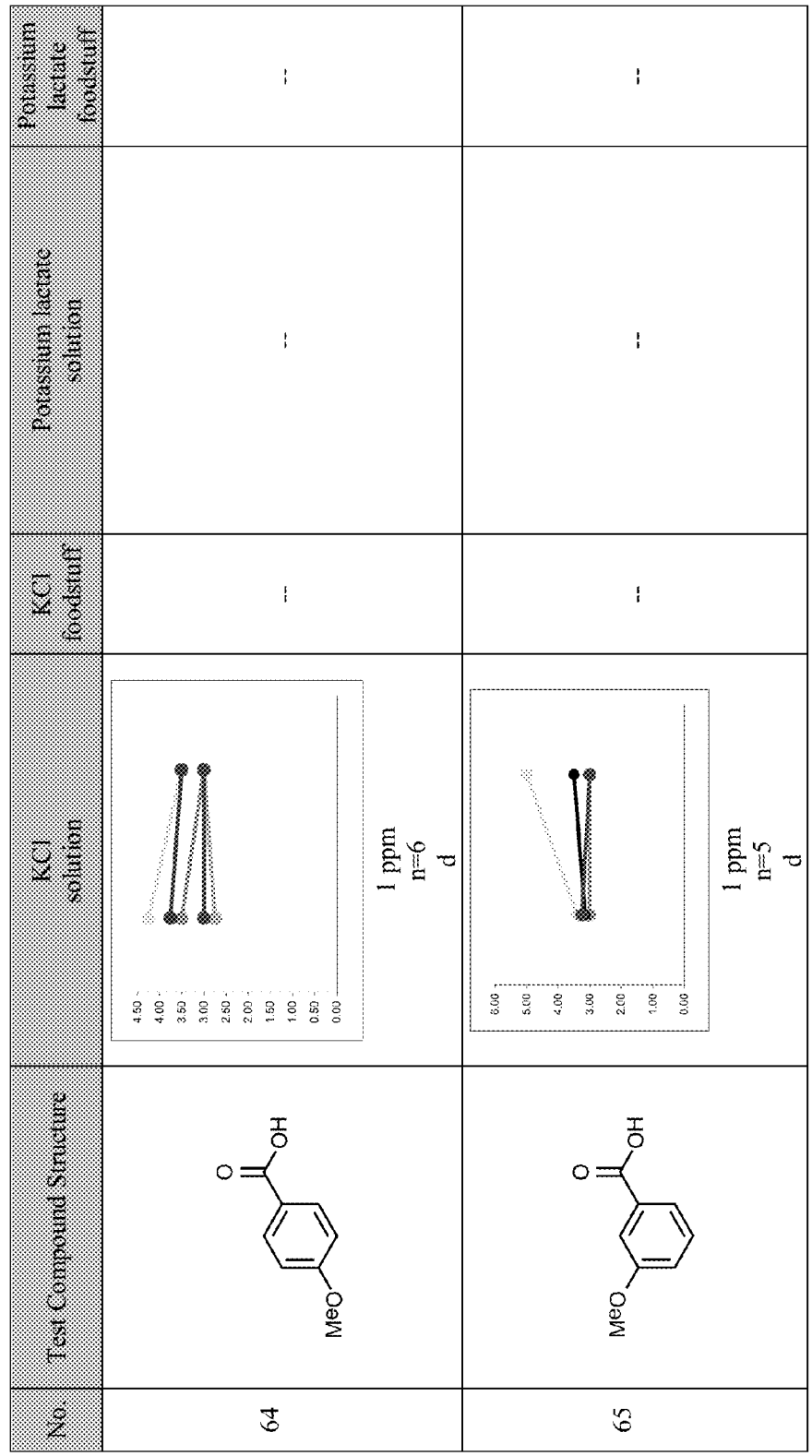
Figure 3G:
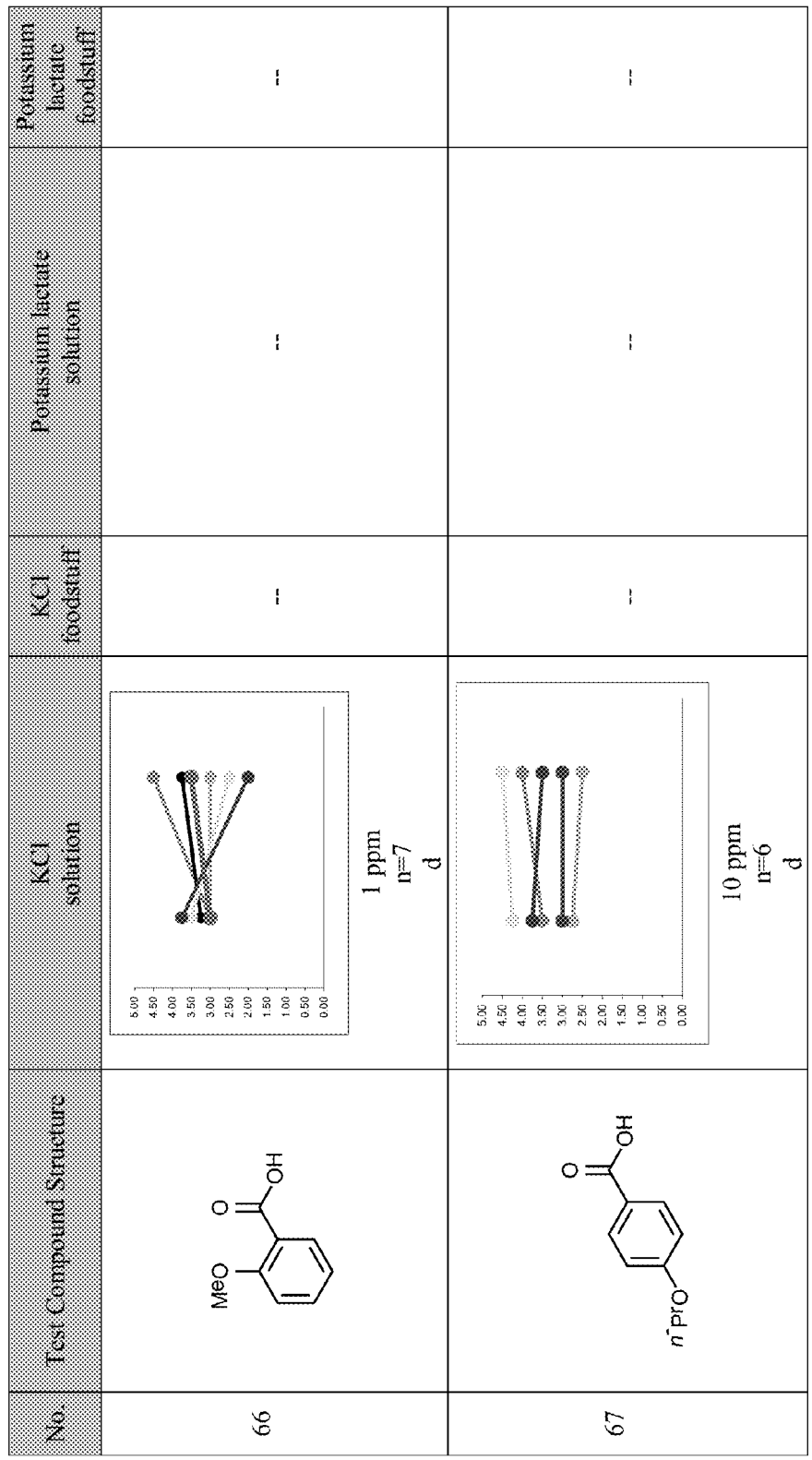
Figure 3H:
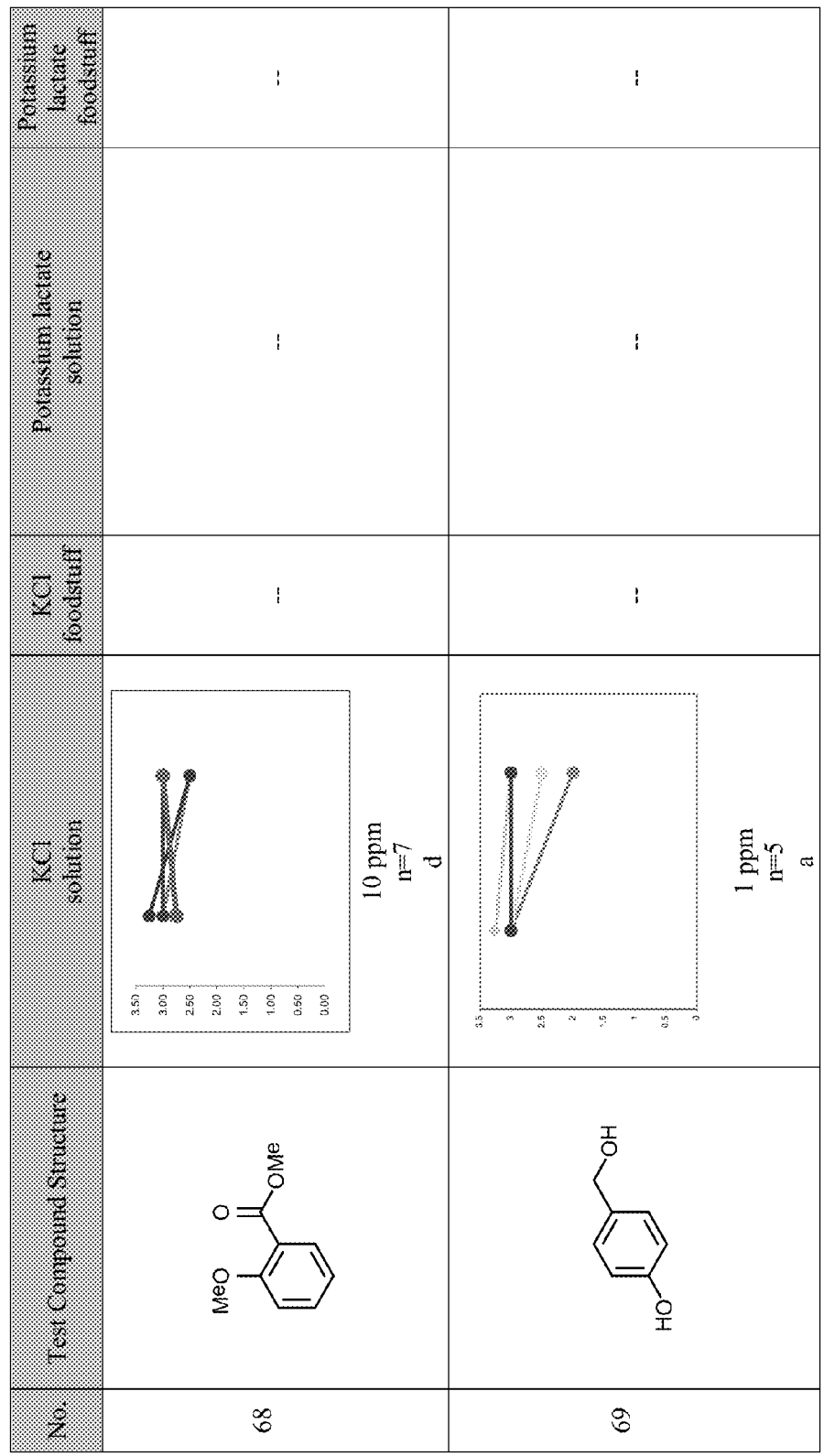
Figure 3I:
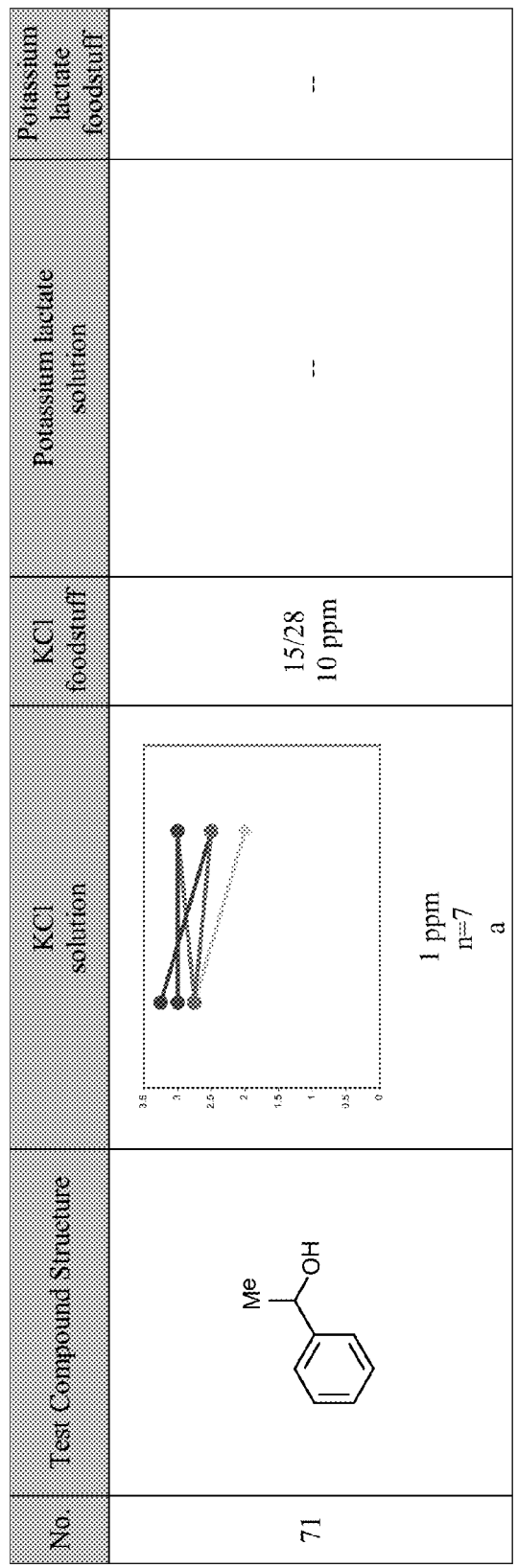
Figure 4D:
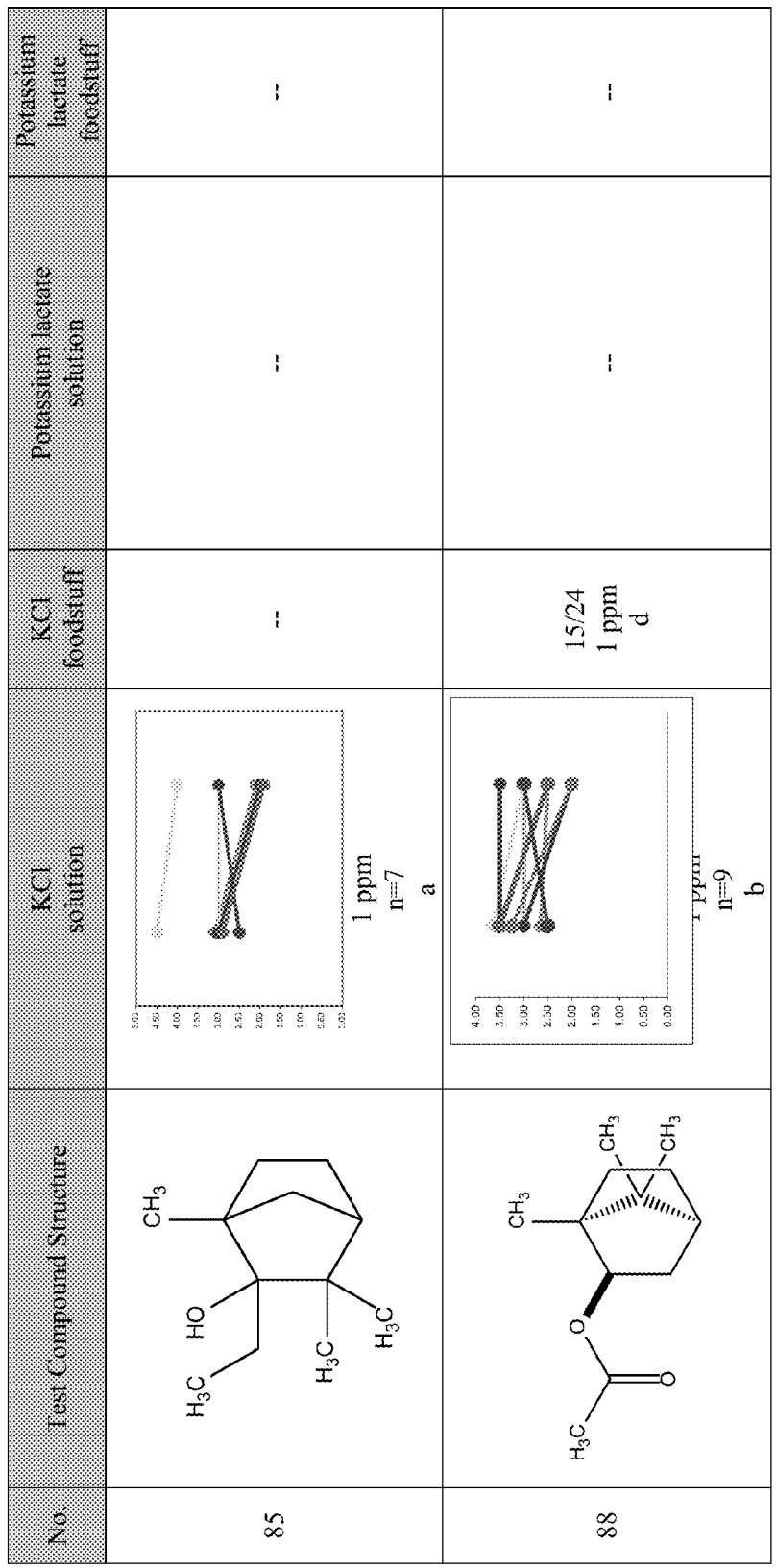
Figure 4E:
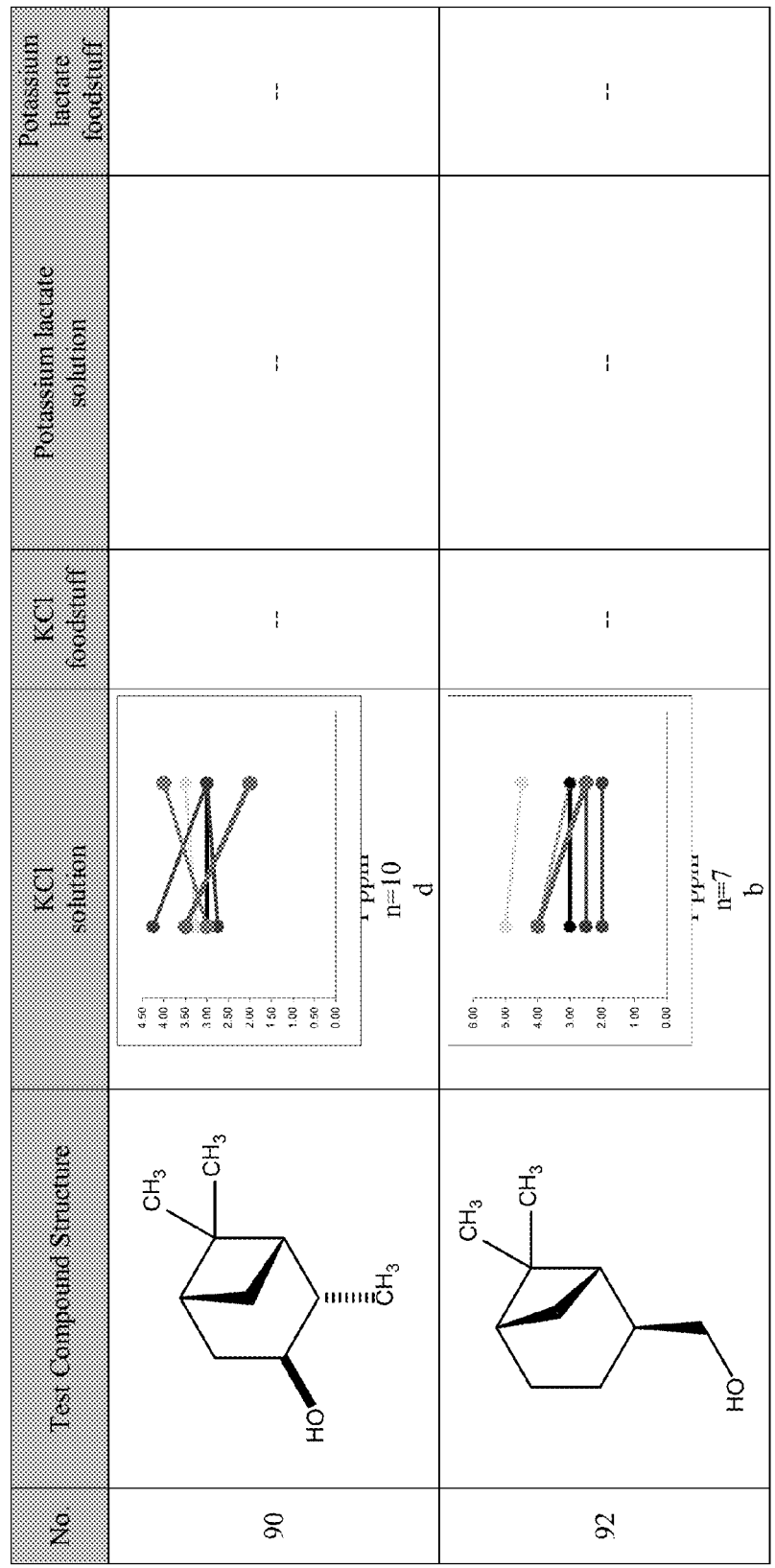
Figure 4G:
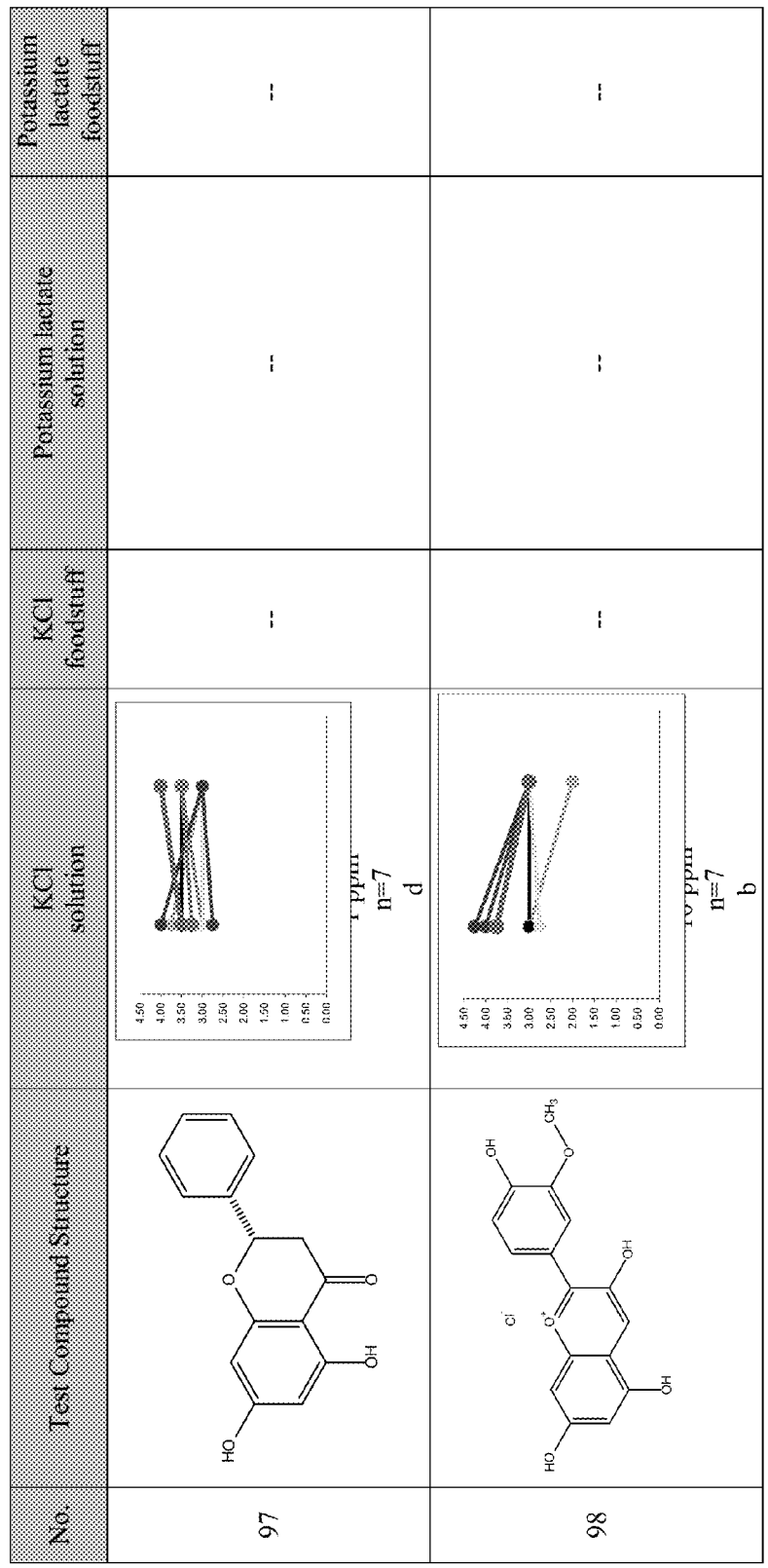
Figure 4H:
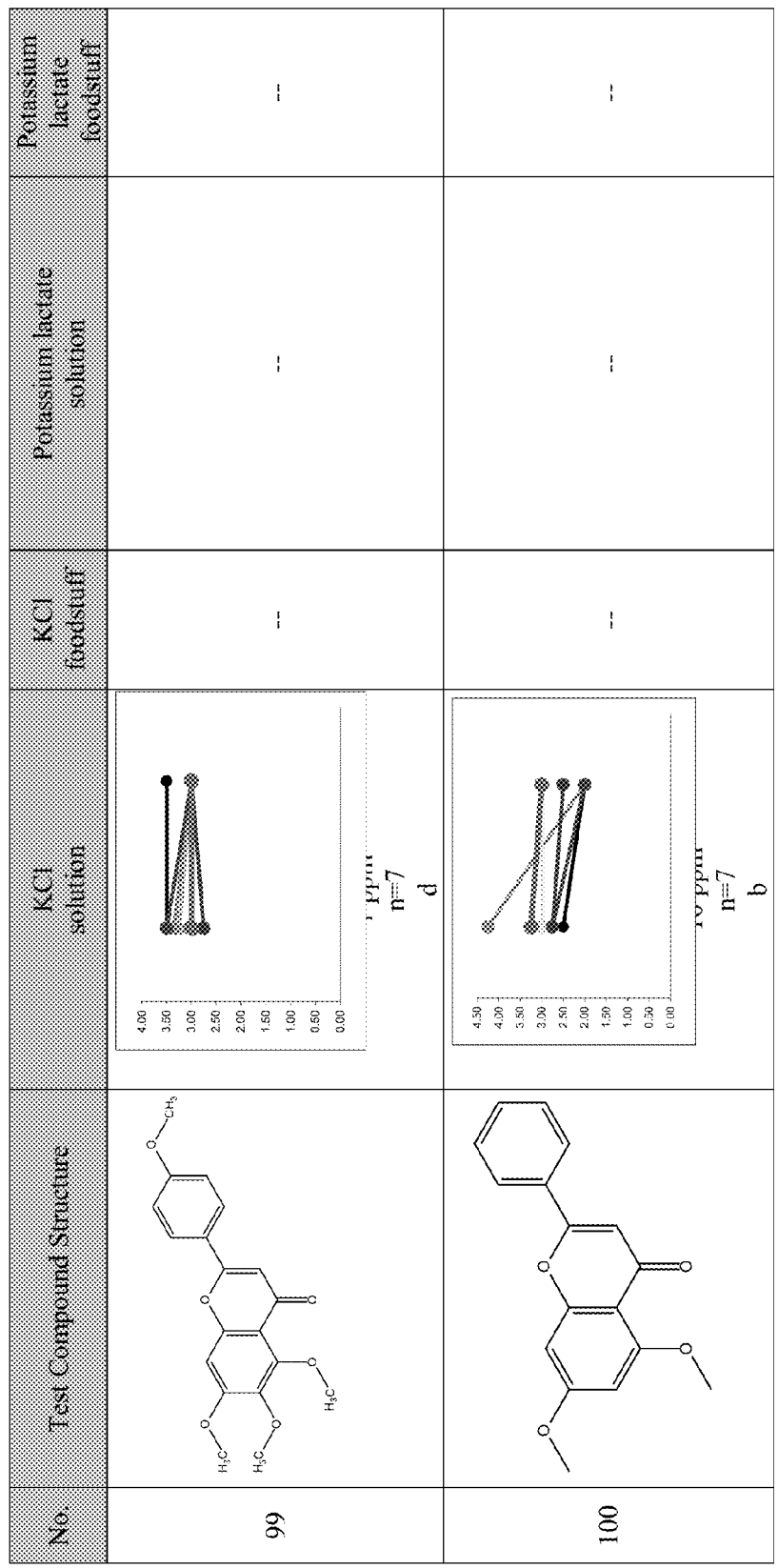
Figure 4I:
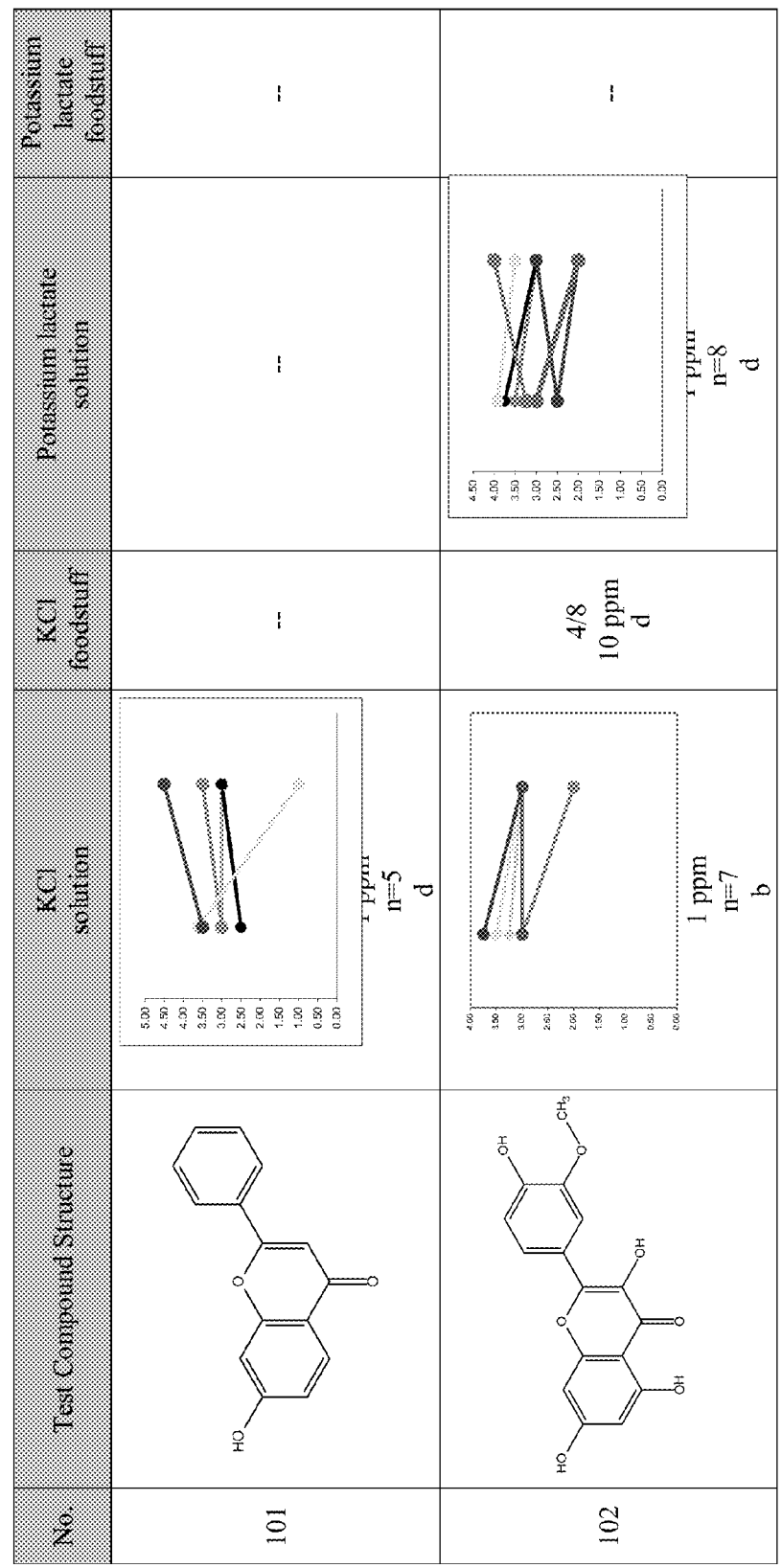
Figure 4J:
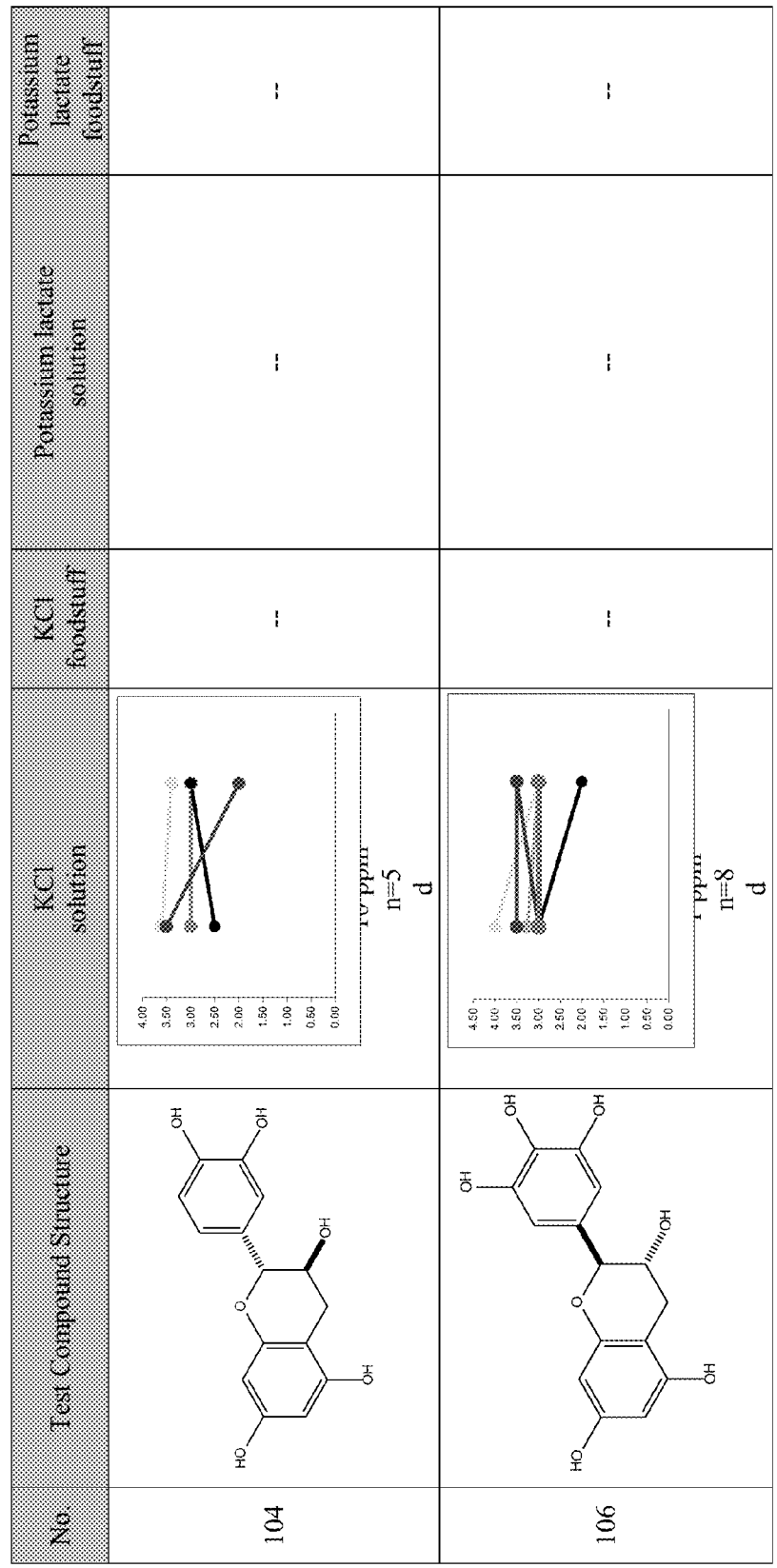
Figure 4P:
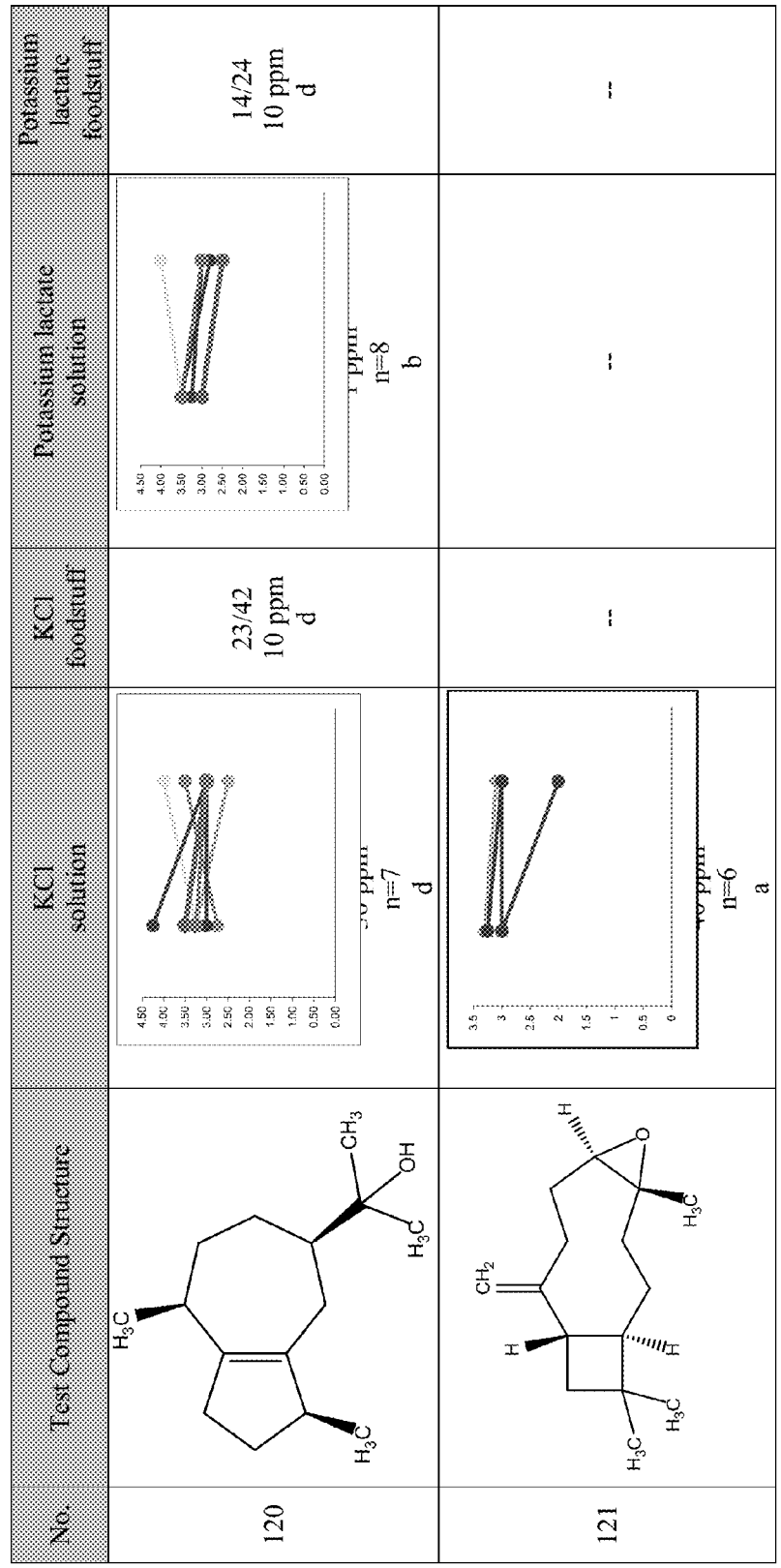
Figure 4S:
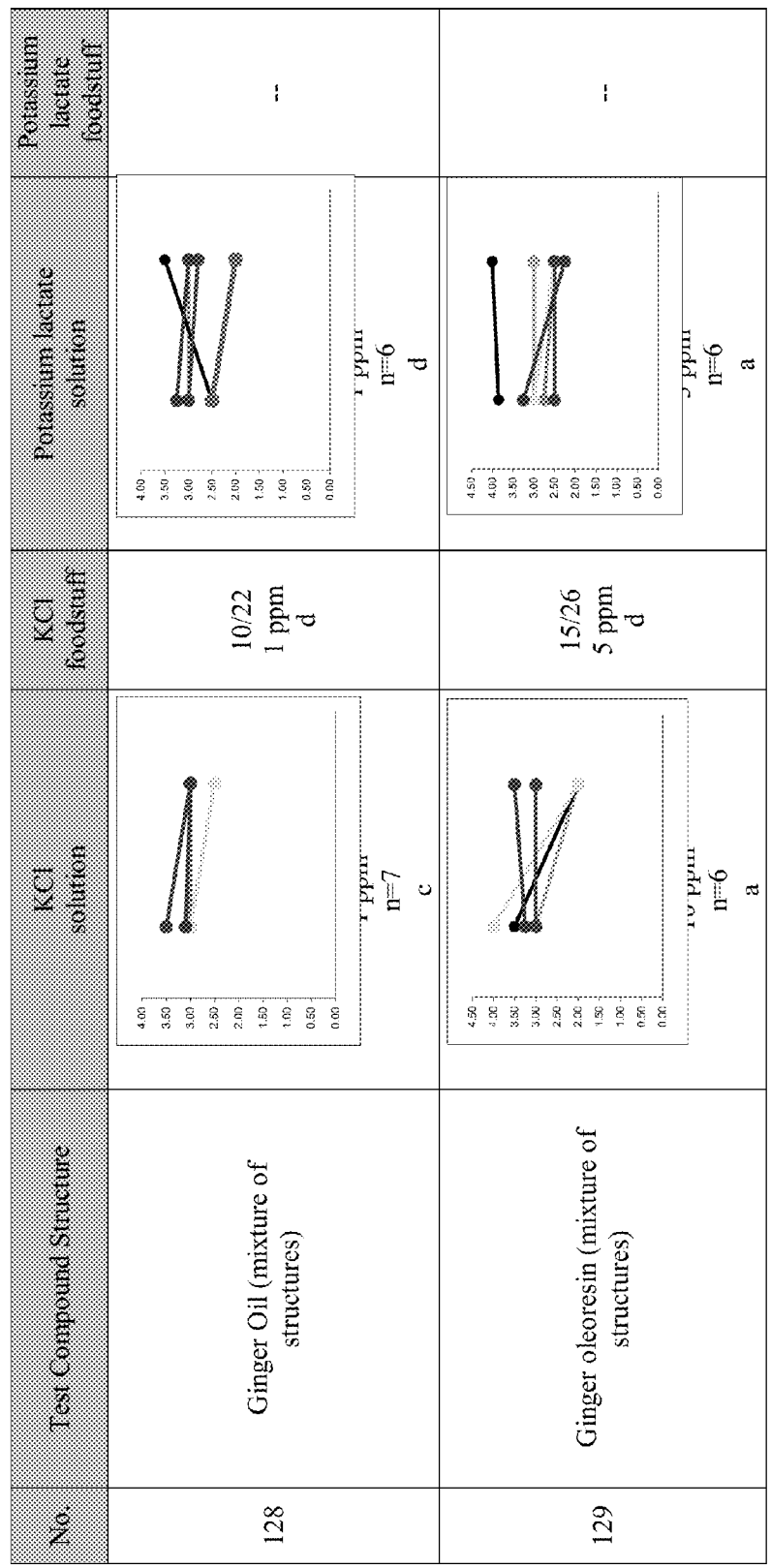
Figure 4U:
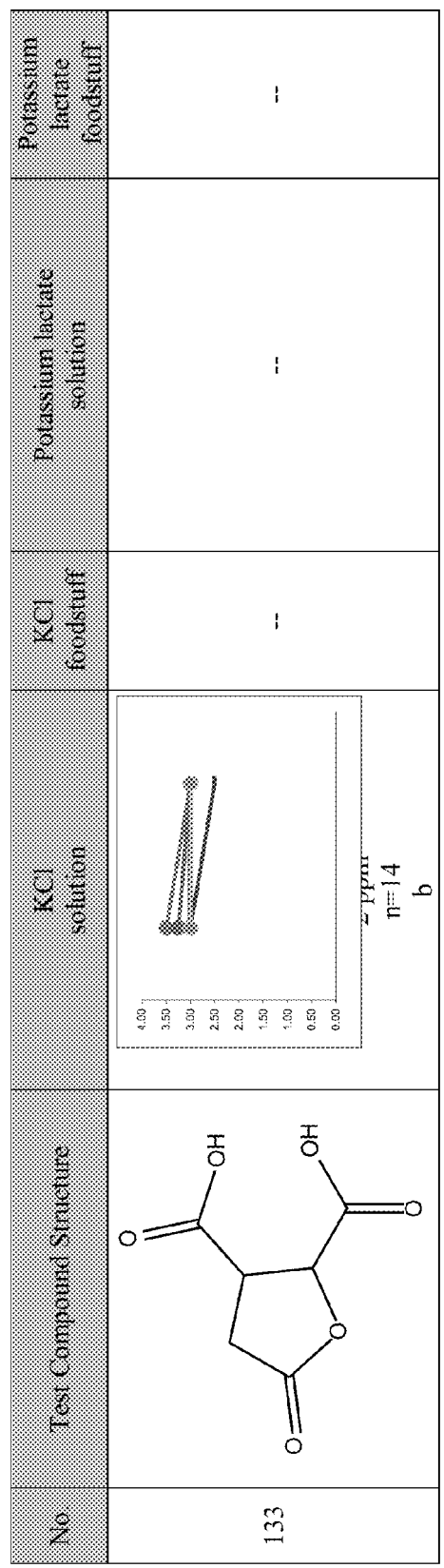

FIG. 4A-U disclose exemplary data for solution and foodstuff taste testing of the compositions comprising compounds of Formula (XI), Formula (XII), and compounds 95-134 of the present invention. Solution Testing—The left data point in the solution charts represents the bitterness or metallic taste/impression score of the KCl/potassium lactate standard. The right data point in the solution charts represents the bitterness or metallic taste/impression score of the Test Solution. The concentration of the Test Compound used in each experiment is recited below the chart. In addition, the statistical significance of the Solution Testing data, determined using a paired T-test analysis, is presented wherein "a" represents $p<0.1$; "b" represents $p<0.05$; "c" represents $p<0.01$; and "d" represents $p>0.1$ (data not shown).

Foodstuff Testing—The fraction represents the number of tasters that discerned a decrease in the bitterness or metallic taste/impression of the Test Foodstuff. In addition, the concentration of the Test Compound used in each experiment is recited. Further, the statistical significance of the Foodstuff Testing data, determined using binomial distribution analysis, is presented wherein "a" represents $p<0.1$; "b" represents $p<0.05$; "c" represents $p<0.01$; and "d" represents $p>0.1$ (data not shown).

"--" denotes that the solution or foodstuff was not tested.

DETAILED DESCRIPTION OF THE INVENTION

In order that the invention described herein may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "acyl" refers to an alkylcarbonyl, alkenylcarbonyl, alkynylcarbonyl or arylcarbonyl substituent, wherein the alkyl, alkenyl, alkynyl or aryl portion may be optionally substituted. Examples of acyl substituents include, but are not limited to, acetyl, propionyl, butyryl and benzoyl.

The term "acyloxy" refers to an —O—C(O)R substituent, wherein R is alkyl, alkenyl, alkynyl or aryl, and wherein the alkyl, alkenyl, alkynyl or aryl portion may be optionally substituted. Examples of acyloxy groups include, but are not limited to, aceloxy, propanoyloxy, butanoyloxy, pentanoyloxy and benzoyloxy.

The term "aliphatic" refers to straight chain or branched hydrocarbons that are completely saturated or that contain one or more units of unsaturation. For example, aliphatic groups include substituted or unsubstituted linear or branched alkyl, alkenyl and alkynyl groups. Unless indicated otherwise, the term "aliphatic" encompasses both substituted and unsubstituted hydrocarbons.

The terms "alkylamide," "alkenylamide and "alkynylamide" refer to amides of the structures alkyl-NR—C(O)—, alkenyl-NR—C(=O)—, and alkynyl-NR—C(=O)—, wherein R may be separately defined, or R is also alkyl, alkenyl or alkynyl.

The term "alkoxy" refers to O-alkyl substituent, wherein the alkyl portion may be optionally substituted. Examples of alkoxy substituents include, but are not limited to, methoxy, ethoxy, n-propoxy, isopropoxy and n-butoxy. Also explicitly included within the scope of the term "alkoxy" are O-alkenyl or O-alkynyl groups. In all cases, the alkyl, alkene and alkyne portions may be optionally substituted.

The term "alkyl" refers to both straight and branched saturated chains containing, for example, 1-3, 1-6, 1-9, or 1-12 carbon atoms. An alkyl group may be optionally substituted.

The term "alkythio" refers to an S-alkyl substituent, wherein the alkyl portion may be optionally substituted. Examples of alkythio substituents include, but are not limited to, methylthio, ethylthio and isopropylthio. Also explicitly included within the scope of the term "alkythio" are S-alkenyl or S-alkynyl groups. In all cases, the alkyl, alkene and alkyne portions may be optionally substituted.

The term "alkenyl" refers to both straight and branched saturated chains containing, for example, 2-3, 2-6, 2-9, or 2-12 carbon atoms, and at least one carbon-carbon double bond. An alkenyl group may be optionally substituted.

The term "alkynyl" refers to both straight and branched saturated chains containing, for example, 2-3, 2-6, 2-9, or 2-12 carbon atoms, and at least one carbon-carbon triple bond. An alkynyl group may be optionally substituted.

The term "aralkyl" refers to an alkyl group substituted by an aryl. Also explicitly included within the scope of the term "aralkyl" are alkenyl or alkynyl groups substituted by an aryl. Examples of aralkyl groups include benzyl and phenethyl. An aralkyl group may be optionally substituted.

The terms "artificial sweetener" and "sugar substitute" refer to a food additive that confers a sweet taste but has less caloric energy than sugar. In some instances, the caloric energy of the "artificial sweetener" or "sugar substitute" is negligible.

The term "aryl" refers to monocyclic or polycyclic aromatic carbon ring systems having five to fourteen members. Examples of aryl groups include, but are not limited to, phenyl (Ph), 1-naphthyl, 2-naphthyl, 1-anthracyl and 2-anthracyl. An aryl group may be optionally substituted.

The term "arylalkoxy" refers to a group having the structure —O—R—Ar, where R is alkyl and Ar is an aromatic substituent. Also explicitly included within the scope of the term "arylalkoxy" are —O—R—Ar groups, wherein R is alkenyl or alkynyl. In all cases, the alkyl, alkene, alkyne and aryl portions may be optionally substituted.

The term "bitter" or "bitter taste" as used herein refers to the perception or gustatory sensation resulting following the detection of a bitter tastant. The following attributes may contribute to bitter taste: astringent, bitter-astringent, metallic, bitter-metallic, as well as off-tastes, aftertastes and undesirable tastes including but not limited to freezer-burn and card-board taste, and/or any combinations of these. It is noted that, in the art, the term "off-taste" is often synonymous with "bitter taste." Without being limited by theory, the diversity of bitter tastes may reflect the large number of bitter receptors and the differential detection of bitter tastants by these receptors. Bitter taste as used herein includes activation of a bitter taste receptor by a bitter tastant. Bitter taste as used herein also includes activation of a bitter taste receptor by a bitter tastant followed by downstream signaling. Bitter taste as used herein also includes activation of a signaling pathway after stimulation by a bitter tastant. Bitter taste as used herein further includes perception resulting from signaling following the detection of a bitter tastant by a bitter taste receptor. Bitter taste as used herein further includes perception resulting from signaling following contacting a bitter taste receptor with a bitter tastant. Bitter taste can be perceived in the brain.

The term "bitter taste receptor" refers to a receptor, typically a cell surface receptor, to which a bitter tastant can bind. Bitter taste receptors may be present in the oral cavity, and/or throughout the gastrointestinal tract, including the stomach, intestines, and colon. Bitter receptors can also be present in vitro, such as in an assay, including but not limited to a cell based assay or a binding assay.

The term "bitter tastant," "bitter ligand," or "bitter compound" refers to a compound that activates or that can be detected by a bitter taste receptor and/or confers the perception of a bitter taste in a subject. A "bitter tastant" also refers to a multiplicity of compounds that combine to activate or be detected by a bitter taste receptor and/or confer the perception of a bitter taste in a subject. A "bitter tastant" further refers to a compound that is enzymatically modified upon ingestion by a subject to activate or be detected by a bitter taste receptor and/or confer the perception of a bitter taste in a subject. Because the perception of bitter taste may vary from individual to individual, some individuals may describe a "bitter tastant" as a compound winch confers a different kind of bitter taste compared to the kind of bitter taste perceived for the same compound by other individuals. The term bitter tastant also reacts to a compound which confers a bitter taste. Those of skill in the art can readily identify and understand what is meant by a bitter tastant Non-limiting examples of bitter tastants or substances including foods that comprise a bitter tastant and taste bitter include coffee, unsweetened cocoa, marmalade, bitter melon, beer, bitters, citrus peel, dandelion greens, escarole, quinine, magnesium salts, calcium salts, potassium salts, KCl, potassium lactate, Acesulfame K, Brussels sprouts, asparagus, bitter gourd, wild cucumber, celery, hops, kohlrabi, radish leaf, ginseng, pumpkin, collard greens, kale, sparteine, caffeine, atropine, nicotine, urea and strychnine.

Further examples of bitter tastants include pharmaceuticals. Non-limiting examples of pharmaceuticals as bitter tastants include acetaminophen, ampicillin, azithromycin, chlorpheniramine, cimetidine, dextromethorphan, diphenylhydramine, erythromycin, ibuprofen, penicillin, phenylbutazone, psuedoephedrine, ranitidine, spironolactone and theophylline all of which have been associated with bitter taste.

The term "carbocyclic" or "carbocyclic," refers to monocyclic or polycyclic non-aromatic carbon ring systems, which may contain a specified number of carbon atoms, preferably from 3 to 12 carbon atoms, which are completely saturated or which contain one or more units of unsaturation. A carbocyclic ring system may be monocyclic, bicyclic or tricyclic. A carbocyclyl ring may be fused to another ring, such as an aryl ring or another carbocyclic ring. Examples of carbocyclic rings could include cyclohexyl, cyclopentyl, cyclobutyl, cyclopropyl, cyclohexenyl, cyclopentenyl, indanyl, tetrahydronaphthyl and the like. The term "carbocyclic" or "carbocyclyl," whether saturated or unsaturated, also refers to rings that are optionally substituted unless indicated. The term "carbocyclic" or "carbocycl" also encompasses hybrids of aliphatic and carbocyclic groups, such as (cycloalkyl)alkyl, (cycloalkenyl(alkyl) and (cycloalkyl)alkenyl.

The term "comestibly or biologically acceptable salt" refers to any comestibly or biologically acceptable salt, ester, or salt of such ester, of a compound of the present invention, which, upon ingestion, is capable of providing (directly or indirectly) a compound of the present invention, or a metabolite, residue or portion thereof, characterized by the ability to reduce the perception of a bitter taste attributed to a bitter tastant. Similarly, the term "comestibly or biologically acceptable derivative" refers to any comestibly or biologically acceptable derivative of a compound of the present invention, which, upon ingestion, is capable of providing (directly or indirectly) a compound of the present invention, or a metabolite, residue or portion thereof, characterized by the ability to reduce the perception of a bitter taste attributed to a bitter tastant. A "comestible product" is a product suitable for oral use, such as eating or drinking. Therefore, a comestibly acceptable compound is an edible compound.

The term "consumer product" refers to health and beauty products for the personal use and/or consumption by a subject. Consumer products may be present in any form including, but not limited to, liquids, solids, semi-solids, tablets, capsules, lozenges, strips, powders, gels, gums, pastes, slurries, syrups, aerosols and sprays. Non-limiting examples of consumer products include nutriceuticals, nutritional supplements, lipsticks, lip balms, soaps, shampoos, gums, adhesives (e.g., dental adhesives), toothpastes, oral analgesics, breath fresheners, mouthwashes, tooth whiteners, and other dentifrices.

The term "diet" collectively refers to the food products and/or beverages consumed by a subject. A subject's "diet" also includes any consumer products or pharmaceutical compositions the subject ingests.

The term "edible composition" refers to a composition suitable for consumption, typically via the oral cavity (although consumption may occur via non-oral means such as inhalation). Edible compositions may be present in any form including, but not limited to, liquids, solids, semi-solids, tablets, lozenges, powders, gels, gums, pastes, slurries, syrups, aerosols and sprays. As used herein, edible compositions include food products, pharmaceutical compositions, and consumer products. The term edible compositions also refers to, for example, dietary and nutritional supplements. As used herein, edible compositions also include compositions that are placed within the oral cavity but not swallowed, including professional dental products, such as dental treatments, fillings, packing materials, molds and polishes.

The term "comestible" refers to similar compositions and is generally used as a synonym to the term "edible."

The term "effective amount" refers to an amount sufficient to produce a desired property or result, for example, an effective amount of a compound of the present invention is an amount capable of reducing the perception of bitter taste associated with a bitter tastant. The term "effective amount" of a compound of the invention also refers to an amount which, when added to an edible composition, reduces the bitter taste of, e.g., a NaCl substitute, thereby allowing for the maintenance of the perception of a desired salty flavor of a said edible composition. The term "effective amount of a compound" also refers to an amount which, when added to an edible composition, allows for the preservation of a food product, while reducing or eliminating bitter taste associated with a bitter tastant in the preservative. The term "effective amount" also refers to the amount of a compound of the present invention capable of reducing or eliminating the perception of a bitter taste or aftertaste associated with either a bitter tastant in a food product or an inherently bitter food product.

The term "flavor modifier" refers to a compound or a mixture of compounds that, when added to an edible composition, such as a food product, modifies (e.g., masks, eliminates, decreases, reduces, or enhances the perception of) a flavor (e.g., sweet, salty, umami, sour, or bitter taste) present in the edible composition.

The term "food product" refers to any composition comprising one or more processed foodstuff. Food products include, but are not limited to, confectionaries, bakery products (including, but not limited to, doughs, breads, biscuits, crackers, cakes, pastries, pies, tarts, quiches, and cookies), ice creams (including but not limited to impulse ice cream, take-home ice cream, frozen yogurt, gelato, sorbet, sherbet and soy, oat, bean and rice-based ice cream), dairy products (including, but not limited to, drinking milk, cheese, yogurt, and sour milk drinks), cheeses (including, but not limited to, natural cheeses and processed cheeses), butter, margarine, sweet and savory snacks (including but not limited to fruit snacks, chips/crisps, tortilla/corn chips, popcorn, pretzels, chocolates, and nuts), hot and cold beverages (including, but not limited to, beverages, beverage mixes, concentrates, juices, carbonated beverages, non-carbonated beverages, alcoholic beverages, non-alcoholic beverages, soft drinks, sports drinks, isotonic drinks, coffees, teas, bottled waters, and beverages prepared from botanicals and botanical extracts (including cold beverages that are prepared with botanical or fungi extracts as ingredients, and drinks that are prepared in various ways, such as infusions, decoctions, or other means of extraction or distillation of various plant parts, including, but not limited to leaves, flowers, stems, fruits, roots, rhizomes, stems, bark, volatile oils, or even the whole plant)), snack bars (including, but not limited to granola bars, muesli bars, protein bars, breakfast bars, energy bars, and fruit bars), meal replacement products, ready meals (including, but not limited to canned meals, preserved meals, frozen meals, dried meals, chilled meals, dinner mixes, frozen pizza, chilled pizza, and prepared salads), soups (including but not limited to broth-like soups and cream-based soups), broth, gravy, soy sauce, meats and fish (including raw, cooked, and dried meats), deli products (including but not limited to meats and cheeses suitable for slicing or pre-sliced meats and cheeses, e.g., turkey, chicken, ham, bologna, salami, bierwurst, capicola, chorizo, corned beef, dutch loaf, Serrano, prosciutto, head cheese, liverwurst, meatloaf (including olive loaf, pepper loaf, pimento loaf, and ham and cheese loaf), mortadella, pastrami, pepperoni, roast beef, roast pork, saucisson, smoked meat, summer sausage, tongue, American cheese, blue cheese, cheddar cheese, Colby cheese, Colby-Jack cheese, gouda, Monterey Jack cheese, muenster cheese mozzarella, parmigiano cheese, pepper jack cheese, provolone, romano cheese, string cheese, spray cheese, and swiss cheese), vegetables (including, but not limited to, raw, pickled, cooked, and dried vegetables, such as french fries), fruits (including raw, cooked, and dried fruits), grains (including, but not limited to, dried cereals and breads), prepared foods (including, but not limited to, dried, canned, or jarred sauces and soups), snack foods, pastas (including, but not limited to, fresh pasta, chilled pasta, frozen pasta, dried pasta), noodles (including, but not limited to, egg noodles, wheat noodles, rice noodles, mung bean noodles, potato noodles, buckwheat noodles, corn noodles, cellophane noodles, chow mein, fettuccini, fusilli, gnocchi, lasagna, linguini, lo mein, macaroni, manicotti, pad thai, penne, ramen, rice vermicelli, rigatoni, soba, spaghetti, spatzle, udon, and ziti), canned roods, frozen foods, dried foods, chilled foods, oils and fats, baby food, spreads, salads, cereals (including, but not limited to, hot and cold cereals), sauces (including, but not limited to, tomato pastes, tomato purees, bouillon cubes, stock cubes, table sauces, boys bases sauces, pasta sauces, cooking sauces, marinades, dry sauces, powder mixes, ketchups, mayonnaises, salad dressings, vinegrettes, mustards, and dips), jellies, jams, preserves, honey, puddings, recipe mixes, syrups, icings, fillings, infused foods, salt-preserved food, marinated foods and condiments (such as ketchup, mustard and steak sauce). In some embodiments, the food product is animal feed. For example, the food product may be a pet food product, i.e. a food product for consumption by a household pet. In other embodiments, the food product is a livestock food product, i.e. a food product for consumption by livestock.

The term "foodstuff" refers to an unprocessed ingredient or a basic nutrient or flavor containing element used to prepare a food product. Non-limiting examples of foodstuffs include: fruits, vegetables, meats, fishes, grains, milks, eggs, tubers, sugars, sweeteners, oils, herbs, snacks, sauces, spices and salts.

The term "halo" or "halogen" refers to a fluorine, chlorine, bromine or iodine substituent The term "heteroaryl" refers to monocyclic or polycyclic aromatic ring systems having five to fourteen members and one or more heteroatoms. One having ordinary skill in the art will recognize that the maximum number of heteroatoms in a stable, chemically feasible heteroaryl ring is determined by the size of the ring and valence. The term "heteroaralkyl" refers to an alkyl group substituted by a heteroaryl. Also explicitly included within the scope of the term "hetetoaralky" are alkenyl or alkynyl groups substituted by a heteroaryl. In general, a heteroaryl ring may have one to four heteroatoms. Heteroaryl groups include, without limitation, 2-furanyl, 3-furanyl, N-imidazolyl, 2imidazolyl, 4-imidazolyl, 5-imidazolyl, 3-isoxazolyl, 4isoxazolyl, 5-isoxazolyl, 2-oxadiazolyl, 5-oxadiazolyl, 2-oxazolyl 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4thiazolyl, 5-thiazolyl, 5-tetrazolyl, 2-triazolyl, 5-triazolyl, 2-thienyl, and 3-thienyl. The term "heteroaryl ring", "heteroaryl group", or "heteroaralkyl" also refers to rings that are optionally substituted. Examples of fused polycyclic heteroaryl and aryl ring systems in which a carbocyclic aromatic ring or heteroaryl ring is fused to one or more other rings include, tetrahydronaphthyl, benzidazolyl, benzothienyl, benzoluranyl, indolyl, quinolinyl, benzothiazolyl, benzoxazolyl, benzoimidazolyl, isoquinolinyl, isoindolyl, acridinyl, benzoisoxazolyl, and the like.

The term "heterocyclic" or "heterocyclyl" refers to non-aromatic saturated or unsaturated monocyclic or polycyclic ring systems containing one or more heteroatoms and with a ring size of three to fourteen. One having ordinary skill in the art will recognize that the maximum number of heteroatoms in a stable, chemically feasible heterocyclic ring is determined by the size of the ring, degree of unsaturation, and valence. In general, a heterocyclic ring may have one to four heteroatoms so long as the heterocyclic ring is chemically feasible and stable and may be fused to another ring, such as a carbocyclic, aryl or heteroaryl ring, or to another heterocyclic ring. A heterocyclic ring system may be monocyclic, bicyclic or tricyclic. Also included within the scope of within the scope of the term "heterocyclic" or "heterocyclyl", as used herein, is a group in which one or more carbocyclic rings are fused to a heteroaryl. Examples of heterocyclic rings include, but are not limited to, 3-1H-benzimidazol-2-one, 3-1H-alkyl-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, benzothiane, aziranyl, oxiranyl, azetidinyl, pyrrolinyl, dioxolanyl, imidazolinyl, imidazolidinyl, pyrazolinyl, pyrazolidinyl, pyranyl, dioxanyl, dithianyl, trithianyl, quinuclidinyl, oxepanyl, succinimidyl and theipanyl.

The term "isoprene" (also referred to as "isoterpene") refers to 2-methyl-1,3-butadiene and is represented by the formula $CH_2C(CH_3)CH=CH_2$.

The terms "parts per million" and "ppm" are used in the food industry to refer to a low concentration of a solution. For example, one gram of solute in 1000 ml of solvent has a concentration of 1000 ppm and one thousandth of a gram (0.001 g) of solute in 1000 ml of solvent has a concentration of 1000 ppm. Accordingly, a concentration of one milligram per liter (i.e. 1 mg/L) is equal to 1 ppm.

The terms "perception of a bitter taste," "perception of saltiness," "perception of a flavor" and similar terms, refer to the awareness of a subject of a particular taste or flavor.

The term "pharmaceutically active ingredient" refers to a compound in a pharmaceutical composition which is biologically active.

The term "potassium salt" relates to a salt wherein potassium is the cation. Potassium salts in the context of the present invention are preferably edible potassium salts including, but not limited to, Acesulfame K (Ace K), aluminum potassium sulfate, dipotassium guanylate, dipotassium inosinate, monopotassium glutamate, potassium acetate, potassium acid tartate, potassium acid tartrate, potassium adipate, potassium alginate, potassium aluminum silicate, potassium ascorbate potassium aspartate, potassium benzoate, potassium bicarbonate, potassium bisulfate, potassium bisulfite, potassium bromate, potassium carbonate, potassium chloride, potassium citrate, potassium dihydrogen citrate, potassium dihydrogen phosphate, potassium ferrocyanide, potassium fumarate, potassium gibberellate, potassium gluconate, potassium hydroxide, potassium hydrogen sulfite, potassium iodide, potassium lactate, potassium malate, potassium metabisulfite, potassium nitrate, potassium nitrite, potassium persulfate, potassium phosphate (dibasic), potassium phosphate (monobasic), potassium phosphate (tribasic), potassium polymetaphosphate, potassium polyphosphates, potassium pyrophosphate, potassium propionate, potassium saccharin, potassium sodium tartrate (e.g., potassium sodium L(+)-tartrate), potassium sorbate, potassium sulfate, potassium sulfite, and potassium tripolyphosphate.

The term "processed foodstuff" refers to a foodstuff has been subjected to any process which alters its original state (excluding, e.g., harvesting, slaughtering, and cleaning). Examples of methods of processing foods include, but are not limited to, removal of unwanted outer layers, such as potato peeling or the skinning of peaches; chopping or slicing; mincing or macerating: liquefaction, such as to produce fruit juice; fermentation (e.g. beer); emulsification; cooking, such as boiling, broiling, frying, heating, steaming or grilling; deep frying; baking; mixing; addition of gas such as an entrapment for bread or gasification of soft drinks; proofing; seasoning (with, e.g., herbs, spices, salts); spray drying; pasteurization; packaging (e.g., canning or boxing); extrusion; puffing; blending; and preservation (e.g., adding salt, sugar, potassium lactate or other preservatives).

The term "replace" or "replacing" refers to substituting one compound for another compound in or in the preparation of, for example, an edible composition, such as food product. It includes complete and partial replacements or substitutions.

The term "salty flavor" refers to the taste elicited by, for example, ions of alkali metals salts (e.g., $Na^+$ and $Cl^-$ in sodium chloride). Non-limiting examples of compositions eliciting a salty flavor include table salt (sodium chloride), sea water, sea salt and potassium chloride. The amount of salty flavor or the saltiness of a composition can be determined by, e.g., taste testing.

The term "sodium" or "sodium salt" refers to the amount of sodium (i.e., sodium salt) ingested or otherwise consumed by a subject. In general, "sodium" or a "sodium salt" refers to a salt or compound wherein sodium is the cation. Sodium salts in the context of the present invention include, but are not limited to, aluminum sodium sulfate, calcium disodium EDTA, dioctyl sodium sulfosuccinate, disodium 5'-ribonucleotides, disodium ethylenediaminetetraacetate, disodium guanylate, disodium inosinate sodium acetate, monosodium glutamate (MSG), potassium sodium tartrate, sodium acid pyrophosphate, sodium adipate, sodium alginate, sodium aluminosilicate, sodium aluminum phosphate (acidic), sodium aluminum phosphate (basic), sodium ascorbate, sodium benzoate, sodium bicarbonate, sodium bisulfate, sodium bisulfite, sodium carbonate, sodium carboxymethylcellulose, sodium caseinate, sodium chloride, sodium citrate, sodium cyclamate, sodium dehydroacetate, sodium diacetate, sodium dehydroacetate, sodium dihydrogen citrate, sodium dihydrogen phosphate, sodium DL-malate, sodium erythorbate, sodium erythorbin, sodium ethyl para-hydroxybenzoate, sodium ferric pyrophosphate, sodium ferrocyanide, sodium formate, sodium fumarate, sodium gluconate, sodium hydrogen carbonate, sodium hydrogen DL-malate, sodium hydrogen acetate, sodium hydrogen sulfite, sodium hydroxide, sodium hypophosphite, sodium tartrate (e.g., sodium L(+)-tartrate), sodium lactate, sodium lauryl sulfate, sodium malate, sodium metabisulfite, sodium metaphosphate, sodium methyl para-hydroxybenzoate, sodium nitrate, sodium nitrite, sodium O-phenylphenol, sodium phosphate (dibasic), sodium phosphate (monobasic), sodium phosphate (tribasic), sodium polyphosphate, sodium potassium tartrate, sodium propionate, sodium propyl para-hydroxybenzoate, sodium pyrophosphate, sodium saccharin, sodium sesquicarbonate, sodium stearoyl lactylate, sodium stearyl fumarate, sodium succinate, sodium sulfate, and starch sodium octenylsuccinate.

The term "sodium intake" refers to the amount of sodium ingested or otherwise consumed by a subject.

The term "stability" or "stable" in the context of a chemical structure refers to the chemical state when a system is in its lowest energy state, or in chemical equilibrium with its environment. Thus, a stable compound (or, e.g., a compound containing a number of atoms or substitutions that are stable) is not particularly reactive in the environment or during normal use, and retains its useful properties on the timescale of its expected usefulness.

The term "subject" refers to a mammal. In preferred embodiments, the subject is human. In some embodiments, a subject is a domestic or laboratory animal, including but not limited to, household pets, such as dogs, cats, pigs, rabbits, rats, mice, gerbils, hamsters, guinea pigs, and ferrets. In some embodiments, a subject is a livestock animal. Non-limiting examples of livestock animals include: alpaca, bison, camel, cattle, deer, pigs, horses, llamas, mules, donkeys, sheep, goats, rabbits, reindeer, and yak.

The term "sugar" refers to a simple carbohydrate, such as a monosaccharide or a disaccharide, that delivers a primary taste sensation of sweetness. Non-limiting examples of sugar include glucose, fructose, galactose, sucrose, lactose, and maltose.

The term "sweet flavor" refers to the taste elicited by, for example, sugars. Non-limiting examples of compositions eliciting a sweet flavor include glucose, sucrose, fructose, saccharin, cyclamate, aspartame, acesulfame potassium, sucralose, alitame, and neotame. The amount of sweet flavor or the sweetness of a composition can be determined by, e.g., taste testing.

The term "terpenes" refers to compounds comprising repeating units of isoprene. The basic molecular formula of a terpene is $(C_5H_8)_n$ where n is the number of linked isoprene units.

The term "terpeneoids" refers to compounds comprising terpenes and derivatives thereof. Thus, in some embodiments, terpenoids have at least one $C_5H_8$ hydrocarbon unit with one or more points of unsaturation. In other embodiments, terpenoids comprise saturated terpene units and derivatives thereof and have no points of unsaturation.

An aryl, aralkyl heteroaryl, or heteroaralkyl group may contain one or more independently selected substituents. Examples of suitable substiutents on the unsaturated carbon atom of an aryl or heteroaryl group include, but are not limited to, halogen, —$CF_3$—, —R', —OR', —OH, —SH, —SR', protected OH (such as acyloxy), —$NO_2$—, —CN, —$NH_2$, —NHR', —N(R')$_2$, —NHCOR', —NHCONH$_2$, NHCONHR', —NHCON(R')$_2$, —NRCOR', —NHCO$_2$H, —NHCO$_2$R', —CO$_2$R, —CO$_2$H, —COR', —CONH$_2$, —CONHR', —CON(R')$_2$, —S(O)$_2$, —S(O)$_2$R', —S(O)$_3$H, —S(O)$_3$R', —S(O)$_2$NH2'-S(O)H, —S(O)R', —S(O)$_2$NHR', —S(O)$_2$N(R')$_2$, —NHS(O)$_2$R', where R' is selected from H, aliphatic, carbocyclyl, heterocyclyl, aryl, aralkyl, heteroaryl, or heteroaralkyl and each R' is optionally substituted with one or more halogen, nitro, cyano, amino, —NH-(unsubstituted aliphatic), —N-(unsubstituted aliphatic)$_2$, carboxy, carbamoyl, hydroxy, —O-(unsubstituted aliphatic), —SH, —S-(unsubstituted aliphatic), $CF_3$, —S(O)$_2$NH$_2$$^1$ unsubstituted aliphatic, unsubstituted carbocyclyl, unsubstituted heterocyclyl, unsubstituted aryl, unsubstituted aralkyl, unsubstituted heteroaryl, or unsubstituted heteroaralkyl.

An aliphatic group, a carbocyclic ring or a heterocyclic ring may contain one or more substituents. Examples of suitable substituents on a saturated or unsaturated carbon of an aliphatic group, a carbocyclic ring or a heterocyclic ring include, but are not limited to, those listed above for the unsaturated carbon as well as the following: =O, =S, =NNHR$^1$, =NN(R$^1$)$_2$, =N—OR$^1$, =NNHCOR$^1$, =NNHCO$_2$R$^1$, =NNHSO$_2$R$^1$, =N—CN, or =NR$^1$, wherein R$^1$ is as defined above. Guided by this specification, the selection of suitable substituents is within the knowledge of one skilled in the art.

As defined herein, the compounds of the invention are intended to include all stereochemical forms of the compound, including geometric isomers (i.e., E, Z) and optical isomers (i.e. R, S). Single stereochemical isomers as well as enantiomeric and diastereomeric mixtures of the present compounds are within the scope of the invention. Unless otherwise stated, formulas depicted herein are also meant to include compounds which differ only in the presence of one or more isotopically enriched atoms. For example, compounds having the present formulas except for the replacement of a hydrogen by a deuterium or tritium, or the replacement of a carbon by a $^{13}$C- or $^{14}$C-enriched carbon are within the scope of this invention.

The present invention provides edible compositions comprising a compound of the present invention, including food products, consumer products, and pharmaceutical compositions comprising said compounds, and methods of preparing a such compositions. The present invention also provides methods of reducing the amount of sodium (e.g., NaCl or sodium lactate) or sugar in a food product, a method of reducing the sodium or sugar intake in a diet, a method of reducing bitter taste, and a method of reducing the activity of a bitter taste receptor. The present invention also includes reducing the amount of sodium in a edible composition or diet by replacing a sodium containing compound or composition with a potassium containing compound or composition. The present invention also includes reducing the amount of sugar in a edible composition or diet by replacing sugar with a potassium containing sweetener, such as Acesulfame K.

Edible Compositions

According to one aspect, the invention provides an edible composition comprising a compound of the invention for reducing bitter taste of a bitter tastant.

Edible Compositions Comprising Terpenoid Compounds

The substituent definitions in this section (i.e., R1, R2, R3, R4, m, n, p and t) refer to compounds of Formula (I), Formula (Ia), Formula (IIa), Formula (IIIa), Formula (IIb), Formula ((IIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh).

All stereochemical forms of the compounds disclosed in this and any section herein are specifically contemplated, including geometric isomers (i.e. E, Z) and optical isomers (i.e., R, S). Single stereochemical isomers as well as enantiomeric and diastereomeric mixtures of the compounds disclosed in this and any section herein are also specifically contemplated.

In some embodiments, the present invention provides an edible composition for reducing bitter taste of a bitter tastant, wherein the composition comprises a terpenoid compound. The terpenoid compounds of this invention are capable of reducing or eliminating bitter taste of a bitter tastant. In some embodiments, the terpenoid compound has a molecular weight less than about 1000, 500, or 300 daltons. In certain embodiments, the terpenoid compound is a compound of Formula (I):

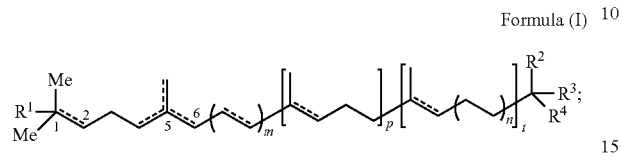

Formula (I)

or a comestibly or biologically acceptable salt or derivative thereof, or an enantiomer or diastereomer thereof.

wherein, as valence and stability permit:
  $R^1$ is absent or is selected from the group consisting of hydrogen, $C_{1-10}$alkyl, $C_{1-10}$haloalkyl, $C_{2-10}$alkenyl, $C_{2-10}$alkynyl, hydroxyl, $C_{1-10}$acylamino, $C_{2-10}$acyloxy, $C_{1-10}$carbonate, $C_{1-10}$alkoxy, phenyloxy, phenyl-$C_{1-6}$ alkyloxy, $C_{1-5}$heteteroaryloxy, $C_{1-5}$heteroaryl-$C_{1-6}$ alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-10}$carbamate, $C_{1-10}$urea, sulfhydryl, $C_{1-10}$alkylthio, sulfate, sulfonate, sulfamoyl, sulfonamido, sulfonyl, wherein heterocyclic or heteroaromatic rings, independently for each occurrence, comprise 1-4 heteroatoms selected from N, O, and S;
  $R^2$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;
  $R^3$ is selected from the group consisting of hydrogen $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;
  $R^4$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocyclyl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;
  or $R^3$ and $R^4$ together form =O or —O—$C_{1-10}$alkyl-O—;
  wherein any of $R^1$, $R^2$, $R^3$, and $R^4$, independently, is optionally substituted with 1-3 substituents selected from the group consisting of $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S; and
  m is 0-2;
  n is 0-2;
  p is 0-2;
  t is 0-2;
  wherein $C_1$ and $C_6$ in formula (I) optionally are bonded together to form a 6-membered ring; and
  wherein all dotted bonds indicate optional carbon-carbon double bonds.

According to some embodiments of compounds of Formula (I),
  as valence and stability permit:
  $R^1$ is absent or is selected from the group consisting of hydroxyl, $C_{1-6}$alkoxy, and $C_{1-6}$acyloxy;
  $R^2$ is selected from the group consisting of hydrogen, $C_{1-6}$alkyl, $C_{2-6}$alkenyl, and $C_{2-6}$alkynyl;
  $R^3$ is selected from the group consisting of hydrogen and $C_{1-6}$alkoxy;
  $R^4$ is selected from the group consisting of hydroxyl, $C_{1-6}$alkoxy, and $C_{1-16}$acyloxy;
  or $R^3$ and $R^4$ together form =O;
  wherein any of $R^1$, $R^2$, $R^3$, and $R^4$, independently, is optionally substituted as in paragraph 1; and
  m is 0-2;
  n is 0-2;
  p is 0-2;
  t is 0-2;

wherein $C_1$ and $C_6$ in Formula (I) optionally are bonded together to form a 6-membered ring; and wherein all dotted bonds indicate optional carbon-carbon double bonds.

According to some embodiments of compounds of Formula (I), as valence and stability permit:

$R^1$ is absent or is selected from the group consisting of hydroxyl, $C_{1-3}$alkoxy, and $C_{1-3}$acyloxy;

$R^2$ is selected from the group consisting of hydrogen, $C_{1-3}$alkyl, $C_{2-3}$alkenyl, and $C_{2-3}$alkynyl;

$R^3$ is selected from the group consisting of hydrogen and $C_{1-3}$alkoxy;

$R^4$ is selected from the group consisting of hydroxyl, $C_{1-3}$alkoxy, and $C_{1-3}$acyloxy;

or $R^3$ and $R^4$ together form =O;

m is 0-2;

n is 0-2;

p is 0-2;

t is 0-2;

wherein $C_1$ and $C_6$ in Formula (I) optionally are bonded together to form a 6-membered ring; and wherein all dotted bonds indicate optional carbon-carbon double bonds.

According to some embodiments of compounds of Formula (I), as valence and stability permit:

$R^1$ is absent or is selected from the group consisting of hydroxyl, $C_{1-3}$alkoxy, and $C_{1-3}$acyloxy;

$R^2$ is selected from the group consisting of hydrogen, $C_{1-3}$alkyl, $C_{2-3}$alkenyl, and $C_{2-3}$alkynyl;

$R^3$ is selected from the group consisting of hydrogen and $C_{1-3}$alkoxy;

$R^4$ is selected from the group consisting of hydroxyl, $C_{1-3}$alkoxy, and $C_{1-3}$acyloxy;

m is 1;

n is 0;

p is 1;

t is 1;

wherein $C_1$ and $C_6$ in Formula (I) optionally are bonded together to form a 6-membered ring; and wherein all dotted bonds indicate optional carbon-carbon double bonds.

According to some embodiments of compounds of Formula (I), as valence and stability permit:

$R^1$ is absent or is selected from the group consisting of hydroxyl, $C_{1-3}$alkoxy, and $C_{1-3}$acyloxy;

$R^2$ is selected from the group consisting of hydrogen, $C_{1-3}$alkyl, $C_{2-3}$alkenyl, and $C_{2-3}$alkynyl;

$R^3$ is selected from the group consisting of hydrogen and $C_{1-3}$alkoxy;

$R^4$ is selected from the group consisting of hydroxyl, $C_{1-3}$alkoxy, and $C_{1-3}$acyloxy;

m is 1;

n is 0;

p is 1;

t is 1;

wherein $C_1$ and $C_6$ in Formula (I) optionally are bonded together to form a 6-membered ring; and wherein all dotted bonds indicate optional carbon-carbon double bonds.

In some embodiments of Formula (I), $R^1$ is absent. For example, in certain embodiments, $R^1$ is absent and $C_3$ is part of a double bond. In other embodiments, $R^1$ is present and is hydrogen, hydroxyl, $C_{1-6}$alkoxy, or $C_{1-6}$acyloxy. In other embodiments, $R^1$ is present and is hydrogen or hydroxyl.

In certain embodiments, the compound of Formula (I) includes a E-double bond between $C_5$ and $C_6$. In other embodiments, the compound of Formula (I) includes a Z-double bond between $C_5$ and $C_6$. In further embodiments, the compound of Formula (I) includes a mixture of E/Z-double bonds between $C_5$ and $C_6$. In yet additional embodiments, the compound of Formula (I) does not include a double bond between $C_5$ and $C_6$. In some embodiments, the compound of Formula (I) includes Z-double in one or more "t" segments. In other embodiments, the compound of Formula (I) includes a double bond in one or more "t" segments. In further embodiments, the compound of Formula (I) includes a mixture of E/Z-double bonds in one or more "t" segments.

In some embodiments, the compound of Formula (I) includes no carbon-carbon double bonds, one carbon-carbon double bond, two carbon-carbon double bonds, three carbon-carbon double bonds, four carbon-carbon double bonds, five carbon-carbon double bonds, or six carbon-carbon double bonds. In some embodiments, the compound of Formula (I) includes no carbon-carbon double bonds, one carbon-carbon double bond, two carbon-carbon double bonds, three carbon-carbon double bonds, four carbon-carbon double bonds. In particular embodiments, the compound of Formula (I) includes no carbon-carbon double bonds, one carbon-carbon double bond, or two carbon-carbon double bonds.

In some embodiments of Formula (I), $R^2$ is hydrogen. In other embodiments, $R^2$ is $C_{1-6}$alkyl, such as methyl, or $C_{2-6}$alkenyl, such as isoallyl (e.g., 1-propenyl).

In certain embodiments of Formula (I), $R^3$ is hydrogen, in other embodiments, $R^3$ is $C_{1-6}$alkoxy, such as methoxy or ethoxy.

In some embodiments of Formula (I), $R^4$ is hydroxyl. In other embodiments, $R^4$ is $C_{1-6}$alkoxy, such as methoxy or ethoxy. In yet further embodiments, $R^1$ is $C_{1-10}$acyloxy, such as $C_{1-6}$acyloxy, e.g., formyloxy, acetyloxy, propionyloxy, butanoyloxy, phenylacetyloxy, etc. In some embodiments, $R^4$ is $C_{1-6}$acyloxy or $C_{1-3}$acyloxy. In other embodiments, $R^4$ is acetyloxy.

In some embodiments of Formula (I), $R^3$ and $R^4$ together form =O.

In certain embodiments of Formula (I), m is 0. In other embodiments, m is 1. In yet further embodiments, m is 2.

In certain embodiments of Formula (I), n is 0. In other embodiments, n is 1. In yet further embodiments, n is 2.

In certain embodiments of Formula (I), p is 0. In other embodiments, p is 1. In yet further embodiments, p is 2.

In certain embodiments of Formula (I), t is 0. In other embodiments, t is 1. In yet further embodiments, t is 2.

In some embodiments of Formula (I), m is 1, n is 0, p is 1, and t is 1.

In certain embodiments, the terpenoid compound is a compound of Formula (Ia):

Formula (Ia)

or a comestibly or biologically acceptable salt or derivative thereof, or an enantiomer or diastereomer thereof, wherein, as valence and stability permit;

$R^1$ is absent or is selected from the group consisting of hydrogen, $C_{1-10}$alkyl, $C_{1-10}$haloalkyl, $C_{2-10}$alkenyl, $C_{2-10}$alkynyl, hydroxyl, $C_{1-10}$acylamino, $C_{2-10}$acyloxy, $C_{1-10}$carbonate, $C_{1-10}$alkoxy, phenyloxy, phenyl-$C_{1-6}$alkyloxy, $C_{1-5}$heteteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-10}$carbamate, $C_{1-10}$urea, sulfhydryl, $C_{1-10}$alkylthio, sulfate, sulfonate, sulfamoyl, sulfonamido, sulfonyl, wherein heterocyclic or heteroaromatic rings, independently for each occurrence, comprise 1-4 heteroatoms selected from N, O, and S;

$R^2$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^3$ is selected from the group consisting of hydrogen $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^4$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

or $R^3$ and $R^4$ together form =O or —O—$C_{1-10}$alkyl-O—;

wherein any of $R^1$, $R^2$, $R^3$, and $R^4$, independently, is optionally substituted with 1-3 substituents selected from the group consisting of $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S; and m is 0-2;

wherein $C_1$ and $C_6$ in formula (Ia) optionally are bonded together to form a 6-membered ring; and wherein all dotted bonds indicate optional carbon-carbon double bonds.

According to some embodiments of compounds of Formula (Ia, as valence and stability permit:

$R^1$ is absent or is selected from the group consisting of hydroxyl, $C_{1-6}$alkoxy, and $C_{1-6}$acyloxy;

$R^2$ is selected from the group consisting of hydrogen, $C_{1-6}$alkyl, $C_{2-6}$alkenyl, and $C_{2-6}$alkynyl;

$R^3$ is selected from the group consisting of hydrogen and $C_{1-6}$alkoxy;

$R^4$ is selected from the group consisting of hydroxyl, $C_{1-6}$alkoxy, and $C_{1-10}$acyloxy;

or $R^3$ and $R^4$ together form =O;

wherein any of $R^1$, $R^2$, $R^3$, and $R^4$, independently, is optionally substituted as noted above; and m is 0-2;

wherein $C_1$ and $C_6$ in Formula (Ia) optionally are bonded together to form a 6-membered ring; and wherein all dotted bonds indicate optional carbon-carbon double bonds.

In some embodiments of Formula (I), $R^1$ is absent. For example, in certain embodiments, $R^1$ is absent and $C_1$ is part of a double bond. In other embodiments, $R^1$ is present and is hydroxyl, $C_{1-6}$alkoxy, or $C_{1-6}$acyloxy, particularly hydroxyl.

In certain embodiments, the compound of Formula (Ia) includes a E-double bond between $C_5$ and $C_6$. In other embodiments, the compound of Formula (Ia) includes a Z-double bond between $C_5$ and $C_6$. In further embodiments, the compound of Formula (Ia) includes a mixture of E/Z-double bonds between $C_5$ and $C_6$. In yet additional embodiments, the compound of Formula (I) does not include a double bond between $C_5$ and $C_6$.

In some embodiments, the compound of Formula (Ia) includes no carbon-carbon double bonds, one carbon-carbon double bond, two carbon-carbon double bonds, three carbon-carbon double bonds, four carbon-carbon double bonds. In particular embodiments, the compound of Formula (Ia) includes no carbon-carbon double bonds, one carbon-carbon double bond, or two carbon-carbon double bonds.

In some embodiments of Formula (Ia), $R^2$ is hydrogen. In other embodiments, $R^2$ is $C_{1-6}$alkyl, such as methyl, or $C_{2-6}$alkenyl, such as isoallyl (e.g., 1-propenyl).

In certain embodiments of Formula (Ia), $R^3$ is hydrogen, in other embodiments, $R^3$ is $C_{1-6}$alkoxy, such as methoxy or ethoxy.

In some embodiments of Formula (Ia), $R^4$ is hydroxyl. In other embodiments, $R^4$ is $C_{1-6}$alkoxy, such as methoxy or ethoxy. In yet further embodiments, $R^1$ is $C_{1-10}$acyloxy, such as $C_{1-6}$acyloxy, e.g., formyloxy, acetyloxy, propionyloxy, butanoyloxy, phenylacetyloxy, etc.

In some embodiments of Formula (Ia), $R^3$ and $R^4$ together form =O.

In certain embodiments of Formula (Ia), m is 0. In other embodiments, m is 1. In yet further embodiments, m is 2.

In some embodiments of the compound of Formula (Ia), $C_1$ and $C_6$ are bonded together to form a 6-membered ring. For example, in certain embodiments, $C_1$ and $C_6$ are bonded together to form a 6-membered ring, and m is 0. For instance, in some embodiments, the compound of Formula (I) is a compound of Formula (IIa):

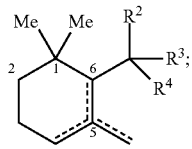

Formula (IIa)

or a comestibly or biologically acceptable salt or derivative thereof, or an enantiomer or diastereomer thereof; wherein, as valence and stability permit, $R^2$, $R^3$, and $R^4$ are as defined above As noted above, in some embodiments, $R^3$ and $R^4$ together form =O. For example, in certain embodiments, the compound of Formula (IIa) is a compound of Formula (IIIa);

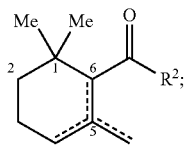

Formula (IIIa)

or a comestibly or biologically acceptable salt or derivative thereof, or an enantiomer or diastereomer thereof, wherein, as valence and stability permit, $R^2$, is as defined above.

As noted above, in some embodiments of the compound of Formula (I), $C_1$ and $C_6$ are bonded together to form a 6-membered ring. For example, in certain embodiments, $C_1$ and $C_6$ are bonded together to form a 6-membered ring, and m is 1. For instance, in some embodiments, the compound of Formula (I) is a compound of Formula (IIb):

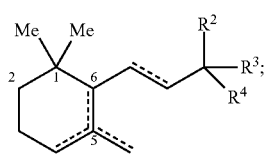

Formula (IIb)

or a comestibly or biologically acceptable salt or derivative thereof or an enantiomer or diastereomer thereof, wherein, as valence and stability permit, $R^2$, $R^3$, and $R^4$ are as defined above. In some embodiments, the exo-cyclic dashed bond is a double bond. In other embodiments, the exo-cyclic dashed bond is a single bond.

As noted above, in some embodiments, $R^3$ and $R^4$ together form =O. For example, in certain embodiments, the compound of formula (IIb) is a compound of Formula (IIIb):

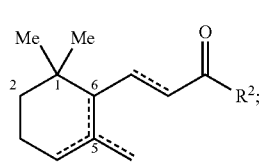

Formula (IIIb)

or a comestibly or biologically acceptable salt or derivative thereof, or an enantiomer or diastereomer thereof, wherein, as valence and stability permit, $R^2$ is as defined above. In some embodiments, the exo-cyclic dashed bond is a double bond. In other embodiments, the exo-cyclic dashed bond is a single bond.

According to other embodiments of the compound of Formula (I), $C_1$ and $C^6$ are not bonded together to form a 6-membered ring and the compound is a substantially linear compound.

As noted above, in certain embodiments, the compound of Formula (I) does not include a double bond between $C_5$ and $C_6$. For example, in certain embodiments, the compound of Formula (I) does not include a double bond between $C_5$ and $C_6$ and $C_1$ and $C_6$ are not bonded together to form a 6-membered ring. For instance, in some embodiments, the compound of Formula (I) is a compound of Formula (IIc):

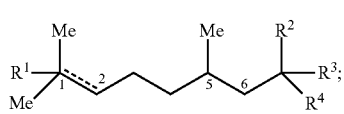

Formula (IIc)

or a comestibly or biologically acceptable salt or derivative thereof, or an enantiomer or diastereomer thereof, wherein, as valence and stability permit, $R^1$, $R^2$, $R^3$, and $R^4$ are as defined above.

As noted above, in some embodiments, $R^1$ is absent and $C_1$ is part of a double bond. For example, in certain embodiments, the compound of Formula (IIc) is a compound of Formula (IIIb);

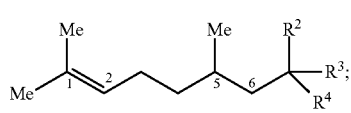

Formula (IIIc)

or a comestibly or biologically acceptable salt or derivative thereof, or an enantiomer or diastereomer thereof, wherein, as valence and stability permit, $R^2$, $R^3$ and $R^4$ are as defined above.

As noted above, in some embodiments, $R^2$ is hydroxyl or $C_{1-10}$acyloxy, such as $C_{1-8}$acyloxy, e.g., formyloxy, acetyloxy, propionyloxy, butanoyloxy, phenyl acetyloxy, etc. For example, in certain embodiments, $R^2$ and $R^3$ are hydrogen and $R^4$ is hydroxyl or $C_{1-16}$acyloxy, such as $C_{6-10}$aryl-$C_{1-6}$ acyl, e.g., phenylacetyloxy. For example, in some embodiments, $R^2$ and $R^3$ are hydrogen and $R^4$ is hydroxyl or $C_{1-16}$acyloxy, such as $C_{1-8}$acyloxy, e.g., formyloxy, acetyloxy, propionyloxy, butanoyloxy, phenyl acetyloxy, etc. For instance, in certain embodiments, the compound of Formula (IIIc) is a compound of Formula (IVc):

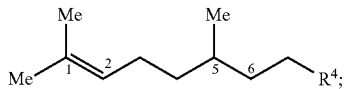

Formula (IVc)

or a comestibly or biologically acceptable salt or derivative thereof, or an enantiomer or diastereomer thereof, wherein, as valence and stability permit, $R^4$ is as defined above.

As noted above, in certain embodiments, the compound of Formula (I) includes a E-double bond between $C_5$ and $C_6$. For example, in certain embodiments, the compound of Formula (I) includes a E-double bond between and $C_5$ and $C_6$ and $C_1$ and $C_6$ are not bonded together to form a 6-membered ring. For instance, in some embodiments, the compound of formula (I) is a compound of Formula (IId):

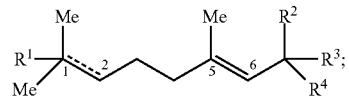

Formula (IId)

or a comestibly or biologically acceptable salt or derivative thereof, or an enantiomer or diastereomer thereof, wherein, as valence and stability permit, $R^1$, $R^2$, $R^3$, and $R^4$ are as defined above.

As noted above, in some embodiments, $R^1$ is absent and $C_1$ is part of a double bond. For example, in certain embodiments, the compound of Formula (IId) is a compound of Formula (IIId):

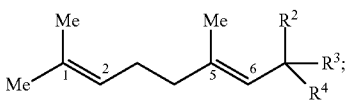

Formula (IIId)

or a comestibly or biologically acceptable salt or derivative thereof, or an enantiomer or diastereomer thereof, wherein, as valence and stability permit, $R^2$, $R^3$ and $R^4$ are as defined above.

As noted above, in some embodiments, $R^2$ is hydroxyl or $C_{1-16}$acyloxy, such as $C_{1-16}$acyloxy-$C_{1-6}$acyl, phenylacetoxy. For example, in some embodiments, $R^4$ is hydroxyl or $C_{1-16}$acyloxy such as $C_{1-8}$acyloxy, e.g., formyloxy, acetyloxy, propionyloxy, butanoyloxy, phenylacetyloxy, etc. For example, in certain embodiments, $R^2$ and $R^3$ are hydrogen and $R^4$ is hydroxyl or $C_{1-16}$acyloxy, such as $C_{6-10}$aryl-$C_{1-6}$acyl, e.g., phenylacetyloxy. For example, in some embodiments, $R^2$ and $R^3$ are hydrogen and $R^4$ is hydroxyl or $C_{1-16}$acyloxy, such as $C_{1-8}$acyloxy, e.g., formyloxy, acetyloxy, propionyloxy, butanoyloxy, phenylacetyloxy, etc. For instance, in some embodiments, the compound of Formula (IIId) is a compound of Formula (IVd):

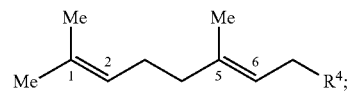

Formula (IVd)

or a comestibly or biologically acceptable salt or derivative thereof, or an enantiomer or diastereomer thereof, wherein, as valence and stability permit, $R^2$ is as defined above.

As noted above, in certain embodiments, the compound of Formula (I) includes a Z-double bond between $C_5$ and $C_6$. For example, in certain embodiments, the compound of Formula (I) includes a Z-double bond between and $C_5$ and $C_6$, and $C_1$ and $C_6$ are not bonded together to form a 6-membered ring. For instance, in some embodiments, the compound of Formula (I) is a compound of Formula (IIe):

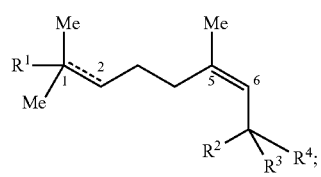

Formula (IIe)

or a comestibly or biologically acceptable salt or derivative thereof, or an enantiomer or diastereomer thereof, wherein, as valence and stability permit, $R^1$, $R^2$, $R^3$, and $R^4$ are as defined above.

As noted above, in some embodiments, $R^1$ is absent and there is a double bond between $C_1$ and $C_2$. For example, in certain embodiments, the compound of Formula (IIe) is a compound of Formula (IIIe):

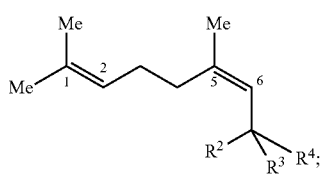

Formula (IIIe)

or a comestibly or biologically acceptable salt or derivative thereof, or an enantiomer or diastereomer thereof, wherein, as valence and stability permit, $R^2$, $R^3$, and $R^4$ are as defined above.

As noted above, in some embodiments, $R^4$ is hydroxyl or $C_{1-16}$acyloxy, such as $C_{6-10}$acyloxy-$C_{1-6}$acyl, phenylacetoxy. For example, in some embodiments, $R^4$ is hydroxyl or $C_{1-16}$acyloxy, such as $C_{1-8}$acyloxy, e.g., formyloxy, acetyloxy, propionyloxy, butanoyloxy, phenylacetyloxy, etc. For example, in certain embodiments, $R^2$ and $R^3$ are hydrogen and $R^4$ is hydroxyl or $C_{1-16}$ acyloxy, such as $C_{6-10}$aryl-$C_{1-6}$acyl, e.g., phenylacetyloxy. For example, in some embodiments, $R^2$ and $R^3$ are hydrogen and $R^4$ is hydroxyl or $C_{1-16}$acyloxy, such as $C_{1-8}$acyloxy, e.g., formyloxy, acetyloxy, propionyloxy, butanoyloxy, phenylacetyloxy, etc. For instance, in some embodiments, the compound of Formula (IIIe) is a compound of Formula (IVe):

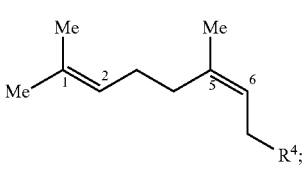

Formula (IVe)

or a comestibly or biologically acceptable salt or derivative thereof, or an enantiomer or diastereomer thereof, wherein, as valence and stability permit, $R^2$ is as defined above.

As noted above, in some embodiments, $R^1$ is present and is hydroxyl, $C_{1-6}$alkoxy, or $C_{1-6}$acyloxy, particularly hydroxyl. For instance, in some embodiments, the compound of Formula (I) is a compound of Formula (IIf):

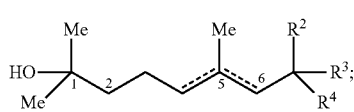

Formula (IIf)

or a comestibly or biologically acceptable salt or derivative thereof, or an enantiomer or diastereomer thereof, wherein, as valence and stability permit, $R^2$, $R^3$, and $R^4$ are as defined above.

In some embodiments of the compound of Formula (I), $R^2$ and $R^3$ are hydrogen and $R^4$ is hydroxyl or $C_{1-16}$acyloxy, such as $C_{6-10}$aryl-$C_{1-6}$acyl, e.g., phenylacetyloxy. For example, in some embodiments, $R^2$ and $R^3$ are hydrogen and $R^4$ is hydroxyl or $C_{1-16}$acyloxy, such as $C_{1-8}$acyloxy, e.g., formyloxy, acetyloxy, propionyloxy, butanoyloxy, phenylacetyloxy, etc. For instance, in some embodiments, the compound of Formula (I) is a compound of Formula (IIg):

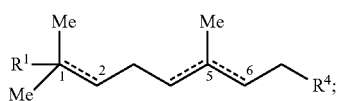

Formula (IIg)

or a comestibly or biologically acceptable salt or derivative thereof, or an enantiomer or diastereomer thereof, wherein, as valence and stability permit, $R^3$ and $R^4$ are as defined above.

In some embodiments of the compound of Formula (I), $R^2$ is hydrogen and $R^3$ and $R^4$ are both $C_{3-6}$alkyloxy, such as methoxy or ethoxy. For instance, in some embodiments, the compound of Formula (I) is a compound of Formula (IIh):

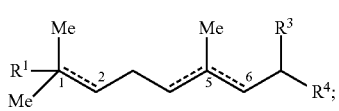

Formula (IIh)

or a comestibly or biologically acceptable salt or derivative thereof, or an enantiomer or diastereomer thereof, wherein, as valence and stability permit, $R^1$, $R^3$, and $R^4$ are as defined above.

In certain embodiments, the compound of Formula (I) is selected from the group consisting of damascone compounds (e.g., β-damascone, trans-α-damascone), ionone compounds (e.g., β-ionoe, α-ionone, γ-ionone, and dihydro-α-ionone, particularly either β-ionone or α-ionone), nerol, geranyl isovalerate, geranyl acetone, neryl acetate, geranyl propionate, geranyl butyrate, citronellyl propionate, citionellyl isobutyrate, citral diethyl acetal, geranyl phenylacetate, geranyl formate, DL-citronellel, neryl isovalerate citronellyl acetate, citral dimethyl acetal, citral, geranial, neral, neryl butyrate, citronellal, hydroxycitronellal, citronellyl valerate, geraniol, neryl isobutyrate, geranyl acetate, citronellyl formate, hydroxycitronellal dimethyl acetal, and phytyl acetate.

In certain embodiments, the compound of Formula (I) is:

| Compound 1 | 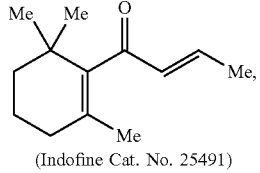 |
|---|---|
| | (Indofine Cat. No. 25491) |
| Compound 2 | 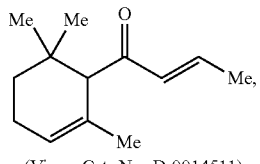 |
| | (Vigon Cat. No. D-0014511) |
| Compound 3 | 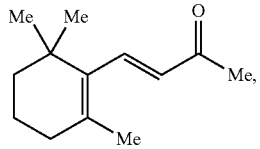 [SMILES: CC(=O)/C=C/C1=C(C)CCCC1(C)C] |
| | |
| Compound 4 | 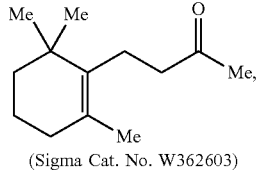 |
| | (Sigma Cat. No. W362603) |

-continued
| | | |
|---|---|---|
| Compound 5 | 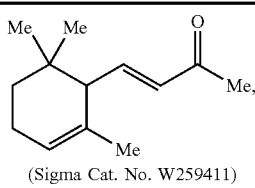 | |
| | (Sigma Cat. No. W259411) | |
| Compound 6 | 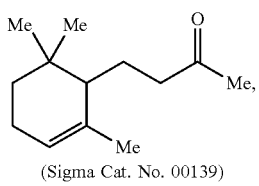 | |
| | (Sigma Cat. No. 00139) | |
| Compound 7 | 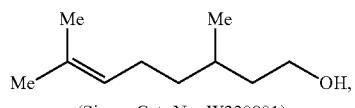 | |
| | (Sigma Cat. No. W230901) | |
| Compound 8 | 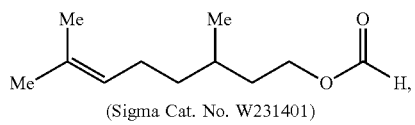 | |
| | (Sigma Cat. No. W231401) | |
| Compound 9 | 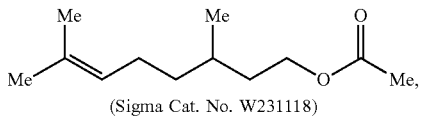 | |
| | (Sigma Cat. No. W231118) | |
| Compound 10 | 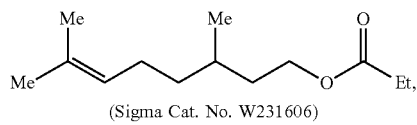 | |
| | (Sigma Cat. No. W231606) | |
| Compound 11 | 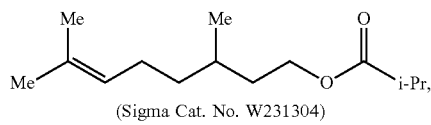 | |
| | (Sigma Cat. No. W231304) | |
| Compound 12 | 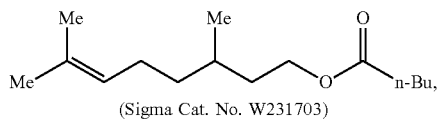 | |
| | (Sigma Cat. No. W231703) | |
| Compound 13 | 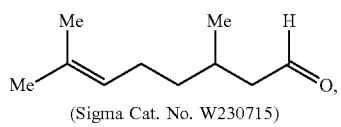 | |
| | (Sigma Cat. No. W230715) | |
| Compound 14 (mixture) | 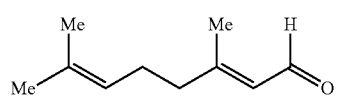 | |
| | 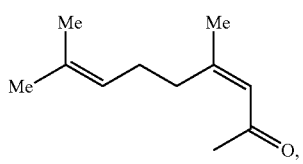 | |

| | |
|---|---|
| Compound 15 (mixture) | 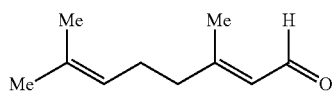<br>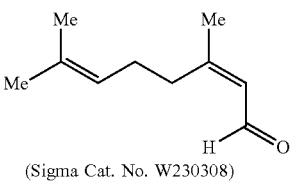<br>(Sigma Cat. No. W230308) |
| Compound 16 | 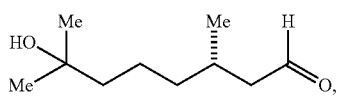 [SMILES: C[C@H](CC=O)CCCC(C)(C)O] |
| Compound 17 | 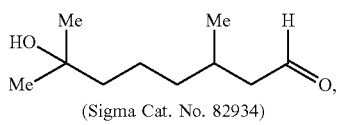<br>(Sigma Cat. No. 82934) |
| Compound 18 | 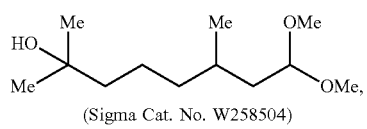<br>(Sigma Cat. No. W258504) |
| Compound 19 | 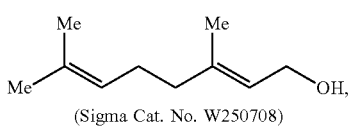<br>(Sigma Cat. No. W250708) |
| Compound 20 | 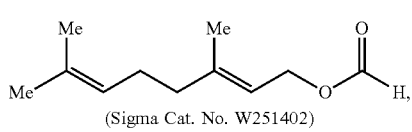<br>(Sigma Cat. No. W251402) |
| Compound 21 | 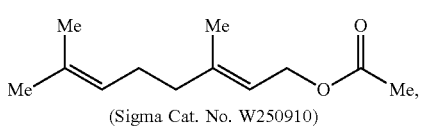<br>(Sigma Cat. No. W250910) |
| Compound 22 | 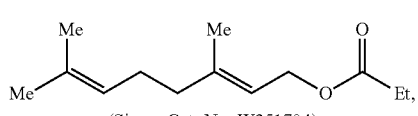<br>(Sigma Cat. No. W251704) |
| Compound 23 | 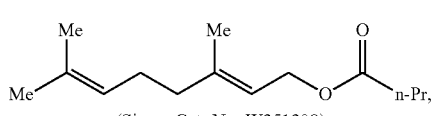<br>(Sigma Cat. No. W251208) |
| Compound 24 | 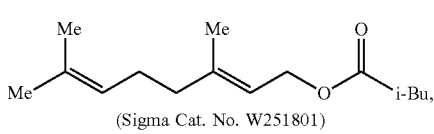<br>(Sigma Cat. No. W251801) |

-continued
| | | |
|---|---|---|
| Compound 25 | 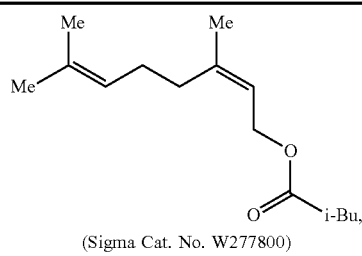 | |
| | (Sigma Cat. No. W277800) | |
| Compound 26 | 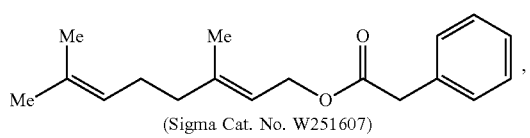 | |
| | (Sigma Cat. No. W251607) | |
| Compound 27 | 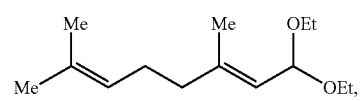 | |
| Compound 28 (mixture) | 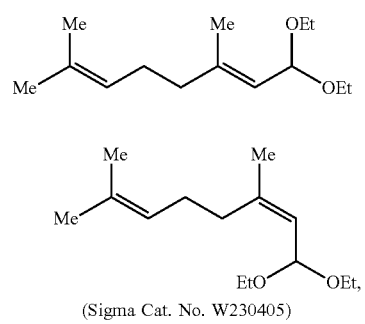 | |
| | (Sigma Cat. No. W230405) | |
| Compound 29 | 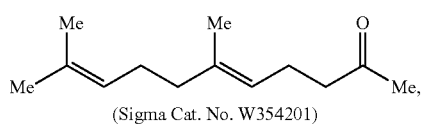 [SMILES: CC(=O)CC/C=C(\C)CCC=C(C)C] | |
| | (Sigma Cat. No. W354201) | |
| Compound 30 | 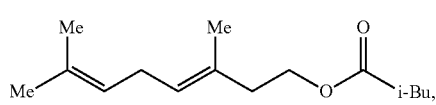 | |
| Compound 31 | 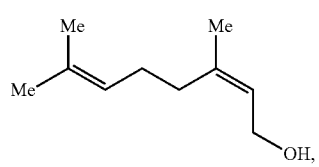 | |
| | (Sigma Cat. No. W277002) | |
| Compound 32 | 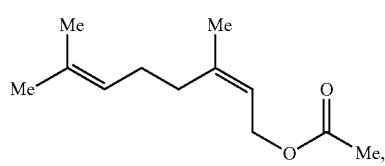 | |
| | (Sigma Cat. No. W277304) | |
| Compound 33 | 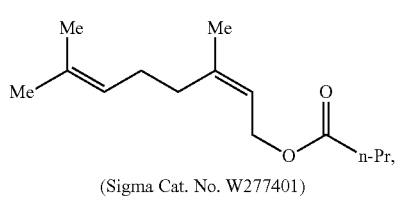 | |
| | (Sigma Cat. No. W277401) | |

-continued

| Compound 34 | 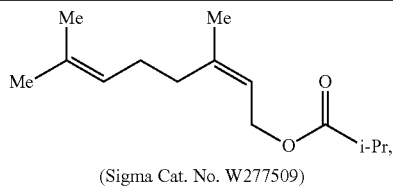
(Sigma Cat. No. W277509) |
| Compound 35 | 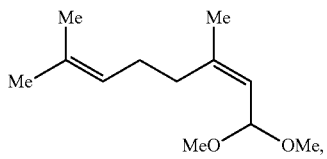 [SMILES: COC(/C=C(/C)CCC=C(C)C)OC] |
| Compound 36 (Mixture) | 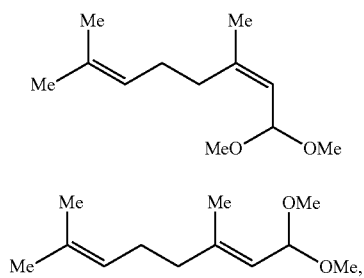
(Sigma Cat. No. W230502) |
| Compound 37 (Mixture) | Nerolie bigarade oil (also referred to as neroli oil, sour orange neroli, orange-blossom oil, bitter orange flower oil, citrus aurantium amara flower oil, and citrus aurantium flower oil) (Sigma Cat. No. W277126), |
| Compound 38 (Mixture) | Citronella oil (Sigma Cat. No. W230840), |
| Compound 39 (Mixture) | Geranium oil (also referred to as Geranium oil Algerian, oil of Geranium, oil of pelargonium, oil of rose geranium, Pelargonium oil, and Rose geranium oil Algerian) (Sigma Cat. No. W250813), |
| Compound 40 (Mixture) | Geranium East Indian oil (also referred to as palmarosa oil, Indian grass oil, oil of Geranium (East Indian), Palmarosa oil, Rusa oil, and Turkish geranium oil) (Sigma Cat. No. W283109), |
| Compound 41 | 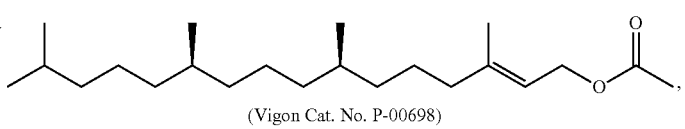
(Vigon Cat. No. P-00698) | or a comestibly or biologically acceptable salt or derivative thereof, or an enantiomer or diastereomer thereof.

Edible Compositions Comprising Chroman Compounds

The substituent definitions in this section (i.e., $R^1$, $R^2$, $R^3$, $R^4$, $R^5$, $R^6$ and n) refer to compounds of Formula (V), Formula (VIa), Formula (VIb), or Formula (VIIa).

All stereochemical forms of the compounds disclosed in this and any section herein are specifically contemplated, including geometric isomers (i.e., E, Z) and optical isomers (i.e., R, S). Single stereochemical isomers as well as enantiomeric and diastereomeric mixtures of the compounds disclosed in this and any section herein are also specifically contemplated.

In some embodiments, the present invention provides an edible composition for reducing bitter taste of a bitter tastant, wherein the composition comprises a chroman compound. The chroman compounds of this invention are capable of reducing or eliminating bitter taste of a bitter tastant. In some embodiments, the chroman compound has a molecular weight less than about 1000, 500, or 300 daltons. In certain embodiments, the chroman compound is a compound of Formula (V);

Formula (V)

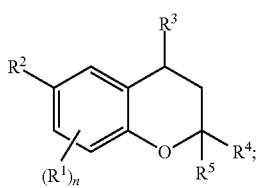

or a comestibly or biologically acceptable salt or derivative thereof, or an enantiomer or diastereomer thereof.

wherein, as valence and stability permit:

$R^1$, independently for each occurrence, is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{2-10}$acyloxy, $C_{1-10}$carbonate, $C_{1-10}$alkoxy, phenyloxy, phenyl-$C_{1-6}$alkyloxy, $C_{3-5}$heteteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-10}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$ alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^2$ is selected from the group consisting of hydrogen, $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^3$ is selected from the group consisting of hydrogen $C_{1-10}$alkyl, $C_{1-10}$haloalkyl, $C_{2-10}$alkenyl, $C_{2-10}$alkynyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^4$ is selected from the group consisting of hydrogen, $C_{1-21}$alkyl, $C_{1-21}$haloalkyl, $C_{2-21}$alkenyl, $C_{2-21}$alkynyl, hydroxyl, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, amino, di$C_{1-10}$alkylamino, mono$C_{1-10}$alkylamino, sulfhydryl, $C_{1-10}$alkylthio, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S;

$R^5$ is selected from the group consisting of hydrogen, $C_{1-21}$alkyl, $C_{1-21}$haloalkyl, $C_{2-21}$alkenyl, $C_{2-21}$alkynyl, hydroxyl, $C_{1-10}$acyloxy, $C_{1-10}$alkoxy, phenyloxy, phenyl-$C_{1-6}$alkyloxy, $C_{1-5}$heteroaryloxy, $C_{1-5}$heteroaryl-$C_{1-6}$alkyloxy, $C_{3-10}$alkenyloxy, amino, di$C_{1-10}$alkylamino, mono$C_{1-10}$alkylamino, sulfhydryl, $C_{1-10}$alkylthio, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S;

or $R^4$ and $R^5$ together form =O or —O—$C_{1-10}$alkyl-O—;

wherein any of $R^1$, $R^2$, $R^3$, and $R^4$, and $R^5$ independently and independently for each occurrence, is optionally substituted with 1-3 substituents selected from the group consisting of $C_{1-10}$alkyl, $C_{1-10}$haloalkyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S; and n is 0-3.

According to some embodiments of compounds of Formula V, as valence and stability permit:

$R^1$, independently occurrence, is selected from the group consisting of halo, hydroxyl, $C_{1-6}$alkyl, $C_{1-6}$alkyl, $C_{2-6}$alkenyl, $C_{2-6}$alkynyl, and $C_{1-6}$alkoxy;

$R^2$ is selected from the group consisting of hydrogen, halo, hydroxyl, $C_{1-6}$alkyl, $C_{1-6}$haloalkyl, $C_{2-6}$alkenyl, $C_{2-6}$alkynyl, $C_{1-6}$alkoxy, $C_{1-6}$acyloxy optionally substituted by hydroxyl, amino, mono- or disubstituted $C_{1-6}$amino, or carboxyl;

$R^3$ is selected from the group consisting of hydrogen, hydroxyl, $C_{1-6}$alkyl. $C_{2-6}$alkenoyl, $C_{2-6}$alkynyl, and $C_{1-6}$alkoxy;

$R^4$ is selected from the group consisting of hydrogen, hydroxyl, $C_{1-21}$alkyl, $C_{2-21}$alkenyl, $C_{2-21}$alkynyl, and $C_{1-4}$alkoxy, wherein $R^4$ is optionally substituted by one or more occurrences of hydroxyl or acetyloxy;

$R^5$ is selected from the group consisting of hydrogen, hydroxyl, $C_{1-21}$alkyl, $C_{2-21}$alkenyl, $C_{2-21}$alkynyl, and $C_{1-4}$alkoxy, wherein $R^5$ is optionally substituted by one or more occurrences of hydroxyl or acetyloxy;

or $R^4$ and $R^5$ together form =O;

wherein any of $R^1$, $R^2$, $R^3$, $R^4$, and $R^5$, independently and independently for each occurrence, is optionally further substituted as noted above; and n is 0-3.

According to some embodiments of the compound of Formula (V), one or more occurrences of $R^1$ is $C_{1-6}$alkyl, such as methyl; $R^2$ is hydrogen; and $R^5$ is $C_{1-6}$alkyl, such as methyl. For example, in certain embodiments, the compound of Formula (V) is a compound of Formula (VIa):

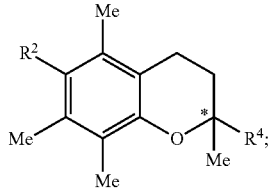

Formula (VIa)

or a comestibly or biologically acceptable salt or derivative thereof, or an enantiomer or diastereomer thereof, wherein, as valence and stability permit, $R^2$ and $R^4$ are as defined above, wherein the carbon marked with * optionally has R or S stereochemistry or is a mixture of R and S stereochemistry.

According to some embodiments, $R^2$ is hydroxyl; $C_{1-6}$alkoxy; or $C_{1-6}$acyloxy optionally substituted by hydroxyl, amino, mono- or disubstituted $C_{1-6}$alkyl amino, or carboxyl; and $R^4$ is $C_{1-21}$alkyl, such as methyl or —$CH_2$ISP wherein ISP represents 1 to 4 saturated isoprene units (particularly 3 isoprene units), or $C_{2-21}$alkenyl, such as —$CH_2$ISP wherein ISP represents 1 to 4 isoprene units wherein one or more isoprene unit optionally includes a carbon-carbon double bond.

For example, in certain embodiments, the compound of Formula (VIa) is a compound Formula (VIIa);

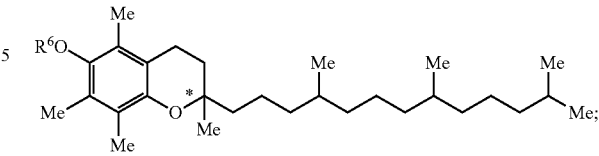

Formula (VIIa)

or a comestibly or biologically acceptable salt or derivative thereof, or an enantiomer or diastereomer thereof, wherein, as valence and stability permit:

$R^6$ is selected from the group consisting of hydrogen, $C_{1-6}$alkyl; or $C_{1-6}$acyl optionally substituted by hydroxyl, amino, mono- or disubstituted $C_{1-6}$alkyl amino, or carboxyl; and wherein the carbon marked with * optionally has R or S stereochemistry or is a mixture of R and S stereochemistry.

In certain embodiments, $R^6$ is hydrogen. In other embodiments, $R^6$ is $C_{1-6}$acyl, such as acetyl or propionyl, optionally substituted by hydroxyl, amino, mono- or disubstituted $C_{1-6}$alkyl amino, or carboxyl. For example, in certain embodiments, $R^6$ is carboxyl-substituted propionyl, such as 3-carboxylpropionyl. In some embodiments, $R^6O$— is succinate.

In certain embodiments, the compound of Formula (V) is:

Compound 42

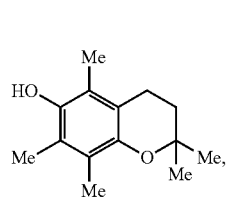

(Sigma Cat No. 430676)

Compound 43

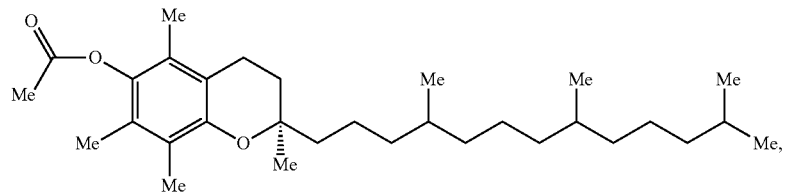

(Sigma Cat No. 90669)

Compound 44

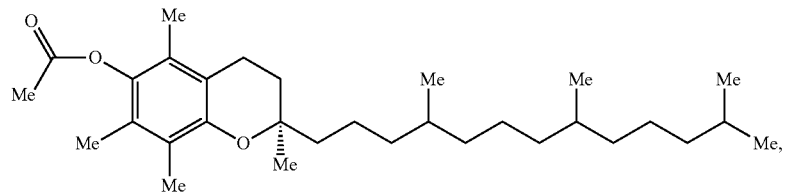

(Sigma Cat No. 248177)

Compound 45

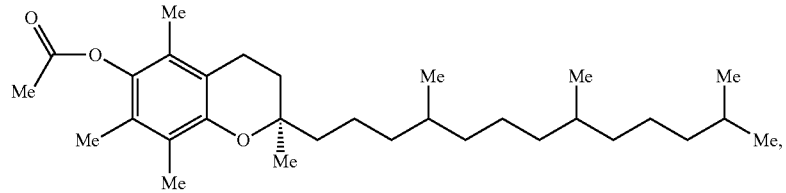

(Sigma Cat. No. T1157)

Compound 46

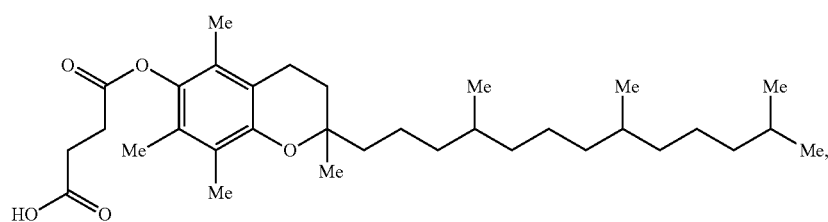

Compound 47

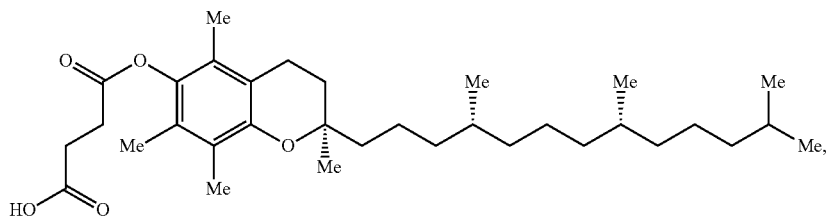

(Sigma Cat No. W381101)

Compound 48

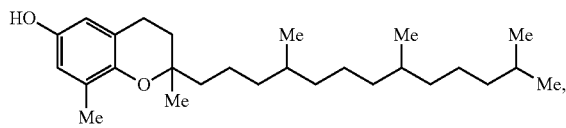

Compound 49

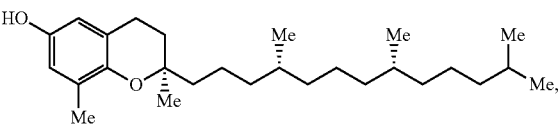

(Sigma Cat No. T2028)

Compound 50

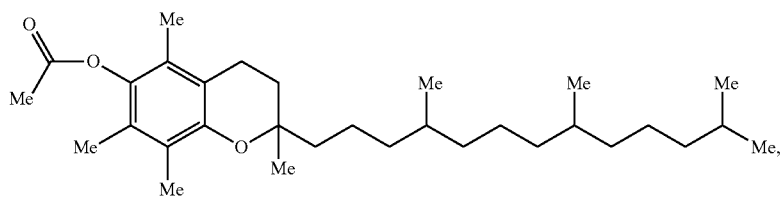

(Sigma Cat No. T3376)

Compound 51

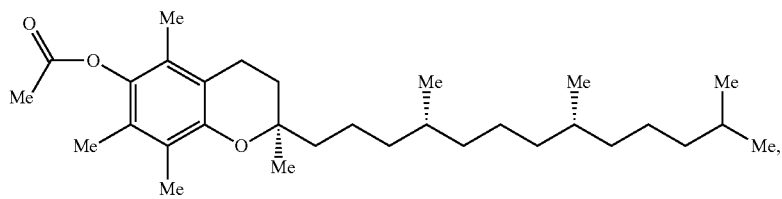

or a comestibly or biologically acceptable salt or derivative thereof, or an enantiomer or diastereomer thereof.

In certain embodiments, the compound of Formula (V) is selected from the group consisting of pentamethyl-6-chromanol, α-tocopherol, (+)-δ-tocopherol, (+)-α-tocopherol acetate, D-α-tocopherol succinate, DL-α-tocopherol acetate, and Vitamin E acetate.

According to some embodiments of the compound of Formula (V), n is 0 and $R^2$ is hydrogen. For example, in certain embodiments, the compound of Formula (V) is a compound of Formula (VIb):

Formula (VIb)

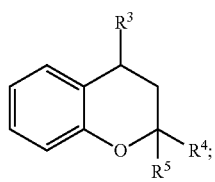

or a comestibly or biologically acceptable salt or derivative thereof, or an enantiomer or diastereomer thereof wherein, as valence and stability permit, $R^3$, $R^4$, and $R^5$ are as defined above.

In some embodiments, $R^3$ is hydrogen. In other embodiments, $R^3$ hydroxyl.

According to certain embodiments, one or both of $R^4$ and $R^5$ is hydrogen, for example, both $R^4$ and $R^5$ are hydrogen. In other embodiments, $R^4$ and $R^5$ together form $=O$.

In certain embodiments, the compound of Formula (V) or Formula (VIb) is:

Compound 52

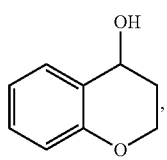

(Sigma Cat No. 303895)

Compound 53

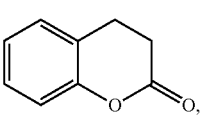

(Sigma Cat No. W238104)

or a comestibly or biologically acceptable salt or derivative thereof, or an enantiomer or diastereomer thereof.

In certain embodiments, the compound of Formula (V) or Formula (VIb) is selected from the group consisting of 4-chromanol and dihydrocoumarin.

Edible Compositions Comprising Benzo Ring-Containing Compounds

The substituent definitions in this section (i.e., R1, R2, R3, R4, m, and n) refer to compounds of Formula (VII), Formula (IXa), Formula (IXb), or Formula (IXc), or Formula (IXd).

All stereochemical forms of the compounds disclosed in this and any section herein are specifically contemplated, including geometric isomers (i.e. E, Z) and optical isomers (i.e., R, S). Single stereochemical isomers as well as enantiomeric and diastereomeric mixtures of the compounds disclosed in this and any section herein are also specifically contemplated.

In some embodiments, the present invention provides an edible composition for reducing bitter taste of a bitter tastant, wherein the composition comprises a benzo-ring-containing compound. The benzo-ring-containing compounds of this invention are capable of reducing or eliminating bitter taste of a bitter tastant. In some embodiments, the benzo-ring-containing compound has a molecular weight less than about 1000, 500, or 300 daltons. In certain embodiments, the benzo-ring-containing compound is a compound of Formula (VIII):

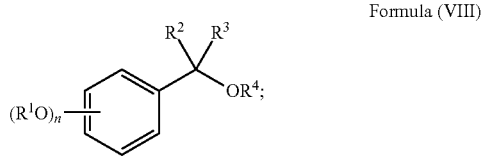

Formula (VIII)

or a comestibly or biologically acceptable salt or derivative thereof, or an enantiomer or diastereomer thereof,
wherein, as valence and stability permit:
$R^1$, independently for each occurrence, is selected from the group consisting of hydrogen, $C_{1-10}$alkyl, $C_{1-10}$haloalkyl, $C_{2-10}$alkenyl, $C_{2-10}$alkynyl, carboxyl, $C_{1-10}$alkoxycarbonyl, $C_{2-10}$alkenyloxycarbonyl, $C_{2-10}$alkynyloxycarbonyl, $C_{1-10}$acyl, phosphoryl, phosphonate, phosphinate, sulfonate, sulfamoyl, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroalkyl, and $C_{1-5}$heteroaryl-$C_{1-6}$alkyl, wherein heterocyclic or heteroaromatic rings, independently for each occurrence, comprise 1-4 heteroatoms selected from N, O, and S;

$R^2$ is selected from the group consisting of hydrogen, $C_{1-10}$alkyl, $C_{1-10}$haloalkyl, $C_{2-16}$alkenyl, $C_{2-16}$alkynyl, hydroxyl, $C_{1-10}$acyloxy, $C_{1-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, amino, di$C_{1-10}$alkylamino, mono$C_{1-10}$alkylamino, sulfhydryl, $C_{1-16}$alkylthio, $C_{3-7}$carbocyclyl, $C_{3-7}$carbocyclyl-$C_{1-6}$alkyl, $C_{1-6}$heterocyclyl, $C_{1-6}$heterocyclyl-$C_{1-6}$alkyl, phenyl, phenyl-$C_{1-6}$alkyl, $C_{1-5}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S;

$R^3$ is selected from the group consisting of hydrogen $C_{1-10}$alkyl, $C_{1-10}$haloalkyl, $C_{2-10}$alkenyl, $C_{2-10}$alkynyl, hydroxyl, $C_{3-10}$acyloxy, $C_{3-10}$alkoxy, phenyloxy, phenyl-$C_{1-6}$-alkyloxy, $C_{1-5}$heteroaryloxy, $C_{1-5}$heteroaryl-$C_{1-6}$alkyloxy, $C_{3-10}$alkenyloxy, $C_{3-10}$alkynyloxy, amino, di$C_{1-10}$alkylamino, mono$C_{1-10}$alkylamino, sulfhydryl, $C_{1-10}$alkylthio, $C_{3-7}$carbocyclyl, $C_{3-7}$carbocyclyl-$C_{1-6}$alkyl, $C_{1-6}$heterocyclyl, $C_{1-6}$heterocycl-$C_{1-6}$alkyl, phenyl, phenyl-$C_{1-6}$alkyl, $C_{1-5}$heteroaryl, and $C_{1-6}$heteroaryl-$C_{1-6}$alkyl, wherein heterocyclic or heteroaromatic rings, independently for each occurrence, comprise 1-4 heteroatoms selected from N, O, and S;

or $R^2$ and $R^3$ together form =O or —O—$C_{1-10}$alkyl-O—;

$R^4$ is selected from the group consisting of hydrogen, $C_{1-10}$alkyl, $C_{1-10}$haloalkyl, $C_{2-10}$alkenyl, $C_{2-10}$alkynyl, carboxyl, $C_{1-10}$alkoxycarbonyl, $C_{2-10}$alkenyloxycarbonyl, $C_{2-10}$alkynyloxycarbonyl, $C_{1-10}$acyl, phosphoryl, phosphonate, phosphinate, cyano, sulfonate, sulfamoyl, sulfonyl, $C_{3-7}$carbocyclyl, $C_{3-7}$carbocycyl-$C_{1-6}$alkyl, $C_{1-6}$heteroaryl, and $C_{1-5}$heteroaryl-$C_{1-6}$alkyl, wherein heterocyclic or heteroaromatic rings, independently for each occurrence, comprise 1-4 heteroatoms selected from N, O, and S;

wherein any of $R^1$, $R^2$, $R^3$, and $R^4$, and $R^5$ independently and independently for each occurrence, is optionally substituted with 1-3 substituents selected from the group consisting of $C_{1-10}$alkyl, $C_{1-10}$haloalkyl, halo, hydroxyl, carboxyl, $C_{1-10}$alkoxycarbonyl, $C_{2-10}$alkenyloxycarbonyl, $C_{2-10}$alkynyloxycarbonyl, $C_{1-10}$acyl, $C_{1-10}$acylamino, $C_{1-10}$acyloxy, $C_{1-10}$carbonate, $C_{1-10}$alkoxy, phenyloxy, phosphoryl, phosphate, phosphonate, phosphinate, amino, di$C_{1-10}$alkylamino, mono$C_{1-10}$alkylamino, $C_{1-13}$amido, $C_{1-10}$imino, $C_{1-10}$carbamate, $C_{1-10}$urea, cyano, nitro, azido, sulfhydryl, $C_{1-10}$alkylthio, sulfate, sulfonate, sulfamoyl, sulfonamido, sulfonyl, $C_{3-7}$carbocyclyl, $C_{3-7}$carbocyclyl-$C_{1-6}$alkyl, $C_{1-6}$heterocyclyl, $C_{1-6}$heterocycl-$C_{3-6}$alkyl, phenyl, phenyl-$C_{1-6}$alkyl, $C_{1-5}$heteroaryl, and $C_{3-5}$heteroaryl-$C_{3-6}$alkyl, wherein heterocyclic or heteroaromatic rings, independently for each occurrence, comprise 1-4 heteroatoms selected from N, O, and S; and n is 3.

According to some embodiments of compounds of Formula (VIII), as valence and stability permit;

$R^1$, independently for each occurrence, is selected from the group consisting of hydrogen, $C_{1-6}$alkyl, $C_{2-6}$alkenyl, $C_{2-6}$alkynyl, and $C_{1-6}$acyl;

$R^1$ is selected from the group consisting of hydrogen, $C_{1-6}$alkyl, $C_{2-6}$alkenyl, and $C_{2-6}$alkynyl;

$R^3$ is selected from the group consisting of hydrogen, $C_{1-10}$alkyl, $C_{2-10}$alkenyl, $C_{2-10}$alkynyl;

or $R^2$ and $R^3$ together form =O;

$R^4$ is selected from the group consisting of hydrogen, $C_{1-6}$alkyl, $C_{2-6}$alkenyl, $C_{2-6}$alkynyl, $C_{3-6}$acyl, and $C_{6-10}$aryl-$C_{1-6}$alkyl;

wherein any of $R^1$, $R^2$, $R^3$, and $R^4$, independently and independently for each occurrence, is optionally further substituted as noted above; and n is 0-3.

According to some embodiments of the compound of Formula (VIII), n is 0, and $R^2$ and $R^3$ together form =O. For example, in certain embodiments, the compound of Formula (VIII) is benzoic acid or a benzoic acid ester. For instance, in some embodiments, the compound of Formula (VIII) is a compound of Formula (IXa):

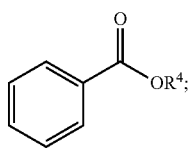

Formula (IXa)

or a comestibly or biologically acceptable salt or derivative thereof, or an enantiomer or diastereomer thereof wherein, as valence and stability permit, $R^4$ is as defined above.

In certain embodiments, $R^4$ is hydrogen. In other embodiments, $R^4$ is $C_{1-6}$alkyl, such as methyl, ethyl, propyl, or butyl, or $C_{3-10}$alkyl-$C_{1-6}$alkyl, such as phenyl-$C_{1-6}$alkyl, e.g., benzyl or dihydrocinnamyl.

In certain embodiments, the compound of Formula (VIII) or Formula (IXa) is:

Compound 54

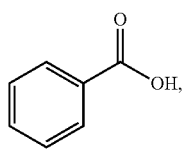

(Sigma Cat No. 12349)

Compound 55

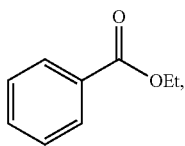

(Sigma Cat No. W242217)

Compound 56

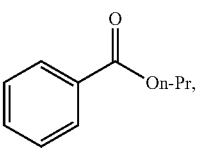

(Sigma Cat No. 307009)

Compound 57

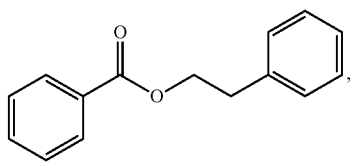

(Sigma Cat No. W286001)

or a comestibly or biologically acceptable salt or derivative thereof, or an enaotiomer or diastereomer thereof.

In certain embodiments, the compound of Formula (VIII) or Formula (IXa) is selected from the group consisting of benzoic acid, ethyl benzoate, propyl benzoate, and phenethyl benzoate.

According to some embodiments of the compound of Formula (VIII), n is 1-3, and $R^2$ and $R^3$ together form =O. For example, in certain embodiments, the compound of Formula (VIII) is a hydroxybenzoic acid or a hydroxybenzoic acid ester. For instance, in some embodiments, the compound of Formula (VIII) is a compound of Formula (IXb):

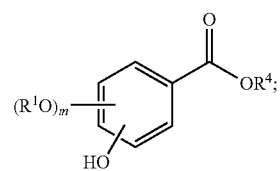

Formula (IXb)

or a comestibly or biologically acceptable salt or derivative thereof, or an enantiomer or diastereomer thereof,
  wherein, as valence and stability permit:
  $R^1$ and $R^2$ are as defined above; and
  m is 0-2.

In certain embodiments, the comported of Formula (VIII) or Formula (IXb) includes a hydroxyl group on the 4-position of the benzo ring. In other embodiments, the compound of Formula (VIII) or Formula (IXb) includes a hydroxyl group on 2-position of the benzo ring.

In certain embodiments, $R^4$ is hydrogen. In other embodiments, $R^4$ is $C_{1-6}$alkyl, such as methyl, ethyl, propyl, or butyl.

In certain embodiments, the compound of Formula (VIII) or Formula (IXb) is:

Compound 58

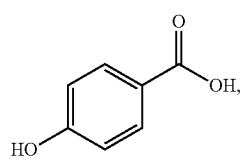

(Sigma Cat No. W398608)

Compound 59

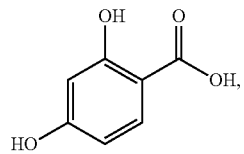

(Sigma Cat No. W379808)

Compound 60

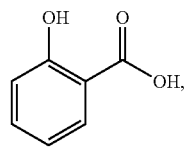

(Sigma Cat No. 84210)

Compound 61

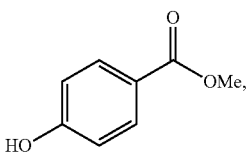

(Sigma Cat No. 54750)

Compound 62

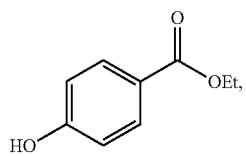

(Sigma Cat No. 111988)

Compound 63

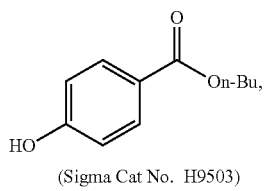

(Sigma Cat No. H9503)

or a comestibly or biologically acceptable salt or derivative thereof, or an enantiomer or diastereomer thereof.

In certain embodiments, the compound of Formula (VIII) or Formula (IXb) is selected from the group consisting of 4-hydroxybenzoic acid, methyl para-hydroxybenzoate, ethyl para-hydroxybenzoate, and butyl paraben.

According to some embodiments of the compound of Formula (VIII), n is 1-3, and $R^2$ and $R^3$ together form =O. For example, in certain embodiments, the compound of Formula (VIII) is a $C_{1-6}$alkylyloxybenzoic acid or a $C_{1-6}$alkylyloxybenzoic acid ester. For instance, in some embodiments, the compound of Formula (VIII) is a compound of Formula (IXc):

Formula (IXc)

$(R^1O)_m$—[benzene ring with $R^5O$ substituent]—C(=O)—$OR^4$;

wherein, as valence and stability permit:

$R^1$ and $R^2$ are as defined above; and $R^5$ is $C_{1-6}$alkyl; and m is 0-2.

In certain embodiments, $R^4$ is hydrogen. In other embodiments, $R^4$ is $C_{1-6}$alkyl, such a methyl.

In certain embodiments, $R^4$ is methyl, ethyl, or propyl. In some embodiments, the compound of Formula (VIII) or Formula (IXc) includes a methoxy group on the 4-position, the 3-position, or the 2-position of the benzo ring.

In certain embodiments, the compound of Formula (VIII) or Formula (IXc) is:

Compound 64

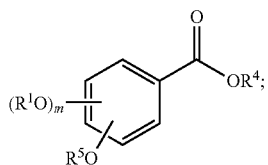

(Sigma Cat No. 117390)

Compound 65

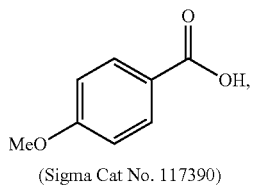

(Sigma Cat No. W394440)

Compound 66

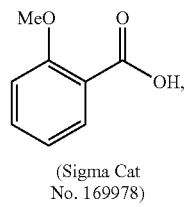

(Sigma Cat No. 169978)

Compound 67

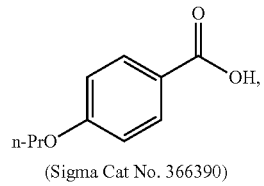

(Sigma Cat No. 366390)

Compound 68

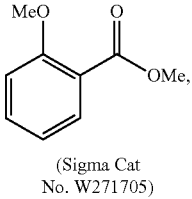

(Sigma Cat No. W271705)

or a comestibly or biologically acceptable salt or derivative thereof, or an enantiomer or diastereomer thereof.

In certain embodiments, the compound of Formula (VIII) or Formula (IXc) is selected from the group consisting of 4-methoxybenzenoic acid, 3-methoxybenzoic acid, 2-methoxybenzoic acid, 4-propoxybenzoic acid, and methyl-ortho-methoxy benzoate.

According to some embodiments of the compound of Formula (VIII), $R^2$ is hydrogen, and at least one occurrence of $R^1$ is H. For example, in certain embodiments, the compound of Formula (VIII) is a compound of Formula (IXd):

Formula (IXd)

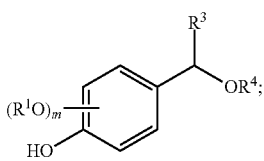

or a comestibly or biologically acceptable salt or derivative thereof, or an enantiomer or diastereomer thereof, wherein, as valence and stability permit:

$R^1$, $R^3$, and $R^4$ are as defined above; and m is 0-2.

In certain embodiments, $R^3$ is hydrogen. In other embodiments, $R^3$ is $C_{1-6}$alkyl, such as methyl.

In some embodiments, $R^4$ is hydrogen.

In certain embodiments, m is 0. In other embodiments, m is 1 or 2, and $R^1$ is $C_{1-6}$alkyl, such as methyl.

In certain embodiments, the compound of Formula (VIII) or Formula (IXd) is:

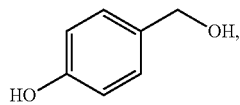

Compound 69

(Sigma Cat No. W398705)

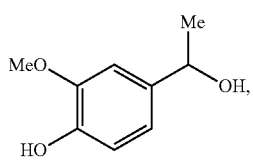

Compound 70

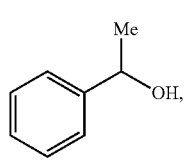

Compound 71

(Sigma Cat No. W268518)

or a comestibly or biologically acceptable salt or derivative thereof, or an enantiomer or diastereomer thereof.

In certain embodiments, the compound of Formula (VIII) or Formula (IXd) is selected from the group consisting of para-hydroxybenzyl alcohol, α-methylbenzyl alcohol, and 4-(1-hydroxyethyl)-2-methoxyphenol.

Edible Compositions Comprising Polycyclic Compounds

The substituent definitions in this section (i.e., R1, R2, R3, R4, $R^5$, $R^6$, $R^7$, and $R^a$, X and Y) refer to compounds of Formula (XI) or Formula (XII).

All stereochemical forms of the compounds disclosed in this and any section herein are specifically contemplated, including geometric isomers (i.e. E, Z) and optical isomers (i.e., R, S). Single stereochemical isomers as well as enantiomeric and diastereomeric mixtures of the compounds disclosed in this and any section herein are also specifically contemplated.

In some embodiments, the present invention provides an edible composition for reducing bitter taste of a bitter tastant, wherein the composition comprises a terpenoid compound. The polycyclic compounds of this invention are capable of reducing or eliminating bitter taste of a bitter tastant. In some embodiments, the polycyclic compound has a molecular weight less than about 1000, 500, 300 or 200 daltons. In certain embodiments, the polycyclic compound has a bicyclic core with a one-carbon transannular bridge, such as a compound of Formula (XI):

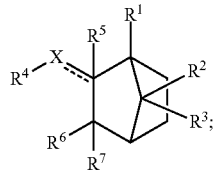

Formula (XI)

or a comestibly or biologically acceptable salt or derivative thereof, or an enantiomer or diastereomer thereof.

wherein, as valence and stability permit:
the bond with a dotted line optionally represents a single or double bond, $R^1$, $R^2$, $R^3$, $R^6$, and $R^7$ are independently selected from the group consisting of hydrogen, $C_{1-10}$alkyl, $C_{2-10}$alkenyl, and $C_{2-10}$alkynyl.

wherein each of $R^1$, $R^2$, $R^3$, $R^6$, and $R^7$ may be optionally independently substituted with one or more substituents selected from the group consisting of halo, —OH, =O, —SH, =S, —NH$_2$, —CO$_2$H, —O(C$_{2-10}$alkyl), —O(C$_{2-10}$alkenyl), —O(C$_{2-10}$alkynyl), —S(C$_{1-10}$alkyl), —S(C$_{2-10}$alkenyl), —S(C$_{2-10}$alkynyl), —NH(C$_{1-10}$alkyl), —NH(C$_{2-10}$alkenyl), —NH(C$_{2-10}$alkynyl), —N(C$_{1-10}$alkyl)$_2$, —N(C$_{2-10}$alkenyl)$_2$, and —N(C$_{2-10}$alkynyl)$_2$, and $R^4$ is absent or selected from the group consisting of hydrogen, $C_{1-10}$alkyl, $C_{1-10}$alkenyl, $C_{2-10}$alkynyl, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester, $C_{1-10}$alkylamide, $C_{1-10}$alkenylamide, $C_{1-10}$alkynylamide, $C_{1-10}$alkylthioester, $C_{1-10}$alkenylthioester, and $C_{1-10}$alkynylthioester;

wherein $R^2$ may be optionally substituted with one or more substituents selected from the group consisting of halo, —OH, =O, —SH, =S, —NH$_2$, —CO$_2$H, —O(C$_{1-10}$alkyl), —O(C$_{2-10}$alkenyl), —O(C$_{2-10}$alkynyl), —S(C$_{1-10}$alkyl), —S(C$_{2-10}$alkenyl), —S(C$_{2-10}$alkynyl), —NH(C$_{1-10}$alkyl), —NH(C$_{2-10}$alkenyl), —NH(C$_{2-10}$alkynyl), —N(C$_{1-10}$alkyl)$_2$, —N(C$_{2-10}$alkenyl)$_2$, —N(C$_{2-10}$alkynyl)$_2$, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester, $C_{1-10}$alkylamide, $C_{1-10}$alkenylamide, $C_{1-10}$alkynylamide, $C_{1-10}$alkylthioester, $C_{1-10}$alkenylthioester, and $C_{1-10}$alkynylthioester, $R^5$ is absent or selected from the group consisting of hydrogen, $C_{1-10}$alkyl, $C_{2-10}$alkenyl, and $C_{2-10}$alkynyl, wherein $R^5$ may be optionally independently substituted with one or more substituents selected from the group consisting of halo, —OH, =O, —SH, =S, —NH$_2$, —CO$_2$H, —O(C$_{1-10}$alkyl), —O(C$_{2-10}$alkenyl), —O(C$_{2-10}$alkynyl), —S(C$_{1-10}$alkyl), —S(C$_{2-10}$alkenyl), —S(C$_{2-10}$alkynyl), —NH(C$_{1-10}$alkyl), —N(C$_{1-10}$alkenyl), —NH(C$_{2-10}$alkynyl), —N(C$_{1-10}$alkyl), —N(C$_{1-10}$alkenyl)$_2$, and —N(C$_{1-10}$alkynyl)$_2$;

wherein $R^6$ and $R^7$ are optionally taken together to form =O, =S or =C($R^a$)$_2$;

wherein each $R^a$ is independently selected from the group consisting of hydrogen, $C_{1-10}$alkyl, $C_{1-10}$alkenyl, and $C_{1-10}$alkynyl, wherein each $C_{1-10}$alkyl, $C_{2-10}$alkenyl, and $C_{2-10}$alkynyl may be optionally independently substituted with one or more substituents selected from the group consisting of halo, —OH, =O, —SH, =S, —NH$_2$, —CO$_2$H, —O(C$_{1-10}$alkyl), —O(C$_{2-10}$alkenyl), —O(C$_{2-10}$alkynyl), —S(C$_{1-10}$alkyl), —S(C$_{2-10}$alkenyl), —S(C$_{2-10}$alkynyl), —NH(C$_{1-10}$alkyl), —N(C$_{1-10}$alkenyl), —NH(C$_{2-10}$alkynyl), —N(C$_{1-10}$alkyl), —N(C$_{2-10}$alkenyl)$_2$, and —N(C$_{2-10}$alkynyl)$_2$;

wherein when the bond with the dotted line represents a double bond and $R^4$ is present, X is selected from the group consisting of =C($R^a$)— and =N—;

wherein when the bond with the dotted line represents a double bond and $R^4$ is absent, X is selected from the group consisting of =O =S; and wherein when the bond with the dotted line represents a single bond, X is selected from the group consisting of —C($R^a$)$_2$—, —N($R^a$)—, —O—, and —S—;

provided that when the bond with the dotted line represents a double bond, $R^3$ is absent, and when the bond with the dotted line represents a single bond, $R^4$ is present.

According to some embodiments of Formula (XI), as valence and stability permit:

$R^1$, $R^2$, $R^3$, $R^6$, and $R^7$ are independently selected from the group consisting of hydrogen, $C_{1-10}$alkyl, $C_{2-10}$alkenyl, and $C_{2-10}$alkynyl.

$R^4$ is absent or selected from the group consisting of hydrogen, $C_{1-10}$alkyl, $C_{1-10}$alkenyl, $C_{2-10}$alkynyl, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester;

$R^5$ is absent or selected from the group consisting of hydrogen, $C_{1-6}$alkyl, $C_{2-6}$alkenyl, and $C_{2-6}$alkynyl;

wherein $R^6$ and $R^7$ are optionally taken together to form $=O$, $=S$ or $=C(R^a)_2$;

wherein each of $R^1$, $R^2$, $R^3$, $R^6$, $R^7$, and $R^a$ are independently optionally substituted as noted above;

wherein when the bond with the dotted line represents a double bond and $R^4$ is present, X is selected from the group consisting of $=C(R^a)-$ and $=N-$;

wherein when the bond with the dotted line represents a double bond and $R^4$ is absent, X is selected from the group consisting of $=O$ $=S$; and wherein when the bond with the dotted line represents a single bond, X is selected from the group consisting of $-C(R^a)_2-$, $-N(R^a)-$, $-O-$, and $-S-$;

provided that when the bond with the dotted line represents a double bond, $R^5$ is absent, and when the bond with the dotted line represents a single bond, $R^4$ is present.

According to some embodiments of Formula (XI), as valence and stability permit;

$R^1$, $R^2$, $R^3$, $R^6$, and $R^7$ are independently selected from the group consisting of hydrogen, $C_{1-6}$alkyl, $C_{2-16}$alkenyl, and $C_{2-6}$alkynyl;

$R^4$ is absent or selected from the group consisting of hydrogen, $C_{1-10}$alkyl, $C_{1-10}$alkenyl, $C_{2-10}$alkynyl, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester;

wherein $R^4$ may be optionally substituted with one or more substituents selected from the group consisting of $-OH$, $=O$, $-SH$, $=S$, $R^5$ is absent or selected from the group consisting of hydrogen, $C_{1-6}$alkyl, $C_{2-6}$alkenyl, and $C_{2-6}$alkynyl;

wherein $R^6$ and $R^7$ are optionally taken together to form $=O$, $=S$ or $=C(R^a)_2$;

wherein each $R^a$ is independently selected from the group consisting of hydrogen, $C_{1-10}$alkyl, $C_{1-10}$alkenyl, and $C_{1-10}$alkynyl, wherein when the bond with the dotted line represents a double bond and $R^4$ is present, X is selected from the group consisting of $=C(R^a)-$ and $=N-$;

wherein when the bond with the dotted line represents a double bond and $R^4$ is absent, X is selected from the group consisting of $=O$ $=S$; and wherein when the bond with the dotted line represents a single bond, X is selected from the group consisting of $-C(R^a)_2-$, $-N(R^a)-$, $-O-$, and $-S-$;

provided that when the bond with the dotted line represents a double bond, $R^5$ is absent, and when the bond with the dotted line represents a single bond, $R^4$ is present.

According to some embodiments of Formula (XI), as valence and stability permit;

$R^1$, $R^2$, $R^3$, $R^6$, and $R^7$ are independently selected from the group consisting of hydrogen, $C_{1-6}$alkyl, $C_{2-16}$alkenyl, and $C_{2-6}$alkynyl;

$R^4$ is absent or selected from the group consisting of hydrogen, $C_{1-6}$alkyl, $C_{2-6}$alkenyl, $C_{2-6}$alkynyl, and $C_{1-6}$acyl;

wherein $R^4$ may be optionally substituted with $=O$ or $=S$;

$R^5$ is absent or selected from the group consisting of hydrogen, $C_{1-3}$alkyl, $C_{2-3}$alkenyl, and $C_{2-3}$alkynyl;

wherein $R^6$ and $R^7$ are optionally taken together to form $=O$, $=S$ or $=C(R^a)_2$;

wherein each $R^a$ is independently selected from the group consisting of hydrogen, $C_{1-3}$alkyl, $C_{2-3}$alkenyl, and $C_{2-3}$alkynyl, wherein when the bond with the dotted line represents a double bond and $R^4$ is present, X is selected from the group consisting of $=C(R^a)-$ and $=N-$;

wherein when the bond with the dotted line represents a double bond and $R^4$ is absent, X is selected from the group consisting of $=O$ $=S$; and wherein when the bond with the dotted line represents a single bond, X is selected from the group consisting of $-C(R^a)_2-$, $-N(R^a)-$, $-O-$, and $-S-$;

provided that when the bond with the dotted line represents a double bond, $R^5$ is absent, and when the bond with the dotted line represents a single bond, $R^4$ is present.

In yet other embodiments of compounds of Formula (XI), as valence and stability permit;

$R^1$, $R^2$, $R^3$, $R^6$, and $R^7$ are independently selected from the group consisting of hydrogen, $C_{1-6}$alkyl, $C_{2-16}$alkenyl, and $C_{2-6}$alkynyl;

$R^4$ is absent or selected from the group consisting of hydrogen, $C_{1-6}$alkyl, $C_{2-6}$alkenyl, $C_{2-6}$alkynyl, and $C_{1-6}$acyl;

wherein $R^4$ may be optionally substituted with $=O$ or $=S$;

$R^5$ is absent or selected from the group consisting of hydrogen, $C_{1-3}$alkyl, $C_{2-3}$alkenyl, and $C_{2-3}$alkynyl;

wherein $R^6$ and $R^7$ are optionally taken together to form $=O$, $=S$ or $=C(R^a)_2$;

wherein each $R^a$ is independently selected from the group consisting of hydrogen, $C_{1-3}$alkyl, $C_{2-3}$alkenyl, and $C_{2-3}$alkynyl, wherein when the bond with the dotted line represents a double bond and $R^4$ is present, X is $=C(R^a)-$;

wherein when the bond with the dotted line represents a double bond and $R^4$ is absent, X is selected from the group consisting of $=O$ $=S$; and wherein when the bond with the dotted line represents a single bond, X is selected from the group consisting of $-C(R^a)_2-$ and $-O-$;

provided that when the dotted line represents a double bond, $R^5$ is absent, and when the bond with the dotted line represents a single bond, $R^4$ is present.

In some embodiments of Formula (XI), $R^1$ is selected from the group consisting of hydrogen, $C_{1-3}$alkyl, $C_{2-3}$alkenyl, and $C_{2-3}$alkynyl. In other embodiments, $R^1$ is methyl, ethyl or propyl, particularly methyl.

In some embodiments of Formula (XI), $R^2$ is selected from the group consisting of hydrogen, $C_{1-3}$alkyl), $C_{2-3}$alkenyl, and $C_{2-3}$alkynyl. In other embodiments, $R^2$ is methyl, ethyl or propyl, particularly methyl, In some embodiments of Formula (XI), $R^3$ is selected from the group consisting of hydrogen, $C_{1-3}$alkyl, $C_{2-3}$alkenyl, and $C_{2-3}$alkynyl. In other embodiments, $R^2$ is methyl, ethyl or propyl particularly methyl.

In some embodiments of Formula (XI), $R^4$ is absent or selected from the group consisting of hydrogen, $C_{1-3}$alkyl, $C_{2-3}$alkenyl, and $C_{2-3}$alkynyl, and $C_{2-6}$acyl, wherein $R^2$ may be optionally substituted with =O or =S. In other embodiments, $R^4$ is absent or $C_{1-6}$acyl. In yet other embodiments, $R^4$ is absent or $C_{3-5}$acyl.

In some embodiments of Formula (XI), $R^5$ is absent or selected from the group consisting of hydrogen, $C_{1-3}$alkyl, $C_{2-3}$alkenyl, and $C_{2-3}$alkynyl. In other embodiments, $R^5$ is absent, methyl, ethyl or propyl, particularly, absent, methyl or ethyl.

In some embodiments of Formula (XI), $R^6$ is selected from the group consisting of hydrogen, $C_{1-3}$alkyl, $C_{2-3}$alkenyl, and $C_{2-3}$alkynyl. In other embodiments, $R^6$ is methyl, ethyl or propyl, particularly methyl.

In some embodiments of Formula (XI), $R^7$ is selected from the group consisting of hydrogen, $C_{1-3}$alkyl, $C_{2-3}$alkenyl, and $C_{2-3}$alkynyl. In other embodiments, $R^7$ is methyl, ethyl or propyl, particularly methyl.

In some embodiments of Formula (XI), $R^6$ and $R^7$ are optionally taken together to form =O, =S or =C($R^a$)$_2$, wherein each $R^a$ is independently selected from the group consisting of hydrogen, $C_{1-3}$alkyl, $C_{2-3}$alkenyl, and $C_{2-3}$alkynyl. In other embodiments, $R^6$ and $R^7$ are optionally taken together to form =O or =C($R^a$)$_2$, wherein each $R^a$ is independently selected from the group consisting of hydrogen, $C_{1-3}$alkyl, $C_{2-3}$alkenyl. In yet other embodiments, $R^6$ and $R^7$ are optionally taken together to form =O or =C($R^a$)$_2$, wherein $R^a$ is hydrogen. In a particular embodiment, $R^6$ and $R^7$ are taken together to form =B($R^a$)—.

In some embodiments of Formula (XI), wherein the bond with the dotted line represents a double bond and $R^a$ is present, X is =C($R^a$)—;

In some embodiments of Formula (XI), wherein when the bond with the dotted line represents a double bond and $R^4$ is absent, X is selected from the group consisting of =O and =S. In other embodiments of Formula (XI), wherein when the bond with the dotted line represents a double bond and $R^4$ is absent, X is selected from the group consisting of =O and =S. In yet other embodiments of Formula (XI), wherein when the bond with the dotted line represents a double bond and $R^4$ is absent, X is =O.

In some embodiments of Formula (XI), wherein when the bond with the dotted line represents a single bond, X is selected from the group consisting of =C($R^a$)$_2$— and —O—.

In certain embodiments, the compound of Formula (XI) is one or more of the following compounds:

Compound 72

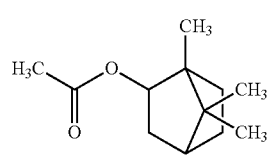

Compound 73

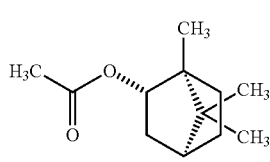

(Sigma Cat. No. W216003)

Compound 74

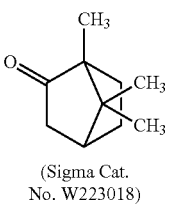

(Sigma Cat. No. W223018)

Compound 75

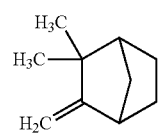

Compound 76

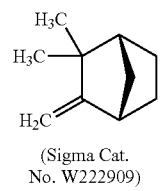

(Sigma Cat. No. W222909)

Compound 77

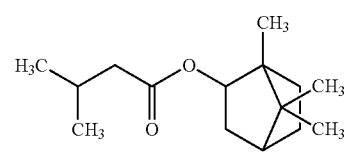

Compound 78

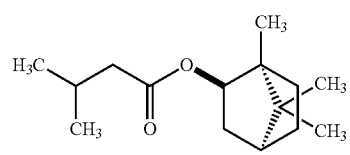

(Sigma Cat. No. W216518)

Compound 79

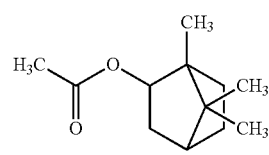

Compound 80

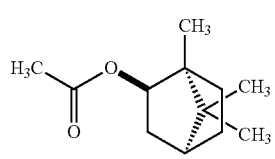

(Sigma Cat. No. W215902)

Compound 81

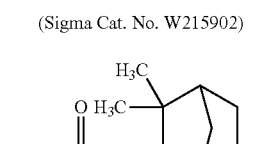

(Sigma Cat. No. W339008)

-continued

Compound 82
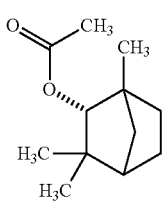

Compound 83
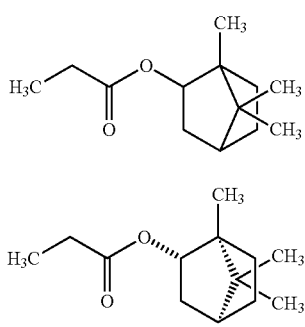

Compound 84

(Sigma Cat. No. W216305)

Compound 85
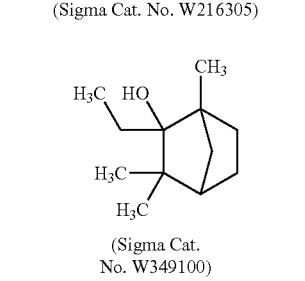

(Sigma Cat. No. W349100)

Compound 86
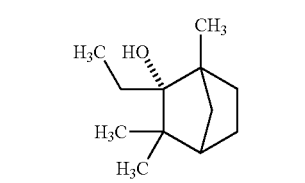

Compound 87
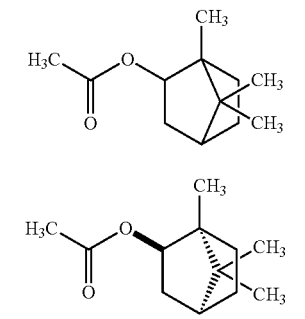

Compound 88

(Sigma Cat. No. B55203)

In certain embodiments, the polycyclic compound is a compound of Formula (XII):

Formula (XII)
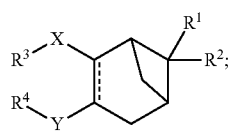

or a comestibly or biologically acceptable salt or derivative thereof, or an enantiomer or diastereomer thereof.

wherein, as valence and stability permit:
the bond with a dotted line optionally represents a single or double bond,
$R^1$ and $R^2$ are independently selected from the group consisting of hydrogen, $C_{1-10}$alkyl, $C_{2-10}$alkenyl, and $C_{2-10}$alkynyl.
  wherein $R^1$ and $R^2$ may be optionally independently substituted with one or more substituents selected from the group consisting of halo, —OH, =O, —SH, =S, —NH$_2$, —CO$_2$H, —O($C_{2-10}$alkyl), —O($C_{2-10}$alkenyl), —O($C_{2-10}$alkynyl), —S($C_{1-10}$alkyl), —S($C_{2-10}$alkenyl), —S($C_{2-10}$alkynyl), —NH($C_{1-10}$alkyl), —NH($C_{2-10}$alkenyl), —NH($C_{2-10}$alkynyl), —N($C_{1-10}$alkyl)$_2$, —N($C_{2-10}$alkenyl)$_2$, and —N($C_{2-10}$alkynyl)$_2$;
$R^3$ and $R^4$ are independently selected from the group consisting of hydrogen, $C_{1-10}$alkyl, $C_{1-10}$alkenyl, $C_{2-10}$alkynyl, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester, $C_{1-10}$alkylamide, $C_{1-10}$alkenylamide, $C_{1-10}$alkynylamide, $C_{1-10}$alkylthioester, $C_{1-10}$alkenylthioester, and $C_{1-10}$alkynylthioester;
  wherein each of $R^3$ and $R^4$ may be optionally substituted with one or more substituents selected from the group consisting of halo, —OH, =O, —SH, =S, —NH$_2$, —CO$_2$H, —O($C_{1-10}$alkyl), —O($C_{2-10}$alkenyl), —O($C_{2-10}$alkynyl), —S($C_{1-10}$alkyl), —S($C_{2-10}$alkenyl), —S($C_{1-10}$alkynyl), —NH($C_{1-10}$alkyl), —NH($C_{2-10}$alkenyl), —NH($C_{2-10}$alkynyl), —N($C_{1-10}$alkyl)$_2$, —N($C_{2-10}$alkenyl)$_2$, —N($C_{2-10}$alkynyl)$_2$, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester, $C_{1-10}$alkylamide, $C_{1-10}$alkenylamide, $C_{1-10}$alkynylamide, $C_{1-10}$alkenylamide, $C_{1-10}$alkynylamide, $C_{1-10}$alkylthioester, $C_{1-10}$alkenylthioester, and $C_{1-10}$alkynylthioester; and
X and Y are independently selected from the group consisting of a direct bond, $C_{1-10}$alkyl, $C_{2-10}$alkenyl, and $C_{2-10}$alkynyl, —N($R^a$)—, —O—, —S—, =O, and =S, provided that when X and Y is =O or =S, then $R^3$ and $R^4$, respectively, are absent,
  wherein $R^1$ is selected from the group consisting of hydrogen, $C_{1-10}$alkyl, $C_{2-10}$alkenyl, and $C_{2-10}$alkynyl;
    wherein each $C_{1-10}$alkyl, $C_{2-10}$alkenyl, and $C_{2-10}$alkynyl may be optionally independently substituted with one or more substituents selected from the group consisting of halo, —OH, =O, —SH, =S, —NH$_2$, —CO$_2$H, —O($C_{1-10}$alkyl), —O($C_{2-10}$alkenyl), —O($C_{2-10}$alkynyl), —S($C_{1-10}$alkyl), —S($C_{2-10}$alkenyl), —S($C_{2-10}$alkynyl), —NH($C_{1-10}$alkyl), —NH($C_{2-10}$alkenyl), —NH($C_{2-10}$alkynyl), —N($C_{1-10}$alkyl), —N($C_{2-10}$alkenyl)$_2$, —N($C_{2-10}$alkynyl), NH($C_{1-10}$alkyl)$_2$, —N($C_{2-10}$alkenyl)$_2$, and —N($C_{2-10}$alkynyl)$_2$.
According to other embodiments of Formula (XII), as valence and stability permit,
the bond with a dotted line optionally represents a single or double bond,
$R^1$ and $R^2$ are independently selected from the group consisting of hydrogen, $C_{1-10}$alkyl, $C_{2-10}$alkenyl, and $C_{2-10}$alkynyl;
$R^3$ and $R^4$ are independently selected from the group consisting of hydrogen, $C_{1-10}$alkyl, $C_{1-10}$alkenyl, $C_{2-10}$alkynyl, $C_{1-10}$acyl, $C_{1-10}$acyloxy, $C_{1-10}$acylamino, $C_{1-10}$acylthioxy, $C_{1-10}$alkylester, $C_{1-10}$alkenylester, $C_{1-10}$alkynylester;
wherein any of $R^1$, $R^2$, $R^3$, $R^4$, and $R^5$, independently and independently for each occurrence, is optionally further substituted as noted above; and wherein R¹ is selected from the group consisting of hydrogen, $C_{1-10}$alkyl, $C_{2-10}$alkenyl, and $C_{2-10}$alkynyl.

According to other embodiments of Formula (XII),
wherein, as valence and stability permit:
the bond with a dotted line optionally represents a single or double bond,
R¹ and R² are independently selected from the group consisting of hydrogen, $C_{1-6}$alkyl, $C_{2-6}$alkenyl, and $C_{2-6}$alkynyl;
R³ and R⁴ are independently selected from the group consisting of hydrogen, $C_{1-6}$alkyl, $C_{1-6}$alkenyl, $C_{2-6}$alkynyl, $C_{1-6}$acyl, $C_{1-6}$acyloxy, $C_{1-6}$alkylester, $C_{1-6}$alkenylester, and $C_{1-6}$alkynylester;
  wherein each of R³ and R⁴ may be optionally independently substituted with one or more substituents selected from the group consisting of —OH, =O, —SH, =S, $C_{1-4}$acyloxy, $C_{1-6}$acylthioxy, $C_{1-4}$alkylester, $C_{1-4}$alkenylester; $C_{1-4}$alkynylester; $C_{1-10}$alkylthioester, $C_{1-10}$alkenylthioester, and $C_{1-10}$alkynylthioester;
X and Y are independently selected from the group consisting of a direct bond, $C_{1-6}$alkyl, $C_{2-6}$alkenyl, and $C_{2-6}$alkynyl, —N(R$^a$)—, —O—, —S—, =O, and =S, provided that when X and Y is =O or =S, then R³ and R⁴, respectively, are absent, and
  wherein R¹ is selected from the group consisting of hydrogen, $C_{1-6}$alkyl, $C_{2-6}$alkenyl, and $C_{2-6}$alkynyl.

According to other embodiments of Formula (XII),
wherein, as valence and stability permit:
the bond with a dotted line optionally represents a single or double bond,
R² and R³ are independently selected from the group consisting of hydrogen, $C_{1-4}$alkyl, $C_{2-4}$alkenyl, and $C_{2-4}$alkynyl;
R³ and R⁴ are independently selected from the group consisting of hydrogen, $C_{1-4}$alkyl, $C_{1-4}$alkenyl, $C_{2-4}$alkynyl, $C_{1-4}$acyl;
  wherein each of R³ and R⁴ may be optionally independently substituted with one or more substituents selected from the group consisting of —OH, =O, —SH, =S, $C_{1-4}$acyloxy, $C_{1-4}$acylthioxy, $C_{1-4}$alkylester, $C_{1-4}$alkenylester; $C_{1-4}$alkynylester; $C_{1-4}$alkylthioester, $C_{1-4}$alkenylthioester, and $C_{1-4}$alkynylthioester; and
X and Y are independently selected from the group consisting of a direct bond, $C_{1-6}$alkyl, $C_{2-6}$alkenyl, $C_{2-6}$alkynyl, —O—, S—, =O, and =S, provided that when either X or Y is =O or =S, then R³ and R⁴, respectively, are absent.

According to other embodiments of Formula (XII),
wherein, as valence and stability permit:
the bond with a dotted line optionally represents a single or double bond,
R¹ and R² are independently selected from the group consisting of hydrogen, $C_{1-4}$alkyl, $C_{2-4}$alkenyl, and $C_{2-4}$alkynyl;
R³ and R⁴ are independently selected from the group consisting of hydrogen, $C_{1-4}$alkyl, $C_{1-4}$alkenyl, and $C_{2-4}$alkynyl, $C_{1-4}$acyl;
  wherein each of R³ and R⁴ may be optionally independently substituted with one or more substituents selected from the group consisting of —OH, =O, —SH, =S, $C_{1-4}$acyloxy, $C_{1-4}$acylthioxy, $C_{1-4}$alkylester, $C_{1-4}$alkenylester; $C_{1-4}$alkynylester; $C_{1-4}$alkylthioester, $C_{1-4}$alkenylthioester, and $C_{1-4}$alkynylthioester; and
X and Y are independently selected from the group consisting of a direct bond, $C_{1-4}$alkyl, $C_{2-4}$alkenyl, $C_{2-4}$alkynyl, —O—, S—, =O, and =S, provided that when either X or Y is =O or =S, then R³ and R⁴, respectively, are absent.

In some embodiments of Formula (XII), R¹ is selected from the group consisting of hydrogen, $C_{1-4}$alkyl, $C_{2-4}$alkenyl, and $C_{2-4}$alkynyl. In other embodiments, R¹ is hydrogen or $C_{1-4}$alkyl, preferably methyl.

In some embodiments of Formula (XII), R² is selected from the group consisting of hydrogen, $C_{1-4}$alkyl, $C_{2-4}$alkenyl, and $C_{2-4}$alkynyl. In other embodiments, R² is hydrogen or $C_{1-4}$alkyl, preferably methyl.

In some embodiments of Formula (XII), R³ is selected from the group consisting of hydrogen, $C_{1-4}$alkyl, $C_{2-4}$alkenyl, $C_{2-4}$alkynyl, and $C_{1-10}$acyl, wherein R³ may be optionally substituted with one or more substituents selected from the group consisting of —OH, =O, —SH, =S, $C_{1-4}$acyloxy, $C_{1-4}$alkylester, $C_{1-4}$alkenylester, $C_{1-4}$alkynylester. In other embodiments of Formula (XII), R³ is hydrogen or $C_{1-4}$alkyl, wherein R³ may be optionally substituted with one or more substituents selected from the group consisting of —OH, =O, —SH, =S, $C_{1-4}$acyloxy. In yet other embodiments of Formula (II), R³ is hydrogen or $C_{1-4}$alkyl, such as methyl, wherein R³ may be optionally substituted with one or more substituents selected from the group consisting of —OH or $C_{1-4}$acyloxy. In some embodiments, R³ is methyl, methyl substituted with —OH or methyl substituted with acetate.

In some embodiments of Formula (XII), R⁴ is selected from the group consisting of $C_{1-4}$alkyl, $C_{2-4}$alkenyl, $C_{2-4}$alkynyl, and $C_{1-10}$acyl, wherein R⁴ may be optionally substituted with one or more substituents selected from the group consisting of —OH, =O, —SH, =S, In other embodiments of Formula (XII), R³ is hydrogen or $C_{1-4}$alkyl, wherein R⁴ may be optionally substituted with one or more substituents selected from the group consisting of —OH, =O, —SH, =S, $C_{1-4}$acyloxy. In yet other embodiments of Formula (II), R⁴ is hydrogen or $C_{1-4}$alkyl, such as methyl, wherein R⁴ may be optionally substituted with one or more substituents selected from the group consisting of —OH, or $C_{1-4}$acyloxy. In yet other embodiments, R⁴ is hydrogen.

In some embodiments of Formula (XII), X is selected from the group consisting of a direct bond, $C_{1-4}$alkyl, $C_{2-4}$alkenyl, $C_{2-4}$alkynyl, —O—, —S—, =O, and =S, provided that when either X or Y is =O or =S, then R³ and R⁴, respectively, are absent. In other embodiments. X is selected from the group consisting of a direct bond, —O—, —S—, =O, and =S, provided that when either X or Y is =O or =S, then R³ and R⁴, respectively, are absent. In other embodiments, Y is selected from the Y is selected from the group consisting of a direct bond, —O—, —S—, =O, and =S, provided that when either when Y is =O or =S, then R³ is absent. In yet other embodiments, Y is a direct bond, —O— or =O, particularly —O—.

In certain embodiments, the compound of Formula (XII) is one or more of the following compounds:

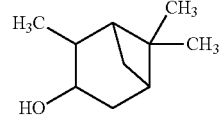

Compound 89

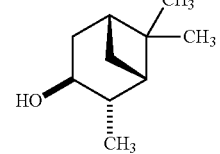

Compound 90

(Indofine Cat. No. 025468S)

Compound 91
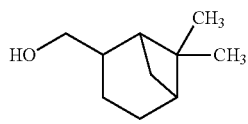
(Sigma Cat. No. 274178)

Compound 92
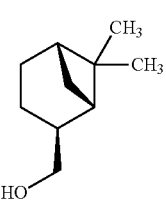

Compound 93
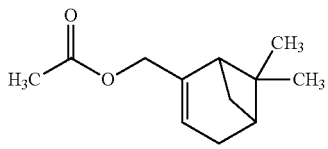

Compound 94
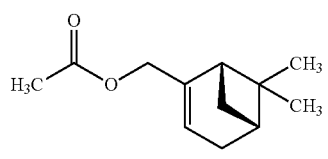
(Sigma Cat. No. W376507)

In certain embodiments, the compound of Formula (XI) or Formula (XII) is selected from the group consisting of Isopinocampheol, Myrtanol, Isobornyl acetate, D-camphor, (+)Camiphene, Myrtenyl acetate, Bornyl isovalerate, Bornyl acetate, 1,3,3 Trimethyl-2-Norbornanyl acetate, Isobornyl propionate, 2 Ethyl 1,3,3 Trimethyl 2 Norbornanol and L-Bornyl acetate.

Edible Compositions Comprising Additional Compounds of the Invention

The present invention includes edible compositions comprising the following compounds or comestibly or biologically acceptable salts or derivatives thereof, or enantiomers or diastereomers thereof. The structural similarity between some of the compounds below would be evident to one of skill in the art. Accordingly, the present invention also includes compounds which are structurally related to those described below. To the extent that the compounds below can be grouped according to structure, the present invention includes such groupings. For example, compounds 95-112 define a genus of compounds with a 2-phenylchromene or 2-phenylchroman core; compounds 113-118 define a genus of benzo-1,3-dioxole compounds; compounds 120, 122, 123, 125, and 126 define a genus of azulene-based compounds; and compounds 132 and 133 define a genus of dihydrofuran-2-one compounds.

All stereochemical forms of the compounds disclosed in this and any section herein are specifically contemplated, including geometric isomers (i.e., E, Z) and optical isomers (i.e., R, S), Single stereochemical isomers as well as enantiomeric and diastereomeric mixtures of the compounds disclosed in this and any section herein are also specifically contemplated In other embodiments, the compound of the present invention is one or more of the following compounds:

Compound 95
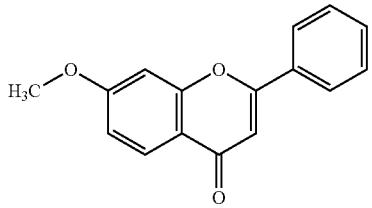
(Indofine Cat. No. M-016)

Compound 96
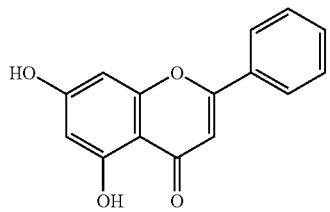 [SMILES: O=c1cc(-c2ccccc2)oc2cc(O)cc(O)c12]

Compound 97
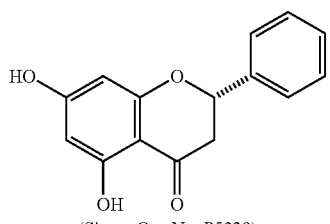
(Sigma Cat. No. P5239)

-continued
Compound 98
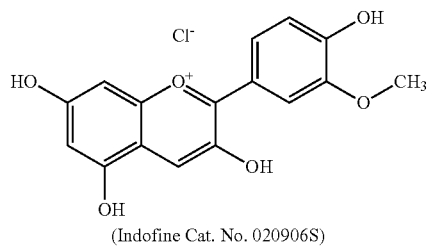 [SMILES: COc1cc(-c2[o+]c3cc(O)cc(O)c3cc2O)ccc1O ; [Cl-]]
(Indofine Cat. No. 020906S)
Compound 99
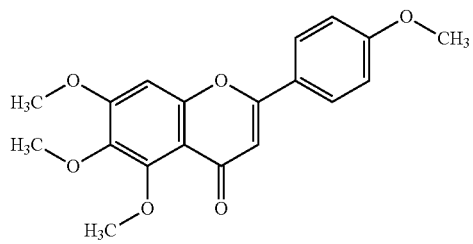
Compound 100
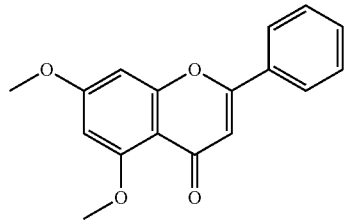
(Indofine Cat. No. 021010)
Compound 101
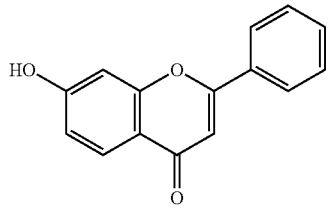 [SMILES: O=c1cc(-c2ccccc2)oc2cc(O)ccc12]
(Sigma Cat. No. H4530)
Compound 102
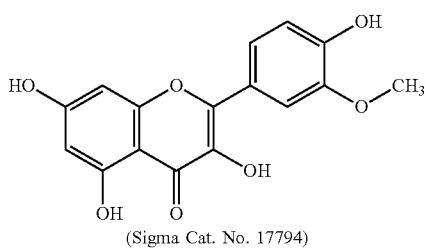
(Sigma Cat. No. 17794)
Compound 103
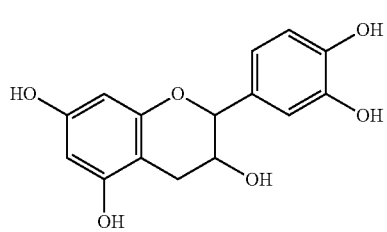 [SMILES: Oc1cc(O)c2c(c1)OC(c1ccc(O)c(O)c1)C(O)C2]

-continued
Compound 104
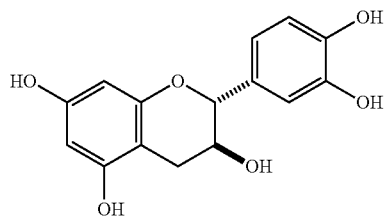 [SMILES: Oc1cc(O)c2c(c1)O[C@H](c1ccc(O)c(O)c1)[C@@H](O)C2]
Compound 105
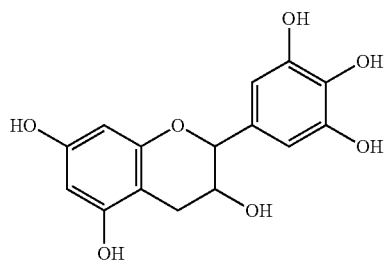 [SMILES: Oc1cc(O)c2c(c1)OC(c1cc(O)c(O)c(O)c1)C(O)C2]
Compound 106
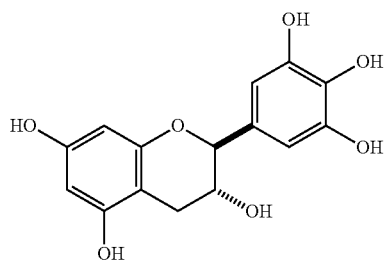 [SMILES: Oc1cc(O)c2c(c1)O[C@@H](c1cc(O)c(O)c(O)c1)[C@H](O)C2]
(Sigma Cat. No. G6657)
Compound 107
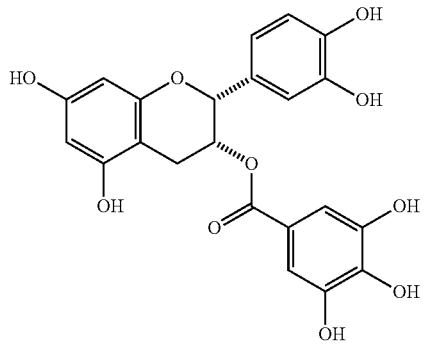
(Sigma Cat. No. E3893)
Compound 108
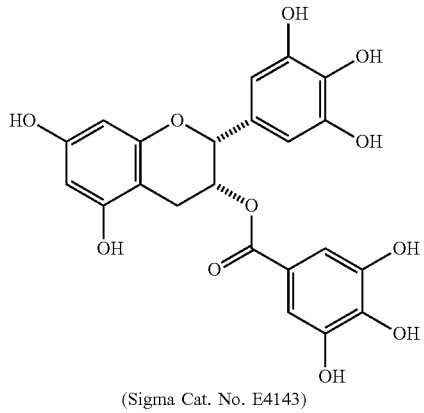
(Sigma Cat. No. E4143)

-continued
Compound 109 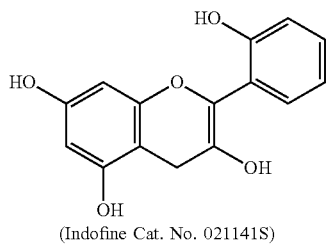
(Indofine Cat. No. 021141S)
Compound 110 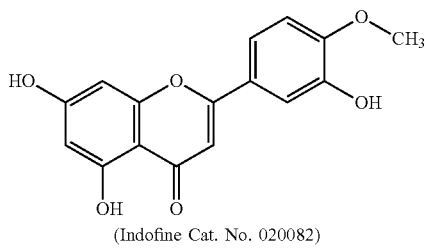
(Indofine Cat. No. 020082)
Compound 111 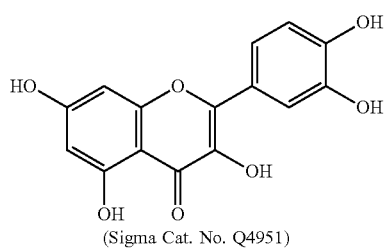
(Sigma Cat. No. Q4951)
Compound 112 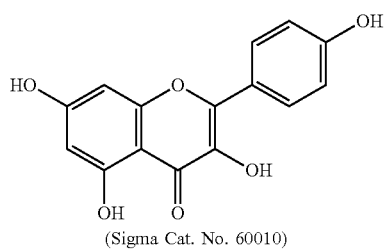
(Sigma Cat. No. 60010)
Compound 113 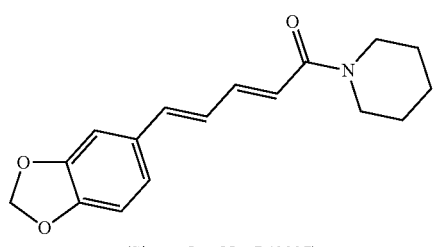
(Sigma Cat. No. P49007)
Compound 114 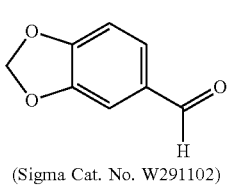
(Sigma Cat. No. W291102)
Compound 115   Black Pepper Oil (mixture of structures)
(Sigma Cat. No. W284505)

-continued
Compound 116 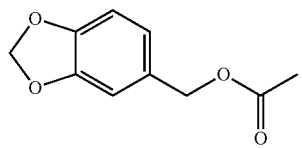
(Sigma Cat. No. W291218)
Compound 117 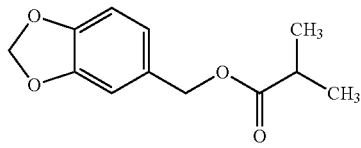 [SMILES: CC(C)C(=O)OCc1ccc2c(c1)OCO2]
(Sigma Cat. No. W291307)
Compound 118 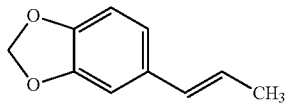
(Sigma Cat. No. 329606)
Compound 119  Camphor Oil (mixture of structures)
(Berje Cat. No. 61484)
Compound 120 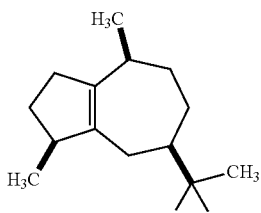
(Sigma Cat. No. 448575)
Compound 121 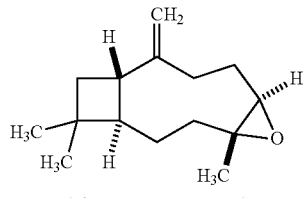 [SMILES: C=C1CC[C@H]2O[C@]2(C)CC[C@@H]2[C@@H]1CC2(C)C]
(Sigma Cat. No. 22076)
Compound 122 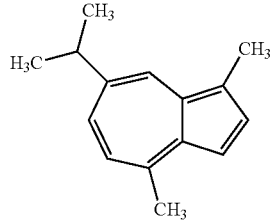
(Sigma Cat. No. G11004)
Compound 123 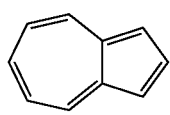
(Sigma Cat. No. A97203)
Compound 124 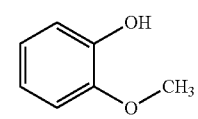
(Sigma Cat. No. W253200)

-continued
Compound 125 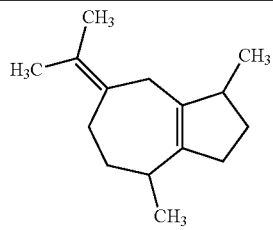
Compound 126 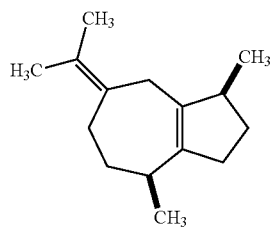
(Vigon Cat. No. G-009751)
Compound 127 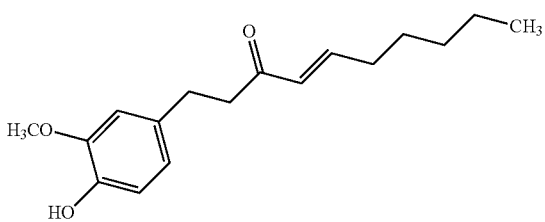 [SMILES: CCCCC/C=C/C(=O)CCc1ccc(O)c(OC)c1]
(Chromadex Cat. No. ASB-00019211)
Compound 128   Ginger Oil (mixture of structures)
(Sigma Cat. No. W252204)
Compound 129   Ginger oleoresin (mixture of structures)
(Vigon Cat. No. G-005210)
Compound 130 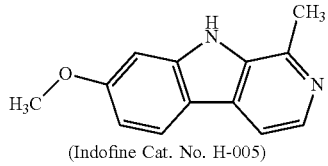
(Indofine Cat. No. H-005)
Compound 131 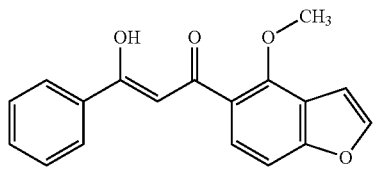 [SMILES: COc1c(C(=O)/C=C(\O)c2ccccc2)ccc2occc12]
Compound 132 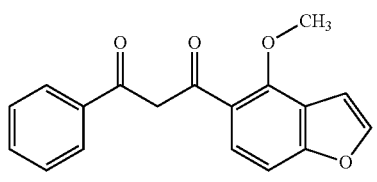 [SMILES: COc1c(C(=O)CC(=O)c2ccccc2)ccc2occc12]
(Chromadex Cat. No. ASB-00016005-050)
Compound 133 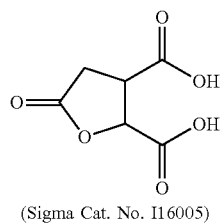
(Sigma Cat. No. I16005)

Compound 134

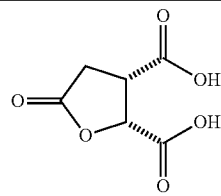

or a comestibly or biologically acceptable salt or derivative thereof, or an enantiomer or diastereomer thereof.

In certain embodiments, the compound of the invention is selected from the group consisting of 7-methoxyflavone, Pinocembrin, Peonidin chloride, Scurellarein tetramethyl ether, Chrysin dimethyl ether, 7-hydroxyflavone, Isorhamnetin, Catechin, Gallocatechin, Epicatechin gallate, Epigallocatechin gallate, Datiscetin, Diosmetin, Querectin, Kaempferol, Piperine, Piperonal, Black pepper oil, Piperonyl acetate, Piperonyl isobutyrate, Isosafrole, Camphor oil, Guaiol, Caryophyllene oxide, Guaiazulene, Azutene, Guaiscol, Guaiene, Shogaol, Ginger oil, Ginger oleoresin, Harmine, Pongamol, and Isocitric acid lactone.

In some embodiments, the edible compositions of this invention comprise terpenoid compounds, chroman compounds, benzo-ring containing compounds, polycyclic compounds, or compounds 95-134 as described herein, or a comestibly or biologically acceptable salt or derivative thereof, or an enantiomer or diastereomer thereof, or mixtures thereof.

If a comestibly or biologically acceptable salt of a compound of the present invention is used, such salt is preferably derived from inorganic or organic acids and bases. Examples of such salts include, but are not limited to, acetate, adipate, alginate, aspartate, benzoate, bezenesulfonate, bisulfate, butyrate, citrate, camphorate, camphorsulfonate, cyclopentanepropionate, digluconate, dedecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, pierate, pivalate, propionate, salicylate, succinate, sulfate, tartrate, thiocyanate, toxylate and undecanoate. Salts derived from appropriate bases include alkali metal (e.g., sodium and potassium), alkaline earth metal (e.g., magnesium), ammonium and $N^+$ ($C_{2-4}$alkyl), salts. This invention also envisions the quaternization of any basic nitrogen-containing groups of the compounds disclosed herein. Water or oil-soluble or dispersible products may be obtained by such quaternization. In some embodiment, the compounds of the present invention are present as sodium, potassium or citrate salts.

Another aspect of the present invention provides edible compositions comprising a) a compound of the invention; and b) a bitter tastant. In some embodiments, the compound is a compound having a molecular weight less than about 1000, 500, or 300 daltons. In certain embodiments, the compound is a compound of Formula (I), Formula (Ia), Formula (IIa), Formula (IIIa), Formula (IIb), Formula ((IIb), Formula (IIc), Formula (IIIc), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof. In some embodiments, the compound of the invention is a compound selected from Compounds 1-134 or combinations thereof. In other embodiments, the compound of the invention is a compound selected from Compounds 1-58 or 61-134, or combinations thereof.

In some embodiments, the bitter tastant present in the edible composition is a bitter tasting salt. In some embodiments, the bitter tastant present in the edible composition is a potassium salt, a magnesium salt, or a calcium salt. In some embodiments, the bitter tastant present in the edible composition is a potassium salt. In some embodiments, the bitter tastant present in the edible composition is KCl. In other embodiments, the bitter tastant present in the edible composition is potassium lactate.

In another embodiment, the edible compositions comprise a) a compound of the invention; and b) a potassium salt. In some embodiments, the potassium salt is KCl or potassium lactate. In specific embodiments, the potassium salt is KCl. In certain embodiments, the compound is a compound of Formula (I), Formula (Ia), Formula (IIa), Formula (IIIa), Formula (IIb), Formula ((IIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

In some embodiments, the compound of the invention is a compound selected from Compounds 1-134 or combinations thereof.

In some embodiments, the edible composition further comprises a sodium salt. In some embodiments, the edible compositions further comprise NaCl. In some embodiments, the edible compositions further comprise sodium lactate. In some embodiments, the edible compositions further comprise sugar.

In some embodiments, the edible composition further comprises one or more additional components selected from the group consisting of preservatives, nutritives, flavorants or additional flavor modifiers, which may lack an inherent flavor.

In some embodiments, the edible composition further comprises one or more emulsifiers. Sodium and potassium based emulsifiers are commonly used as emulsifiers in the food art. Sodium-based emulsifiers include, e.g., sodium salts of fatty acids, sodium alginate, sodium aluminum phosphate, sodium caseinate, sodium metaphosphate, sodium phosphate (dibasic), sodium phosphate (monobasic), sodium phosphate (tribasic) sodium polyphosphate, sodium pyrophosphate, and sodium stearoyl lactylate. Potassium-based emulsifiers include, e.g., potassium salts of fatty acids, potassium alginate, potassium citrate, potassium phosphate (dibasic), potassium phosphate (monobasic), potassium phosphate (tribasic), potassium polyphosphate, potassium polymetaphosphate, and potassium pyrophosphate. Accordingly, some embodiments of the present invention include replacing a sodium-based emulsifier with a potassium based emulsifier and adding a compound of the present invention.

In some embodiments, the edible composition further comprises a surfactant to increase or decrease the effectiveness of the compounds of the present invention. Suitable surfactants include, but are not limited to, non-ionic surfactants (e.g., mono and diglycerides, fatty acid esters, sorbitan esters, propylene glycol esters, and lactylate esters) anionic surfactants (e.g., sulfosuccinates and lecithin) and cationic surfactants (e.g., quaternary ammonium salts).

In some embodiments wherein the edible compositions further comprises a preservative, the preservative improves the shelf life of the edible composition. Suitable preservatives include, but are not limited to, ascorbic acid, benzoic acid, butyl p-hydroxybenzoate, calcium benzoate, calcium disodium EDTA, calcium hydrogen sulfite, calcium propionate, calcium sorbate, chitosan, cupric sulfate, dehydroacetic acid, diethyl pyrocarbonate, dimethyl dicarbonate, disodium EDTA, E-polylysine glycine, erythorbic acid, ethyl p-hydroxybenzoate, formic acid, gum guaiac, heptylparaben, hinokitiol, isobutyl paraoxybenzoate, Japanese styrax benzoin extract, methylparaben, milt protein extract, natamycin, nisin, peplin extract, 2-phenylphenol, pimaricin, potassium acetate, potassium benzoate, potassium lactate, potassium metabisulfite, potassium nitrate, potassium nitrite, potassium pyrosulfite, potassium sorbate, potassium sulfite, propionic acid, propyl p-hydroxybenzoate, propyl p-oxybenzoate, propylene oxide, propylparaben, sodium benzoate, sodium bisulfite, sodium dehydroacetate, sodium diacelate, sodium erythorbate, sodium hydrogen sulfite, sodium hypophosphite, sodium hyposulfite, sodium metabisulfite, sodium nitrate, sodium nitrite, sodium o-phenylphenol, sodium propionate, sodium pyrosulfite, sodium sulfite, sodium thiocyanate, sorbic acid and sulfur dioxide. In some embodiments, the preservative has a bitter flavor.

In some embodiments, the composition may further comprise one or more additional components selected from the group consisting of flow agents, processing agents, sugars, amino acids, other nucleotides, and sodium or potassium salts of organic acids such as citrate and tartrate. Such additional ingredients may add flavor, or aid in blending, processing or flow properties of the edible composition.

In some embodiments, the rate of release of the compound of the present invention is regulated. The release rate of the compound of the present invention can be altered by, for example, varying its solubility in water. Rapid release can be achieved by encapsulating the compound of the present invention with a material with high water solubility. Delayed release of the compound of the present invention can be achieved by encapsulating the compound of the present invention with a material with low water solubility. The compound of the present invention can be co-encapsulated with carbohydrates or masking tastants such as sweeteners. The rate of release of the compound of the present invention can also be regulated by the degree of encapsulation. In some embodiments, the compound of the present invention is fully encapsulated. In other embodiments, the compounds of the present invention are partially encapsulated. In some condiments, the rate of release is regulated so as to release with the bitter tastant.

The edible compositions of this invention are prepared according to techniques well-known in the art. In general, an edible composition of the invention is prepared by mixing a component or ingredient of the edible composition with a compound of the invention. Alternatively, a compound of the invention can be added directly to the edible composition. In some embodiments, a bitter tastant is added simultaneously or sequentially with a compound of the invention. If sequentially, the bitter tastant may be added before or after the compound of the invention. In some embodiments, the edible composition is a food product. In some embodiments, the edible composition is a pharmaceutical composition. In some embodiments, the edible composition is a consumer product.

The amount of both a compound of the present invention and a bitter tastant used in an edible composition depends upon a variety of factors, including the purpose of the composition and the desired or acceptable perception of bitterness, saltiness, or sweetness. The amount may depend on the nature of the edible composition, the particular compound added, the bitter tastant, other compounds present in the composition, the method of preparation (including amount of heat used), and the pH of the edible composition. It will be understood that those of skill in the art will know how to determine the amounts needed to produce the desired taste(s).

In general, a compound of the present invention in an edible composition may be present in a concentration between about 0.001 ppm and 1000 ppm. In some embodiments, the edible composition comprises between about 0.005 to 500 ppm; 0.01 to 100 ppm; 0.05 to 50 ppm; 0.1 to 5 ppm; 0.1 to 10 ppm; 1 to 10 ppm; 1 to 30 ppm; 1 to 50 ppm: 10 to 30 ppm; 10 to 50 ppm; or 30 to 50 ppm of a compound of the present invention. In yet other embodiments, the edible composition comprises about 0.1 to 30 ppm, 1 to 30 ppm or 1 to 50 ppm of a compound of the present invention. In additional embodiments, the edible composition comprises about 0.1 to 5 ppm; 0.1 to 4 ppm; 0.1 to 3 ppm; 0.1 to 2 ppm; 0.1 to 1 ppm; 0.5 to 5 ppm; 0.5 to 4 ppm; 0.5 to 3 ppm; 0.5 to 2 ppm; 0.5 to 1.5 ppm; 0.5 to 1 ppm; 5 to 15 ppm; 6 to 14 ppm; 7 to 13 ppm; 8 to 12 ppm; 9 to 11 ppm: 25 to 35 ppm; 26 to 34 ppm; 27 to 33 ppm; 28 to 32 ppm; or 29 to 31 ppm.

In yet other embodiments, the edible composition comprises about 0.1 ppm, about 0.5 ppm, about 1 ppm, about 2 ppm, about 3 ppm, about 4 ppm, about 5 ppm, about 6 ppm, about 7 ppm, about 8 ppm, about 9 ppm, or about 10 ppm of a compound of the present invention. In other embodiments, the edible composition comprises about 11 ppm, about 12 ppm, about 13 ppm, about 14 ppm, about 15 ppm, about 16 ppm, about 17 ppm, about 18 ppm, about 19 ppm, about 20 ppm, about 21 ppm, about 22 ppm, about 23 ppm, about 24 ppm, about 25 ppm, about 26 ppm, about 27 ppm, about 28 ppm about, 29 ppm, or about 30 ppm of a compound of the present invention.

In still other embodiments, the edible composition comprises about 31 ppm, about 32 ppm, about 33 ppm, about 34 ppm, about 35 ppm, about 36 ppm, about 37 ppm, about 38 ppm, about 39 ppm, about 40 ppm, about 41 ppm, about 42 ppm, about 43 ppm, about 44 ppm, about 45 ppm, about 46 ppm, about 47 ppm, about 48 ppm, about 49 ppm, or about 50 ppm of a compound of the present invention.

In other embodiments, the edible composition comprises more than about 0.5 ppm, 1 ppm, 5 ppm, 10 ppm, 15 ppm, 20 ppm, 25 ppm, or 30 ppm of a compound of the present invention, up to, for example, about 30 ppm or 50 ppm. In additional embodiments, the edible composition comprises less than about 50 ppm, 30 ppm, 25 ppm, 20 ppm, 15 ppm, 10 ppm, 5 ppm, 1 ppm, or 0.5 ppm of a compound of the present invention. In yet additional embodiments, the edible composition comprises less than about 30 ppm, 10 ppm, or 1 ppm of a compound of the present invention.

When the edible composition comprises KCl, the amount of KCl will vary depending on the nature of the edible composition, the amount of perceived saltiness desired and the presence of other compounds in the composition. In some embodiments, KCl is present at a concentration between about 0.001-5% w/w; 0.01-5% w/w; 0.1-5% w/w; 1-5% w/w; 0.5-4.8% w/w; 0.5-4% w/w; 0.5-3% w/w; 0.75-3% w/w; 1-2.5% w/w; or 1-2% w/w. In some embodiments, KCl is present at a concentration of about 0.5% w/w, about 1% w/w, about 1.5% w/w, about 2% w/w, about 2.5% w/w, about 3% w/w, about 3.5% w/w, about 4% w/w, about 4.5% w/w, or about 5% w/w. In some embodiments, KCl is present at a concentration of up to about 0.5% w/w, up to about 1% w/w, up to about 1.5% w/w, up to about 2% w/w, up to about 2.5% w/w, up to about 3% w/w, up to about 3.5% w/w, up to about 4% w/w, up to about 4.5% w/w, of up to about 5% w/w. In some embodiments, KCl is present at a concentration of about 2% w/w.

In some embodiments, KCl is added to the edible composition as a salt substitute in an amount sufficient to replace NaCl. For example, the amount of KCl in the edible compositions may range from about 0.5 to about 1.5 times the replaced NaCl depending upon the application, e.g., if about 0.5 mg of NaCl is replaced, about 0.25 to about 0.75 mg of KCl is added. Typically, KCl is added in the same weight amount as the NaCl being replaced.

Similarly, when the edible composition comprises potassium lactate, the amount of potassium lactate added varies depending on the nature of the edible composition, the amount of preservation required and the presence of other compounds in the composition. Potassium lactate may be present at a concentration between about 0.001-5% w/w; 0.01-5% w/w; 0.1-5% w/w; 0.5-4.8% w/w; 0.5-4% w/w; 0.5-3% w/w; 0.75-3% w/w; 1-2.5% w/w; or 1-2% w/w.

In some embodiments, potassium lactate is added to the edible composition in an amount sufficient to replace sodium lactate. For example, the amount of potassium lactate in the food or beverage after the sodium lactate substitute is added may range from about 0.5 to about 1.5 times the replaced sodium lactate depending upon the application, e.g., if about 0.5 mg of sodium lactate is replaced, about 0.25 to about 0.75 mg of potassium lactate is added. Typically, potassium lactate will be added in the same weight amount as the sodium lactate being replaced.

Further, when the edible composition comprises an artificial sweetener, such as Acesulfame K, the amount of the sweetener added varies depending on the nature of the edible composition, the amount of sweetness required and the presence of other compounds in the composition, Acesulfame K, for example, may be present at a concentration between about 1-200 ppm, 10-200 ppm, 50-150 ppm, 50-125 ppm, 75-125 ppm, and 75-100 ppm, preferably about 75 ppm.

In some embodiments, an artificial sweetener is added to the edible composition in an amount sufficient to replace sugar. In some embodiments, the artificial sweetener has a bitter taste or aftertaste. In some embodiments, the artificial sweetener is Acesulfame K. For example, the amount of Acesulfame K in the edible composition may range from about 0.001 to about 0.01 times the replaced sugar depending upon the application, e.g., if about 100 mg of sugar is replaced, about 0.1 to about 1 mg of Acesulfame K is added. Typically, Acesulfame K will be added in about 0.005 times the amount of sugar being replaced.

In some embodiments, the edible compositions are included in a package, in some embodiments, the edible composition is packaged in bulk, in which the package contains more of the compositions that would typically be used for a single dish or serving of food or beverage. Such bulk packages can be in the form of paper, plastic, or cloth bags or cardboard boxes or drains. Such bulk packages may be fitted with plastic or metal spouts to facilitate the dispensing of the edible composition.

In some embodiments, the package contains an edible composition comprising a compound of the present invention and a bitter tastant. In some embodiments, the package contains an edible composition comprising a compound of the present invention and bitter tasting salt. In some embodiments, the package contains an edible composition comprising a compound of the present invention and a potassium salt, a magnesium salt, or a calcium salt. In some embodiments, the package contains an edible composition comprising a compound of the present invention and a potassium salt. In some embodiments, the package contains an edible composition comprising a compound of the present invention and KCl. In other embodiments, the package contains an edible composition comprising a compound of the present invention and potassium lactate. In some embodiments, the package contains an edible composition comprising a compound of the present invention a potassium salt, and a sodium salt. In other embodiments, the package contains an edible composition comprising a compound of the present invention, KCl and NaCl. In yet other embodiments, the package contains an edible composition comprising a compound of the present invention, potassium lactate and sodium lactate. In other embodiments, the package contains an edible composition comprising a compound of the present invention and Acesulfame K and sugar. In other embodiments, the package contains an edible composition comprising a compound of the present invention, potassium lactate, KCl and NaCl.

In some embodiments, the edible compositions of the present invention are compositions suitable to be used as seasonings, as ingredients in food products or as condiments. In such embodiments, the edible composition may or may not contain a bitter tastant. For example, the edible composition may be used in, e.g., a seasoning which comprises a bitter tastant such as, e.g., KCl. Such seasonings can be used in the place of table salt (i.e., NaCl) to season prepared food products. Alternatively, the edible composition may be used in, e.g., a seasoning which does not contain a bitter tastant. Such seasonings can be used to season prepared food products which contain a bitter tastant (either inherently present or added during preparation) in order to reduce the bitter taste associated with the bitter tastant. In some embodiments, the edible composition is a seasoning comprising KCl and a compound of the invention. In some embodiments, the edible composition is a seasoning comprising KCl, NaCl and a compound of the invention. In some embodiments the seasoning further comprises a spice or a blend of spices.

Alternatively, the edible compositions may be used for medicinal or hygienic purposes, for example, in soaps, shampoos, mouthwash, medicines, pharmaceuticals, cough syrup, nasal sprays, toothpaste, dental adhesives, tooth whiteners, glues (e.g., on stamps and envelopes), and toxins used in insect and rodent control.

Food Product

In some embodiments, the edible composition is a food product. According to such embodiments, the food product comprises (a) a food stuff; and (b) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof.

In some embodiments, the food product further comprises a bitter tastant, as described herein. In some embodiments, the bitter tastant is a potassium salt, such as KCl or potassium lactate. In specific embodiments, the potassium salt is KCl.

In some embodiments, the food product further comprises one or more additional flavor modifiers.

In some embodiments, the food product further comprises one or more additional components selected from the group consisting of preservatives, nutritives, flavorants or additional flavor modifiers, which may lack an inherent flavor.

Pharmaceutical Composition

In some embodiments, the edible composition is a pharmaceutical composition. According to such embodiments, the pharmaceutical composition comprises (a) a bitter tasting pharmaceutically active ingredient; and (b) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof.

According to some embodiments, the pharmaceutical composition can comprise any bitter tasting pharmaceutically active ingredient. Non-limiting examples of bitter pharmaceutical compounds include: acetaminophen, ampicillin, azithromycin, chlorpheniramine, cimetidine, dextromethorphan, diphenyhydramine, erythromycin, ibuprofen, penicillin, phenylbutazone, psuedoephedrine, ranitidine, spironolactone, statins (including, but not limited to, atorvastatin, ceirvastatin, fluvastatin, louvastalin, mevastatin, pitavastatin, pravastatin, rosuvastatin, and simvastatin) and theophylline.

In other embodiments, the invention provides a pharmaceutical composition comprising (a) a pharmaceutically active ingredient; (b) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof; and (c) a bitter tastant. In such embodiments, the pharmaceutical compositions may comprise any pharmaceutically active ingredient.

In other embodiments, the invention provides a pharmaceutical composition comprising (a) a pharmaceutically active ingredient; (b) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof; and (c) a potassium salt. In some embodiments, the potassium salt is KCl or potassium lactate. In some embodiments, the potassium salt is KCl.

In some embodiments, the pharmaceutical composition further comprises one or more additional flavor modifiers.

In some embodiments, the pharmaceutical composition further comprises one or more additional components selected from the group consisting of preservatives, nutritives, flavorants or flavor modifiers, which may lack an inherent flavor.

Consumer Product

In some embodiments, the edible compositions is a consumer product. According to such embodiments, the consumer product composes (a) a bitter tastant; and (b) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof.

In another embodiment, the invention provides a consumer product comprising (a) a potassium salt; and (b) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof. In some embodiments, the potassium salt is KCl or potassium lactate. In some embodiments, the potassium salt is KCl.

In other embodiments, the invention provides a consumer product for reducing bitter taste of a bitter tastant, wherein said consumer product comprises a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof; and (c) a potassium salt. In some embodiments, the potassium salt is KCl or potassium lactate. In some embodiments, the potassium salt is KCl.

In some embodiments, the consumer product further comprises one or more additional flavor modifiers.

In some embodiments, the consumer product further comprises one or more additional components selected from the group consisting of preservatives, nutritives, flavorants or additional flavor modifiers, which may lack an inherent flavor.

Method of Preparing an Edible Compound

According to another aspect, the invention provides a method of preparing an edible composition. The method comprises: (a) providing a comestibly acceptable carrier; and (b) adding to the comestibly acceptable carrier of (a) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof, with the comestibly acceptable carrier. In some embodiments, the compound of the invention has been dissolved in a solvent prior to the addition step (b).

In some embodiments, the comestibly acceptable carrier in (a) is inherently bitter. In such embodiments, the comestibly acceptable carrier may inherently contain a bitter tastant. In some embodiments, the inherent bitter tastant is a bitter tasting salt. In some embodiments, the inherent bitter tastant is a potassium salt, a magnesium salt, or a calcium salt. In some embodiments, the inherent bitter tastant is a potassium salt. In some embodiments, the inherent bitter tastant is KCl. In other embodiments, the inherent bitter tastant is potassium lactate.

In some embodiments, the method of preparing a edible composition further comprises: (c) adding a bitter tastant. In some embodiments, the bitter tastant is a potassium salt. In some embodiments, the potassium salt is KCl or potassium lactate. In specific embodiments, the potassium salt is KCl. In some embodiments, the bitter tastant is added before the compound of the present invention. In other embodiments, the bitter tastant is added after the compound of the present invention. In some embodiments, the compounds of the present invention are combined with the bitter tastant and then combined with the comestibly acceptable carrier. In other embodiments, the compound of the present invention is combined sequentially with the comestibly acceptable carrier and then the bitter tastant. In yet other embodiments, the compounds of the present invention are combined with a mixture of the bitter tastant and the comestibly acceptable carrier.

In some embodiments, a compound of the invention and the bitter tastant, if present, are mixed with the comestibly acceptable carrier. In other embodiments, the compound and the bitter tastant, if present, are sprayed onto or coat the comestibly acceptable carrier. In some embodiments, the compound of the invention is plated on a carbohydrate or salt, encapsulated on a salt or a carbohydrate (spray dried), or co-crystallized with a potassium salt to create a "topping" salt.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the edible composition further comprises a sodium salt. In some embodiments, the edible composition further comprises NaCl. In other embodiments, the edible composition further comprises sodium lactate. In further embodiments, the edible composition further comprises sugar.

In some embodiments, the methods of preparing an edible composition further comprise adding one or more additional components selected from the group consisting of preservatives, nutritives, flavorants or flavor modifiers, which may lack an inherent flavor. In some embodiments, the methods of preparing an edible composition further comprise adding one or more additional flavor modifiers.

In some embodiments, the edible composition is a consumer product.

Method of Preparing a Food Product

According to another aspect, the invention provides a method of preparing an edible composition, wherein the edible composition is a food product. The method comprises: (a) providing a foodstuff; and (b) adding to the foodstuff of (a) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof. In some embodiments, the compound of the invention is added in the form of an edible composition comprising the compound of the invention.

In some embodiments, the foodstuff in (a) is inherently bitter. In such embodiments, the food stuff may inherently contain a bitter tastant. In some embodiments, the inherent bitter tastant is a bitter tasting salt. In some embodiments, the inherent bitter tastant is a potassium salt, a magnesium salt, or a calcium salt. In some embodiments, the inherent bitter tastant is a potassium salt. In some embodiments, the inherent bitter tastant is KCl. In other embodiments, the inherent bitter tastant is potassium lactate.

In some embodiments, the method comprises: (a) providing a food product; and (b) adding to the food product of (a) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof. In some embodiments, the compound of the invention is added in the form of an edible composition comprising the compound of the invention.

In some embodiments, the food product in (a) comprises a bitter tastant. In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the method of preparing a food product further comprises: (c) adding a bitter tastant. In some embodiments, the bitter tastant is a potassium salt, such as KCl or potassium lactate. In specific embodiments, the potassium salt is KCl. In some embodiments, the bitter tastant is added before the compound of the present invention. In other embodiments, the bitter tastant is added after the compound of the present invention. In some embodiments, the compound of the invention is added with the bitter tastant. In some embodiments, the compound of the present invention is combined with the bitter tastant and then combined with the foodstuff or food product. In other embodiments, the compound of the present invention is combined sequentially with the foodstuff or food product and then the bitter tastant. In yet other embodiments, the compound of the present invention is combined with a mixture of the bitter tastant and the foodstuff or food product.

In some embodiments, the compound and the bitter tastant, if present are mixed with the foodstuff. In other embodiments, the compound and the bitter tastant, if present, are sprayed onto or coat the foodstuff. In some embodiments, the compound of the invention is plated on a carbohydrate or salt, encapsulated on a salt or a carbohydrate (spray dried), or co-crystallized with a potassium salt to create a "topping" salt.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the food product further comprises a sodium salt. In some embodiments, the food product further comprises NaCl. In other embodiments, the food product further comprises sodium lactate. In further embodiments, the food product further comprises sugar.

In some embodiments, the methods of preparing a food product further comprise adding one or more additional components selected from the group consisting of preservatives, nutritives, flavorants or flavor modifiers, which may lack an inherent flavor.

Method of Preparing a Pharmaceutical Composition

According to another aspect, the invention provides a method of preparing an edible composition, wherein the edible composition is a pharmaceutical composition. The method comprises: (a) providing a pharmaceutically active ingredient; and (b) adding to the pharmaceutically active ingredient of (a) a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof with the pharmaceutically active ingredient. In some embodiments, the compound of the invention is added in the form of an edible composition comprising the compound of the invention.

In some embodiments, the pharmaceutically active ingredient in (a) is inherently bitter. In such embodiments, the pharmaceutically active ingredient may inherently contain a bitter tastant. In some embodiments, the inherent bitter tastant is a bitter tasting salt. In some embodiments, the inherent bitter tastant is a potassium salt, a magnesium salt, or a calcium salt. In some embodiments, the inherent bitter tastant is a potassium salt.

In some embodiments, the method of preparing a pharmaceutical composition further comprises: (c) adding a bitter tastant. In some embodiments, the bitter tastant is a potassium salt. In some embodiments, the potassium salt is KCl or potassium lactate. In specific embodiments, the potassium salt is KCl. In some embodiments, the bitter tastant is added before the compound of the present invention. In other embodiments, the bitter tastant is added after the compound of the present invention. In some embodiments, the bitter tastant is added with the compound of the invention. In some embodiments, the compound of the present invention is combined with the bitter tastant and then combined with the pharmaceutically active ingredient. In other embodiments, the compound of the present invention is combined sequentially with the pharmaceutically active ingredient and then the bitter tastant. In yet other embodiments, the compound of the present invention is combined with a mixture of the bitter tastant and the pharmaceutically active ingredient.

In some embodiments, the compound and the bitter tastant if present, are mixed with the pharmaceutically active ingredient. In other embodiments, the compound and the bitter tastant, if present, are sprayed onto or coat the pharmaceutical composition. In some embodiments, the compound of the invention is encapsulated with the pharmaceutically active ingredient. In some embodiments, the compound of the invention is in a form such that the rate of release is regulated vis a vis the rate of release of the bitter tastant, which in some embodiments is the pharmaceutically active ingredient.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the pharmaceutical composition further comprises a sodium salt. In some embodiments, the pharmaceutical composition further comprises NaCl. In other embodiments, the pharmaceutical composition further comprises sodium lactate. In further embodiments, the pharmaceutical composition further comprises sugar.

In some embodiments, the pharmaceutical composition further comprises a pharmaceutically acceptable carrier. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidine, cellulose-based substances, polyethylene glycol, sodium carboxymethylcellulose, polyacrylates, waxes, polyethylene-polyoxypropylene-block polymers, polyethylene glycol and wool fat.

In some embodiments, the methods of preparing a pharmaceutical composition further comprise adding one or more additional components selected from the group consisting of preservatives, nutritives, flavorants or flavor modifiers, which may lack an inherent flavor.

Method of Reducing or Eliminating the Perception of Bitter Taste in a Subject According to another aspect, the invention provides a method of reducing or eliminating the perception of bitter taste in a subject. The method comprises the use of an edible composition comprising a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof.

The method can be used to reduce or eliminate bitter taste in any edible composition, including a foodstuff, food product, pharmaceutical composition or consumer product. The edible composition may be in any form. In some embodiments, the composition is in the form of, for example, a gum, lozenge, sauce, condiment, meat matrix, meat slurry, paste, suspension, spread, coating, a liquid, a gel, an emulsion, granules, or seasoning.

In some embodiments the edible composition is utilized by, for example, placement in the oral cavity or by ingestion. In some embodiments, the edible composition is placed in the oral cavity or ingested before a bitter food stuff, food product, pharmaceutical composition or consumer product. In some embodiments, the edible composition is placed in the oral cavity or ingested concurrently with a bitter food stuff, food product, pharmaceutical composition or consumer product, either as a separate edible composition or by incorporation in the bitter food stuff, food product, pharmaceutical composition or consumer product. In some embodiments, the edible composition is placed in the oral cavity or ingested after a bitter food stuff, food product, pharmaceutical composition or consumer product. For example, a compound of the invention can be combined with foodstuffs or food products to reduce the bitter taste of a food product. Alternatively, a compound of the invention can be used, for example, in a lozenge or gum for use after exposure to a bitter food stuff, food product, pharmaceutical composition or consumer product (e.g., to reduce or eliminate a bitter aftertaste).

Method of Reducing the Amount of Sodium in an Edible Composition

According to another embodiment, the invention provides a method of reducing the amount of sodium in an edible composition, such as a food product, a pharmaceutical composition or a consumer product. In some embodiments, the invention provides a method of reducing the amount of a sodium containing compound in an edible composition, such as a food product, a pharmaceutical composition or a consumer product. In another embodiment, the invention provides a method of reducing the amount of NaCl in an edible composition, such as a food product, a pharmaceutical composition or a consumer product. In another embodiment, the invention provides a method of reducing the amount of sodium lactate in an edible composition, such as a food product, a pharmaceutical composition or a consumer product. In some embodiments, the sodium salt is replaced with a non-sodium salt. In some embodiments, the non-sodium salt is a calcium salt, a magnesium salt, or a potassium salt. In some embodiments, the non-sodium salt is a potassium salt.

In some embodiments, the method comprises: (a) replacing an amount of a sodium salt used in preparing an edible composition with an amount of a potassium salt; and (b) incorporating into the edible composition an effective amount of a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof with the pharmaceutically active ingredient. In some embodiments, the compound of the invention is added in the form of an edible composition comprising the compound of the invention.

In some embodiments, the method of reducing the amount of sodium in an edible composition comprises the steps of; (a) ingesting a first edible composition, in which an amount of a sodium salt has been replaced with an amount of a potassium salt; and (b) ingesting a second edible compound, which comprises a compound of the invention. In some embodiments, the first edible composition is ingested before the second edible composition. In some embodiments, the first edible composition is ingested after the second edible composition. In some embodiments, the first edible composition is ingested concurrently with the second edible composition.

In some embodiments, the edible composition is a food product. In some embodiments, the edible composition is a pharmaceutical composition. In some embodiments, the edible composition is a consumer product.

In some embodiments, the potassium salt is added to the edible composition prior to addition of an effective amount of a compound of the invention. In some embodiments, the potassium salt is added to the edible composition subsequent to addition of an effective amount of a compound of the invention. In some embodiments, the potassium salt is added to the edible composition concurrent with addition of an effective amount of a compound of the invention.

In some embodiments, the amount of sodium replaced in the edible composition in step (a) is an amount sufficient to maintain or restore the health of a subject. In some embodiments, the amount of sodium replaced in the edible composition is an amount sufficient to decrease hypertension in a subject. In some embodiments, the amount of sodium replaced by potassium in the edible composition is an amount to sufficient to change the texture or freezing point of the edible composition. In some embodiments, the amount of sodium replaced is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the amount of compound added in step (b) reduces the perception of bitter taste in the subject. The bitter taste is completely reduced or partially reduced. In some embodiments, the perception of salty taste is maintained.

In some embodiments, the amount of compound added in step (b) is sufficient to permit replacement of up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80% 85%, 90%, 95% or 100% of the amount of sodium present in the edible composition with potassium. These amounts are not meant to be limiting, and increments between the recited percentages are specifically envisioned as part of the invention. In some embodiments, the amount of compound added in step (b) is sufficient to permit replacement of up to 25% of the amount of sodium present in the edible composition with potassium. In other embodiments, the amount of compound added in step (b) is sufficient to permit replacement of up to 50% of the amount of sodium present in the edible composition with potassium. In other embodiments, the amount of compound added in step (b) is sufficient to permit replacement of up to 75% of the amount of sodium present in the edible composition with potassium, in yet other embodiments, the amount of compound added in step (b) is sufficient to permit replacement of up to 100% of the amount of sodium present in the edible composition with potassium.

In some embodiments, the method of reducing the amount of sodium in an edible composition further comprises adding one or more additional components selected from the group consisting of preservatives, nutritives, flavorants or flavor modifiers, which may lack an inherent flavor.

In some embodiments, the method comprises: (a) replacing an amount of NaCl used in preparing an edible composition with an amount of KCl; and (b) incorporating into the edible composition an effective amount of a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof.

In some embodiments, the method of reducing the amount of sodium in an edible composition comprises the steps of: (a) ingesting a first edible composition, in which an amount of NaCl has been replaced with an amount of KCl; and (b) ingesting a second edible compound, which comprises a compound of the invention. In some embodiments, the first edible composition is ingested before the second edible composition. In some embodiments, the first edible composition is ingested after the second edible composition. In some embodiments, the first edible composition is ingested concurrently with the second edible composition.

In some embodiments, the edible composition is a food product, in some embodiments, the edible composition is a pharmaceutical composition. In some embodiments, the edible composition is a consumer product.

In some embodiments, the KCl is added to the edible composition prior to addition of an effective amount of a compound of the invention. In some embodiments, the KCl is added to the edible composition subsequent to addition of an effective amount of a compound of the invention. In some embodiments, the KCl is added to the edible composition concurrent with addition of an effective amount of a compound of the invention.

In some embodiments, the amount of NaCl replaced by KCl in the edible composition in step (a) is an amount sufficient to maintain or restore the health of a subject. In some embodiments, the amount of NaCl replaced by KCl in the edible composition is an amount sufficient to decrease hypertension in a subject. In some embodiments, the amount of NaCl replaced by KCl in the edible composition is an amount so sufficient to change the texture or freezing point of the edible composition. In some embodiments, the amount of NaCl replaced by KCl is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the amount of compound added in step (b) reduces the perception of bitter taste in the subject. The bitter taste is completely reduced or partially reduced. In some embodiments, the perception of salty taste is maintained.

In some embodiments, the amount of compound added in step (b) is sufficient to permit replacement of up to 1%, 2%, 3%, 4%, 5%, 6%, 7%, 8%, 9%, 10%, 15%, 20%, 25%, 30%, 35%, 40%, 45%, 50%, 55% 60%, 65%, 70% 75%, 80%, 85%, 90%, 95% or 100% of the amount of NaCl present in the edible composition with KCl. These amounts are not meant to be limiting, and increments between the recited percentages are specifically envisioned as part of the invention. In some embodiments, the amount of compound added in step (b) is sufficient to permit replacement of up to 25% of the amount of NaCl present in the edible composition with KCl. In other embodiments, the amount of compound added in step (b) is sufficient to permit replacement of up to 50% of the amount of NaCl present in the edible composition with KCl. In other embodiments, the amount of compound added in step (b) is sufficient to permit replacement of up to 75% of the amount of NaCl present in the edible composition with KCl. In yet other embodiments, the amount of compound added in step (b) is sufficient to permit replacement of up to 100% of the amount of NaCl present in the edible composition with KCl.

In some embodiments, the method of reducing the amount of NaCl in an edible composition or food product comprises maintaining a salty flavor.

In some embodiments, the method of reducing the amount of NaCl in an edible composition further comprises adding one or more additional components selected from the group consisting of preservatives, nutritives, flavorants or flavor modifiers, which may lack an inherent flavor.

In other embodiments, the method of reducing the amount of sodium in an edible composition comprises: (a) replacing an amount of sodium lactate present in the edible composition with an amount of potassium lactate; and (b) incorporating into the edible composition an effective amount of a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof.

In some embodiments, the method of reducing the amount of sodium in an edible composition comprises the steps of: (a) ingesting a first edible composition, in which an amount of sodium lactate has been replaced with an amount of potassium lactate; and (b) ingesting a second edible compound, which comprises a compound of the invention. In some embodiments, the first edible composition is ingested before the second edible composition. In some embodiments, the first edible composition is ingested after the second edible composition. In some embodiments, the first edible composition is ingested concurrently with the second edible composition.

In some embodiments, the edible composition is a food product. In some embodiments, the edible composition is a pharmaceutical composition. In some embodiments, the edible composition is a consumer product.

In some embodiments, the potassium lactate is added to the edible composition prior to addition of an effective amount of a compound of the invention. In some embodiments, the potassium lactate is added to the edible composition subsequent to addition of an effective amount of a compound of the invention. In some embodiments, the potassium lactate is added to the edible composition concurrent with addition of an effective amount of a compound of the invention.

In some embodiments, the amount of sodium lactate replaced by potassium lactate in the edible compound in step (a) is an amount sufficient to maintain or restore the health of a subject. In some embodiments, the amount of sodium lactate replaced by potassium lactate in the edible composition is an amount sufficient to decrease hypertension in a subject. In some embodiments, the amount of sodium lactate replaced by potassium lactate in the edible composition is an amount to sufficient to change the texture or freezing point of the edible composition. In some embodiments, the amount of sodium lactate replaced by potassium lactate is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the amount of compound added in step (b) reduces the perception of bitter taste in the subject. The bitter taste is completely reduced or partially reduced. In some embodiments, the perception of salty taste is maintained.

In some embodiments, the amount of compound added in step (b) is sufficient to permit replacement of up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100% of the amount of sodium lactate present in the edible composition with potassium lactate. These amounts are not meant to be limiting, and increments between the recited percentages are specifically envisioned as part of the invention. In some embodiments, the amount of compound added in step (b) is sufficient to permit replacement of up to 25% of the amount of sodium lactate present in the edible composition with potassium lactate. In other embodiments, the amount of compound added in step (b) is sufficient to permit replacement of up to 50% of the amount of sodium lactate present in the edible composition with potassium lactate. In other embodiments, the amount of compound added in step (b) is sufficient to permit replacement of up to 75% of the amount of sodium lactate present in the edible composition with potassium lactate. In yet other embodiments, the amount of compound added in step (b) is sufficient to permit replacement of up to 100% of the amount of sodium lactate present in the edible composition with potassium lactate.

In some embodiments, the method of reducing the amount of sodium lactate in an edible composition or food product comprises maintaining the preservation of the food product.

In some embodiments, the method of reducing the amount of sodium lactate in an edible composition further comprises adding one or more additional components selected from the group consisting of preservatives, nutritives, flavorants or flavor modifiers, which may lack an inherent flavor.

Method of Reducing the Amount of Sugar in an Edible Composition or Food Product

According to another embodiment, the invention provides a method of reducing the amount of sugar in an edible composition. In some embodiments, the method comprises: (a) replacing an amount of sugar used in preparing an edible composition with an amount of Acesulfame K; and (b) incorporating into the edible composition an effective amount of a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof.

In some embodiments, the edible composition is a food product. In some embodiments, the edible composition is a pharmaceutical composition. In some embodiments, the edible composition is a consumer product.

In some embodiments, the Acesulfame K is added to the edible composition prior to addition of an effective amount of a compound of the invention. In some embodiments, the Acesulfame K is added to the edible composition subsequent to addition of an effective amount of a compound of the invention. In some embodiments, the Acesulfame K is added to the edible composition concurrent with addition of an effective amount of a compound of the invention.

In some embodiments, the amount of sugar replaced in the edible composition in (a) is an amount sufficient to maintain or restore the health of a subject. In some embodiments, the amount of sugar replaced in the edible composition is an amount sufficient to result in weight loss in a subject. In some embodiments, the amount of sugar replaced by Acesulfame K in the edible composition is an amount to sufficient to alleviate the effects of, or treat, a disease associated with sugar consumption or excessive weight of the subject (e.g., diabetes). In some embodiments, the amount of sugar replaced by Acesulfame K is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the amount of compound added in (b) reduces the perception of bitter taste in the subject. The bitter taste is completely reduced or partially reduced. In some embodiments, the perception of sweet taste is maintained.

In some embodiments, the amount of compound added in step (b) is sufficient to permit replacement of up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100% of the amount of sugar present in the edible composition with Acesulfame K. These amounts are not meant to be limiting, and increments between the recited percentages are specifically envisioned as part of the invention. In some embodiments, the amount of compound added in step (b) is sufficient to permit replacement of up to 25% of the amount of sugar present in the edible composition with Acesulfame K. In other embodiments, the amount of compound added in step (b) is sufficient to permit replacement of up to 50% of the amount of sugar present in the edible composition with Acesulfame K. In other embodiments, the amount of compound added in step (b) is sufficient to permit replacement of up to 75% of the amount of sugar present in the edible composition with Acesulfame K. In yet other embodiments, the amount of compound added in step (b) is sufficient to permit replacement of up to 100% of the amount of sugar present in the edible composition with Acesulfame K.

In some embodiments, the method of reducing the amount of sugar in an edible composition comprises maintaining a sweet flavor.

In some embodiments, the method of reducing the amount of sugar in an edible composition or food product further comprises adding one or more additional components selected from the group consisting of preservatives, nutritives, flavorants or flavor modifiers, which may lack an inherent flavor.

Method of Reducing Sodium Intake of a Subject

According to another embodiment, the invention provides a method of reducing sodium intake of a subject. In some embodiments, the method comprises the step of providing an edible composition of the present invention to the subject, wherein all or a portion of the sodium salts in the edible composition is replaced with one or more non-sodium salts, and wherein the edible composition comprises a compound of the present invention. In some embodiments, the non-sodium salt is a calcium salt, a magnesium salt, or a potassium salt. In some embodiments, the non-sodium salt is a potassium salt. In some embodiments, the edible composition is a food product. In some embodiments, the edible composition is a pharmaceutical composition. In some embodiments, the edible composition is a consumer product. In some embodiments the sodium salt is NaCl and the potassium salt is KCl. In some embodiments, the sodium salt is sodium lactate and the potassium salt is potassium lactate.

In some embodiments, the methods of reducing sodium intake of a subject further comprise the step of identifying a subject in need thereof. The skilled worker would be able to identify a subject in need of reducing sodium intake. Non-limiting examples of such subjects include subjects that suffer from any one or more of the following disorders: hypernatremia, hypertension, cardiovascular disease, edema, seizures due to cerebral edema, dehydration (due to excess sweating, diarrhea, urinary tract disorders or diuretics), diabetes insipidus. Conn's syndrome, and Cushing's syndrome.

In some embodiments, the amount of the sodium salt replaced by a potassium salt in the edible composition is an amount sufficient to maintain or restore the health of a subject. In some embodiments, the amount of the sodium salt replaced by a potassium salt in the edible composition is an amount sufficient to decrease hypertension in a subject. In some embodiments, the amount of the sodium salt replaced by a potassium salt in the edible composition is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, a subject's daily sodium intake is less than 2500 mg/day, less than 2000 mg/day, less than 1500 mg/day, less than 1000 mg/day, or less than 500 mg/day, where desirable.

In some embodiments, the amount of the compound of the invention added to the edible composition is sufficient to permit reduction of a subject's sodium intake by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, the amount of compound of the invention added to the edible composition is sufficient to permit reduction of the subjects sodium intake by up to 25%. In other embodiments, the amount of compound of the invention added to the edible composition is sufficient to permit reduction of the subject's sodium intake by up to 50%. In other embodiments, the amount of compound of the invention added to the edible composition is sufficient to permit reduction of the subject's sodium intake by up to 75%. In yet other embodiments, the amount of compound of the invention added to the edible composition is sufficient to permit reduction of the subject's sodium intake by up to 100%.

In some embodiments, the method of reducing sodium intake of a subject further comprises adding one or more additional components selected from the group consisting of preservatives, nutritives, flavorants or flavor modifiers, which may lock an inherent flavor.

Method of Reducing Sugar Intake of a Subject

According to another embodiment, the invention provides a method of reducing sugar intake of a subject. In some embodiments, the method comprises the step of providing an edible composition of the present invention to the subject, wherein all or a portion of the sugar in the edible composition is replaced with Acesulfame K, and wherein the edible composition comprises a compound of the present invention. In some embodiments, the edible composition is a food product. In some embodiments, the edible composition is a pharmaceutical composition. In some embodiments, the edible composition is a consumer product.

In some embodiments, the methods of reducing sugar intake of a subject further comprise the step of identifying a subject in need thereof. The skilled worker would be able to identify a subject in need of reducing sugar intake. Non-limiting examples of such subjects include subjects that suffer from any one or more of the following disorders: diabetes, pre-diabetes, insulin resistance, obesity, excessive weight, and hyperglycemia.

In some embodiments, the amount of sugar replaced by Acesulfame K in the edible composition is an amount sufficient to maintain or restore the health of a subject. In some embodiments, the amount of sugar replaced by Acesulfame K in the edible composition is an amount sufficient to result in weight loss in a subject. In some embodiments, the amount of sugar replaced by Acesulfame K in the edible composition is an amount to sufficient to alleviate the effects of, or treat, a disease associated with sugar consumption or excessive weight of the subject (e.g., diabetes). In some embodiments, the amount of sugar replaced by Acesulfame K in the edible composition is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%, These amounts are not meant to be limiting, and increments between the recited percentages are specifically envisioned as part of the invention. In some embodiments, the subject's daily sugar intake is less than 250 g/day, less than 200 g/day, less man 175 g/day, less than 150 g/day, less than 125 g/day, less than 100 g/day, less than 75 g/day, less than 50 g/day or less than 25 g/day.

In some embodiments, the amount of compound of the invention added to the edible composition is sufficient to permit reduction of a subject's sugar intake by up to 1%, 2%, 3%, 4%, 5%, 6% 7%, 8%, 9%, 10%, 15%, 20%, 25%, 30%, 35%, 40%, 45%, 50% 55%, 60%, 65% 70% 75%, 80%, 85%, 90%, 95% or 100%. These amounts are not meant to be limiting, and increments between the recited percentages are specifically envisioned as part of the invention. In some embodiments, the amount of compound of the invention added to the edible composition is sufficient to permit reduction of a subject's sugar intake by up to 25%. In other embodiments, the amount of compound of the invention added to the edible composition is sufficient to permit reduction of a subject's sugar intake by up to 50%. In other embodiments, the amount of compound of the invention added to the edible composition is sufficient to permit reduction of a subject's sugar intake by up to 75%. In yet other embodiments, the amount of compound of the invention added to the edible composition is sufficient to permit reduction of a subject's sugar intake by up to 100%.

In some embodiments, the method of method of reducing sugar intake of a subject further comprises adding one or more additional components selected from the group consisting of preservatives, nutritives, flavorants or flavor modifiers, which may lack an inherent flavor.

Method of Reducing Bitter Taste of an Edible Composition

According to another embodiment, the invention provides methods of reducing the bitter taste in an edible composition. In some embodiments, the edible composition is a food product. In some embodiments, the edible composition is a pharmaceutical composition. In some embodiments, the edible composition is a consumer product.

In one embodiment, the method comprises: (a) adding an effective amount of a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof, to an edible composition such that the bitter taste is reduced.

In alternate embodiments, the method comprises: (a) ingesting an effective amount of a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof, before, along with, or after the edible composition such that bitter taste is reduced.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate. In some embodiments, the bitter tastant is inherent in the edible composition, such as in an inherently bitter foodstuff.

In some embodiments, the bitter taste is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, the bitter taste is reduced by up to 25%. In other embodiments, the bitter taste is reduced by up to 50%. In other embodiments, the bitter taste is reduced by up to 75%. In other embodiments, the bitter taste is reduced by up to 100%.

In some embodiments, the method of reducing the bitter taste attributed to a bitter tastant in an edible composition further comprises adding one or more additional components selected from the group consisting of preservatives, nutritives, flavorants or flavor modifiers (which lack an inherent flavor).

Method of Preserving an Edible Composition

According to another embodiment, the invention provides a method of preserving an edible composition an edible composition comprising:
(a) providing an edible composition; and
(b) combining with the edible composition of (a) a preservative and an effective amount of compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof.

In another embodiment, the method of preserving an edible composition comprises:
(a) providing an edible composition; and
(b) combining with the edible composition of (a) a preservative and an effective amount of any one of Compounds 1-134, or combinations thereof.

According to the invention, the preservative can be any bitter-tasting preservative. In some embodiments, the preservative in (a) is a potassium salt. In some embodiments, the preservative in (a) is potassium lactate.

In some embodiments, the edible composition is a food product. In some embodiments, the edible composition is a pharmaceutical composition. In some embodiments, the edible composition is a consumer product.

In some embodiments, the method of preserving an edible composition further comprises adding one or more additional components selected from the group consisting of preservatives, nutritives, flavorants or flavor modifiers, which may lack an inherent flavor.

Method of Reducing the Amount of Sodium in an Edible Composition while Preserving the Edible Composition According to another embodiment, the invention provides a method of reducing the amount of sodium in an edible composition while preserving the edible composition. In some embodiments, the method comprises replacing an amount of sodium containing preservative used in preparing an edible composition with an amount of potassium containing preservative and adding an effective amount of a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof.

In some embodiments, the method comprises replacing an amount of sodium lactate used in preparing an edible composition with an amount of potassium lactate and adding an effective amount of a compound of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof.

In some embodiments, the edible composition is a food product. In some embodiments, the edible composition is a pharmaceutical composition. In some embodiments, the edible composition is a consumer product.

In some embodiments, the effective amount of the compound is sufficient to permit reduction of the amount of sodium lactate typically used in preparing an edible composition by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, the effective amount of the compound is sufficient to permit reduction of the amount of sodium lactate typically present in an edible composition by up to 25%. In other embodiments, the effective amount of the compound is sufficient to permit reduction of the amount of sodium lactate typically present in an edible composition by up to 50%. In other embodiments, the effective amount of the compound is sufficient to permit reduction of the amount of sodium lactate typically present in an edible composition by up to 75%. In yet other embodiments, the effective amount of the compound is sufficient to permit reduction of the amount of sodium lactate typically present in an edible composition by up to 100%.

In some embodiments, the method of reducing the bitter taste attributed to a bitter tastant in an edible composition further comprises adding one or more additional components selected from the group consisting of preservatives, nutritives, flavorants or flavor modifiers, which may lack an inherent flavor. In some embodiments, the method of reducing the amount of sodium lactate in an edible composition while preserving the food product further comprises adding one or more additional flavor modifiers.

According to another embodiment, the invention provides a method of inhibiting or reducing activation and/or signaling of a bitter taste receptor. In some embodiments, the method comprises contacting a bitter taste receptor with a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof. In some embodiments, the method comprises contacting a bitter taste receptor with any one of Compounds 1-58, or 61-134, or combinations thereof.

In some embodiments, the method comprises contacting a bitter taste receptor with an edible composition comprising a compound according to Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), Formula (V), Formula (VIa), Formula (VIb), Formula (VIIa), Formula (VIII), Formula (IXa), Formula (IXb), Formula (IXc), Formula (IXd), Formula (XI) or Formula (XII), as described herein, or combinations thereof, or any one of Compounds 1-134, as described above, or combinations thereof, or any one of Compounds 1-134, as described above, or combinations thereof.

In some embodiments, the edible composition is a food product. In some embodiments, the edible composition is a pharmaceutical composition. In some embodiments, the edible composition is a consumer product.

In some embodiments, the bitter taste receptor is an ex vivo receptor present in, for example, an assay. In some embodiments, the bitter taste receptor is an in vitro receptor present in, for example, an assay. In other embodiments, the bitter taste receptor is an in vivo receptor present in a subject. In some embodiments, the bitter taste receptor is present in the oral cavity or gastrointestinal tract of a subject. In some embodiments, the bitter receptor is in the oral cavity of a human. In some embodiments, the bitter receptor is in the oral cavity of a non-human animal. In some embodiments, the bitter receptor is in the oral cavity of an animal model.

In some embodiments, inhibition of a bitter taste receptor will affect a physiological process or condition. Non-limiting examples of physiological processes and conditions affected by inhibition of bitter taste receptors include bitter taste, hypertension, nausea, emesis, effects on the gastrointestinal tract appetite, nutrition, nutrient absorption, satiety, hunger, diabetes, obesity, blood glucose levels, blood glucose regulation, metabolism, diet, and eating disorders.

Preparation of the Compounds of the Invention

Terpenoid Compounds

In some embodiments, one or more of the compounds of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), as described herein, is commercially available, for example from commercial sources such as Sigma-Aldrich® of St. Louis, Mo., USA; TCI America, Portland, Oreg., USA; and Aeros Organics, Geel, Belgium; among others.

In other embodiments, one or more of the compounds of Formula (I), Formula (Ia), Formula (IIa), Formula (IIIa), Formula (IIb), Formula (IIIb), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), Formula (IIh), is prepared from commercially available reagents by routine methods in synthetic organic chemistry.

In one embodiment, one or more compounds of Formula (I), Formula (Ia), Formula (IIa), Formula (IIIa), Formula (IIb), or Formula (IIb) is prepared by in a multi-step sequence beginning with epoxidation of diene A1 to afford epoxide P1, which then undergoes Brønsted acid or Lewis acid catalyzed cyclization to afford cyclohexene P2 after quenching of the cation by deprotonation Reduction of the olefin of P2 followed by elimination of the hydroxy group affords olefin product P3 (Scheme I):

by the use of a directing group on the —C(R²)(R³)(R⁴) moiety, such as a hydroxy group. Moreover, epoxidation of A1 can also be stereoselective through the use of chiral reagents and/or catalysts, such as those used in the Jacobsen epoxidation or the Sharpless epoxidation. Stereoselective epoxidation can afford an enantiomerically enriched cyclization product P3 as the stereochemistry of the epoxide can be transferred during the cyclization step.

In some instances, the cyclization step in Scheme I is promoted by the presence of Brønsted acids, such as inorganic acids (e.g., HCl, $H_2SO_4$, etc.) or organic acids (acetic acid, trifluoroacetic acid, triflic acid, etc.). In certain embodiments, the cyclization step in Scheme I is promoted by the use of Lewis acids, such as boron compounds (e.g., $Bu_2BOTf$ or $BF_3.Et_2O$), titanium compounds (e.g., $TiCl_4$ or titanium alkoxides), aluminum compounds (e.g., $AlCl_3$ or aluminium alkoxides), silicon compounds (e.g., trialkylsilyl triflates, such as TMS-OTf, trialkylsilyl halides, etc.), and the like.

Suitable reducing conditions include those known in the art for reducing olefins, such as hydrogenolysis with hydrogen and palladium, such as palladium on carbon.

During the final elimination step of Scheme I, the hydroxy group may be converted to a leaving group to facilitate the elimination. Suitable leaving groups include those recognized in the art for elimination reactions, such as halide (e.g., chloro, bromo, iodo), alkoxy, aryloxy, activated leaving groups, and the like. In some embodiments, elimination conditions also employ an inorganic or organic base. Suitable bases include those recognized in the art for such reactions, and include but are not limited to alkaline and alkaline earth metal hydroxides (such as NaOH, LiOH, etc.), carbonates (such as $Na_2CO_3$, $K_2CO_3$, $CaCO_3$, etc.) and

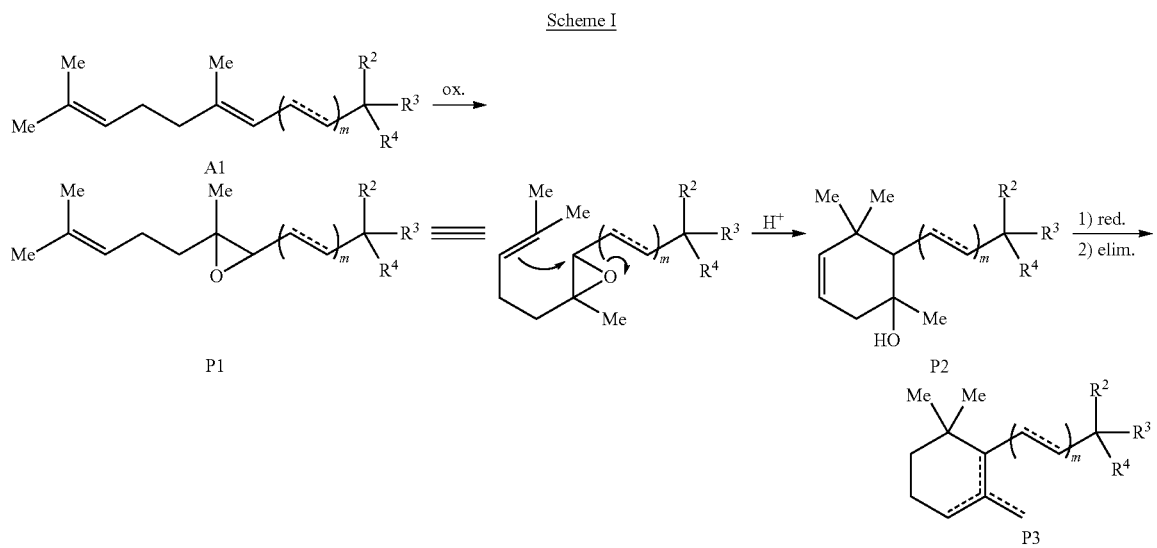

Scheme I

Suitable epoxidation conditions include those known in the art for epoxidizing olefins, such as use of hydrogen peroxide, peroxycarboxylic acids (e.g., perbenzoic acids, such as m-CPBA), alkyl hydroperoxides (e.g., tert-butylperoxide), acetone peroxide, or transition metal reagents, such as osmium tetroxide, manganese with sodium hypochlorite (Jacobsen epoxidation), or titanium with tartrate ester (Sharpless epoxidation). In one embodiment, selective epoxidation of the internal olefin of A1 is achieved bicarbonates (such as $NaHCO_3$, $KHCO_3$, etc.), Other suitable bases include aprotic amine bases, such as triethylamine, pyrridine, 2,6-lutidine, 1,8-diazabicycloundec-7-ene (DBU), 4-(dimethylamino-pyridine, etc. In some instances, suitable bases include strong bases such as alkoxides (such as sodium or potassium tert-butoxide), lithium diisopropyl amide (LDA), lithium bis(trimethylsilyl)amide (LiHMDS), sodium bis(trimethylsilyl)amide (NaHMDS), and the like. In other instances, the elimination employs acidic conditions. Suitable acids include inorganic acids (e.g., HCl, H₂SO₄, etc.) or organic acids (acetic acid, trifluoroacetic acid, triflic acid, etc.), Although in Scheme I the cation formed during the cyclization step is quenched by deprotonation resulting in an olefin, in other embodiments, the cation is quenched by addition of water. The resulting hydroxy group can also be eliminated and the resulting olefin reduced.

In one embodiment, one or more compounds of Formula (I), formula (Ia), Formula (IIa), Formula (IIIa), Formula (IIb), or Formula (IIIb) is prepared by nucleophilic attack by nucleophile A2 on aldehyde P3, wherein $R^3$ and $R^4$ together form =O, followed by oxidation of the resulting alcohol P4 to afford product P5 (Scheme II):

Scheme II

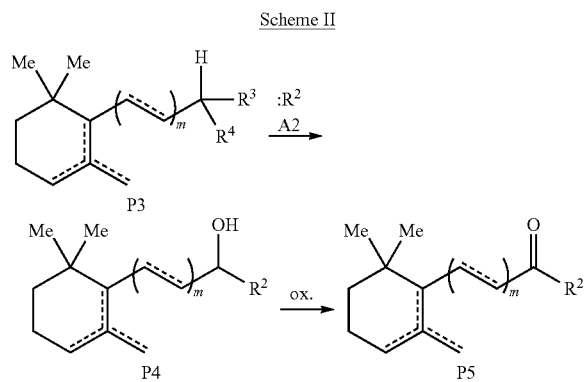

Oxidation can be carried out using routine methods known in the art, such as Swern oxidation, PC, TPAP/NMO, Dess-Martin periodinane, IBX, TEMPO, etc.

In another embodiment, one or more compounds of Formula (I), Formula (Ia), Formula (IIa), Formula (IIIa), Formula (IIb), or Formula (IIIb) is prepared by nucleophilic attack by nucleophile A2 on acyl compound P3, wherein $R^3$ and $R^4$ together form =O, to displace leaving group LG to afford product P5 (Scheme III):

Scheme III

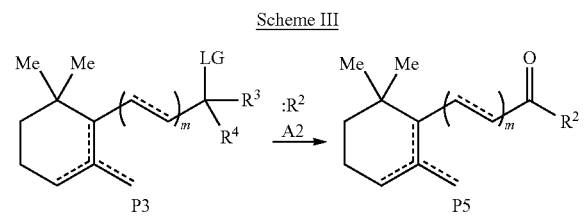

Suitable leaving groups include those recognized in the art for acylation reactions, such as halide (e.g., chloro, bromo, iodo), alkoxy, aryloxy, leaving groups associated with activated esters (e.g., N-succinamide or that associated with dicyclohexylcarbodiimide), and the like. In some embodiments, acylation conditions also employ an inorganic or organic base. Suitable bases include those recognized in the art for such reactions, and include but are not limited to alkaline and alkaline earth metal hydroxides (such as NaOH, LiOH, etc.), carbonates (such as Na₂CO₃, K₂CO₃, CaCO₃, etc.), and bicarbonates (such as NaHCO₃, KHCO₃, etc.). Other suitable bases include amine bases, such as ammonia, ammonium hydroxide, triethylamine, pyridine, piperidine, pyrrolidine, 2,6-lutidine, 1,8-diazabicycloundec-7-ene (DBU), 4-(dimethylamino)-pyridine, etc.

In one particular embodiment, compound P3 is an acid halide, such as an acid chloride or bromide, and the acylation reaction proceeds in the presence of an aprotic amine base, such as triethylamine, pyridine, 2,6-lutidine, 1,8-diazobicycloundec-7-ene (DBU), 4-(dimethylamino)-pyridine. When P3 is an acid halide, compound P3 can be prepared from the corresponding carboxylic acid using routine methods known in the art.

In one embodiment, one or more compounds of Formula (I), Formula (IIc), Formula (IIIc), Formula (IId), Formula (IIId), Formula (IIe), Formula (IIIe), or Formula (IIf) is prepared by oxidation of alcohol A3 to aldehyde P6 (Scheme IV):

Scheme IV

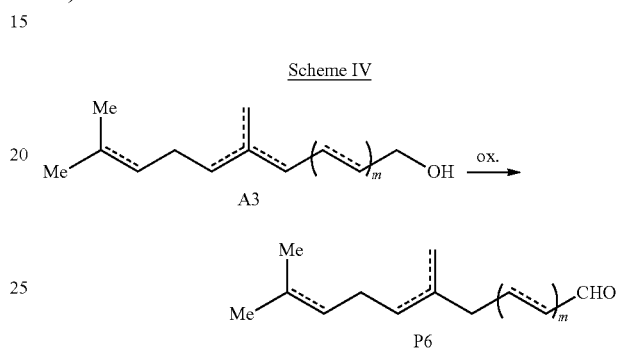

Oxidation can be carried out using routine methods known in the art, such as Swern oxidation PC, TPAP/NMO, Dess-Martin periodinane, IBX, TEMPO, etc.

In another embodiment, one or more compounds of Formula (I), Formula (IIc), Formula (IIIc), Formula (IId), Formula (IIId), Formula (IIe), Formula (IIIe), or Formula (IIf) is prepared by nucleophilic attack by nucleophile A2 on aldehyde P6 followed by oxidation of the resulting alcohol P7 to afford product P8 (Scheme V):

Scheme V

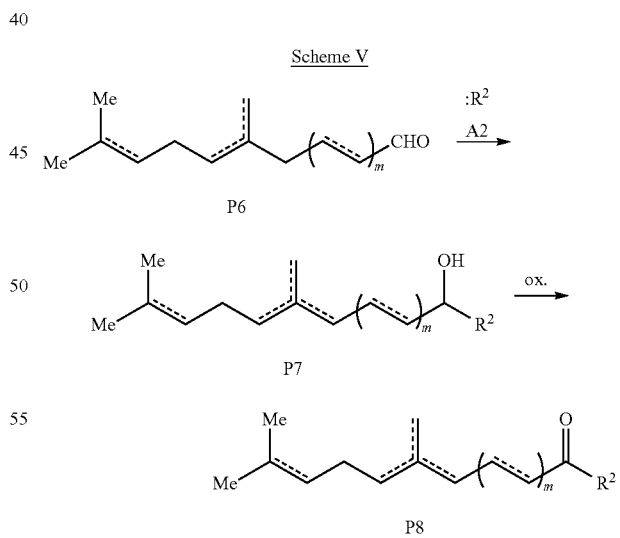

In some embodiments, one or more compounds of Formula (I), Formula (IIc), Formula (IIIc), Formula (IId), Formula (IIId), Formula (IIe), Formula (IIIe), or Formula (IIf) is prepared by nucleophilic attack by nucleophile A2 on acyl compound A4 to displace leaving group LG to afford product P8 (Scheme VI):

157

Scheme VI

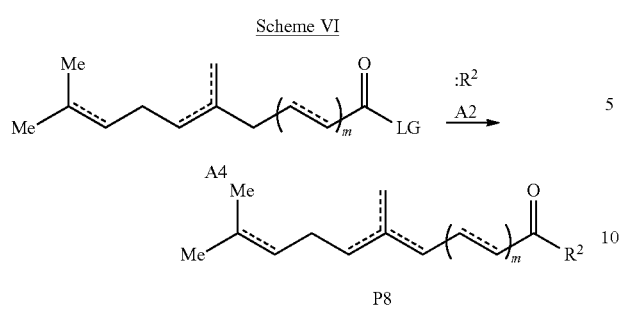

P8

Suitable leaving groups include those recognized in the art for acylation reactions, such as halide (e.g., chloro, bromo, iodo, alkoxy, aryloxy, leaving groups associated with activated esters (e.g., N-succinamide or that associated with dicyclohexylcarbodiimide and the like. In some embodiments, acylation conditions also employ an inorganic or organic base. Suitable bases include those recognized in the art for such reactions, and include but are not limited to alkaline and alkaline earth metal hydroxides (such as NaOH, LiOH, etc.), carbonates (such as $Na_2CO_3$, $K_2CO_3$, $CaCO_3$, etc.), and bicarbonates (such as $NaHCO_3$, $KHCO_3$, etc.). Other suitable bases include amine bases, such as ammonia, ammonium hydroxide, triethylamine, pyridine, piperidine, pyrrolidine, 2,6-lutidine, 1,8-diazabicycloundec-7-ene (DBU), 4-(dimethylamino)-pyridine, etc.

In one particular embodiment, compound P3 is an acid halide, such as an acid chloride or bromide, and the acylation reaction proceeds in the presence of an aprotic amine base, such as triethylamine, pyridine, 2,6-lutidine, 1,8-diazobicyclounder-7-ene (DBU), 4-(dimethylamino)-pyridine. When A4 is an acid halide, compound A4 can be prepared from the corresponding carboxylic acid using routine methods known in the art.

In some embodiments, compound A4 is prepared from the corresponding carboxylic acid using routine methods known in the art. In other embodiments, compound A4 is prepared from alcohol A3 by oxidation using methods known in the art.

In one embodiment, one or more compounds of Formula (I), Formula (IIc), Formula (IIIc), Formula (IId), Formula (IIId), Formula (IIe), Formula (IIIe), Formula (IIf), or Formula (IIh) is prepared by acetal formation under acidic conditions between aldehyde P6 and nucleophile A2, when $R^2$ represents alkoxy, to afford acetal product P9 (Scheme VII):

Scheme VII

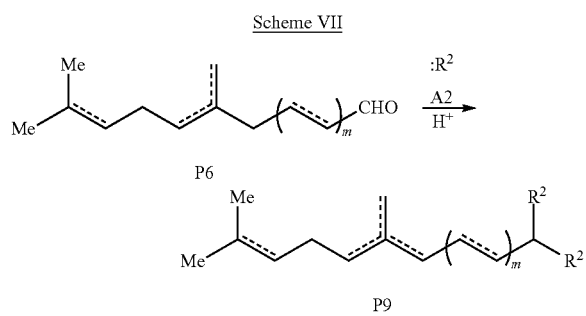

Suitable acids for acetal formation include inorganic acids (e.g., HCl, $H_2SO_4$, etc.) and organic acids (acetic acid, trifluoroacetic acid, triflic acid, etc.),

158

In one embodiment, one or more compounds of Formula (I), Formula (IIc), Formula (IIIc), Formula (IVc), Formula (IId), Formula (IIId), Formula (IVd), Formula (IIe), Formula (IIIe), Formula (IVe), Formula (IIf), Formula (IIg), or Formula (IIh), wherein $R^2$ is —OC(O)—R, is prepared by acylation of alcohol A3 with acyl compound A5 bearing leaving group LG to afford product P10 (Scheme VIII):

Scheme VIII

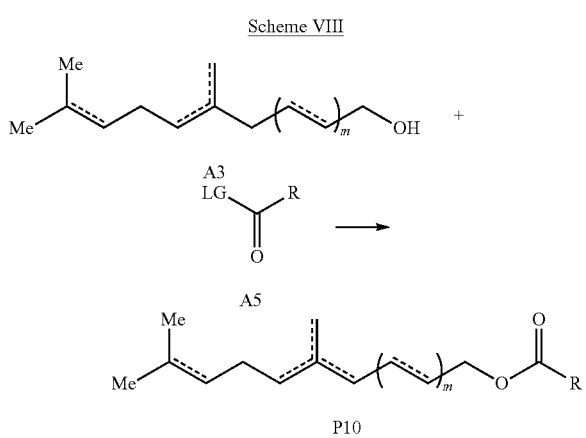

P10

Suitable leaving groups include those recognized in the art for acylation reactions, such as halide (e.g., chloro, bromo, iodo), aryloxy, leaving groups associated with activated esters (e.g., N-succinamide or that associated with dicyclohexylcarbodimiide), and the like. In certain embodiments, acyl compound A5 is an acid anhydride; that is LG is —OC(O)R. In some embodiments, acylation conditions also employ an inorganic or organic base. Suitable bases include those recognized in the art for such reactions, and include but are not limited to alkaline and alkaline earth metal carbonates carbonates (such as $Na_2CO_3$, $K_2CO_3$, $CaCO_3$, etc.), and bicarbonates (such as $NaHCO_3$, $KHCO_3$, etc.). Other suitable bases include amine bases, such as ammonia, ammonium hydroxide, triethylamine, pyridine, piperidine, pyrrolidine, 2,6-lutidine, 1,8-diazabicycloundec-7-ene (DBU), 4-(dimethylamino)-pyridine, etc.

In one particular embodiment, compound A5 is an acid halide, such as an acid chloride or bromide, and the acylation reaction proceeds in the presence of an amine base, such as triethylamine, pyridine, 2,6-lutidine, 1,8-diazabicyclounder-7-ene (DBU), 4-(dimethylamino)-pyridine, etc.

In another embodiment, compound A2 is an activated ester and acylation proceeds under mild conditions that do not result in the generation of strong acids.

Compound A5 can be prepared from the corresponding carboxylic acid using routine methods known in the art.

Chroman Compounds

In some embodiments, one or more of the compounds of Formula (V), Formula (VIa), Formula (VIb), or Formula (VIIa), as described herein, is commercially available, for example from commercial sources such as Sigma-Aldrich® of St. Louis, Mo., USA; TCI America, Portland, Oreg., USA; and Aeros Organics, Geel, Belgium; among others.

In other embodiments, one or more of the compounds of Formula (V), Formula (VIa), Formula (VIb), or Formula (VIIa), is prepared from commercially available reagents by routine methods in synthetic organic chemistry.

In one embodiment, one or more compounds of Formula (V), Formula (VIa), Formula (VIb), or Formula (VIIa) is prepared by cyclization of phenol A21 by intramolecular displacement of leaving group LG (Scheme IX):

Scheme IX

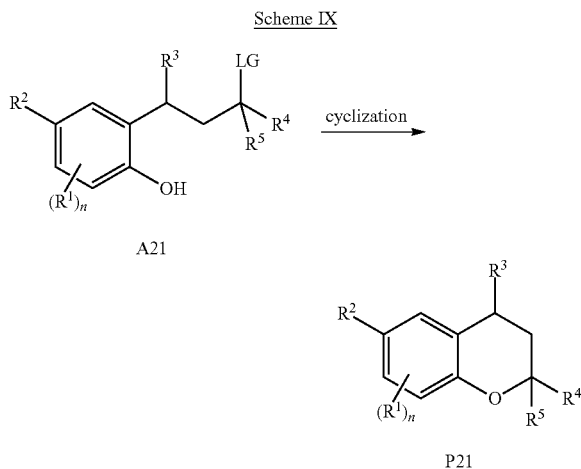

Suitable leaving groups include those recognized in the art for acylation reactions, such as halide (e.g., chloro, bromo, iodo), triflate, mesylate, tosylate, alkoxy, acyloxy, and the like. In some instances, the displacement reaction employs an inorganic or organic base in order to deprotonate the phenol. Suitable bases include those recognized in the art for such reactions, and include but are not limited alkaline and alkaline earth metal carbonates carbonates (such as $Na_2CO_3$, $K_2CO_3$, $CaCO_3$, etc.), and bicarbonates (such as $NaHCO_3$, $KHCO_3$, etc.). Other suitable bases include amine bases, such as ammonia, ammonium hydroxide, triethylamine, pyridine, piperidine, pyrrolidine, 2,6-lutidine, 1,8-diazabicycloundec-7-ene (DBU), 4-(dimethylamino)-pyridine, etc. In some embodiments, LG is hydroxy and the cyclization is promoted by acidic conditions, such as with inorganic acids (e.g., HCl, $H_2SO_4$, etc.) or organic acids (acetic acid, trifluoroacetic acid, triflic acid, etc.), In certain embodiments, phenol A21 is prepared in two steps, first by nucleophilic attack on ketone A22 with nucleophile A23 to give alcohol P22, second by conversion of the tertiary alcohol of P22 to leaving group LG (Scheme X):

Scheme X

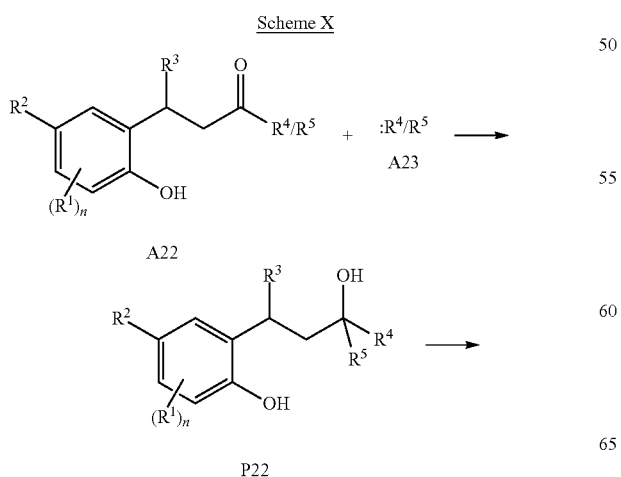

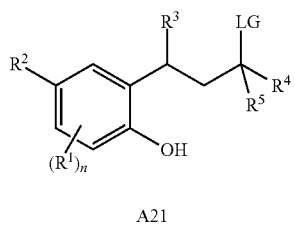

Conversion of the tertiary alcohol of P22 to leaving group LG can be performed by routine methods known in the art, such as conversion to a halide, mesylate, toxylate, or triflate, acylation, or treatment with inorganic acids (e.g., HCl, $H_2SO_4$, etc.) or organic acids (acetic acid, trifluoroacetic acid, triflic acid, etc.), In certain embodiments, phenol A21, wherein $R^4$ or $R^5$ is H, is prepared in two steps, first by nucleophilic attack on aldehyde A24 with nucleophile A23 to give alcohol P23, second by conversion of the secondary alcohol of P23 to leaving group LG (Scheme XI):

Scheme XI

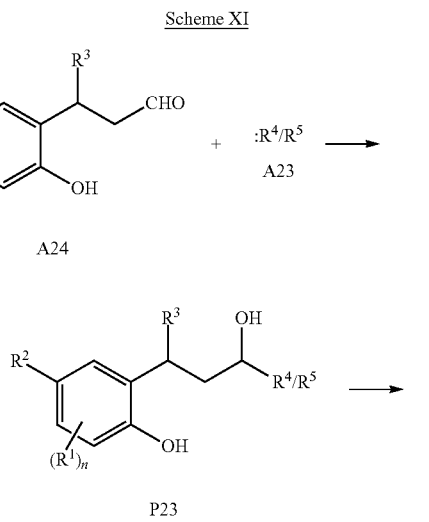

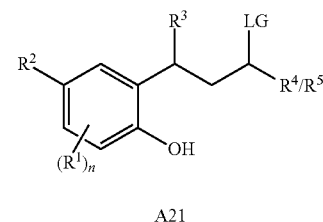

Conversion of the secondary alcohol of P23 to leaving group LG can be performed by routine methods known in the art, such as conversion to a halide, mesylate, toxylate, or triflate, acylation, or treatment with inorganic acids (e.g., HCl, $H_2SO_4$, etc.) or organic acids (acetic acid, trifluoroacetic acid, triflic acid, etc.), In some embodiments, aldehyde A24 is prepared by oxidation of primary alcohol A25 (Scheme XII):

Scheme XII

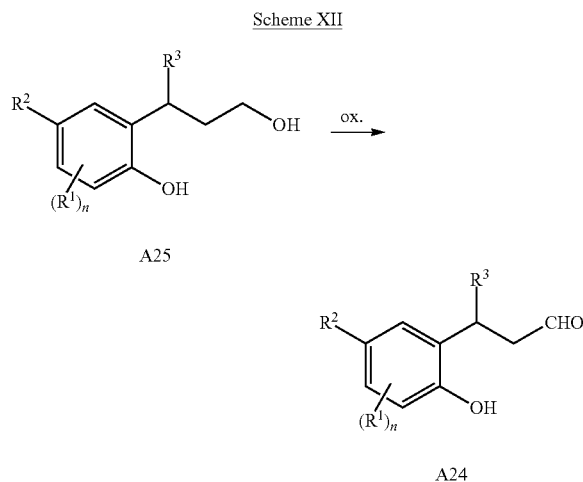

Oxidation can be carried out using routine methods known in the art, such as Swern oxidation, PC, TPAP/NMO, Dess-Martin periodinane, IBX, TEMPO, etc.

In another embodiment, one or more compounds of Formula (V) or Formula (VIb) is prepared by lactonization between the phenol and activated carboxyl group —C(O)-LG of A26 resulting in loss of leaving group LG to afford lactone P24 (Scheme XIII):

Scheme XIII

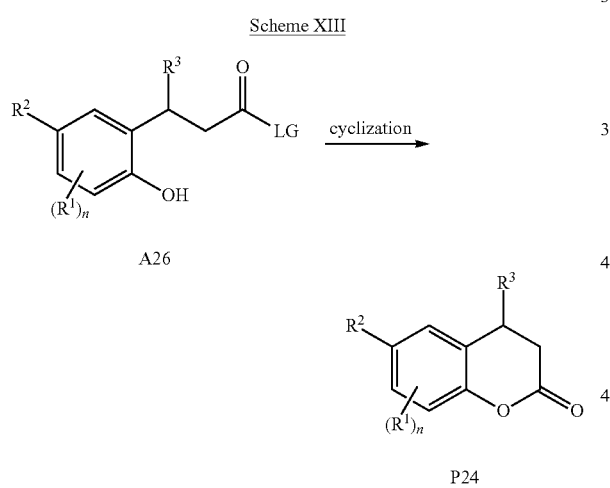

Suitable leaving groups include those recognized in the art for acylation reactions, such as halide (e.g., chloro, bromo), alkoxy, acyloxy, activated groups (e.g., —O—N-succinamide, or that generated by the use of dicyclohexylcarbodiimide, DC), and the like. When LG is halide, suitable lactonization conditions often employ an inorganic or organic base. Suitable bases include those recognized in the art for such reactions, and include but are not limited to alkaline and alkaline earth metal carbonates (such as $Na_2CO_3$, $K_2CO_3$, $CaCO_3$, etc.), and bicarbonates (such as $NaHCO_3$, $KHCO_3$, etc.). Other suitable bases include amine bases, such as ammonia, ammonium hydroxide, triethylamine, pyridine, piperidine, pyrrolidine, 2,6-lutidine, 1,8-diazabicycloundec-7-ene (DBU), 4-(dimethylamino)-pyridine, etc.

In another embodiment, compound A22 is prepared by nucleophilic attack of nucleophile A23 on lactone P24 (Scheme XIV):

Scheme XIV

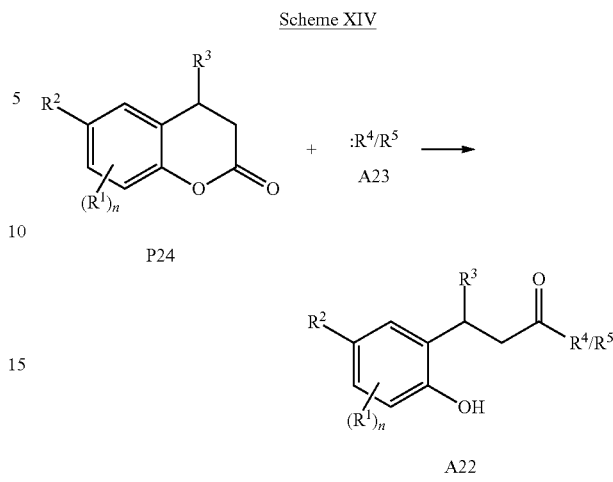

In another embodiment, ketone A22 is prepared by oxidation of secondary alcohol P23 (Scheme XV):

Scheme XV

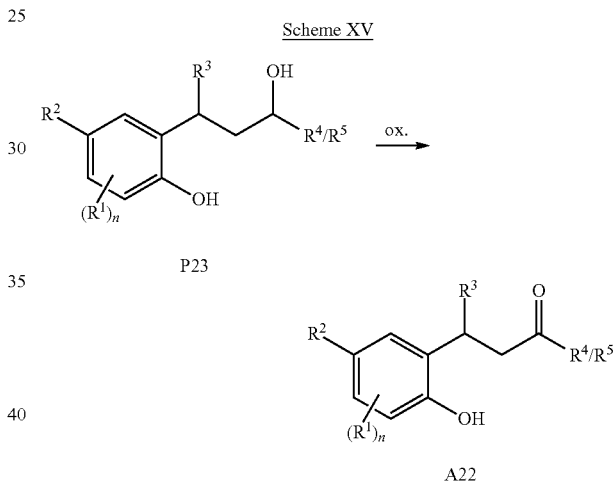

Oxidation can be carried out using routine-methods known in the art, such as Swern oxidation, PC, TPAP/NMO, Dess-Martin periodinane, IBX, TEMPO, etc.

In another embodiment, one or more compounds of Formula (V) or Formula (VIb), wherein $R^4$ and $R^5$ are H, is prepared by redaction of lactone P24 to the corresponding cyclic ether P25 (Scheme XVI):

Scheme XVI

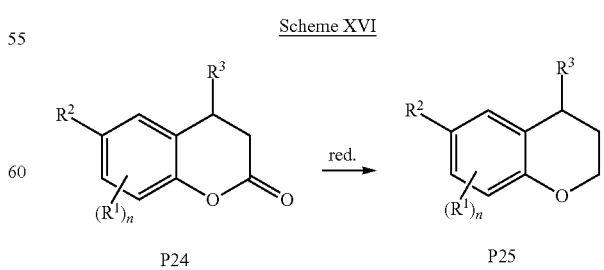

Suitable reduction conditions include those known in the art for reducing esters, such as treatment with hydride sources, such as lithium aluminum hydride (LiAlH$_4$), diisobutylaluminum hydride (DIBAL), and various borane compounds.

The skilled artisan will appreciate that any of the above reactions in which a stereogenic center is formed can be performed under enantioselective conditions that produce a product enriched in one enantiomer, for example, with greater than about 25, 50, 70, 80, 90, 95, 97, 98, or 99%. Such stereoselectivity can be induced through the use of chiral auxiliaries, reagents, and catalysts as known in the art.

Benzo Ring-Containing Compounds

In some embodiments, one or more of the compounds of Formula (VIII), Formula (IXa), Formula (IXb), Formula (IXc), or Formula (IXd), as described herein, is commercially available, for example from commercial sources such as Sigma-Aldrich® of St. Louis, Mo., USA; TCI America, Portland, Oreg., USA; and Aeros Organics, Geel, Belgium; among others.

In other embodiments, one or more of the compounds of Formula (VIII), Formula (IXa), Formula (IXb), Formula (IXe), or Formula (IXd) is prepared from commercially available reagents by routine methods in synthetic organic chemistry.

In one embodiment, one or more compounds of Formula (VIII, Formula (IXa), Formula (IXb), or Formula (IXe) is prepared by esterification of benzoic acid A31 (when X is OH) or of acid halide A31 (when X is halide) with alcohol A32 to afford ester P31 (Scheme XVII):

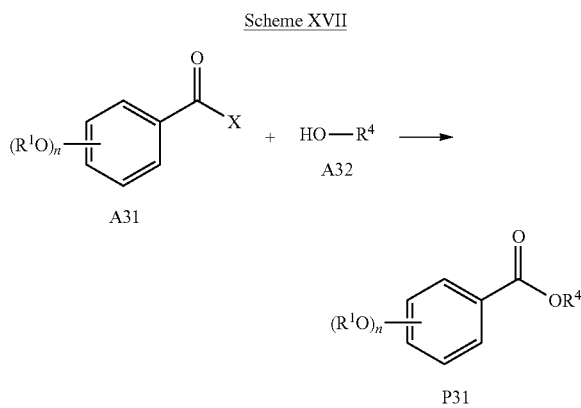

Suitable esterification conditions when X is OH include those known in the art, such as Fischer esterification, Steglich esterification (i.e., using dicyclohexylcarbodiimide, DC), as well as ethers involving activated esters (when X is an activated group, such as —O—N-succinamide). When X is halide, suitable esterification conditions often employ an inorganic or organic base. Suitable bases include those recognized in the art for such reactions, and include but are not limited to alkaline and alkaline earth metal carbonates (such as Na$_2$CO$_3$, K$_2$CO$_3$, CaCO$_3$, etc.), and bicarbonates (such as NaHCO$_3$, KHCO$_3$, etc.). Other suitable bases include amine bases, such as ammonia, ammonium hydroxide, triethylamine, pyridine, piperidine, pyrrolidine, 2,6-lutidine, 1,8-diazabicycloundec-7-ene (DBU), 4-(dimethylamino)-pyridine, etc.

Compound A31 (when X is halide) can be prepared from the corresponding carboxylic acid using routine methods known in the art.

Although not pictured, in some instances, one or more compounds of Formula (VIII, Formula (IXa), Formula (IXb), or Formula (IXe) is prepared by esterification of benzoic acid A31 (when X is OH) or of acid halide A31 (when X is halide) with alcohol A32 to afford ester P31. When utilizing an acid anhydride, suitable esterification conditions often employ an inorganic or organic base. Suitable bases include those recognized in the art for such reactions, and include but are not limited to alkaline and alkaline earth metal carbonates (such as Na$_2$CO$_3$, K$_2$CO$_3$, CaCO$_3$, etc.), and bicarbonates (such as NaHCO$_3$, KHCO$_3$, etc.). Other suitable bases include amine bases, such as ammonia, ammonium hydroxide, triethylamine, pyridine, piperidine, pyrrolidine, 2,6-lutidine, 1,8-diazabicycloundec-7-ene (DBU), 4-(dimethylamino)-pyridine, etc. In some instances, reaction with acid anhydrides also includes use of a reagent that reacts with the acid anhydride to generate an activated ester in situ.

In another embodiment, one or more compounds of Formula (VIII), Formula (IXa), Formula (IXb), or Formula (IXe) is prepared by alkylation of benzoate A31 (when X is O$^-$) with compound A33 by displacement of the leaving group LG of A33 to afford ester P31 (Scheme XVIII):

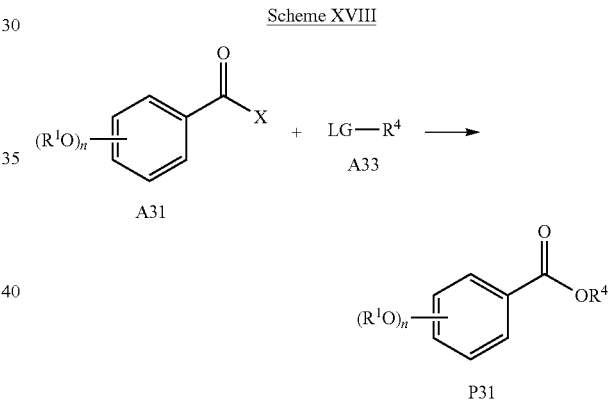

In some instances, the benzoate is generated by deprotonating benzoic acid A31 (when X is OH) with an inorganic or organic base. Suitable bases include those recognized in the art for such reactions, and include but are not limited to alkaline and alkaline earth metal carbonates (such as Na$_2$CO$_3$, K$_2$CO$_3$, CaCO$_3$, etc.) and bicarbonates (such as NaHCO$_3$, KHCO$_3$, etc.), Other suitable bases include amine bases, such as ammonia, ammonium hydroxide, triethylamine, pyrridine, piperidine, pyrrolidine, 2,6-lutidine, 1,8-diazabicycloundec-7-ene (DBU), 4-(dimethylamino-pyridine, etc. Suitable leaving groups include those recognized in the art, such as halide e.g., chloro, bromo, iodo), triflate, mesylate, tosylate, and the like.

In certain embodiments, one or more compounds of Formula (VIII) or Formula (IXd) is prepared by nucleophilic addition of one or more nucleophiles A34 to ester P31 to afford alcohol P32, which can optionally under go etherification with compound A33 by displacement of leaving group LG to afford ether P33 (Scheme XIX):

Scheme XIX

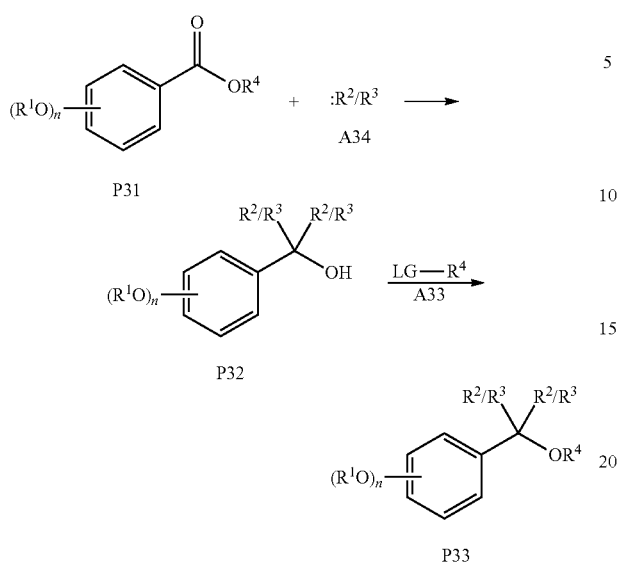

Suitable leaving groups include those recognized in the art, such as halide e.g., chloro, bromo, iodo), triflate, mesylate, toxylate, and the like. In some instances, the displacement reaction employs an inorganic or organic base. Suitable bases include those recognized in the art for such reactions, and include but are not limited to alkaline and alkaline earth metal carbonates (such as $Na_2CO_3$, $K_2CO_3$, $CaCO_3$, etc.) and bicarbonates (such as $NaHCO_3$, $KHCO_3$, etc.), Other suitable bases include amine bases, such as ammonia, ammonium hydroxide, triethylamine, pyrridine, piperidine, pyrrolidine, 2,6-lutidine, 1,8-diazabicycloundec-7-ene (DBU), 4-(dimethylamino-pyridine, etc. In some instances, suitable bases include strong bases such as alkoxides (such as sodium or potassium tert-butoxide), lithium diisopropyl amide (LDA), lithium bis(trimethylsilyl)amide (LiHMDS), sodium bis(trimethylsilyl)amide (NaHMDS), and the like.

In another embodiment, one or more compounds of Formula (VIII) or Formula (IXd) is prepared by nucleophilic addition of nucleophile A34 to aldehyde A35 to afford alcohol P34 (Scheme XX):

Scheme XX

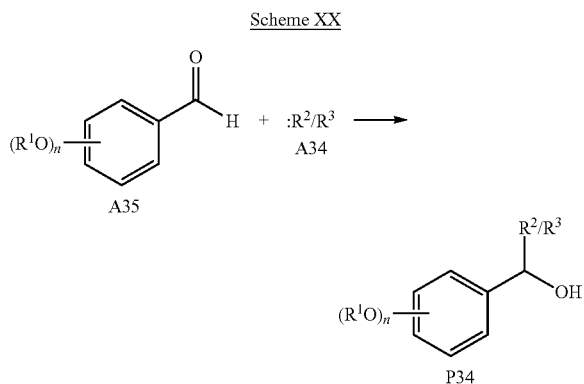

In certain embodiments, alcohol P34 is oxidized to a carbonyl (e.g., using routine methods known in the art, such as Swern oxidation, PC, TPAP/NMO, Dess-Martin periodi-nane, IBX, TEMPO, etc.), which is then subjected to nucleophilic attack by nucleophile A34 (which can be the same or different from A34 in Scheme XX) to afford alcohol P32, which, as noted above, can optionally undergo etherification with compound A33 to afford ether P33 (Scheme XXI):

Scheme XXI

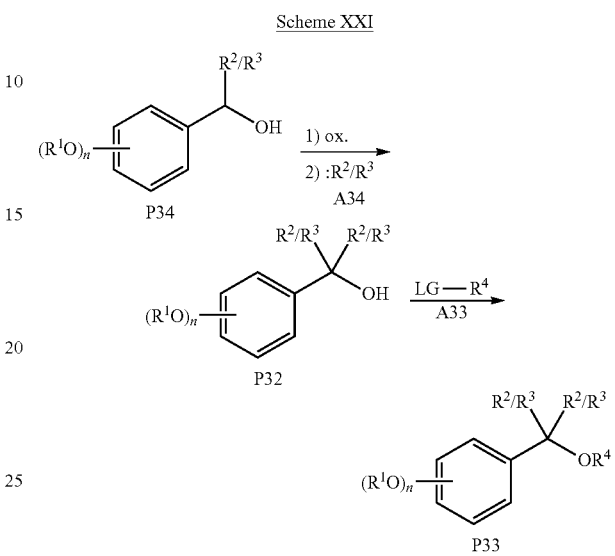

In some embodiments, one or more compounds of formula (VIII) or formula (IXd) is prepared by etherification of alcohol P34 with compound A33 by displacement of the leaving group LG to afford ether P35 (Scheme XXII):

Scheme XXII

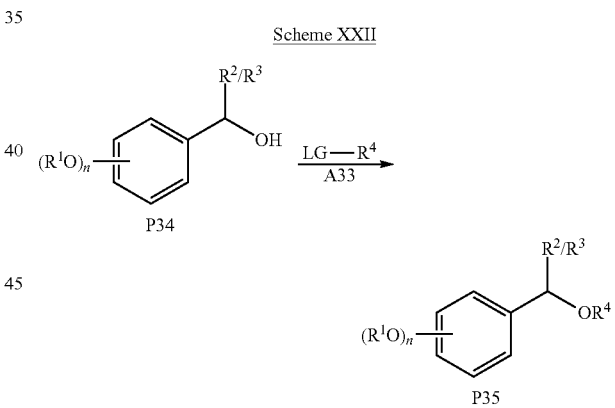

Suitable leaving groups include those recognized in the art, such as halide e.g., chloro, bromo, iodo), triflate, mesylate, toxylate, and the like. In some instances, the displacement reaction employs an inorganic or organic base. Suitable bases include those recognized in the art for such reactions, and include but are not limited to alkaline and alkaline earth metal carbonates (such as $Na_2CO_3$, $K_2CO_3$, $CaCO_3$, etc.) and bicarbonates (such as $NaHCO_3$, $KHCO_3$, etc.), Other suitable bases include amine bases, such as ammonia, ammonium hydroxide, triethylamine, pyrridine, piperidine, pyrrolidine, 2,6-lutidine, 1,8-diazabicycloundec-7-ene (DBU), 4-(dimethylamino-pyridine, etc. In some instances, suitable bases include strong bases such as alkoxides (such as sodium or potassium tert-butoxide), lithium diisopropyl amide (LDA), lithium bis(trimethylsilyl)amide (LiHMDS), sodium bis(trimethylsilyl)amide (NaHMDS), and the like.

In some embodiments, one or more compounds of Formula (VIII) or Formula (IXd), wherein $R^2$ and/or $R^3$ is hydrogen, is prepared by reduction of ester P31 to ether P36 (Scheme XXIII):

Scheme XXIII

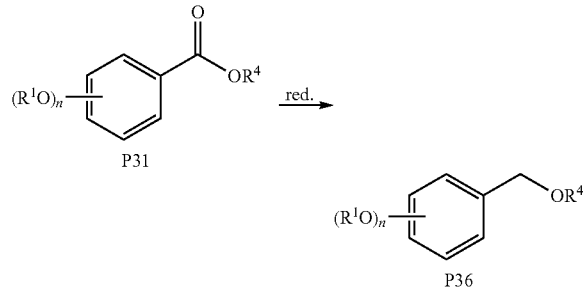

Suitable reduction conditions include those known in the art for reducing esters, such as treatment with hydride sources, such as lithium aluminum hydride (LiAlH$_4$), diisobutylaluminum hydride (DIBAL), and various borane compounds.

In certain embodiments, one or more compounds of Formula (VIII) or Formula (IXd), wherein $R^2$ and/or $R^3$ is hydrogen, is prepared by etherification of benzyl alcohol A36 with compound A33 by displacement of the leaving group LG to afford to ether P36 (Scheme XXIV):

Scheme XXIV

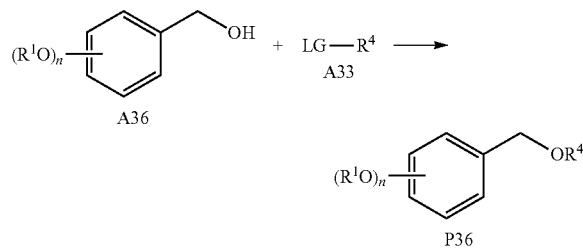

Suitable leaving groups include those recognized in the art, such as halide e.g., chloro, bromo, iodo), triflate, mesylate, toxylate, and the like. In some instances, the displacement reaction employs an inorganic or organic base. Suitable bases include those recognized in the art for such reactions, and include but are not limited to alkaline and alkaline earth metal carbonates (such as Na$_2$CO$_3$, K$_2$CO$_3$, CaCO$_3$, etc.) and bicarbonates (such as NaHCO$_3$, KHCO$_3$, etc.), Other suitable bases include amine bases, such as ammonia, ammonium hydroxide, triethylamine, pyrridine, piperidine, pyrrolidine, 2,6-lutidine, 1,8-diazabicycloundec-7-ene (DBU), 4-(dimethylamino-pyridine, etc. In some instances, suitable bases include strong bases such as alkoxides (such as sodium or potassium tert-butoxide), lithium diisopropyl amide (LDA), lithium bis(trimethylsilyl)amide (LiHMDS), sodium bis(trimethylsilyl)amide (NaHMDS), and the like.

In alternate embodiments, one or more compounds of Formula (VIII) or Formula (IXd), wherein $R^2$ and/or $R^3$ is hydrogen, is prepared by etherification of alcohol A32 with compound A37 by displacement of the leaving group LG to afford to ether P36 (Scheme XXV);

Scheme XXV

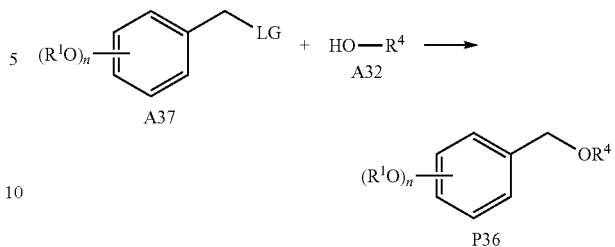

Suitable leaving groups include those recognized in the art, such as halide e.g., chloro, bromo, iodo), triflate, mesylate, toxylate, and the like. In some instances, the displacement reaction employs an inorganic or organic base. Suitable bases include those recognized in the art for such reactions, and include but are not limited to alkaline and alkaline earth metal hydroxides (such as Na$_2$CO$_3$, LiOH, etc.), carbonates (such as NaHCO$_3$, K$_2$CO$_3$, CaCO$_3$, etc.), and bicarbonates (such as NaHCO$_3$, KHCO$_3$, etc.), Other suitable bases include amine bases, such as ammonia, ammonium hydroxide, triethylamine, pyrridine, piperidine, pyrrolidine, 2,6-lutidine, 1,8-diazabicycloundec-7-ene (DBU), 4-(dimethylamino-pyridine, etc. In some instances, suitable bases include strong bases such as alkoxides (such as sodium or potassium tert-butoxide), lithium diisopropyl amide (LDA), lithium bis(trimethylsilyl)amide (LiHMDS), sodium bis(trimethylsilyl)amide (NaHMDS), and the like.

Polycyclic Compounds

In some embodiments, one or more of the compounds of Formula (XI) or Formula (XII) is as described herein, is commercially available, for example from commercial sources such as Sigma-Aldrich® of St. Louis, Mo., USA; TCI America, Portland, Oreg., USA; and Aeros Organics, Geel, Belgium; among others.

In other embodiments, one or more of the compounds of Formula (XI) or Formula (XII) is prepared from commercially available reagents by routine methods in synthetic organic chemistry.

In one embodiment, one or more compounds of Formula (XI) is prepared by reduction of a commercially available ketone A41, such as camphor (e.g., where $R^1$, $R^2$, and $R^3$ are methyl and $R^6$ and $R^7$ are hydrogen) to afford alcohol P41 (i.e., wherein $R^4$ is hydrogen) (Scheme XVI). Ketones such as A41 are commercially available in racemic and enantiomerically enriched forms. The alcohol product P41 is optionally etherified or acylated with compound A42 by displacement of the leaving group LG to afford to ether or acyl compound P42 (Scheme XXVI):

Scheme XXVI

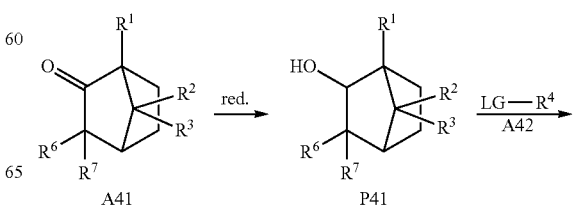

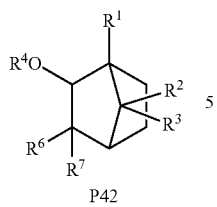

P42

Suitable reduction conditions include those known in the art for reducing esters, such as treatment with hydride sources, such as lithium aluminum hydride (LiAlH$_4$), diisobutylaluminum hydride (DIBAL), and various borane compounds. In some instances, reduction of the ketone is diastereoselective such that an excess of one diastereomeric product is prepared, such as an excess of the endo alcohol or the exo alcohol.

Suitable leaving groups include those recognized in the art, such as halide e.g., chloro, bromo, iodo), triflate, mesylate, toxylate, and the like. In some instances, the displacement reaction employs an inorganic or organic base. Suitable bases include those recognized in the art for such reactions, and include but are not limited to alkaline and alkaline earth metal hydroxides (such as Na$_2$CO$_3$, LiOH, etc.), carbonates (such as NaHCO$_3$, K$_2$CO$_3$, CaCO$_3$, etc.), and bicarbonates (such as NaHCO$_3$, KHCO$_3$, etc.), Other suitable bases include amine bases, such as ammonia, ammonium hydroxide, triethylamine, pyridine, piperidine, pyrrolidine, 2,6-lutidine, 1,8-diazabicycloundec-7-ene (DBU), 4-(dimethylamino-pyridine, etc. In some instances, suitable bases include strong bases such as alkoxides (such as sodium or potassium tert-butoxide), lithium diisopropyl amide (LDA), lithium bis(trimethylsilyl)amide (LiHMDS), sodium bis(trimethylsilyl)amide (NaHMDS), and the like.

In some embodiments, when alcohol P41 is acylated, compound A42 is a acylhalide or an acid anhydride. In one particular embodiment, compound A42 is an acid halide, such as an acid chloride or bromide, and the acylation reaction proceeds in the presence of an aprotic amine base, such as triethylamine, pyridine, 2,6-lutidine, 1,8-diazabicycloundec-7-ene (DBU), 4-(dimethylamino)-pyridine. When A42 is an acid halide, compound A42 can be prepared from the corresponding carboxylic acid using routine methods known in the art.

In another embodiment, one or more compounds of Formula (XI) is prepared by nucleophilic addition of nucleophile A43 (e.g., Grignard reagent, alkyllithium reagent) to ketone A41 to afford alcohol P43 (Scheme XXVII). As noted above for the alcohol product P41, the alcohol product P43 is optionally etherified or acylated with compound A42, by displacement of the leaving group LG to afford to ether or acyl compound P44 (Scheme XXVII):

Scheme XXVII

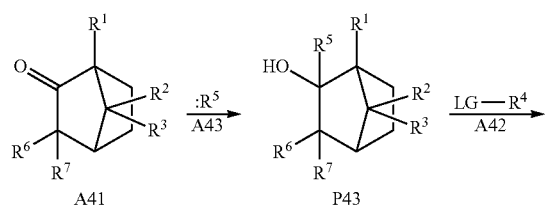

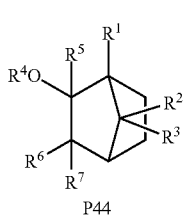

P44

In another embodiment, one or more compounds of Formula (XI), is prepared by enolizing commercially available ketone A41' (e.g., wherein one or both of R$^6$ and R$^7$ is hydrogen) with a strong base, optionally in the presence of a Lewis acid. The resulting enolate intermediate can then be reacted with electrophile A44 to afford product P4S (Scheme XXVIII):

Scheme XXVIII

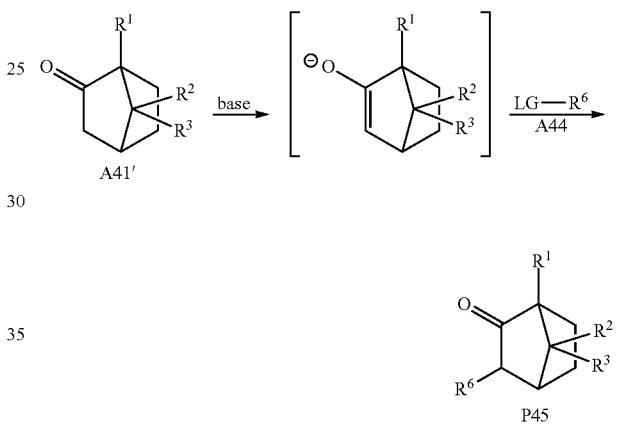

Examples of suitable bases for enclizing ketone A41' include strong bases such as alkoxides (such as sodium or potassium tert-butoxide), lithium diisopropyl amide (LDA), lithium bis(trimemylsilyl)amide (LiHMDS), sodium bis(t-rimethylsilyl)amide (NaHMDS), and the like.

Examples of suitable Lewis acids for promoting the enolization of ketone A41 include boron compounds (e.g., Bu$_2$BOTf or BF$_3$.Et$_2$O), titanium compounds (e.g., TiCl$_4$ or titanium alkoxides), aluminum compounds (e.g., AlCl$_3$ aluminum alkoxides), silicon compounds (e.g., trialkylsilyl triflates, such as TMS-OTf, trialkylsilyl halides, etc.), and the like.

With product ketone P45 in hand, the ketone can be reduced and optionally etherated or acylated as in Scheme XVI above or subject to nucleophilic attack and optionally etherated or acylated as in Scheme XVII above to give products P41, P42, P43, and P44.

In another embodiment, one or more compounds of Formula (XI), is prepared by enolizing product P45, as with alcohol A41 above, e.g., with a strong base, optionally in the presence of a Lewis acid. The resulting enolate intermediate is then be reacted with electrophile A45 to afford product P46, which has the structure of A41 (Scheme XXIX).

Scheme XXIX

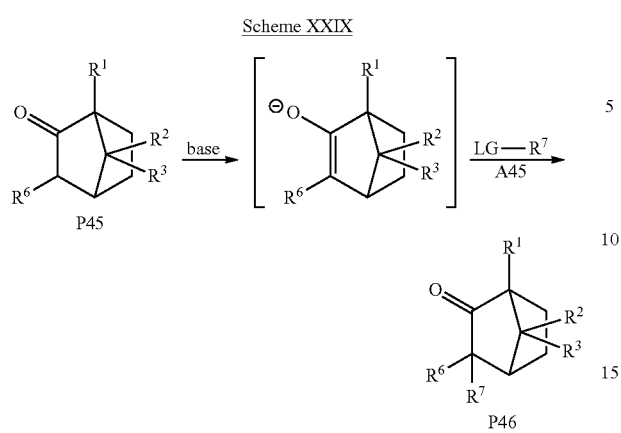

In another embodiment, one or more compounds of formula (XI) are prepared by imine formation between compounds A41, P45, or P46 and amine A46 to afford imine product P47 (Scheme XXX). Imine P47 is optionally reduced to afford amine product P48 (Scheme XXX):

Scheme XXX

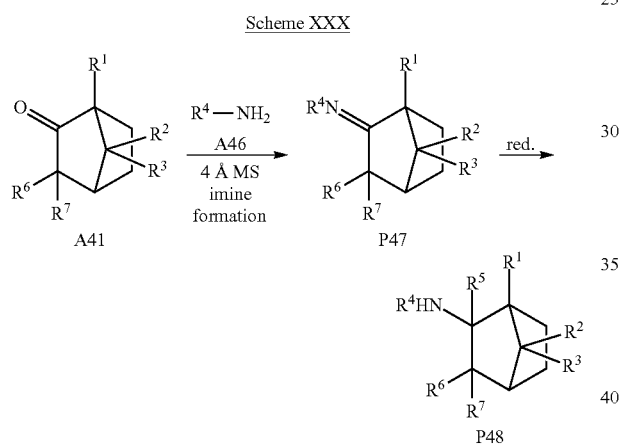

In some embodiments, imine formation conditions employ dehydrating agents, such as molecular sieves, heat, and/or the use of an azeotrope to remove water.

Suitable imine reducing conditions include those known in the art for reducing imine and iminimum ions, such as hydrogenolysis with hydrogen and palladium, such as palladium on carbon. Another suitable source of hydrogen includes formic acid.

In one embodiment, one or more compounds of Formula (XII) is prepared by hydroboration of a commercially available olefin A48, such as β-pinene (e.g., where $R^4$ is hydrogen and Y is a direct bond, and $R^1$ and $R^2$ are methyl) to give product organoborane P49, which is optionally oxidatively cleaved to afford alcohol P410 (Scheme XXXI).

Scheme XXXI

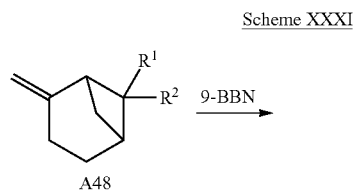

Suitable imine hydroboration conditions include the use of reagents such as borane, diborane, 9-BBN, among others. Oxidative cleavage of the organoborane P49 is carried out by standard methods, e.g., with hydrogen peroxide. The organoborane P9 is also optionally used in a Suzuki coupling with a suitable organohalide.

Olefins such as A48 are commercially available in racemic and enatiomerically enriched forms. Examples include α-pinene and β-pinene, pinenone, and pinenol.

In some embodiments, and in similar fashion as described above for Scheme XXVI, compounds of Formula (XVII) are prepared by etherifying or acylating the alcohol product P410 with electrophilic compound A49 by displacement of the leaving group LG to afford to ether or acyl compound P411 (Scheme XXXII):

Scheme XXXII

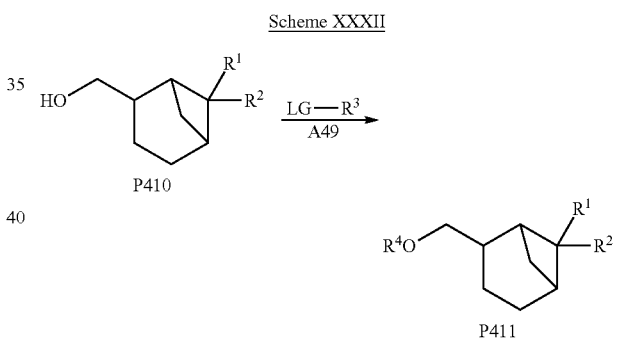

In other embodiments, one or more compounds of Formula (XII) is prepared by oxidative cleavage of a commercially available olefin A48 to give product ketone P412 (Scheme XXXIII). Ketone P412 is then able to under go reactions similar to those described for the ketones in Schemes XXVI-XXX above, such as enolate formation with base followed by nucleophilic attack on electrophile A410 to give product ketone P413, followed by reduction of the ketone P413 to give product alcohol P414, which is optionally etherified or acylation with electrophile A411 (Scheme XXXIII):

Scheme XXXIII

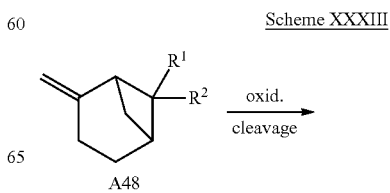

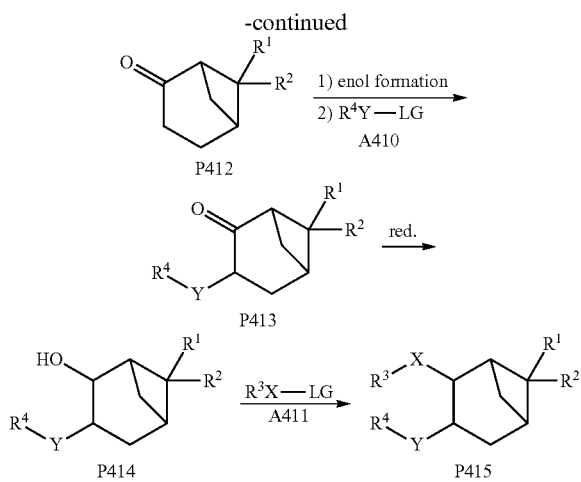

Suitable oxidative cleavage conditions include the use of catalytic ruthenium or osmium in combination with excess oxidants, such as oxone, sodium periodate, sodium perchlorate, bleach, and the like.

In other embodiments, one or more compounds of Formula (XII), wherein the bond with a dotted line is a double bond is prepared by elimination of the leaving group LG in compound A412 under basic or acidic conditions (Scheme XXXIV). Compound A412 is prepared from the corresponding alcohol P415 by conversion of the hydroxy group into the leaving group LG (Scheme XXXIV):

Scheme XXXIV

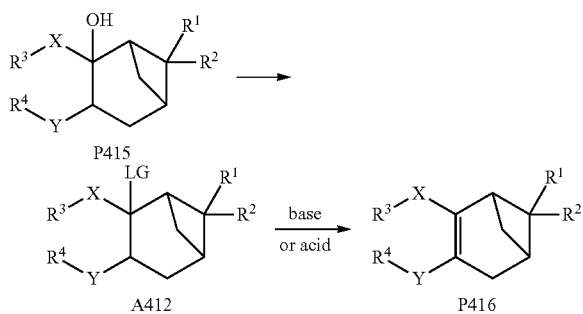

Conversion of the hydroxy group of P415 to leaving group LG can be performed by routine methods known in the art, such as conversion to a halide, mesylate, tosylate, or triflate, acylation, or treatment with inorganic acids (e.g., HCl, H$_2$SO$_4$, etc.) or organic acids (acetic acid, trifluoroacetic acid, triflic acid, etc.), Suitable bases for elimination of leaving group LG of A412 to afford olefin P416 include strong bases such as alkaline and alkaline earth metal hydroxides (such as NaOH, LiOH, etc.), alkoxides (such as sodium or potassium tert-butoxide), lithium diisopropyl amide (LDA), lithium bis(trimethylsilyl)amide (LiHMDS), sodium bis(trimethylsilyl)amide (NaHMDS), and the like. Depending on the leaving group, suitable bases also include milder bases, such as alkaline and alkaline earth metal carbonates (such as Na$_2$CO$_3$, K$_2$CO$_3$, CaCO$_3$, etc.), and bicarbonates (such as NaHCO$_2$, KHCO$_3$, etc.), as well as amine bases, such as ammonia, ammonium hydroxide, triethylamine, pyridine, piperidine, pyrrolidine, 2,6-lutidine, 1,8-diazabicycloundec-7-ene (DBU), 4-(dimethylamino-pyridine, etc.

In some instances elimination of leaving group LG of A412 to afford olefin P416 occurs by treatment with inorganic acids (e.g., HCl, H$_2$SO$_4$, etc.) or organic acids (acetic acid, trifluoroacetic acid, triflic acid, etc.), in some embodiments, olefin P416 can be obtained directly from alcohol P415 by treatment with an inorganic or organic acid.

The alcohol P415 is obtained by nucleophilic attack of a nucleophile R$^3$—X$^-$ on the ketone P413, which is described above.

Regarding each of the synthetic schemes above, the skilled artisan will appreciate that aryl and/or heteroaryl, alkenyl, alkynyl, aralkyl, heteroaralkyl, allyl, and propargyl moieties herein may be readily coupled directly using Stille, Suzuki, Heck, Negishi, Sonongashira, Kumada, Glaser, or other related reactions, such as palladium-mediated cross-coupling reactions. Aryl and/or heteroaryl moieties herein may also be readily coupled through a heteroatom, e.g., using reactions such as the Ullmann reaction, any of various palladium-mediated reactions developed by S. Buchwald and others, by nucleophilic aromatic substitution, or other such reactions. Similarly, amines, alcohols, thiols, and other such heteroatom-bearing compounds herein may be coupled to aryl and/or heteroaryl moieties using palladium-mediated reactions developed by S. Buchwald and others, nucleophilic aromatic substitution, etc. Aryl and/or heteroaryl moieties linked by substituted or unsubstituted hydrocarbon chains herein may also be prepared by Stifle, Suzuki, Heck, Friedel-Crafts, and other reactions as will be apparent to those of skill in the art.

It will be understood that the various substituents on the compounds in the above syntheses can be protected from the reaction conditions as necessary using the proper protecting groups, such as those disclosed in Greene, T. W.; Wuts, P. G. M. *Greene's Protective Groups in Organic Synthesis,* 4th ed.; Wiley-Interscience: New York, 2006.

EXAMPLE

In order that this invention be more fully understood, the following examples are set forth. These examples are for the purpose of illustration only and are not to be construed as limiting the scope of the invention in any way.

The test compounds used in the following examples were obtained from commercial vendors for synthetic and natural compounds, including VitasM, ChemDiv, ChemBridge, Chromadex, Sigma Aldrich, Penta, Spectrum Chemical, Vigon, and Indofine.

The taste test panelists used in the following examples were screened based upon and selected for their ability to perceive the bitter taste associated with potassium chloride. Only panelists capable of perceiving bitter taste participated in the following taste tests.

Due to the complex nature of taste perception in subjects and the inherently subjective nature of the following experiments, individual taste test trials may yield different results for a given compound. The data presented in the following Examples is illustrative of the taste testing results observed. It is noted that the data presented in the Figures represents a subset of the data presented in the Examples below.

The taste testing experiments below were conducted with panels of varying size (i.e., panels comprising varying numbers of panelists).

Example 1 Generation of KCl Test Solutions

Edible KCl solution compositions ("KCl test solutions") were prepared by first dissolving varying amounts of the test compounds in an amount of ethanol or water (depending on the solubility of the compound) to create a 5 mg/mL stock compound solution. An amount of this stock compound solution is then added to an aqueous KCl solution. Enough EtOH is then added to the resulting stock compound/KCl solution so that the final KCl test solution contains 1% EtOH. KCl solution standards were similarly prepared by dissolving various amounts of KCl in water and ethanol without adding any test compound. NaCl solution standards were similarly prepared by dissolving various amounts of NaCl in water and ethanol without adding any test compound (NaCl solution standards did not contain any KCl).

TABLE 1

KCl Taste Test Solution

| Compound No. | Conc. Of KCl | Conc. of Compound Tested (ppm) | Conc. Where Decrease in Bitter Taste Was Discerned (ppm) | Conc. Where Decrease in Bitter Taste Discerned and $p \leq 0.1$ (ppm) |
|---|---|---|---|---|
| 1 | 4.85 g/L | 0.1 | 0.1 | 0.1 |
| 2 | 4.85 g/L | 1; 10 | 1; 10 | 10 |
| 4 | 4.85 g/L | 1; 10 | 1; 10 | 1 |
| 5 | 4.85 g/L | 0.1 | 0.1 | 0.1 |
| 6 | 4.85 g/L | 1; 10 | 1; 10 | 1 |
| 7 | 4.85 g/L | 1; 10 | 10 | — |
| 8 | 4.85 g/L | 1; 10 | 10 | — |
| 9 | 4.85 g/L | 1; 10 | 10 | — |
| 10 | 4.85 g/L | 1; 10 | 1; 10 | 1 |
| 11 | 4.85 g/L | 1; 10 | 1; 10 | 10 |
| 12 | 4.85 g/L | 1; 10 | 10 | — |
| 13 | 4.85 g/L | 1; 10 | 1 | — |
| 15 | 4.85 g/L | 1 | 1 | 1 |
| 17 | 4.85 g/L | 1; 10 | 1 | — |
| 18 | 4.85 g/L | 1; 10 | 10 | — |
| 19 | 4.85 g/L | 1; 10 | 1; 10 | — |
| 20 | 4.85 g/L | 1; 10 | — | — |
| 21 | 4.85 g/L | 1; 10 | 10 | — |
| 22 | 4.85 g/L | 1; 10 | 1; 10 | 1 |
| 23 | 4.85 g/L | 1; 10 | 1; 10 | 1 |
| 24 | 4.85 g/L | 1; 10 | 10 | — |
| 25 | 4.85 g/L | 1; 10 | 1; 10 | 1 |
| 26 | 4.85 g/L | 1; 10 | 1; 10 | 1 |
| 28 | 4.85 g/L | 1; 10 | 1; 10 | — |
| 29 | 4.85 g/L | 1; 10 | 1 | — |
| 31 | 4.85 g/L | 1; 10 | 1; 10 | 10 |
| 32 | 4.85 g/L | 1; 10 | 1; 10 | — |
| 33 | 4.85 g/L | 1; 10 | 1 | — |
| 34 | 4.85 g/L | 1; 10 | 1; 10 | 1; 10 |
| 36 | 4.85 g/L | 1; 10 | 1 | 1 |
| 37 | 4.85 g/L | 0.1; 1; 5; 10 | 0.1; 1; 10 | 0.1; 1; 10 |
| 38 | 4.85 g/L | 1; 10 | 1; 10 | — |
| 39 | 4.85 g/L | 1; 10 | 1; 10 | — |
| 40 | 4.85 g/L | 1; 10 | 10 | — |
| 41 | 4.85 g/L | 1; 10 | 10 | 10 |
| 42 | 4.85 g/L | 0.1; 1; 10 | 0.5; 1; 10 | 0.5; 10 |
| 43 | 4.85 g/L | 0.1; 1; 10 | 1 | 1 |
| 44 | 4.85 g/L | 1; 10 | — | — |
| 45 | 4.85 g/L | 1; 10 | 1 | — |
| 47 | 4.85 g/L | 1; 10 | — | — |
| 49 | 4.85 g/L | 10 | 10 | — |
| 50 | 4.85 g/L | 1; 10 | 1 | — |
| 52 | 4.85 g/L | 0.1; 1; 5 | 0.1; 1 | — |
| 53 | 4.85 g/L | 1; 10 | 1; 10 | 10 |
| 54 | 4.85 g/L | 1; 10 | 10 | — |
| 55 | 4.85 g/L | 1; 10 | 1; 10 | — |
| 56 | 4.85 g/L | 1; 10 | 1 | — |
| 57 | 4.85 g/L | 1; 10 | — | — |
| 58 | 4.85 g/L | 10 | 10 | 10 |
| 59 | 4.85 g/L | 1; 10 | 1 | — |
| 60 | 4.85 g/L | 1; 10 | 1; 10 | — |
| 61 | 4.85 g/L | 1; 10 | 1 | — |
| 62 | 4.85 g/L | 1; 10 | 10 | — |
| 63 | 4.85 g/L | 0.1; 1; 10 | 0.1; 1; 10 | 1 |
| 64 | 4.85 g/L | 1; 10 | 1; 10 | — |
| 65 | 4.85 g/L | 1; 10 | — | — |
| 66 | 4.85 g/L | 1; 10 | — | — |
| 67 | 4.85 g/L | 1; 10 | — | — |
| 68 | 4.85 g/L | 1; 10 | 10 | — |
| 69 | 4.85 g/L | 1; 10 | 1; 10 | 1 |
| 71 | 4.85 g/L | 1; 10 | 1; 10 | 1 |
| 73 | 4.85 g/L | 1; 10 | — | — |
| 74 | 4.85 g/L | 1; 10 | 1; 10 | 1; 10 |

TABLE 1-continued

KCl Taste Test Solution

| Compound No. | Conc. Of KCl | Conc. of Compound Tested (ppm) | Conc. Where Decrease in Bitter Taste Was Discerned (ppm) | Conc. Where Decrease in Bitter Taste Discerned and $p \leq 0.1$ (ppm) |
|---|---|---|---|---|
| 76 | 4.85 g/L | 1; 10 | 1; 10 | — |
| 78 | 4.85 g/L | 1; 10 | 1 | — |
| 80 | 4.85 g/L | 1; 10 | — | — |
| 81 | 4.85 g/L | 1; 10 | 10 | — |
| 84 | 4.85 g/L | 1; 10 | — | — |
| 85 | 4.85 g/L | 1; 10 | 1; 10 | 1 |
| 88 | 4.85 g/L | 1; 10 | 1; 10 | 1 |
| 90 | 4.85 g/L | 1 | 1 | — |
| 92 | 4.85 g/L | 1 | 1 | 1 |
| 94 | 4.85 g/L | 1; 10 | 10 | — |
| 95 | 4.85 g/L | 0.1; 1; 10 | 0.1; 1; 10 | 0.1; 1 |
| 97 | 4.85 g/L | 1 | 1 | — |
| 98 | 4.85 g/L | 10 | 10 | 10 |
| 99 | 4.85 g/L | 1 | 1 | — |
| 100 | 4.85 g/L | 10 | 10 | — |
| 101 | 4.85 g/L | 1; 10 | 1 | — |
| 102 | 4.85 g/L | 1; 10 | 1 | 1 |
| 104 | 4.85 g/L | 1; 10 | 10 | — |
| 106 | 4.85 g/L | 1; 10 | 1 | — |
| 107 | 4.85 g/L | 1; 10 | 10 | — |
| 108 | 4.85 g/L | 1; 10 | 1 | — |
| 109 | 4.85 g/L | 1; 10 | — | — |
| 110 | 4.85 g/L | 1; 10 | — | — |
| 111 | 4.85 g/L | 1; 10 | 1; 10 | 10 |
| 112 | 4.85 g/L | 1; 10 | — | — |
| 113 | 4.85 g/L | 1 | 1 | — |
| 114 | 4.85 g/L | 1; 10 | 1; 10 | 1; 10 |
| 115 | 4.85 g/L | 1; 10 | — | — |
| 116 | 4.85 g/L | 1; 10 | 1; 10 | — |
| 117 | 4.85 g/L | 1; 10 | 10 | — |
| 118 | 4.85 g/L | 1; 10 | 1; 10 | 1; 10 |
| 119 | 4.85 g/L | 1; 10 | 10 | — |
| 120 | 4.85 g/L | 30 | — | — |
| 121 | 4.85 g/L | 40 | 40 | 40 |
| 122 | 4.85 g/L | 0.1; 1; 10 | — | — |
| 123 | 4.85 g/L | 0.1; 1; 10 | 0.1; 1; 10 | — |
| 124 | 4.85 g/L | 0.1; 1; 10 | — | — |
| 126 | 4.85 g/L | 1; 10 | 1; 10 | 1; 10 |
| 127 | 4.85 g/L | | | |
| 128 | 4.85 g/L | 1; 10 | 1; 10 | 1 |
| 129 | 4.85 g/L | 1; 10 | 10 | 10 |
| 130 | 4.85 g/L | 40 | 40 | — |
| 132 | 4.85 g/L | 1 | 1 | — |
| 133 | 4.85 g/L | 2 | 2 | 2 |
| Standard | 4.85 g/L | | | |

Example 2 Effect of Test Compounds on the Perception of Bitter Taste of Aqueous KCl Solutions in Humans The effect of the test compounds an the perception of the bitter taste of an aqueous solution of KCl in humans was evaluated using a "sip and spit" test as follows.

A set of KCl solution standards was developed and each standard solution was assigned a bitterness taste score of 0-15 (corresponding to aqueous KCl concentrations of 0 mM-120 mM). Panelists were trained to recognize these standards. In addition, before each day of testing, panelists were tested to see if they could determine differences in taste between the standard solutions. If a panelist was unable to recognize a change in KCl concentration, they were excluded from the panel for that day.

In a blind taste test, panelists were asked to compare the bitter taste of a small quantity (e.g., 8 ml) of each of the KCl Test Solutions to the taste of a KCl solution standard, without swallowing (see, e.g., Table 1). Specifically, panelists were asked to rate the bitterness of each KCl Test Solution on a scale of 0-15 using the same scale developed for the KCl solution standards. Each sample was tested in 2-4 discrete taste test experiments. Panelists were asked to rinse with water, eat a cracker, and wait approximately 10 minutes between samples.

Illustrative results of the aqueous solution testing are presented in FIGS. 1-4 and Table 1.

Example 3 Generation of Potassium Lactate Test Solutions

Edible potassium lactate solution compositions ("potassium lactate test solutions") were prepared by first dissolving varying amounts of the test compounds in an amount of ethanol or water (depending on the solubility of the compound) to create a 5 mg/mL stock compound solution. An amount of this stock compound solution is then added to an aqueous potassium lactate solution. Enough EtOH is then added to the resulting stock compound/potassium lactate solution so that the final potassium lactate test solution contains 1% EtOH. Potassium lactate solution standards were similarly prepared by dissolving various amounts of potassium lactate in water and ethanol without adding any test compound. Sodium lactate solution standards were similarly prepared by dissolving various amounts of sodium lactate in water and ethanol without adding any test compound (sodium lactate solution standards did not contain any potassium lactate).

TABLE 2

Potassium Lactate Taste Test Solutions

| Compound No. | Conc. Of KLae | Conc. of Compound Tested (ppm) | Conc. Where Decrease in Bitter Taste Was Discerned (ppm) | Conc. Where Decrease in Bitter Taste Discerned and $p \leq 0.1$ (ppm) |
|---|---|---|---|---|
| 2 | 41 g/L | 1; 10 | 1 | — |
| 4 | 41 g/L | 1; 10 | — | — |
| 6 | 41 g/L | 1; 10 | 1; 10 | — |
| 10 | 41 g/L | 0.1; 1 | 0.1 | — |
| 11 | 41 g/L | 5; 10 | — | — |
| 22 | 41 g/L | 0.1; 1; 5; 10 | 1; 10 | 1 |
| 23 | 41 g/L | 0.1; 1 | — | — |
| 26 | 41 g/L | 0.1; 1; 10 | 10 | 10 |
| 31 | 41 g/L | 5; 10 | 5; 10 | 10 |
| 34 | 41 g/L | 1; 10 | 1; 10 | 1 |
| 37 | 41 g/L | 0.1; 10 | — | — |
| 41 | 41 g/L | 1; 5 | 5 | — |
| 42 | 41 g/L | 1; 10; 30 | 1 | 1 |
| 43 | 41 g/L | 1; 5 | 1 | 1 |
| 53 | 41 g/L | 5; 10 | 10 | 10 |
| 58 | 41 g/L | 1; 10; 30 | 1; 10; 30 | 10; 30 |
| 63 | 41 g/L | 1; 10; 30 | 1; 10; 30 | — |
| 74 | 41 g/L | 1; 10 | 1 | 1 |
| 85 | 41 g/L | 1; 5 | 5 | 5 |
| 88 | 41 g/L | 1; 5 | 1; 5 | 1; 5 |
| 95 | 41 g/L | 1; 10; 30 | 1; 10 | 1 |
| 102 | 41 g/L | 0.1; 1 | 1 | — |
| 114 | 41 g/L | 1; 5 | 1; 5 | — |
| 118 | 41 g/L | 1; 5 | 1 | — |
| 120 | 41 g/L | 1; 10; 30 | 1; 10; 30 | 1; 10 |
| 128 | 41 g/L | 1; 5 | 1; 5 | — |
| 129 | 41 g/L | 5; 10 | 5; 10 | 5 |
| Standard | 41 g/L | — | | |

Example 4 Effect of Test Compounds on the Perception of Bitter Taste of Aqueous Potassium Lactate Solutions in Humans The effect of the test compounds on the perception of the bitter taste of an aqueous solution of potassium lactate in humans was evaluated using the "sip and spit" test described in Example 2.

Illustrative results of the aqueous solution testing are presented in FIGS. 1-4 and to Table 2.

Example 5 Generation of KCl) Test Foodstuff Slurries

Edible KCl food compositions ("KCl test foodstuff slurries") were prepared as follows. Dehydrated, salt-free turkey powder was weighed and mixed with various amounts of KCl and/or NaCl and then solubilized with boiling water to create a homogenized solubilized turkey slurry. Varying amounts of the test compounds were dissolved in an amount of ethanol or water (depending on the solubility of the compound) to create a 5 mg/mL stock compound solution. An amount of this stock compound solution was then added to the turkey slurry. Enough EtOH is then added to the resulting stock compound/turkey slurry so that the slurry contains 1% EtOH. The slurry was again homogenized by boiling and mixing and allowed to cool to yield the final KCl test foodstuff slurry for taste testing KCl foodstuff slurry standards were similarly prepared without any test compound. NaCl foodstuff slurry standards were similarly prepared without adding any test compound (NaCl foodstuff slurry standards did not contain any KCl).

TABLE 3

KCl Foodstuff Slurry Compositions

| Compound No. | Conc. Of KCl | Conc. of Compound Tested (ppm) | Conc. at Which At Least 50% of Panelist Discerned Decrease in Bitter Taste (ppm) | Conc. at Which At Least 50% of Panelist Discerned Decrease in Bitter Taste and $p \leq 0.1$ (ppm) |
|---|---|---|---|---|
| 2 | 1.6% | 1; 10 | — | — |
| 4 | 1.6% | 1; 10 | — | — |
| 8 | 1.6% | 1; 10 | 1 | — |
| 10 | 1.6% | 0.1; 1 | 0.1 | — |
| 11 | 1.6% | 5; 10 | — | — |
| 21 | 1.6% | 1; 10 | 10 | — |
| 22 | 1.6% | 1; 5 | — | — |
| 23 | 1.6% | 1; 10 | — | — |
| 26 | 1.6% | 0.1; 1 | — | — |
| 31 | 1.6% | 5; 10 | 10 | — |
| 33 | 1.6% | 1; 10 | 1; 10 | — |
| 34 | 1.6% | 1; 10 | — | — |
| 37 | 1.6% | 0.1; 10 | — | — |
| 41 | 1.6% | 1; 10 | 1; 10 | — |
| 42 | 1.6% | 1; 10; 30 | 1; 10; 30 | 30 |
| 43 | 1.6% | 1; 5 | 5 | — |
| 53 | 1.6% | 1; 5; 10 | — | — |
| 58 | 1.6% | 1; 10; 30 | 1; 10; 30 | 10; 30 |
| 63 | 1.6% | 1; 10; 30 | 1; 10; 30 | 30 |
| 65 | 1.6% | 10 | | |
| 69 | 1.6% | 1; 10 | 1; 10 | 10 |
| 74 | 1.6% | 1; 10 | 10 | — |
| 88 | 1.6% | 1; 10 | 1 | — |
| 95 | 1.6% | 1; 10; 30 | 1; 10; 30 | — |
| 102 | 1.6% | 10 | 10 | — |
| 111 | 1.6% | 1; 10 | 1 | — |
| 114 | 1.6% | 1; 10 | 1; 10 | — |
| 118 | 1.6% | 1; 10 | — | — |
| 120 | 1.6% | 1; 10; 30 | 10 | — |
| 128 | 1.6% | 1; 5 | — | — |
| 129 | 1.6% | 5; 10 | 5 | — |
| Standard | 1.6% | — | | |

Example 6 Effect of Test Compounds on the Perception of Bitter Taste of KCl Foodstuff Slurries in Humans Using a Two-Alternative Forced Choice Method (2AFC)

The effect of the test compounds on the perception of the bitter taste of KCl foodstuff slurries in humans was evaluated using a two-alternative-forced-choice "sip and spit" test as follows.

In a blind taste test, panelists received two portions of turkey slurry—one portion being the KCl foodstuff slurry standard and the other being one of the KCl test foodstuff slurries (each prepared as described in Example 5). The panelists tasted each of the portions by sipping and spitting. Each sample was tested in 2-4 discrete taste test experiments. Panelists were asked to rinse with water, eat a cracker, and wait about 10 minutes between samples. In each case, the panelists were asked to compare the bitter taste of the two turkey samples to each other (i.e., panelists were asked to indicate which sample was less bitter).

Illustrative results of the foodstuff testing are presented in FIGS. 1-4 and in Table 3.

Example 7 Generation of Potassium Lactate Test Foodstuff Slurries

Edible potassium lactate food compositions ("potassium lactate test foodstuff slurries") were prepared as follows. Dehydrated, salt-free turkey powder was weighed and mixed with various amounts of potassium lactate and/or sodium lactate and then solubilized with boiling water to create a homogenized solubilized turkey slurry. Varying amounts of the test compounds were dissolved in an amount of ethanol or water depending on the solubility of the compound) to create a 5 mg/mL stock compound solution. An amount of this stock compound solution was then added to the turkey slurry. Enough EtOH is then added to the resulting stock compound/turkey slurry so that the final slurry contains 1% EtOH. The final slurry was again homogenized by boiling and mixing and allowed to cool to yield the final slurry for taste testing. Potassium lactate foodstuff slurry standards were similarly prepared without any test compound. Sodium lactate foodstuff slurry standards were similarly prepared without adding any test compound (sodium lactate foodstuff slurry standards did not contain any potassium lactate).

TABLE 4

Potassium Lactate Foodstuff Slurry Compositions

| Compound No. | Conc. Of KLac | Conc. of Compound Tested (ppm) | Conc. at Which At Least 50% of Panelist Discerned Decrease in Bitter Taste (ppm) | Conc. at Which At Least 50% of Panelist Discerned Decrease in Bitter Taste and $p \leq 0.1$ (ppm) |
|---|---|---|---|---|
| 34 | 4.5% | 1; 10 | — | — |
| 42 | 4.5% | 1; 10; 30 | 1; 10; 30 | 30 |
| 43 | 4.5% | 30 | 30 | 30 |
| 53 | 4.5% | 5 | 5 | — |
| 63 | 4.5% | 1; 10; 30 | — | — |
| 74 | 4.5% | 1; 10 | 1 | — |
| 95 | 4.5% | 1; 10; 30 | 1; 10 | 10 |
| 120 | 4.5% | 1; 10; 30 | 10 | — |
| Standard | 4.5% | — | | |

Example 8 Effect of Test Compounds on the Perception of Bitter Taste of Potassium Lactate Foodstuff Slurries in Humans Using a Two-Alternative Forced Choice Method (2AFC)

The effect of the test compounds on the perception of the bitter taste of potassium lactate foodstuffs in humans was evaluated using the two-alternative-forced-choice "sip and spit" test described in Example 6.

Illustrative results of the foodstuff test are presented in FIGS. 1-4 and in Table 4.

Example 9 Effect of Test Compounds on the Perception of Bitter Taste of KCl Foodstuff Slurries in Humans Using a Latin Square Two-Alternative Forced Choice Method (Latin Square 2AFC)

The effect of the test compounds on the perception of the bitter taste of an aqueous solution of KCl in humans was evaluated using a "sip and spit" test using a Latin Square-2AFC testing method as follows.

In a blind taste test, panelists were asked to compare the bitter taste of a small quantity (e.g., 8 ml) of a KCl Test Solution to the taste of a KCl solution standard (prepared as described in Example 1), without swallowing. NaCl solution standards were prepared as described in Example 1.

In order to eliminate any effects of sample order, a complete Latin Square design was employed so that each possible order of sample presentation was utilized across subjects. Each sample was tested in several discrete taste test experiments. Panelists were asked to rinse with water, eat a cracker, and wait about 10 minutes between samples. In each case, the panelists were asked to choose the sample which tasted "less bitter." Illustrative results of the aqueous solution Latin Square-2AFC testing are presented in Table 5.

TABLE 5

KCl Latin Square-2AFC Taste Test Solution

| Compound No. | Conc. Of KCl | Conc. of Compound Tested (ppm) | Conc. at Which At Least 50% of Panelist Discerned Decrease in Bitter Taste (ppm) | Conc. at Which At Least 50% of Panelist Discerned Decrease in Bitter Taste and $p \leq 0.1$ (ppm) |
|---|---|---|---|---|
| 2 | 4.85 g/L | 0.2; 0.6; 2; 6.5; 20 | 2 | — |
| 4 | 4.85 g/L | 0.25; 1; 2.5; 10; 25 | — | — |
| 10 | 4.85 g/L | 0.25; 1; 2.5; 10; 25 | — | — |
| 11 | 4.85 g/L | 0.25; 1; 2.5; 10; 25 | 1 | — |
| 22 | 4.85 g/L | 0.25; 0.5; 1; 2; 4 | 0.25; 2 | 0.25 |
| 25-1 | 4.85 g/L | 0.4; 1.2; 4; 12; 40 | 0.4; 1.2; 4 | |
| 25-2 | 4.85 g/L | 0.5; 1; 2; 4 | 0.5; 1; 4 | — |
| 26-1 | 4.85 g/L | 0.4; 1.2; 4; 12; 40 | 4; 12; 40 | |
| 26-2 | 4.85 g/L | 0.5; 1; 2; 4; 8 | 0.5; 1 | |
| 31-1 | 4.85 g/L | 0.6; 2; 6; 20; 50 | — | — |
| 31-2 | 4.85 g/L | 0.25; 0.5; 1; 2; 4 | 0.25 | |
| 34-1 | 4.85 g/L | 0.6; 1.8; 6; 18; 50 | 0.6; 1.8; 6 | 6 |

TABLE 5-continued

KCl Latin Square-2AFC Taste Test Solution

| Compound No. | Conc. Of KCl | Conc. of Compound Tested (ppm) | Conc. at Which At Least 50% of Panelist Discerned Decrease in Bitter Taste (ppm) | Conc. at Which At Least 50% of Panelist Discerned Decrease in Bitter Taste and $p \leq 0.1$ (ppm) |
|---|---|---|---|---|
| 34-2 | 4.85 g/L | 1; 3; 5; 7; 9 | 1; 7 | — |
| 36 | 4.85 g/L | 0.25; 1; 2.5; 10; 25 | — | — |
| 37 | 4.85 g/L | 0.25; 0.5; 1; 2.5; 5 | — | — |
| 41 | 4.85 g/L | 0.1; 0.25; 1; 2.5; 5; 10 | 0.25; 1; 2.5 | 1 |
| 43 | 4.85 g/L | 1; 5; 10; 25; 50 | 10 | — |
| 53 | 4.85 g/L | 0.25; 1; 2.5; 10; 25 | 1 | — |
| 69-1 | 4.85 g/L | 0.6; 2; 6; 20; 40 | 0.6; 2; 6 | 2 |
| 69-2 | 4.85 g/L | 0.25; 1; 2; 4; 10 | 0.25; 2; 4 | — |
| 74 | 4.85 g/L | 0.25; 0.5; 1; 2; 4 | 0.25; 0.5; 1; 4 | 1 |
| 85 | 4.85 g/L | 0.005; 0.01; 0.05; 0.17 | 0.005 | — |
| 114 | 4.85 g/L | 0.25; 1; 2.5; 10; 25 | 0.25; 1; 25 | 25 |
| 128 | 4.85 g/L | 0.1; 0.25; 0.5; 1; 2 | 1 | — |
| 129 | 4.85 g/L | 0.25; 1; 2.5; 5; 10 | — | — |
| Standard | 4.85 g/L | | | |

Example 10 Effect of Test Compounds on the Perception of Bitter Taste of KCl Foodstuff Slurries in Humans Using a Two-Alternative Forced Choice Method (Latin Square-2AFC)

The effect of the test compounds on the perception of the bitter taste of KCl foodstuff slurries in humans was evaluated using a "sip and spit" test using a Latin Square-2AFC testing method as follows.

In a blind taste test, panelists received two portions of turkey slurry—one portion being the KCl foodstuff slurry standard and the other being one of the KCl test foodstuff slurries (prepared as described in Example 5). NaCl foodstuff slurry standards were prepared as described in Example 1.

The panelists tasted each of the portions by sipping and spitting. In order to eliminate any effects of sample order, a complete Latin Square design was employed so that each possible order of sample presentation was utilized across subjects. Each sample was tested in several discrete taste test experiments. Panelists were asked to rinse with water, eat a cracker, and wait about 10 minutes between samples. In each case, the panelists were asked to choose the sample that tasted less bitter.

Illustrative results of the foodstuff Latin Square-2AFC testing are presented in Table 6.

TABLE 6

KCl Latin Square-2AFC Taste Test Turkey Slurry

| Compound No. | Conc. Of KCl | Conc. of Compound Tested (ppm) | Conc. at Which At Least 50% of Panelist Discerned Decrease in Bitter Taste (ppm) | Conc. at Which At Least 50% of Panelist Discerned Decrease in Bitter Taste and $p \leq 0.1$ (ppm) |
|---|---|---|---|---|
| 2 | 1.6% | 0.2; 0.25; 0.6; 1; 2; 2.5; 6.5; 10; 20; 25 | 25 | — |
| 22 | 1.6% | 0.5; 1.5; 5; 15; 50 | — | — |
| 26 | 1.6% | 0.2; 0.6; 2; 6.5; 20 | 0.6 | — |
| 31 | 1.6% | 0.6; 2; 6; 20; 50 | — | — |
| 69 | 1.6% | 0.6; 2; 6; 20; 50 | 0.6; 2; 6; 20 | 0.6; 2 |
| Standard | 1.6% | | | |

Example 11 Effect of Test Compounds on the Perception of Bitter Taste of KCl Foodstuff Slurries in Humans Using a Two-Alternative Forced Choice Method (Latin Square-2AFC)

The effect of the test compounds on the perception of the bitter taste of KCl in solid-matrix foodstuffs in humans was evaluated using a "chew and spit" test using a Latin Square-2AFC testing method as follows.

Two types of marinades containing Prague powder, sugar, Evian™ water, KCl and/or NaCl in water were prepared. One marinade contained 80% KCl, 20% NaCl (by weight) (i.e., marinade concentration of 1-6% KCl). A second marinade contained 60% KCl:40% NaCl (by weight) (i.e., marinade concentration of 1.2% KCl). Compound stock solutions were prepared by dissolving an amount of test compound in ethanol or water (depending on the solubility of the compound) to create a 5 mg/mL stock compound solution. Enough ethanol was added to each stock compound solution to generate a final stock compound solution containing 1% ethanol. The marinade, the stock compound solution and ground turkey were added to a mixing bowl, mixed at low-speed for about 2 minutes, and then mixed at high-speed for about 5 minutes. The marinated turkey mixture was divided into one pound aliquots, vacuum sealed into food saver bags, and allowed to marinate for about 2 hours in a refrigerator. The vacuum-sealed turkey was then cooked in an about 86° C. water bath for about 30 minutes. If after about 30 minutes, the internal turkey temperature had not reached about 170° F., the vacuum-sealed turkey was cooked for about an additional 5 minutes. The vacuum-sealed turkey was then refrigerated for about two weeks before taste testing. KCl standards were similarly prepared by dissolving KCl in the marinade without adding any test compound during the turkey preparation. NaCl standards were similarly prepared by dissolving NaCl in the marinade without adding any test compound during the turkey preparation (NaCl standards did not contain any KCl).

The panelists tasted portions by chewing and spitting. In order to eliminate any effects of sample order, a complete Latin Square design was employed so that each possible order of sample presentation was utilized across subjects. Each simple was tested in several discrete taste test experiments. Panelists were asked to rinse with water, cat a cracker, and wait about 10 minutes between samples. In each case, the panelists were asked to choose the sample that tasted less bitter. Illustrative results presented in Table 7.

TABLE 7

KCl Latin Square-2AFC Taste Solid Turkey

| Compound No. | Conc. Of KCl | Conc. of Compound Tested (ppm) | Conc. at Which At Least 50% of Panelist Discerned Decrease in Bitter Taste (ppm) | Conc. at Which At Least 50% of Panelist Discerned Decrease in Bitter Taste and p ≤ 0.1 (ppm) |
|---|---|---|---|---|
| 2 | 1.6% | 0.5; 2; 5; 10 | 10 | — |
| 4 | 1.6% | 1; 2; 4; 10 | — | — |
| 6 | 1.6% | 0.5; 1; 2; 4 | 0.5; 1; 2 | — |
| 10 | 1.6% | 0.5; 2; 5; 10 | 0.5 | — |
| 11 | 1.6% | 2; 5; 10; 20 | 2; 10 | — |
| 19 | 1.6% | 0.1; 1; 2; 4 | — | — |
| 22 | 1.6% | 1; 2; 4; 10 | — | — |
| 23 | 1.6% | 0.01; 0.05; 0.1; 0.3; 0.5 | 0.05; 3 | — |
| 25 | 1.6% | 2; 5; 10; 20 | 2; 20 | — |
| 26 | 1.6% | 2; 5; 10; 20 | — | — |
| 31 | 1.6% | 0.5; 1; 2; 4 | 0.5; 1; 4 | 4 |
| 34 | 1.6% | 1; 2; 4; 10 | 2 | — |
| 36 | 1.6% | 2; 5; 10; 20 | — | — |
| 37 | 1.6% | 0.5; 1; 2.5; 5; 10; 25 | 0.5; 1; 10 | — |
| 41 | 1.6% | 0.1; 0.5; 1; 2.5; 5; 10 | 0.1; 0.5; 2.5 | 2.5 |
| 43 | 1.6% | 0.1; 0.5; 1; 2; 4; 8 | 0.1; 0.5; 1; 2; 4 | 0.1; 1; 2 |
| 53 | 1.6% | 2; 5; 10; 20 | — | — |
| 69 | 1.6% | 0.5; 1; 2; 4; 10 | 0.5; 1; 2; 4; 10 | 1 |
| 74 | 1.6% | 1; 2; 5; 10; 20 | 1; 2; 10; 20 | 10 |
| 85 | 1.6% | 0.1; 0.25; 0.5; 1; 2; 4; 10 | 0.5; 1 | 1 |
| 114 | 1.6% | 0.01; 0.05; 0.1; 0.5 | — | — |
| 126 | 1.6% | 1; 2; 10; 20 | — | — |
| 128 | 1.6% | 0; 0.4; 1.2; 2.4; 3.6 | — | — |
| 128 | 1.2% | 0.1; 0.25; 0.4; 0.5; 1; 1.2; 2.4; 3.6; 4.8 | 0.1; 1 | — |
| 129 | 1.6% | 0.5; 1; 2; 4; 5; 15 | — | — |
| Standard | 1.6% | | | |

We claim:

1. A composition comprising a bitter tastant selected from KCl and potassium lactate; and a compound according to Formula (I):

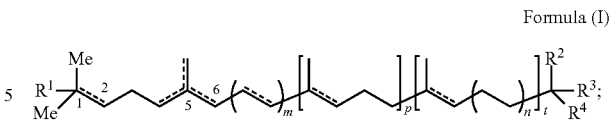

or a comestibly or biologically acceptable salt thereof, or an enantiomer or diastereomer thereof, wherein, as valence and stability permit:

$R^1$ is absent or is selected from the group consisting of hydrogen, hydroxyl, $C_{1-3}$alkoxy, and $C_{1-3}$acyloxy;

$R^2$ is selected from the group consisting of hydrogen, $C_{1-3}$alkyl, $C_{2-3}$alkenyl, and $C_{2-3}$alkynyl;

$R^3$ is selected from the group consisting of hydrogen and $C_{1-3}$alkoxy;

$R^4$ is selected from the group consisting of hydroxyl, $C_{1-3}$alkoxy, and $C_{1-3}$acyloxy;

m is 1;

n is 0;

p is 1; and t is 1;

wherein all dotted bonds indicate optional carbon-carbon double bonds; and wherein the composition is edible and the bitter taste due to KCl or potassium lactate is reduced.

2. The composition according to claim 1, wherein said compound is Compound 41 and having the structure:

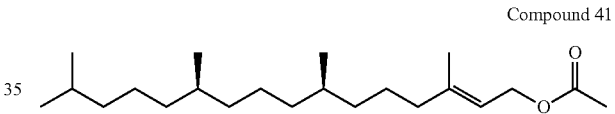

or comestibly or biologically acceptable salts thereof, or enantiomers or diastereomers thereof.

3. The composition of claim 1 or 2, wherein the composition further comprises one or more component selected from the group consisting of: NaCl and sodium lactate.

4. A food product comprising the composition of any one of claim 1 or 2.

5. A method of preparing an edible composition comprising KCl or potassium lactate, said method comprising:
 (a) providing a comestibly acceptable carrier; and
 (b) adding to said comestibly acceptable carrier a compound according to Formula (I) as defined in claim 1, or combinations thereof.

6. The method according to claim 5, wherein the edible composition further comprises one or more component selected from NaCl and sodium lactate.

7. A method of reducing the amount of sodium salt in an edible composition comprising:
 (a) replacing an amount of sodium salt used in preparing said edible composition with an amount of potassium salt; and
 (b) incorporating into the edible composition an effective amount of a compound according to Formula (I) as defined in claim 1, or combinations thereof, to produce an edible composition with reduced sodium salt.

8. The method according to claim 7, wherein the amount of compound incorporated into the edible composition is sufficient to permit replacement of the amount of 100% of the sodium salt in the edible composition.

9. The method according to claim 7, wherein the edible composition with reduced sodium salt maintains a salty flavor.

10. The method according to claim 7, wherein the edible composition with reduced sodium salt has the same shelf life as an edible composition comprising the full amount sodium salt.

11. The method according to any one of claim 5 or 7, wherein the edible composition is selected from the group consisting of a food product, a consumer product, and a pharmaceutical composition.

12. The method according to claim 7, wherein the sodium salt is selected from NaCl and sodium lactate, or a combination thereof, and the potassium salt is selected from KCl and potassium lactate, or a combination thereof.

13. The method according to claim 7, wherein the edible composition with reduced sodium salt has the same shelf life as an edible composition comprising the full amount sodium salt and further wherein the sodium salt is selected from NaCl and sodium lactate, or a combination thereof, and the potassium salt is selected from KCl and potassium lactate, or a combination thereof.

14. The method according to claim 7, wherein the amount of compound incorporated into the edible composition is sufficient to permit replacement of the amount of 25% of the sodium salt in the edible composition.

15. The method according to claim 7, wherein the amount of compound incorporated into the edible composition is sufficient to permit replacement of the amount of 50% of the sodium salt in the edible composition.

16. The method according to claim 7, wherein the amount of compound incorporated into the edible composition is sufficient to permit replacement of the amount of 75% of the sodium salt in the edible composition.

* * * * *